(12) United States Patent
Schaetzer et al.

(10) Patent No.: US 12,281,095 B2
(45) Date of Patent: Apr. 22, 2025

(54) PESTICIDALLY ACTIVE DIAZINE-AMIDE COMPOUNDS

(71) Applicant: SYNGENTA CROP PROTECTION AG, Basel (CH)

(72) Inventors: Jürgen Harry Schaetzer, Stein (CH); Andrew Edmunds, Stein (CH); Julien Daniel Henri Gagnepain, Stein (CH); Roger Graham Hall, Stein (CH); André Jeanguenat, Stein (CH); Amandine Kolleth Krieger, Stein (CH); Camille Le Chapelain, Stein (CH); Shrikant Palwe, Goa (IN); Mangala Phadte, Goa (IN); Thomas Pitterna, Stein (CH); Sebastian Rendler, Stein (CH); Christopher Charles Scarborough, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 834 days.

(21) Appl. No.: 17/593,969

(22) PCT Filed: Mar. 27, 2020

(86) PCT No.: PCT/EP2020/058701
§ 371 (c)(1),
(2) Date: Sep. 29, 2021

(87) PCT Pub. No.: WO2020/201079
PCT Pub. Date: Oct. 8, 2020

(65) Prior Publication Data
US 2022/0185789 A1 Jun. 16, 2022

(30) Foreign Application Priority Data

Mar. 29, 2019 (EP) .................... 19166323
Oct. 22, 2019 (EP) .................... 19204721
Jan. 14, 2020 (EP) .................... 20151657

(51) Int. Cl.
C07D 401/04 (2006.01)
A01N 43/60 (2006.01)
C07D 401/14 (2006.01)
C07D 403/04 (2006.01)

(52) U.S. Cl.
CPC .......... *C07D 401/04* (2013.01); *A01N 43/60* (2013.01); *C07D 401/14* (2013.01); *C07D 403/04* (2013.01)

(58) Field of Classification Search
None
See application file for complete search history.

(56) References Cited

U.S. PATENT DOCUMENTS

| 9,730,447 B2 | 8/2017 | Bereznak et al. | |
| 2021/0395228 A1* | 12/2021 | Schaetzer | ............. A01P 7/04 |
| 2022/0159958 A1* | 5/2022 | Schaetzer | ............. A01N 53/00 |
| 2022/0169629 A1* | 6/2022 | Schaetzer | ............. A01N 43/60 |
| 2022/0389000 A1* | 12/2022 | Hueter | ............. C07D 409/14 |

FOREIGN PATENT DOCUMENTS

| WO | 2004047722 A2 | 6/2004 | |
| WO | 2007041643 A1 | 4/2007 | |
| WO | WO-2013152150 A1 * | 10/2013 | ........... C07D 401/12 |
| WO | 2015/078800 A1 | 6/2015 | |
| WO | 2017153380 A1 | 9/2017 | |
| WO | 2017192385 A1 | 11/2017 | |
| WO | 2019197468 A1 | 10/2019 | |

OTHER PUBLICATIONS

Notification on the necessity on filing additional documents issued in Eurasian Application No. 202192597 dated Nov. 21, 2022, with English translation.
Karnozhitskii, "Organicheskie perekisi" [Organic peroxides], Izdatelstvo inostrannoi literatury [Foreign Literature Publishing House], Moscow, pp. 38-39, 1961.
Written Opinion of the International Searching Authority and International Search Report for PCT/EP2020/058701, mailed on Jun. 15, 2020.
Extended European Search Report for EP 19204721.5 dated Apr. 1, 2020.

\* cited by examiner

*Primary Examiner* — Jeffrey S Lundgren
*Assistant Examiner* — Anthony Joseph Seitz
(74) *Attorney, Agent, or Firm* — BakerHostetler; Toni-Junell Herbert

(57) ABSTRACT

Compounds of formula I (1) wherein the substituents are as defined in claim 1, and the agrochemically acceptable salts, stereoisomers, enantiomers, tautomers and N-oxides of those compounds, can be used as insecticides.

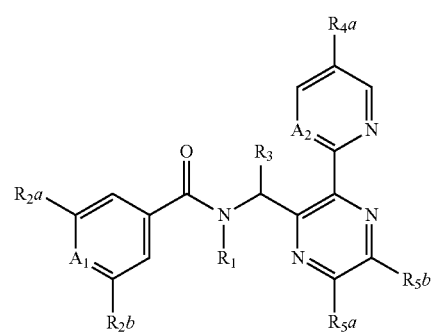

22 Claims, No Drawings

PESTICIDALLY ACTIVE DIAZINE-AMIDE COMPOUNDS

CROSS-REFERENCE TO RELATED APPLICATIONS

This application is a 371 National Stage application of International Application No. PCT/EP2020/058701 filed Mar. 27, 2020, which claims priority to EP 19166323.6 filed Mar. 29, 2019, EP 19204721.5 filed Oct. 22, 2019, and EP 20151657.2 filed Jan. 14, 2020, the entire contents of these applications are hereby incorporated by reference.

The present invention relates to pesticidally active, in particular insecticidally active diazine-amide compounds, to processes for their preparation, to compositions comprising those compounds, and to their use for controlling animal pests, including arthropods and in particular insects or representatives of the order Acarina.

WO2017192385 describes certain heteroaryl-1,2,4-triazole and heteroaryl-tetrazole compounds for use for controlling ectoparasites in animals (such as a mammal and a non-mammal animal).

There have now been found novel pesticidally active-diazine amide compounds.

The present invention accordingly relates, in a first aspect, to a compound of the formula I

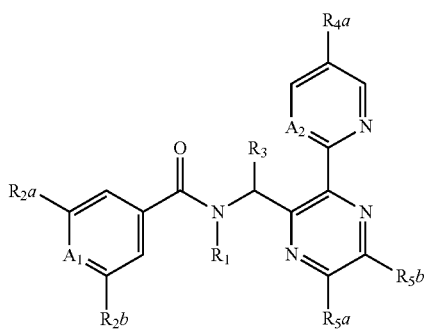

wherein
$R_1$ is H, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_6$haloalkyl, $C_2$-$C_6$alkenyl, $C_2$-$C_6$haloalkeny, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halo atoms, oxetan-3-yl-$CH_2$—, benzyl or benzyl substituted with halo or $C_1$-$C_6$haloalkyl;
$A_1$ is N or C—$R_{2c}$;
$R_{2c}$ is H, halogen, $C_1$-$C_3$alkyl, $C_1$-$C_3$haloalkyl, $C_1$-$C_3$alkoxy, or $C_1$-$C_3$haloalkoxy;
$R_{2a}$ is $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkoxy substituted with one to three substituents independently selected from $C_1$-$C_3$alkyl, $C_1$-$C_3$haloalkyl, cyano, and halogen, $C_3$-$C_6$cycloalkyl$C_1$-$C_4$alkyl, $C_3$-$C_6$cycloalkyl$C_1$-$C_4$alkoxy, $C_3$-$C_6$cycloalkyl$C_1$-$C_4$alkyl substituted with one to five substituents independently selected from $C_1$-$C_3$alkyl, $C_1$-$C_3$haloalkyl, $C_1$-$C_3$alkoxy, cyano, and halogen, $C_3$-$C_6$cycloalkyl$C_1$-$C_4$alkoxy substituted with one to five substituents independently selected from $C_1$-$C_3$alkyl, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, or $C_1$-$C_4$haloalkylsulfinyl;
$R_{2b}$ is H, halogen, $C_1$-$C_3$alkyl, $C_1$-$C_3$haloalkyl, $C_1$-$C_3$haloalkylthio, $C_1$-$C_3$alkoxy, $C_1$-$C_3$haloalkoxy, $SF_5$, or CN;
$R_3$ is $C_1$-$C_3$alkyl or $C_1$-$C_3$haloalkyl;
$A_2$ is $CR_{4b}$ or N;
$R_{4b}$ is hydrogen, or halogen;
$R_{4a}$ is cyano, or $C_1$-$C_3$haloakoxy;
$R_{5a}$ and $R_{5b}$ are, independently of each other, selected from hydrogen, halogen, CN, $C_1$-$C_3$alkyl, $C_1$-$C_3$haloalkyl, $C_3$-$C_4$cycloalkyl, $C_1$-$C_3$alkoxy, and $C_1$-$C_3$haloalkoxy; or agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "*Heterocyclic N-oxides*" by A. Albini and S. Pietra, CRC Press, Boca Raton 1991.

The compounds of formula I according to the invention also include hydrates which may be formed during the salt formation.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2, 2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "C$_1$-C$_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "C$_1$-C$_2$fluoroalkyl" would refer to a C$_1$-C$_2$alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "C$_1$-C$_n$alkoxy" as used herein refers to a straight-chain or branched saturated alkyl radical having 1 to n carbon atoms (as mentioned above) which is attached via an oxygen atom, i.e., for example, any one of the radicals methoxy, ethoxy, n-propoxy, 1-methylethoxy, n-butoxy, 1-methylpropoxy, 2-methylpropoxy or 1,1-dimethylethoxy. The term "haloC$_1$-C$_n$alkoxy" as used herein refers to a C$_1$-C$_n$alkoxy radical where one or more hydrogen atoms on the alkyl radical is replaced by the same or different halo atom(s)—examples include tnfluoromethoxy, 2-fiuoroetlioxy, 3-fluoropropoxy, 3,3,3-trifluoropropoxy, 4-chlorobutoxy.

The term "C$_1$-C$_n$cyanoalkyl" as used herein refers to a straight chain or branched saturated C$_1$-C$_n$alkyl radical having 1 to n carbon atoms (as mentioned above), where one of the hydrogen atoms in these radicals is be replaced by a cyano group: for example, cyanomethyl, 2-cyanoethyl, 2-cyanopropyl, 3-cyanopropyl, 1-(cyanomethyl)-2-ethyl, 1-(methyl)-2-cyanoethyl, 4-cyanobutyl, and the like.

The term "C$_3$-C$_n$cycloalkyl" as used herein refers to 3 to n membered cycloalkyl groups such as cyclopropane, cyclobutane, cyclopentane and cyclohexane. The term "C$_3$-C$_n$cycloalkoxy" refers to a cycloalkyl groups (as mentioned above) which is attached via an oxygen atom to the rest of the molecule.

The term "C$_3$-C$_n$cycloalkyl-C$_1$-C$_n$alkyl-" as used herein refers to 3 to n membered cycloalkyl group with a 1 to n alkyl group, which alkyl group is connected to the rest of the molecule. In the instance, the C$_3$-C$_4$cycloalkyl-C$_1$-C$_2$alkyl- group is substituted, the substituent(s) can be on the cycloalkyl group or the alkyl part. The term "C$_3$-C$_n$cycloalkyl-C$_1$-C$_n$alkoxy-" refers to the alkyl group of the cycloalkyl-alkyl substitutent being connected to an oxygen atom, which oxygen atom forms the attachment to the rest of the molecule.

The term "aminocarbonylC$_1$-C$_n$alkyl" as used herein refers to an alkyl radical where one of the hydrogen atoms in the radical is replaced by CONH2 group.

The term "hydroxycarbonylC$_1$-C$_n$alkyl" as used herein refers to an alkyl radical where one of the hydrogen atoms in the radical is replaced by COOH group.

The term "C$_1$-C$_n$nitroalkyl" as used herein refers to an alkyl radical where one of the hydrogen atoms in the radical is replaced by NO2 group.

The term "C$_1$-C$_n$haloalkylthio" as used herein refers to a C$_1$-C$_3$haloalkyl moiety linked through a sulfur atom.

The term "trimethylsilaneC$_1$-C$_n$alkyl" as used herein refers to an alkyl radical where one of the hydrogen atoms in the radical is replaced by a —Si(CH$_3$)$_3$ group.

The term "C$_2$-C$_n$alkenyl" as used herein refers to a straight or branched alkenyl chain having from two to n carbon atoms and one or two double bonds, for example, ethenyl, prop-I-enyl, but-2-enyl.

The term "C$_2$-C$_n$haloalkenyl" as used herein refers to a C$_2$-C$_n$alkenyl moiety substituted with one or more halo atoms which may be the same or different.

The term "C$_2$-C$_n$alkynyl" as used herein refers to a straight or branched alkynyl chain having from two to n carbon atoms and one triple bond, for example, ethynyl, prop-2-ynyl, but-3-ynyl, The term "C$_2$-C$_n$haloalkynyl" as used herein refers to a C$_2$-C$_n$alkynyl moiety substituted with one or more halo atoms which may be the same or different.

Halogen is generally fluorine, chlorine, bromine or iodine. This also applies, correspondingly, to halogen in combination with other meanings, such as haloalkyl As used herein, the term "controlling" refers to reducing the number of pests, eliminating pests and/or preventing further pest damage such that damage to a plant or to a plant derived product is reduced.

The staggered line as used herein, for example, in K-1 and L-1, represent the point of connection/attachment to the rest of the compound.

As used herein, the term "pest" refers to insects, and molluscs that are found in agriculture, horticulture, forestry, the storage of products of vegetable origin (such as fruit, grain and timber); and those pests associated with the damage of man-made structures. The term pest encompasses all stages in the life cycle of the pest.

As used herein, the term "effective amount" refers to the amount of the compound, or a salt thereof, which, upon single or multiple applications provides the desired effect.

An effective amount is readily determined by the skilled person in the art, by the use of known techniques and by observing results obtained under analogous circumstances. In determining the effective amount a number of factors are considered including, but not limited to: the type of plant or derived product to be applied; the pest to be controlled & its lifecycle; the particular compound applied; the type of application; and other relevant circumstances.

As one of ordinary skill in the art will appreciate, compounds of formula I contain a stereogenic centre which is indicated with an asterisk in the structure below:

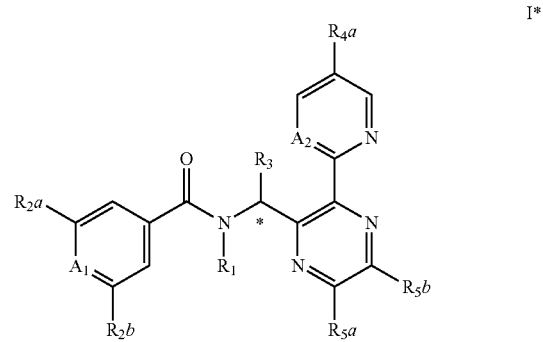

where $R_1$, $R_{2a}$, $R_{2b}$, $R_3$, $R_{4a}$, $R_{5a}$, $R_{5b}$, $A_1$ and $A_2$ are as defined in the first aspect.

The present invention contemplates both racemates and individual enantiomers. Compounds having preferred stereochemistry are set out below.

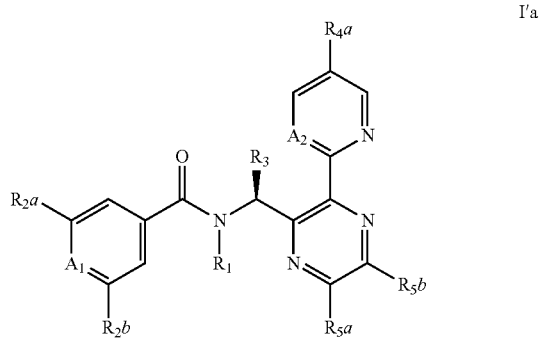

I'a

Particularly preferred compounds of the present invention are compounds of formula I'a: where $R_1$, $R_{2a}$, $R_{2b}$, $R_3$, $R_{4a}$, $R_{5a}$, $R_{5b}$, $A_1$ and $A_2$ are as defined in the first aspect, and stereoisomers, enantiomers, tautomers and N-oxides of the compounds of formula (I'a), and agrochemically acceptable salts thereof.

The term "optionally substituted" as used herein means that the group referenced is either unsubstituted or is substituted by a designated substituent, for example, "$C_3$-$C_4$cycloalkyl is optionally substituted with 1 or 2 halo atoms" means $C_3$-$C_4$cycloalkyl, $C_3$-$C_4$cycloalkyl substituted with 1 halo atom and $C_3$-$C_4$cycloalkyl substituted with 2 halo atoms.

Embodiments according to the invention are provided as set out below.

In an embodiment of each aspect of the invention, $A_1$ is
A. N; or
B. C—$R_{2c}$, where $R_{2c}$ is hydrogen or halogen (such as Cl, F, Br and I); preferably hydrogen.

In an embodiment of each aspect of the invention, $R_{2a}$ is
A. $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkyl$C_1$-$C_4$alkyl substituted with one to five substituents independently selected from halogen and $C_1$-$C_3$haloalkyl, $C_1$-$C_5$cyanoalkyl, $C_3$-$C_6$cycloalkoxy, $C_1$-$C_4$haloalkylsulfonyl or $C_1$-$C_4$haloalkylsulfinyl; or
B. $C_3$-$C_4$cycloalkyl, $C_3$-$C_4$cycloalkoxy, $C_3$-$C_4$cycloalkyl substituted with one to three substituents independently selected from $C_1$-$C_2$alkyl, $C_1$-$C_2$haloalkyl, $C_1$-$C_2$alkoxy, cyano, and halogen, $C_3$-$C_4$cycloalkyl$C_1$-$C_2$alkyl substituted with one to five substituents independently selected from halogen and $C_1$-$C_3$haloalkyl, $C_1$-$C_3$cyanoalkyl, $C_3$-$C_4$cycloalkoxy, $C_1$-$C_3$haloalkylsulfonyl or $C_1$-$C_3$haloalkylsulfinyl; or
C. cyclopropyl, cyclopropyl substituted with one to three substituents independently selected from methyl, triflurormethyl, methoxy, cyano, fluoro and chloro, cyclopropylmethyl substituted with one to five fluoro substituents, $C_1$-$C_3$cyanoalkyl, cyclopropoxy, trifluoromethylsulfonyl or trifluoromethyl sulfinyl; or
D. cyclopropyl, cyclopropyl substituted with one to three substituents independently selected from methyl, trifluorormethyl, methoxy, cyano, fluoro and chloro, cyclopropylmethyl substituted with one or two fluoro substituents on the methyl part, $C_1$-$C_3$cyanoalkyl, trifluoromethylsulfonyl or trifluoromethyl sulfinyl; or
E. cyclopropyl, cyclopropyl substituted with one to three substituents independently selected from trifluororomethyl, methoxy, cyano, fluoro and chloro, cyclopropylmethyl substituted with one or two fluoro substituents on the methyl part, $C_1$-$C_3$cyanoalkyl, trifluoromethylsulfonyl.

In an embodiment of each aspect of the invention, $R_{2b}$ is
A. halogen, $C_1$-$C_3$haloalkyl, $C_1$-$C_3$haloalkylthio, $C_1$-$C_3$alkoxy, $C_1$-$C_3$haloalkoxy, or CN; or
B. halogen, $C_1$-$C_3$haloalkyl, or $C_1$-$C_3$haloalkoxy; or
C. chlorine, fluorine, difluoromethyl, trifluoromethyl, difluoromethoxy or trifluoromethoxy; or
D. difluoromethyl or trifluoromethyl.

In an embodiment of each aspect of the invention, $R_1$ is
A. hydrogen, methyl, ethyl, n-propyl, isobutyl, cyclopropylmethyl or HCH≡CCH$_2$—; or
B. hydrogen, methyl, or cyclopropylmethyl; or
C. hydrogen.

In an embodiment of each aspect of the invention, $R_3$ is
A. $C_1$-$C_3$alkyl or $C_1$-$C_3$haloalkyl; or
B. methyl.

In an embodiment of each aspect of the invention, $A_2$ is
A. N; or
B. C—$R_{4b}$, where $R_{4b}$ is hydrogen or halogen (such as Cl, F, Br and I); preferably $R_{4b}$ is hydrogen.

In an embodiment of each aspect of the invention, $R_{4a}$ is
A. cyano, or $C_1$-$C_3$fluoroalkoxy; or
B. cyano, trifluoromethoxy, difluoromethoxy, 2,2,2-trifluoroethoxy, or 2,2-difluoroethoxy.

In an embodiment of each aspect of the invention, $R_{5a}$ and $R_{5b}$, independent of each other, are selected from
A. hydrogen, halogen, $C_1$-$C_3$alkyl, and $C_1$-$C_3$alkoxy;
B. selected from hydrogen, bromo, chloro, methyl, methoxy; or
C. hydrogen.

The present invention, accordingly, makes available a compound of formula I having the substituents $R_1$, $R_{2a}$, $R_{2b}$, $R_3$, $R_{4a}$, $R_{5a}$, $R_{5b}$, $A_1$ and $A_2$ as defined above in all combinations/each permutation. Accordingly, made available, for example, is a compound of formula I with $A_1$ being of the first aspect (i.e. $A_1$ is N or C—$R_{2c}$, where $R_{2c}$ is H, halogen, $C_1$-$C_3$alkyl, $C_1$-$C_3$haloalkyl, $C_1$-$C_3$alkoxy, or $C_1$-$C_3$haloalkoxy); $R_1$ being embodiment B (i.e. hydrogen, methyl, cyclopropylmethyl); $R_{2a}$ being an embodiment C (i.e. cyclopropyl, cyclopropyl substituted with one to three substituents independently selected from methyl, triflurormethyl, cyano, fluoro and chloro, cyclopropylmethyl substituted with one to five fluoro substituents, $C_1$-$C_3$cyanoalkyl, $C_3$-$C_6$cyclopropoxy, trifluoromethylsulfonyl or trifluoromethyl sulfinyl); $R_{2b}$ being embodiment B (i.e. halogen, $C_1$-$C_3$haloalkyl, or $C_1$-$C_3$haloalkoxy); $R_3$ being embodiment B (i.e. methyl); $A_2$ being embodiment B (i.e. C—$R_{4b}$, where $R_{4b}$ is hydrogen or halogen (such as Cl, F, Br and I); preferably $R_{4b}$ is hydrogen); $R_{4a}$ being embodiment A (i.e. cyano, or $C_1$-$C_3$fluoroalkoxy); and $R_{5a}$ being embodiment B (i.e selected from hydrogen, bromo, chloro, methyl, methoxy); and $R_{5b}$ being embodiment C (i.e hydrogen).

In an embodiment, the compound of formula I can be represented as

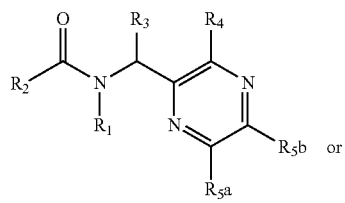
I-A

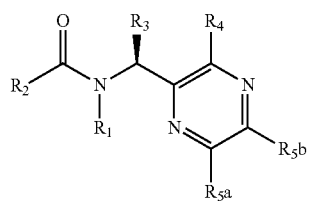
I'-A wherein $R_1$, $R_3$, $R_{5a}$, and $R_{5b}$ are as defined in the first aspect, $R_2$ is the the cyclic group containing $A_1$ and the substituents $R_{2a}$ and $R_{2b}$ as defined in the first aspect, and $R_4$ is the cyclic group containing $A_2$ and the substituent $R_{4a}$ as defined in the first aspect.

In an embodiment of each aspect of the invention, the $R_2$ (the cyclic group containing $A_1$ and the substituents $R_{2a}$ and $R_{2b}$) is A. selected from K-1 to K-16

K-1
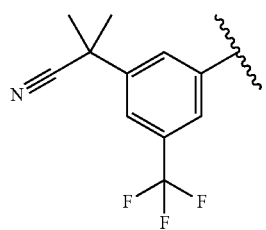 [SMILES: *c1cc(C(F)(F)F)cc(C(C)(C)C#N)c1]

K-2
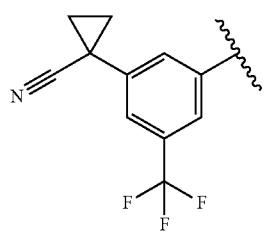

K-3
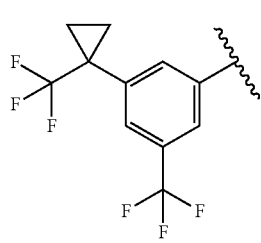

K-4
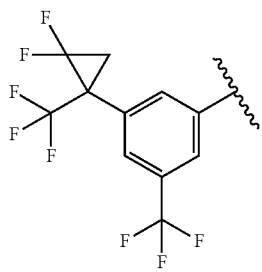

K-5
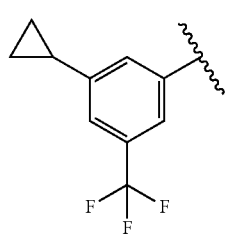 [SMILES: *c1cc(C2CC2)cc(C(F)(F)F)c1]

K-6
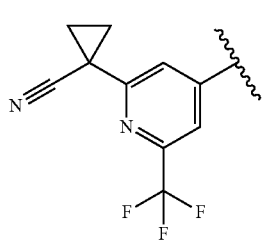

K-7
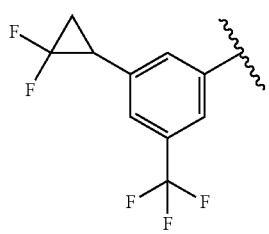

K-8
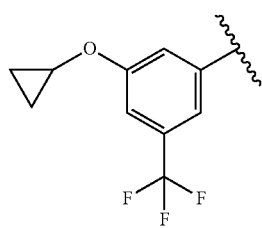

K-9
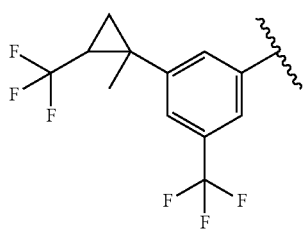

-continued

K-10 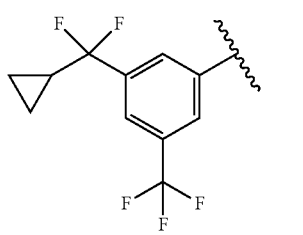

K-11 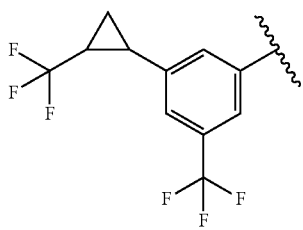 [SMILES: *c1cc(C2CC2C(F)(F)F)cc(C(F)(F)F)c1]

K-12 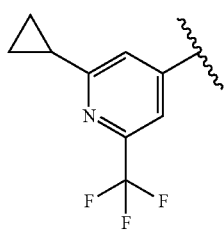

K-13 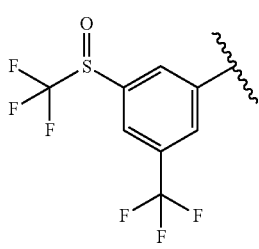 [SMILES: *c1cc(S(=O)C(F)(F)F)cc(C(F)(F)F)c1]

K-14 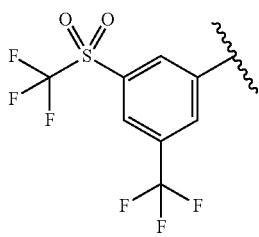

K-15 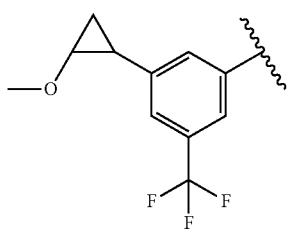

-continued

K-16 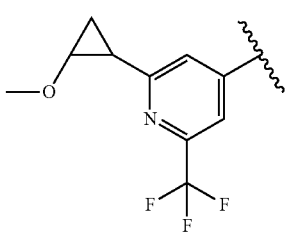

B. selected from K-1, K-2, K-3, K-5, K-6, K-10, K-11, K-12, K,-14, K-15 and K-16; or
C. selected from K-1, K-2, K-6, K-10, K-12, K-14, K-15 and K-16; or
D. selected from K-1, K-2, K-5, K-10, K-11, K-14, K-15 and K-16: or
E. selected from K-1, K-2, K-5, K-6, K-10, K-14, K-15 and K-16; or
F. selected from K-1, K-2, K-6, K-10, K-14, K-15 and K-16; or
G. selected from K-2, K-6 and K-10; or
H. selected from K-5, K-10, K-14 and K-15; or
I. selected from K-2, K-6, K-14 and K-15.

In an embodiment of each aspect of the invention, the $R_4$ (the cyclic group containing $A_2$ and the substituent $R_{4a}$) is
A. selected from L-1 to L-9

L-1 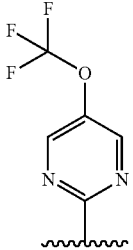

L-2 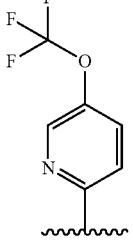

L-3 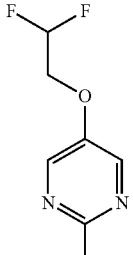

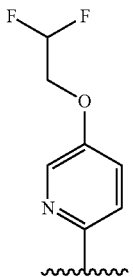

L-4

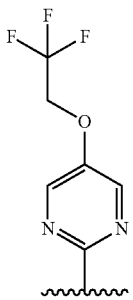

L-5

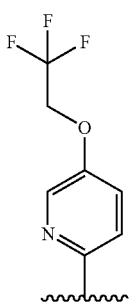

L-6

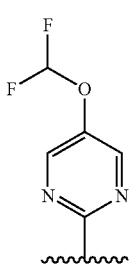

L-7

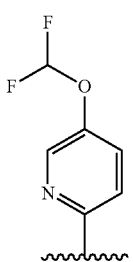

L-8

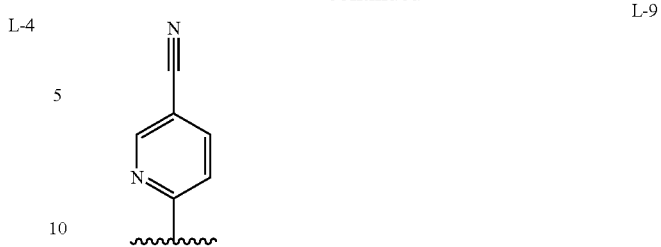

B. selected from L-1, L-2, L-7, L-8, and L-9; or
C. selected from L-3, L-5, L-6, L-7, L-8 and L-9; or
D. selected from L5, L-7, L-8 and L-9; or
E. selected from L-3, L-5, L-7 and L-9; or
F. L-8 and L-9; or
G. L-5 and L-9; or
H. L-7 or L-9; or
I. L-1 or L-9.

In an embodiment of each aspect of the invention, the compound of formula I-A or I'-A has as $R_1$ hydrogen, methyl, ethyl, n-propyl, isobutyl, cyclopropylmethyl or HCH≡CCH$_2$—; as $R_2$ one of K-1 to K-16: as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1 to K-16: as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen; as $R_2$ one of K-1 to K-16: as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1, K-2, K-3, K-5, K-6, K-10, K-11, K-12, K-14, K-15 and K-16; as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1, K-2, K-5, K-10, K-11, K-14; K-15 and K-16; as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1, K-2, K-5, K-10, K-11, K-14, K-15 and K-16; as $R_3$ methyl; as $R_4$ one of L-1, L-2, L-7, L-8, and L-9; and as $R_{5a}$ and $R_{5b}$, independently selected from hydrogen, halogen, and methyl.

In an embodiment of each aspect of the invention, the compound formula I-A or I'-A has as $R_1$ hydrogen, methyl, or cyclopropylmethyl; as $R_2$ one of K-1, K-2, K-5, K-10, K-11, K-14, K-15 and K-16; as $R_3$ methyl; as $R_4$ one of L-1, L-2, L-7, L-8, and L-9; and as $R_{5a}$ and $R_{5b}$, each hydrogen.

In an embodiment of each aspect of the invention, the compound of formula I-A or I'-A has as $R_1$ hydrogen, methyl, or cyclopropylmethyl; as $R_2$ one of K-5, K-10, K-14 and K-15; as $R_3$ methyl; as $R_4$ one of L-1 or L-9; and as $R_{5a}$ and $R_{5b}$, each hydrogen.

In an embodiment of each aspect of the invention, the compound of formula I-A or I'-A has as $R_1$ hydrogen, methyl, or cyclopropylmethyl; as $R_2$ one of K-1, K-2, K-6, K-10, K-12, K-14, K-15 and K-16; as $R_3$ methyl; as $R_4$ one of L-1 to L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1, K-2, K-6, K-10, K-12, K-14, K-15 and K-16; as $R_3$ methyl; as $R_4$ one of L-3, L-5, L-7 and L-9; and as $R_{5a}$ and $R_{5b}$, independently selected from hydrogen, halogen, and methyl.

In an embodiment of each aspect of the invention, the compound of formula I-A or I'-A has as $R_1$ hydrogen, methyl, or cyclopropylmethyl; as $R_2$ one of K-1, K-2, K-6, K-10, K-12, K-14, K-15 and K-16; as $R_3$ methyl; as $R_4$ one of L-3, L-5, L-7 and L-9; and as $R_{5a}$ and $R_{5b}$, each hydrogen.

In an embodiment of each aspect of the invention, the compound of formula I-A or I'-A has as $R_1$ hydrogen, methyl, or cyclopropylmethyl; as $R_2$ one of K-2, K-6, K-14 and K-15; as $R_3$ methyl; as $R_4$ one of L-1 or L-9; and as $R_{5a}$ and $R_{5b}$, each hydrogen.

In a second aspect, the present invention makes available a composition comprising a compound of formula I as defined in the first aspect, one or more auxiliaries and diluent, and optionally one more other active ingredient.

In a third aspect, the present invention makes available a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in the first aspect or a composition as defined in the second aspect.

In a fourth aspect, the present invention makes available a method for the protection of plant propagation material from the attack by insects, acarines, nematodes or molluscs, which comprises treating the propagation material or the site, where the propagation material is planted, with an effective amount of a compound of formula I as defined in the first aspect or a composition as defined in the second aspect.

In a fifth aspect, the present invention makes available a plant propagation material, such as a seed, comprising, or treated with or adhered thereto, a compound of formula I as defined in the first aspect or a composition as defined in the second aspect.

The present invention in a further aspect provides a method of controlling parasites in or on an animal in need thereof comprising administering an effective amount of a compound of the first aspect. The present invention further provides a method of controlling ectoparasites on an animal in need thereof comprising administering an effective amount of a compound of formula I as defined om the first aspect. The present invention further provides a method for preventing and/or treating diseases transmitted by ectoparasites comprising administering an effective amount of a compound of formula I as defined in the first aspect, to an animal in need thereof.

Compounds of formula I can be prepared by those skilled in the art following known methods. More specifically compounds of formulae I, and I'a, and intermediates therefor can be prepared as described below in the schemes and examples. Certain stereogenic centers have been left unspecified for the clarity and are not intended to limit the teaching of the schemes in any way.

The process according to the invention for preparing compounds of formula I is carried out by methods known to those skilled in the art.

Compounds of formula I

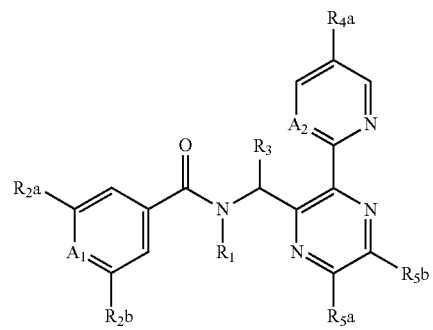

can be prepared by reaction of an amine of formula II

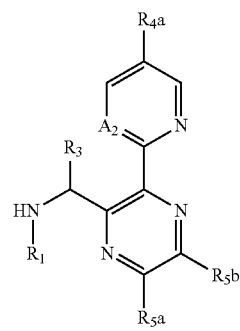

wherein $R_1$, $R_3$, $A_2$, $R_{4a}$, $R_{5a}$, and $R_{5b}$ are as described in formula I, with a carboxylic acid derivative of formula III

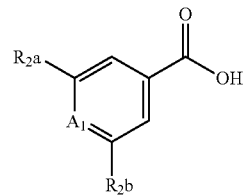

wherein $A_1$, $R_{2a}$ and $R_{2b}$ are described as above under formula I. The chemistry is described in more detail in Scheme 1.

Scheme 1

(COCl)$_2$, inert solvent, e.g. CH$_2$Cl$_2$ rt
or SOCl$_2$, CH$_2$Cl$_2$ rt
or DCC, EDC, THF or pyridine, rt to 120° C.
or T3P®, pyridine
or HATU, base, DMF

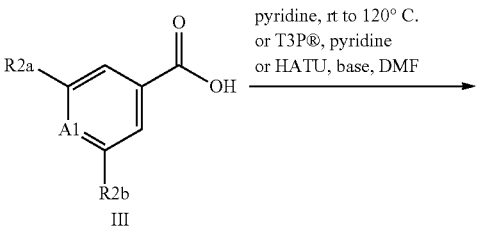

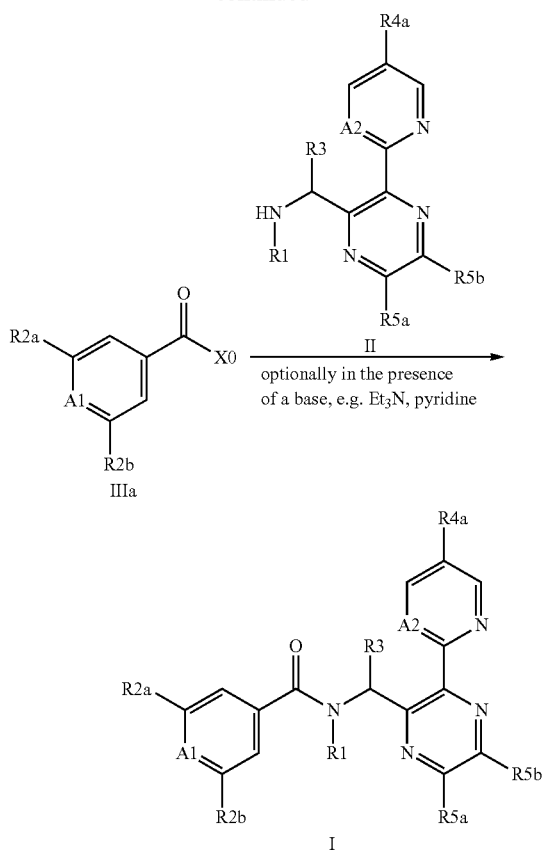

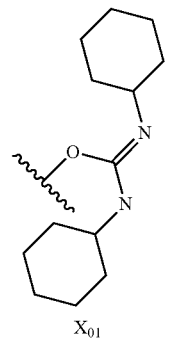

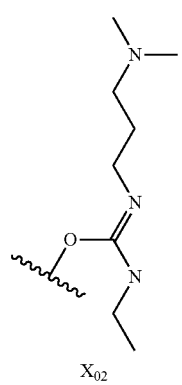

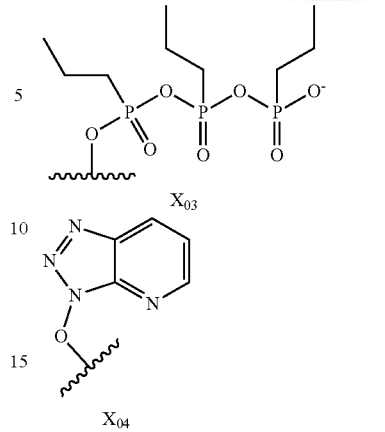

In Scheme 1 compounds of formula III, wherein $A_1$, $R_{2a}$ and $R_{2b}$ are described in formula I, are activated to compounds of formula IIIa by methods known to those skilled in the art and described for example in *Tetrahedron*, 61 (46), 10827-10852, 2005. For example, compounds where $X_0$ is halogen are formed by treatment of compounds of formula III with for example, oxalyl chloride or thionyl chloride in the presence of catalytic quantities of DMF in inert solvents such as methylene dichloride or THF at temperatures between 20° C. to 100° C., preferably 25° C. Treatment of IIIa with compounds of formula II, wherein $R_1$, $R_3$, $A_2$, $R_{4a}$, $R_{5a}$, and $R_{5b}$ are as defined in formula I, optionally in the presence of a base, e.g. triethylamine or pyridine leads to compounds of formula I. Alternatively, compounds of formula I can be prepared by treatment of compounds of formula III with dicyclohexyl carbodiimide (DCC) or 1-ethyl-3-(3-dimethylaminopropyl)carbodiimide (EDC) to give the activated species IIIa, wherein $X_0$ is $X_{01}$ or $X_{02}$, in an inert solvent, e.g. pyridine, or THF optionally in the presence of a base, e.g. triethylamine, at temperatures between 50-180° C. In addition, an acid of the formula III can also be activated by reaction with a coupling reagent such as propanephosphonic acid anhydride (T3P®) or O-(7-Aza-1-benzotriazolyl)-N,N,N',N'-tetramethyluronium-hexafluorophosphat (HATU) to provide compounds of formula IIIa wherein $X_0$ is $X_{03}$ and $X_{04}$ as described for example in Synthesis 2013, 45, 1569 and Journal Prakt. Chemie 1998, 340, 581. Subsequent reaction with an amine of the formula II provides compounds of formula I.

Intermediates of formula II, wherein $R_1$, $R_3$, $A_2$, $R_{4a}$, $R_{5a}$ and $R_{5b}$ are as defined in formula I can be prepared according to Scheme 2:

Scheme 2

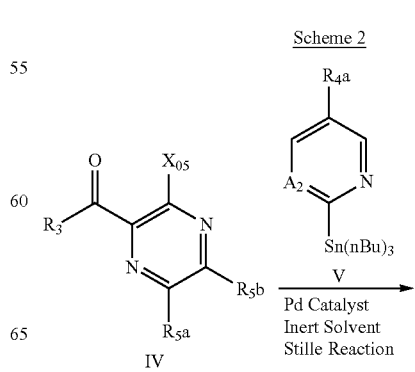

-continued

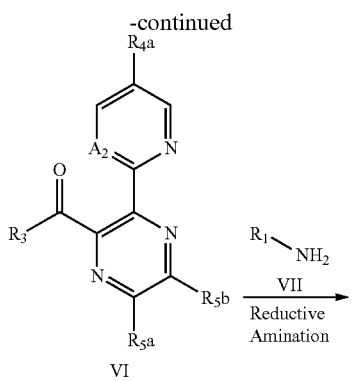

VI

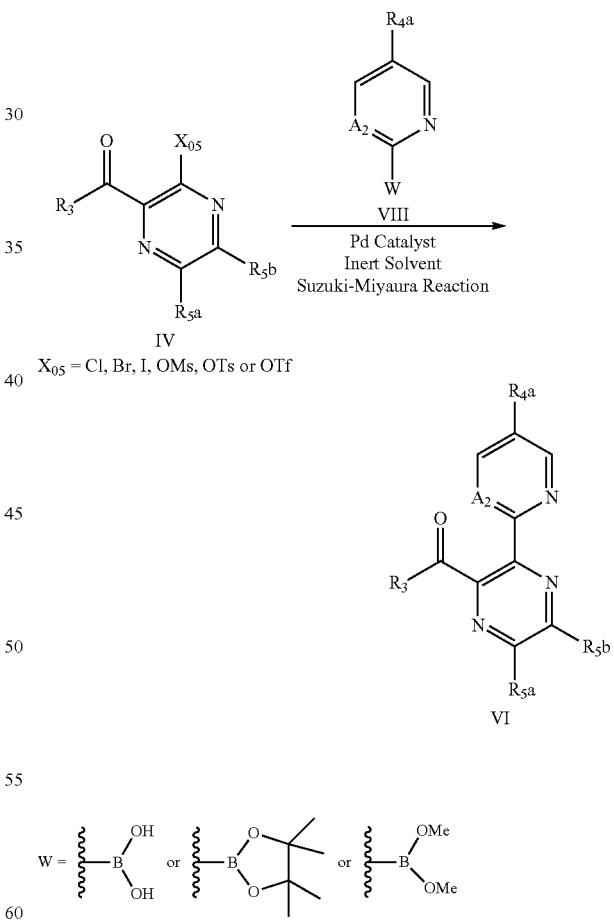

$X_{05}$ = Cl, Br, I, OMs, OTs or OTf

In Scheme 2, compounds of formula II, wherein $R_1$, $R_3$, $A_2$, $R_{4a}$, $R_{5a}$ and $R_{5b}$ are as defined in formula I, can be prepared by treatment of compounds of formula VI, wherein $R_3$, $A_2$, $R_{4a}$, $R_{5a}$ and $R_{5b}$ are as defined in formula I, with compounds of formula VII (wherein $R_1$ is as defined in formula I), e.g. in the presence of $NaBH(OAc)_3$ or $NaBH_3CN$, preferably with $NaBH_3CN$ as reductive reagent, in a suitable solvent, preferably in acetic acid at room temperature analog to WO2002/088073, page 35. Alternatively, another reagent system for the reductive amination uses a combination of $Ti(i\text{-}OiPr)_4$ and $NaBH_4$ in the presence of an amine of formula VII can also provide compounds of formula II (see Synthesis 2003 (14), 2206).

Compounds of formula VI, wherein $R_3$, $A_2$, $R_{4a}$, $R_{5a}$, and $R_{5b}$ are as defined in formula I, can be prepared by a Stille reaction between compounds of formula IV, wherein $X_{05}$ is a leaving group, such as chlorine, bromine, iodine, arysulfonate, alkylsulfonate or trifluoromethanesulfonate and $R_3$, $R_{5a}$ and $R_{5b}$ are as defined in formula I, and tin compounds of formula V (wherein $A_2$ and $R_{4a}$ are as defined in formula I) in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent, such as DMF, acetonitrile, or dioxane, optionally in the presence of an additive, such as potassium, cesium fluoride, or lithium chloride, and optionally in the presence of a further catalyst, for example copper(I)iodide. Such Stille coupling reactions are well known to those skilled in the art, and have been described in for example J. Org. Chem., 2005, 70, 8601, J. Org. Chem., 2009, 74, 5599, Angew. Chem. Int. Ed., 2004, 43, 1132, Heterocycles 2010, 80, 1215 and J. Am. Chem. Soc. 2004, 126, 16433.

Alternatively, compounds of formula VI (wherein $R_3$, $A_2$, $R_{4a}$, $R_{5a}$, and $R_{5b}$ are as defined in formula I) can also be prepared by a Suzuki reaction (Scheme 3), which involves for example, reacting compounds of formula IV (wherein $R_3$, $R_{5a}$, and $R_{5b}$ are as defined in formula I and $X_{05}$ is a leaving group like, for example, chlorine, bromine, iodine, arysulfonate, alkylsulfonate or trifluoromethanesulfonate) with compounds of formula VIII, wherein W can be a boron-derived functional group, as for example $B(OH)_2$ or a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, dioxane and water, or DMF and water preferably under inert atmosphere. The reaction temperature can preferentially range from room temperature to the boiling point of the reaction mixture. Such Suzuki reactions are well known to those skilled in the art and have been reported, for example in J. Organomet. Chem. 576, 1999, 147-168, Science of Synthesis 2010, 45b, 547, Eur. J. Org. Chem. 2012, (31), 6248 and Synthesis 2017, 49, 4372.

Scheme 3

Compounds of formula IV are generally commercially available.

Alternatively compounds of formula VI, wherein $R_3$, $A_2$, $R_{4a}$, $R_{5a}$, and $R_{5b}$ are as defined in formula I, is outlined in Scheme 4.

Scheme 4

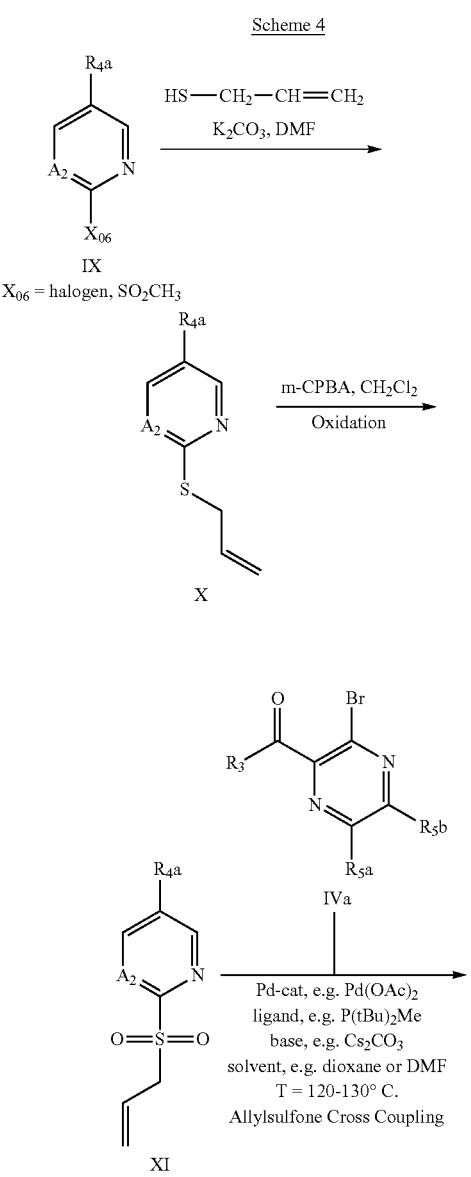

with compounds of formula XI, wherein $A_2$ and $R_{4a}$ are defined in formula I, in suitable solvents, preferable dioxane or DMF, in the presence of a Pd-catalyst, preferable palladium acetate, a ligand, e.g. ditert-butyl(methyl)phosphane, and a base, e.g. $Cs_2CO_3$ usually upon heating at temperatures between 120 to 130° C. Such processes have been described, for example, in *J. Am. Chem. Soc.* 2018, 140, 15916.

The required intermediates of formula XI can be obtained from compounds of formula IX (wherein $A_2$ and $R_{4a}$ are defined as for formula I and $X_{06}$ is a leaving group and stands for halogen and methyl sulfone) through nucleophilic substitution with prop-2-ene-1-thiol and subsequent oxidation with mCPBA. Such transformation are well known and reported, for instance, in J. Am. Chem. Soc. 2018, 140, 15916.

Alternatively compounds of formula VI, wherein $R_3$, $A_2$, $R_{4a}$, $R_{5a}$, and $R_{5b}$ are as defined in formula I, is outlined in Scheme 5.

Compounds of formula VI (wherein $R_3$, $A_2$, $R_{4a}$, $R_{5a}$, and $R_{5b}$ are as defined in formula I) may be prepared by treatment of compounds of formula XIV with a Grignard reagent $R_3MgBr$, e.g. MeMgBr at lower temperatures, preferable at 0 to 25° C. in a suitable solvent such as THF or diethyl ether.

Weinreb amides of formula XIV (wherein $A_2$, $R_{4a}$, $R_{5a}$, and $R_{5b}$ are as defined in formula I) can be prepared in three steps from compounds of formula XIII wherein $A_2$, $R_{4a}$, $R_{5a}$, and $R_{5b}$ are as defined in formula I and Z is $C_1$-$C_6$alkyl. Compounds of formula XIII are converted to carboxylic acids by methods known in the art (see e.g. WO2011/143365, page 138) and activation (see Scheme 1) of the subsequent carboxylic acids followed by treatment with N-methoxy-N-methylamine (according to Weinreb et al. Tet. Lett. 1981, 39, 3815) lead to compounds of formula XIV.

Compounds of formula XIII, wherein $A_2$, $R_{4a}$, $R_{5a}$, and $R_{5b}$ are as defined in formula I and Z is $C_1$-$C_6$alkyl, can be prepared by reaction of compounds of formula XII (wherein $R_{5a}$, and $R_{5b}$ are as defined in formula I, Z is $C_1$-$C_6$alkyl, and $X_{07}$ is a leaving group like, for example, chlorine, bromine, iodine) with compounds of formula V (Stille reaction) or compounds of formula VIII (Suzuki-Miyaura reaction) in the presence of a palladium catalyst as described in detail in Schemes 2 and 3.

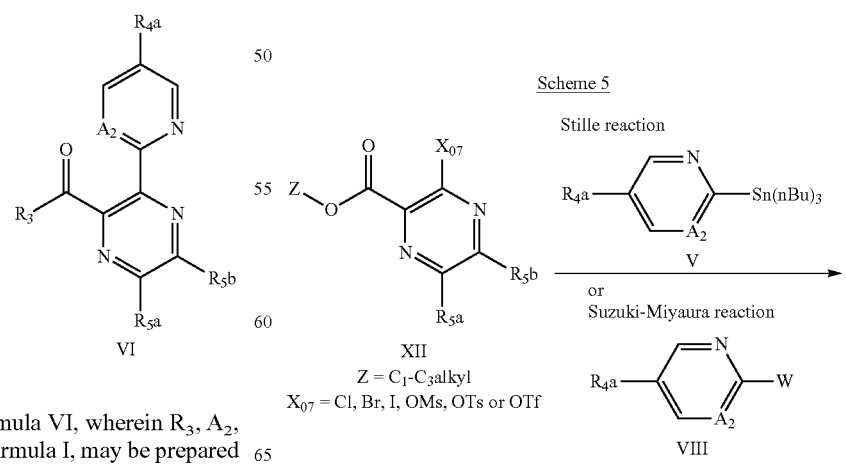

For example, compounds of formula VI, wherein $R_3$, $A_2$, $R_{4a}$, $R_{5a}$, and $R_{5b}$ is as defined in formula I, may be prepared by allyl sulfone coupling reaction of compounds of formula IVa (wherein $R_3$, $R_{5a}$, and $R_{5b}$ are as defined in formula I)

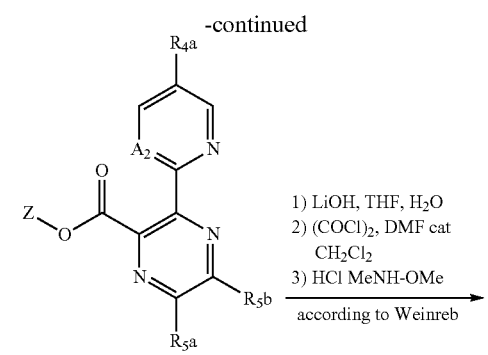

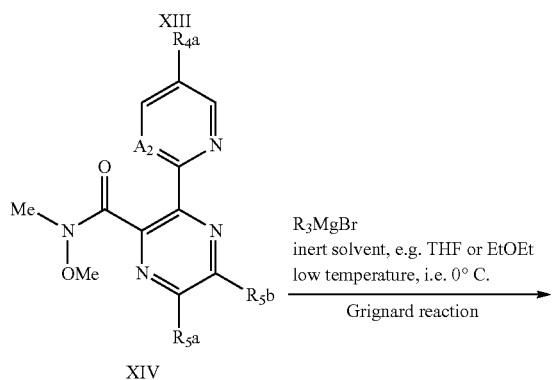

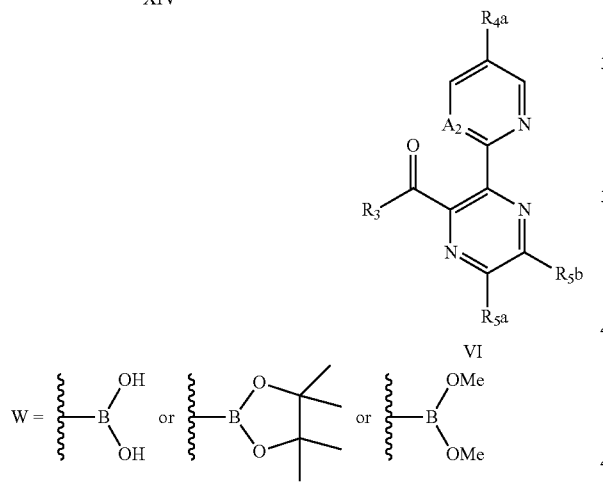

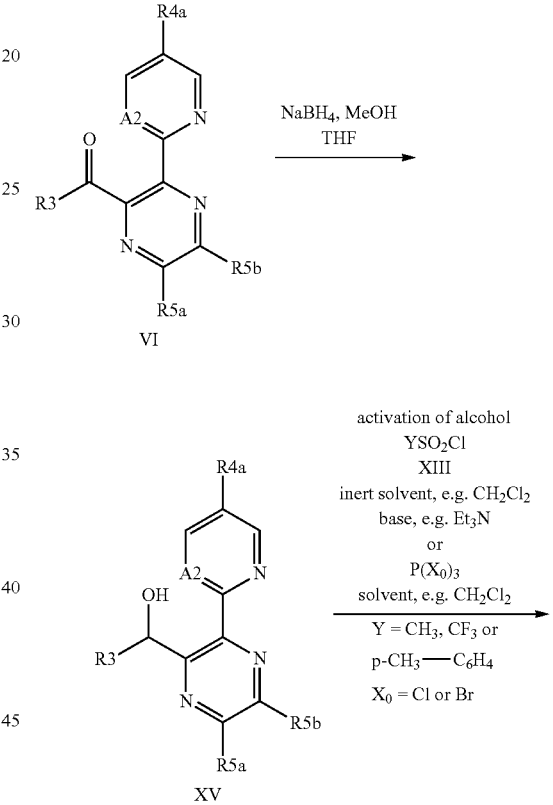

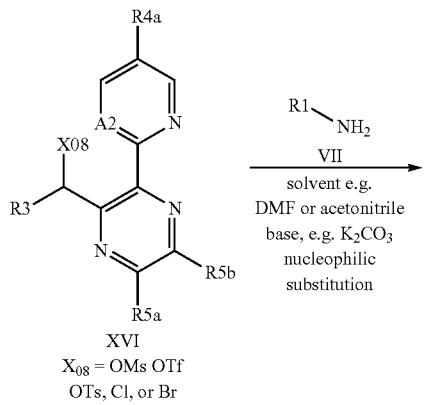

halides XVI (wherein $X_{08}$ is Cl or Br) by treatment with phosphorous compounds, e.g. $P(X_0)_3$, wherein $X_0$ is chlorine or bromine, by methods known to those skilled in the art. Such general functional group transformations are described for example in Organische Chemie. 4. Auflage, Wiley-VCH Verlag, Weinheim 2005, p. 393 ff and Chem Commun. 2014, 50, 5756.

Compounds of formula XV wherein $R_3$, $A_2$, $R_{4a}$, $R_{5a}$ and $R_{5b}$ are defined as in formula I may be prepared by reduction of ketones VI (wherein $R_3$, $A_2$, $R_{4a}$, $R_{5a}$, and $R_{5b}$ are as defined in formula I) for example with $NaBH_4$ in the usual manner (see e.g. WO2012/082997, page 141), preferably in MeOH as solvent.

In an alternative process (Scheme 6), compounds of formula II, wherein $R_1$, $R_3$, $A_2$, $R_{4a}$, $R_{5a}$, and $R_{5b}$ are defined as in formula I, may be prepared by nucleophilic substitution reaction of compound of formula XVI, wherein $R_3$, $A_2$, $R_{4a}$, $R_{5a}$, and $R_{5b}$ are as defined in formula I and $X_{08}$ is OMs, OTs or OTf, with amines of formula VII in suitable solvents that may include, for example, acetonitrile or DMF, in the presence of a suitable base, such as sodium, potassium or caesium carbonate, usually upon heating at temperatures between room temperature and 200° C., preferably between 40° C. to the boiling point of the reaction mixture, optionally under microwave heating conditions.

Compounds of formula XVI, wherein $R_3$, $A_2$, $R_{4a}$, $R_{5a}$, $R_{5b}$ are defined as in formula I and $X_{08}$ is OMs, OTs or OTf, may be prepared by activation of the alcohols of formula XV wherein $R_3$, $A_2$, $R_{4a}$, $R_{5a}$ and $R_{5b}$ are defined as in formula I with compounds of formula XIII wherein Y is $CH_3$, $CF_3$ or p-$CH_3$—$C_6H_4$ in an inert solvent, preferably in methylene dichloride and in the presence of a base, e.g. triethyl amine. Alcohols of formula XV may be also be activated to alkyl -continued

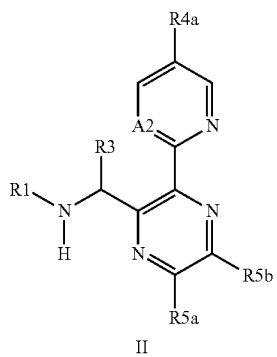

II

Yet another methodology to prepare compounds of general formula of IIa is outlined in Scheme 7.

-continued

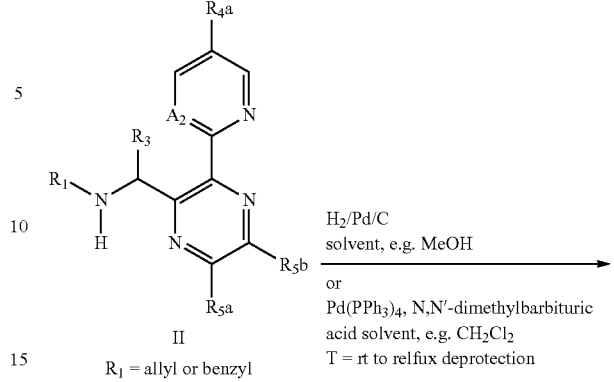

$R_1$ = allyl or benzyl

Thus, nucleophilic substitution reaction of compound of formula XVI with amines of formula VII furnishes compounds of formula II (wherein $R_1$, $R_3$, $A_2$, $R_{4a}$, $R_{5a}$, and $R_{5b}$ are defined as in formula I) as already described in detail in Scheme 6. Compounds of formula II suited with a protecting group, e.g. $R_1$ is benzyl, can be hydrogenated with hydrogen in the presence of palladium (on charcoal) in a solvent, e.g. MeOH or EtOH, to give compounds of formula IIa wherein $R_3$, $A_2$, $R_{4a}$, $R_{5a}$, and $R_{5b}$ is defined as in formula I (see e.g. Synlett, 2010, (18), page 2708). Compounds of formula II, wherein $R_1$ is allyl, and $R_3$, $A_2$, $R_{4a}$, $R_{5a}$, and $R_{5b}$ are as defined in formula I, can also be converted to compounds of formula IIa by reaction with N'N'dimethylbarbituric acid in the presence of a Pd-catalyst, preferable tetrakis(triphenylphosphine)palladium(0), in a suitable solvent, for example $CH_2Cl_2$ to provide compounds of formula IIa according to J. Org. Chem. 1993, 58, 6109.

Formation of compounds of formula V, wherein $A_2$ and $R_{4a}$ are as defined in formula I, is outlined in Scheme 8.

Compounds of formula V, wherein $A_2$ and $R_{4a}$ are as defined in formula I, may be prepared by treatment of compounds of formula IX with a palladium source such as for example $Pd(Ph_3)_4$ and bis(tributyltin) in a suitable solvent such as DMF usually upon heating at temperatures between 100 to 130° C. Such processes have been described, for example, in Molecular Pharmacology, 90(3), 177-187; 2016. Alternatively compounds of formula V can also be prepared by treatment of compounds of formula IX with n-Butyllithium and tributyltin chloride in a suitable solvent such as THF, usually at lower temperature such as −78° C. to 0° C. Such processes have been described, for example, in US20180273562.

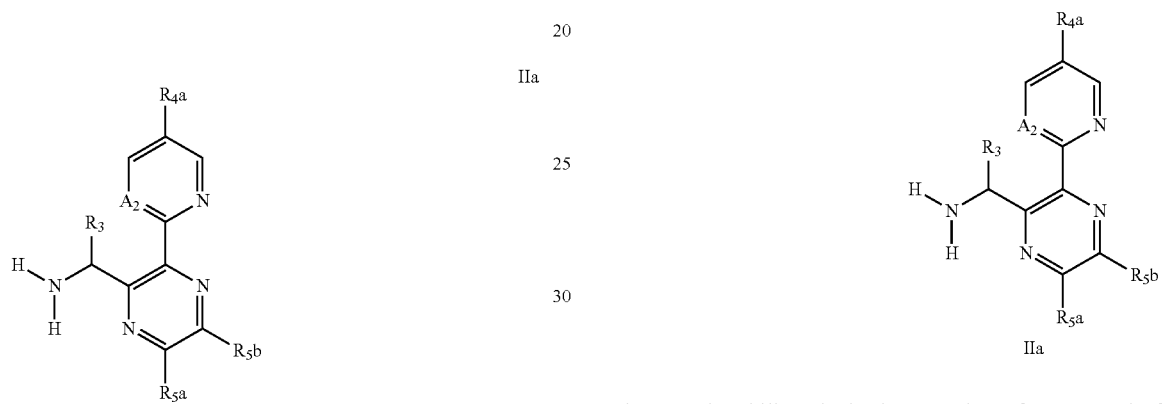

Scheme 7

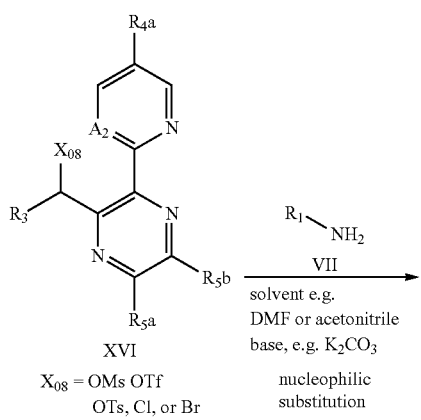

Scheme 8

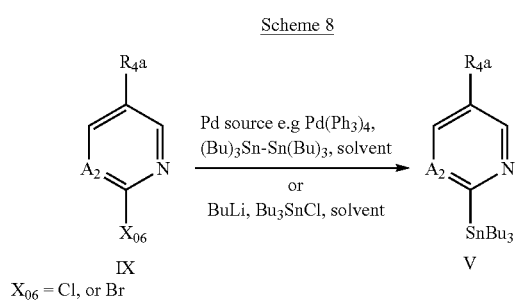

$X_{06}$ = Cl, or Br

Compounds formula IXa and IXaa wherein $A_2$ and $R_{4a}$ are as defined in formula I and $X_{06}$ is a leaving group, such as Cl, Br and Q is $C_1$-$C_3$haloalkyl, are either commercially available or can be prepared according to well-known methods as shown in Scheme 9.

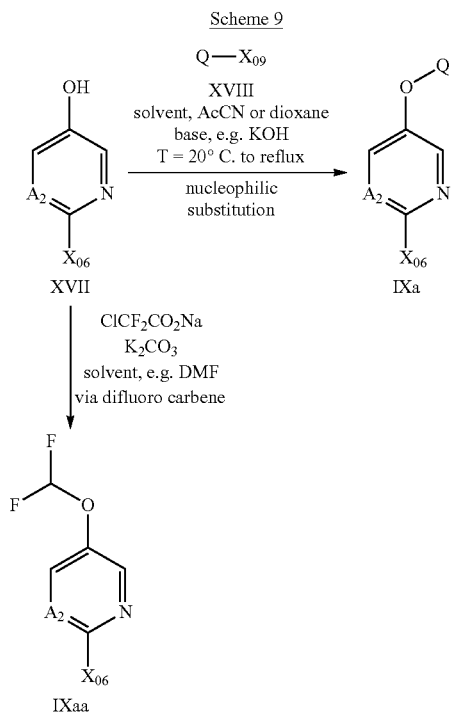

Thus compounds of formula IXa, wherein $A_2$ and $R_{4a}$ are as defined in formula I, $X_{06}$ is a leaving group, such as Cl or Br, and Q is $C_1$-$C_3$haloalkyl, can be obtained by alkylation of compounds XVII with a compound of formula XVIII, wherein Q is $C_1$-$C_3$haloalkyl and $X_{09}$ is a leaving group, such as Cl, Br, F, I, $OSO_2CF_3$, or $OSO_2CH_3$, in the presence of a suitable base, for example cesium or potassium carbonate, in a solvent such as acetonitrile or DMF at temperatures between 20-80° C. Such reactions are well known to those skilled in the art and have been reported for example in see e.g. Med. Chem. Letts., 2017, 8(5), p 543-548 and Bio. Med. Chem. Letts., 2017, 27(11), 2420-2423.

Compounds of formula IXaa wherein $A_2$ and $R_{4a}$ are as defined in formula I, $X_{06}$ is a leaving group, such as Cl or Br, can be prepared from compounds of formula XVII by treatment with a difluorocarbene source e.g. $ClCF_2CO_2Na$ or $CF_2SO_2OCHF_2$ in the presence of a base such as KOH, potassium carbonate and the like, in an inert solvent at temperatures between 20-80° C. Such procedures have been described for example in J. Fluor. Chem. 2017, 203, 155, and US2013/0225552, page 128, and Org. Process Res. Dev., 2011, 15, 721.

Compounds of formula XVII are commercially available.

Carboxylic acids of formula IIIb, wherein $R_{2b}$ and $A_1$ are as defined in formula I, are useful intermediates for the preparation of final compounds (see Scheme 1) and may be prepared by the process shown in Scheme 10.

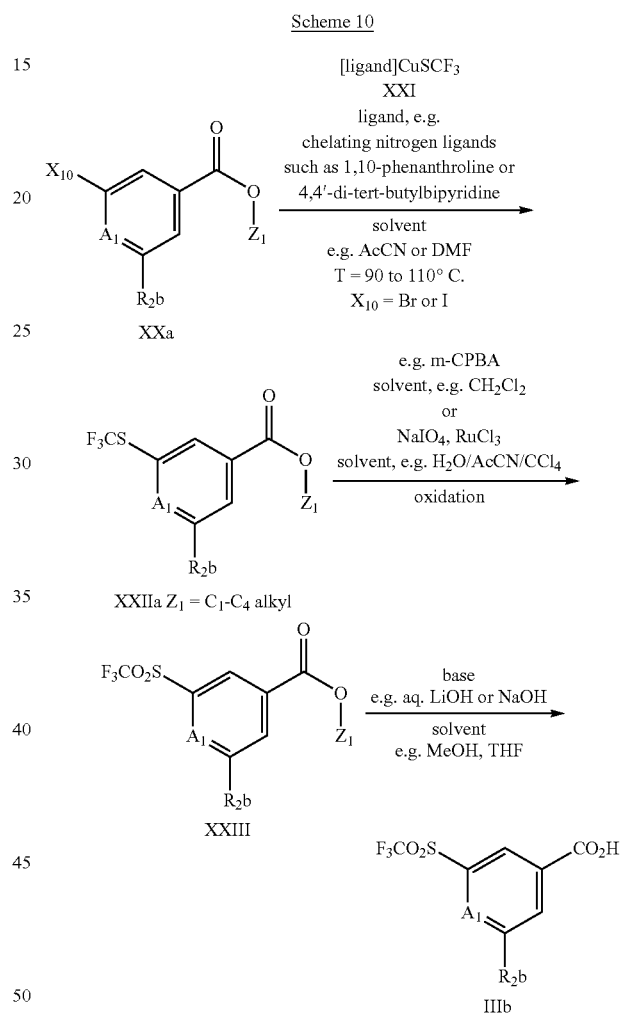

Accordingly, compounds of formula IIIb, wherein $R_{2b}$ and $A_1$ are as defined in formula I, can be prepared by reaction of compounds of formula XXIII (wherein $R_{2b}$ and $A_1$ are as defined in formula I and $Z_1$ is $C_1$-$C_4$alkyl) with a suitable base such as sodium or lithium hydroxide, in a suitable solvent like MeOH, THF, and $H_2O$ or a mixture of them, usually upon heating at temperatures between room temperature and reflux. Compounds of formula XXIII are prepared through oxidation of compounds of formula XXIIa (wherein $R_{2b}$ and $A_1$ are as defined in formula I and $Z_1$ is $C_1$-$C_4$alkyl), e.g. with m-CPBA or $NaIO_4$/$RuCl_3$, in a solvent, preferable $CH_2Cl_2$, or $CHCl_3$ or a mixture of $H_2O$, AcCN and $CCl_4$. Such transformations are known to those skilled in the art and described for example in J. Med. Chem. 2008, 51, 6902 or WO2004/9086, pages 24-25.

Finally, compounds of formula XXIIa, wherein $R_{2b}$ and $A_1$ are as defined in formula I and $Z_1$ is $C_1$-$C_4$alkyl, may be prepared by reaction of compounds of formula XX with a suitable trifluoromethylthiolation copper reagent of formula XXI (wherein $R_{2b}$ and $A_1$ are as defined in formula I and $X_{10}$ is Br or Cl), ligands being. e.g. 1,10-phenanthroline or 4,4'-di-tert-butylbipyridine, in suitable solvents, for example, acetonitrile or DMF, usually upon heating at temperatures between 20 to 150° C., preferably between 40° C. to the boiling point of the reaction mixture. Such processes have been described previously, for example, in Angew. Chem. Int. Ed. 2013, 52, 1548-1552, Angew. Chem. Int. Ed. 2011, 50, 3793, Org. Lett. 2014, 16, 1744, J. Org. Chem. 2017, 82, 11915.

Further carboxylic acids of formula IIIb, wherein $R_{2b}$, and $A_1$ are as defined in formula I and $R_{2a}$ is as defined in formula I but excluding $C_1$-$C_4$alkylsulfonyl, $C_1$-$C_4$-haloalkylsulfonyl, $C_1$-$C_4$-alkylsulfinyl, $C_1$-$C_4$-haloalkylsulfinyl, are generally known or can be easily prepared by those skilled in the art.

A typical example of such a synthesis of compounds of formula IIIc, wherein $R_{2b}$, and $A_1$ are defined as in formula I and $R_{2a}$ is as defined in formula I but excluding $C_1$-$C_4$alkylsulfonyl, $C_1$-$C_4$-haloalkylsulfonyl, $C_1$-$C_4$-alkylsulfinyl, $C_1$-$C_4$-haloalkylsulfinyl, is shown in Scheme 11.

a suitable solvent like MeOH, THF, and $H_2O$ or a mixture of them, usually upon heating at temperatures between room temperature and reflux.

Compounds of formula XXV, wherein $R_{2a}$, $R_{2b}$, and $A_1$ and $Z_1$ are as defined in scheme 11, may be prepared by reaction of compounds of formula XX, wherein $R_{2b}$ and $A_1$ are as defined in scheme 11 and $X_{11}$ represents a leaving group (such as, chlorine, bromine, iodine, OMs, OTs and OTf), with compounds of formula XXIV, wherein $R_{2a}$ is as defined in scheme 11, in the presence of a palladium catalyst, for example, $Pd(PPh_3)_4$, in suitable solvents, for example, toluene/water, 1,4-dioxane/water, in the presence of a suitable base, such as sodium, potassium or caesium carbonate or tripotassium phosphate usually upon heating at temperatures between room temperature and 200° C., preferably between 20° C. to the boiling point of the reaction mixture, optionally under microwave heating conditions. Such processes have been described previously, for example, in Tetrahedron Letters 2002, 43, 6987-6990.

Compounds of formula XXV, wherein $R_{2a}$, $R_{2b}$, and $A_1$ and $Z_1$ are as defined in scheme 11, may also be prepared by reaction of compounds of formula XXVII, wherein $R_{2b}$ and $A_1$ and $Z_1$ are as defined in scheme 11, and compounds of formula XXVIII, wherein $R_{2a}$ is as defined in scheme 11 and $X_{11}$ is a leaving group, for example, bromine or iodine, in the presence of a palladium catalyst, for example, $PdCl_2(dppf)$,

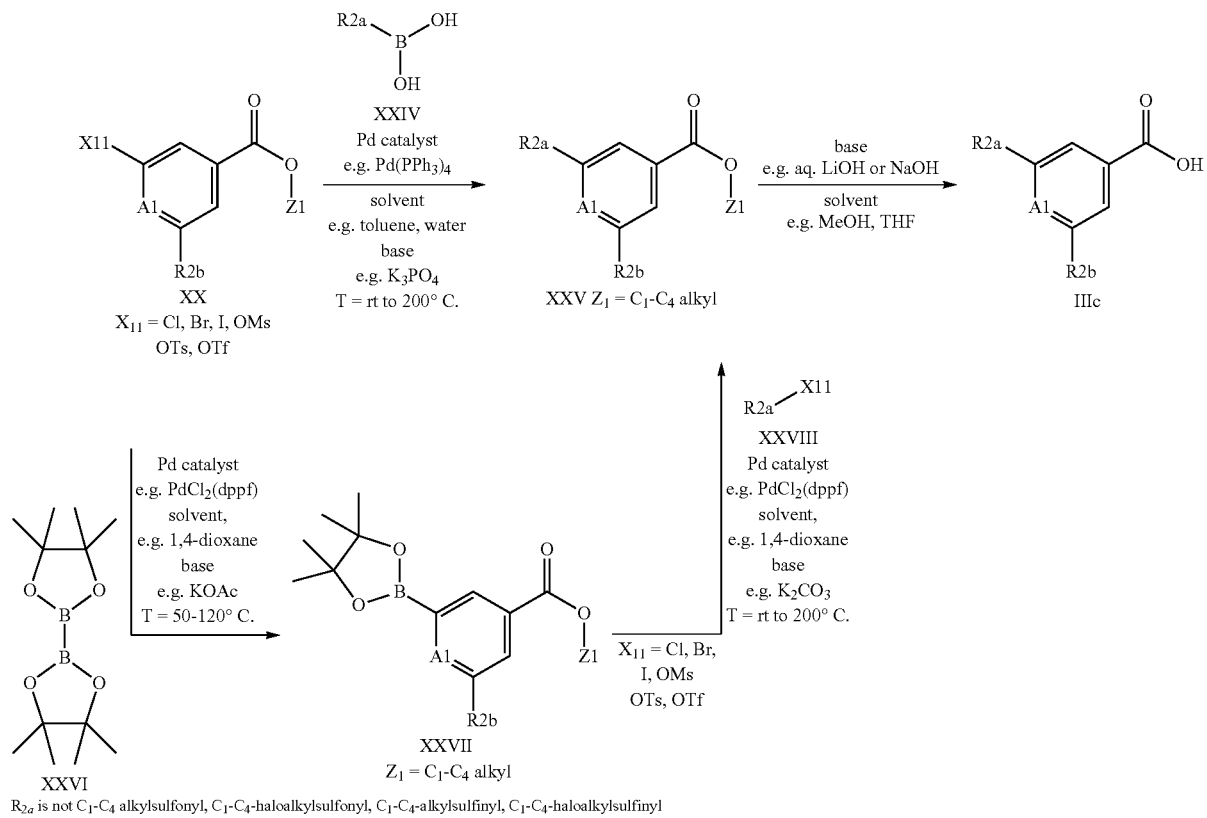

For example, compounds of formula IIIc can be prepared by reaction of compounds of formula XXV (wherein $R_{2a}$, $R_{2b}$ and $A_1$ are as defined in scheme 11 and $Z_1$ is $C_1$-$C_4$alkyl) with a suitable base such as sodium or lithium hydroxide, in in suitable solvents that may include, for example, toluene/water, 1,4-dioxane/water, in the presence of a suitable base, such as sodium, potassium or caesium carbonate or tripotassium phosphate usually upon heating at temperatures between room temperature and 200° C., preferably between 20° C. to the boiling point of the reaction mixture, optionally under microwave heating conditions. Such processes have been described previously, for example, in WO12139775, page 73.

Compounds of formula XXVII, wherein $R_{2b}$ and $A_1$ and $Z_1$ are as defined in scheme 11, may be prepared by reaction of compounds of formula XX, wherein $R_{2b}$ and $A_1$ and $Z_1$ are as defined in scheme 11 and $X_{11}$ is Cl, Br, I, OMs, OTs or OTf, with compound of formula XXVI, e.g. bis(pinacolato)diboron ($B_2pin_2$), in the presence of a palladium catalyst, for example, $PdCl_2(dppf)$, in suitable solvents that may include, for example, toluene/water, 1,4-dioxane/water, in the presence of a suitable base, such as sodium, potassium or caesium carbonate or potassium acetate, usually upon heating at temperatures between room temperature and 200° C., preferably between 20° C. to the boiling point of the reaction mixture, optionally under microwave heating conditions. Such processes have been described previously, for example, in Bioorg. Med. Chem. Lett. 2015, 25, 1730, and WO12139775, page 67.

Carboxylic acids of formula IIId, wherein $R_{2b}$ and $A_1$ are as defined in formula I and $R_{2a}$ is H, $C_1$-$C_3$alkyl, $C_1$-$C_3$haloalkyl, cyano or halogen, may be prepared as described in Scheme 12.

Compounds of formula XXX, wherein $R_{2a}$, $R_{2b}$ and $A_1$ are as defined in scheme 12 and $Z_1$ is $C_1$-$C_4$alkyl, may be prepared by treatment of compounds of formula XXIX, which are either commercially available or can be prepared by methods known to those skilled in the art (see e.g. Angew. Chem. Int. Ed. 2004, 43, 1132 and Pure Appl. Chem. 1985, 57, 1771) with compound of formula XXXI, e.g. (trifluoroethyl)-diphenyl-sulfonium triflate ($Ph_2S^+CH_2CF_3^-OTf$) in the presence of an Fe-catalyst and a base, preferably CsF at temperatures between 0 to 50°, preferable 20° C. in DMA as solvent (analog to Org. Lett. 2016, 18, 2471). Compounds of formula XXIX are obtained as mixture of stereoisomers with the trans isomer being the major isomer.

An alternative (see Scheme 12) to prepare compounds of formula XXX, wherein $R_{2a}$, $R_{2b}$ and $A_1$ and $Z_1$ are as defined in scheme 12, uses trifluoroethylamine hydrochloride/$NaNO_2$/NaOAc in the presence of an Fe-catalyst; this reaction is conducted at room temperature in $H_2O$; or in a mixture of $CH_2Cl_2$ and $H_2O$, see e.g. Angew. Chem. Int. Ed. 2010, 49, 938 and Chemm. Commun. 2018, 54, 5110.

Carboxylic acids of formula IIIe, wherein $R_{2a}$, $R_{2b}$ and $A_1$ are as defined in scheme 12, may be prepared in quite a similar manner as already shown in Scheme 12 (see scheme 13).

Scheme 12

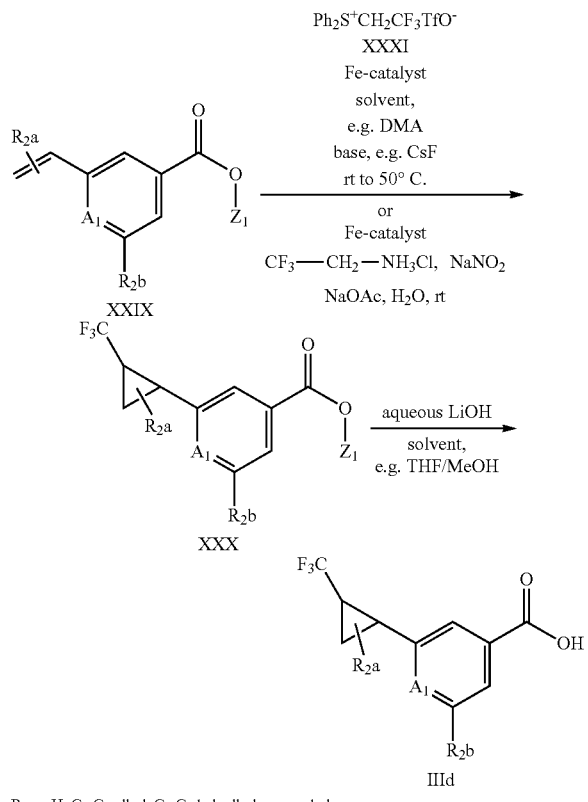

$R_{2a}$ = H, $C_1$-$C_3$ alkyl, $C_1$-$C_3$ haloalkyl, cyano, halogen

Scheme 13

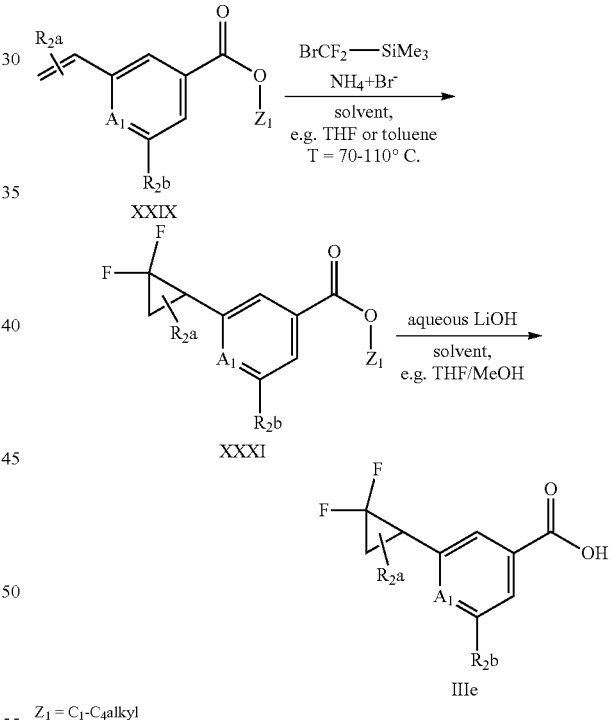

$Z_1$ = $C_1$-$C_4$alkyl
$R_{2a}$ = H, $C_1$-$C_3$alkyl, $C_1$-$C_3$haloalkyl, cyano, halogen Compounds of formula IIId may be prepared from compound of formula XXX analogs, by treatment with, for example aqueous LiOH, NaOH or KOH, in suitable solvents that may include, for example, THF/MeOH mixture, usually upon heating at temperatures between room temperature and 100° C., preferably between 20° C. to the boiling point of the reaction mixture.

Thus, compounds of formula XXXI, wherein $R_{2a}$, $R_{2b}$ and $A_1$ are as defined in scheme 13 and $Z_1$ is $C_1$-$C_4$alkyl, are prepared by reaction of compounds of formula XXIX (synthesized analog to ACS Med. Chem. Lett. 2013, 4, 514 or Tetrahedron Lett. 2001, 42, 4083) with (bromodifluoromethyl)-trimethylsilane in the presence of $NH_4^+Br^-$ in a suitable solvent, preferable in THF or toluene at temperatures between 70 to 110° C. Subsequent saponification of the ester intermediates XXXI provide compounds of formula IIIe (Scheme 13).

Carboxylic acids of formula IIIf, wherein $R_{2b}$ and $A_1$ are as defined in formula I and $R_{2a}$ is H, $C_1$-$C_3$alkyl, $C_1$-$C_3$haloalkyl, cyano or halogen, can also be prepared according to reaction Scheme 14.

Scheme 14

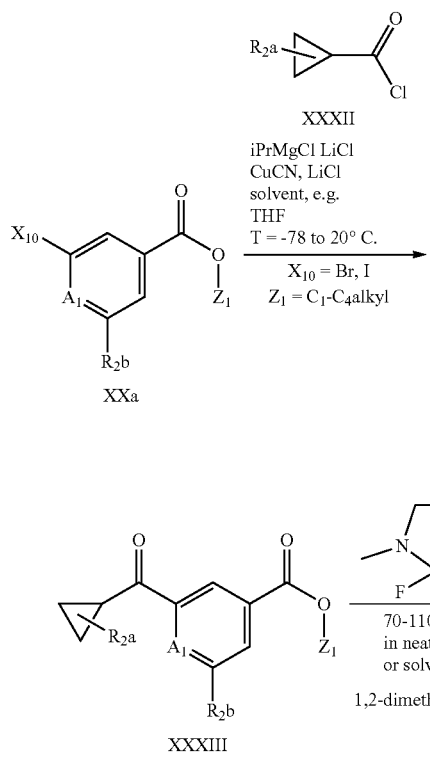

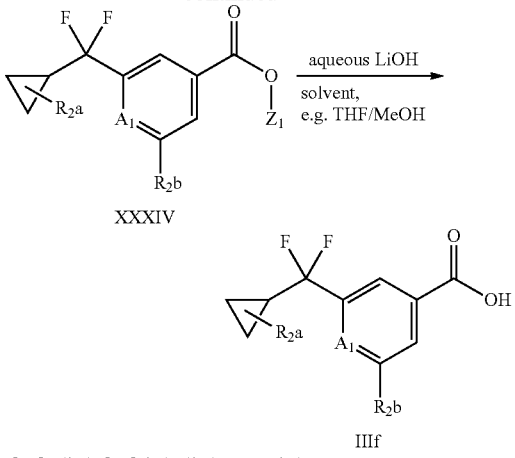

XXXIV $R_{2a}$ = H, $C_1$-$C_3$alkyl, $C_1$-$C_3$haloalkyl, cyano, halogen

Thus, compounds of formula XXa, wherein $R_{2b}$ and $A_1$ are as defined in formula I, $Z_1$ is $C_1$-$C_4$alkyl and $X_{10}$ represents a leaving group (such as bromine or iodine), were treated with iPrMgCl/LiCl-complex; subsequent reaction with CuCN and quenching with cyclopropane carbonyl chlorides of formula XXXII wherein $R_{2a}$ is defined above provided compounds of formula XXXIII (analog to WO2006/067445, page 148). Following fluorination of compounds XXXIII with 2,2-difluoro-1,3-dimethylimidazoline either in a solvent, e.g. in 1,2-dimethoxy-ethane or in neat (see Chem. Commun. 2002, (15), 1618) afforded compound of formula XXXIV. Subsequent hydrolysis using e.g. LiOH as already described gived carboxylic acids of formula IIIf.

Carboxylic acids of formula IIIg, wherein $R_{2b}$ and $A_1$ are as defined in formula I, can be prepared according to reaction Scheme 15.

Scheme 15
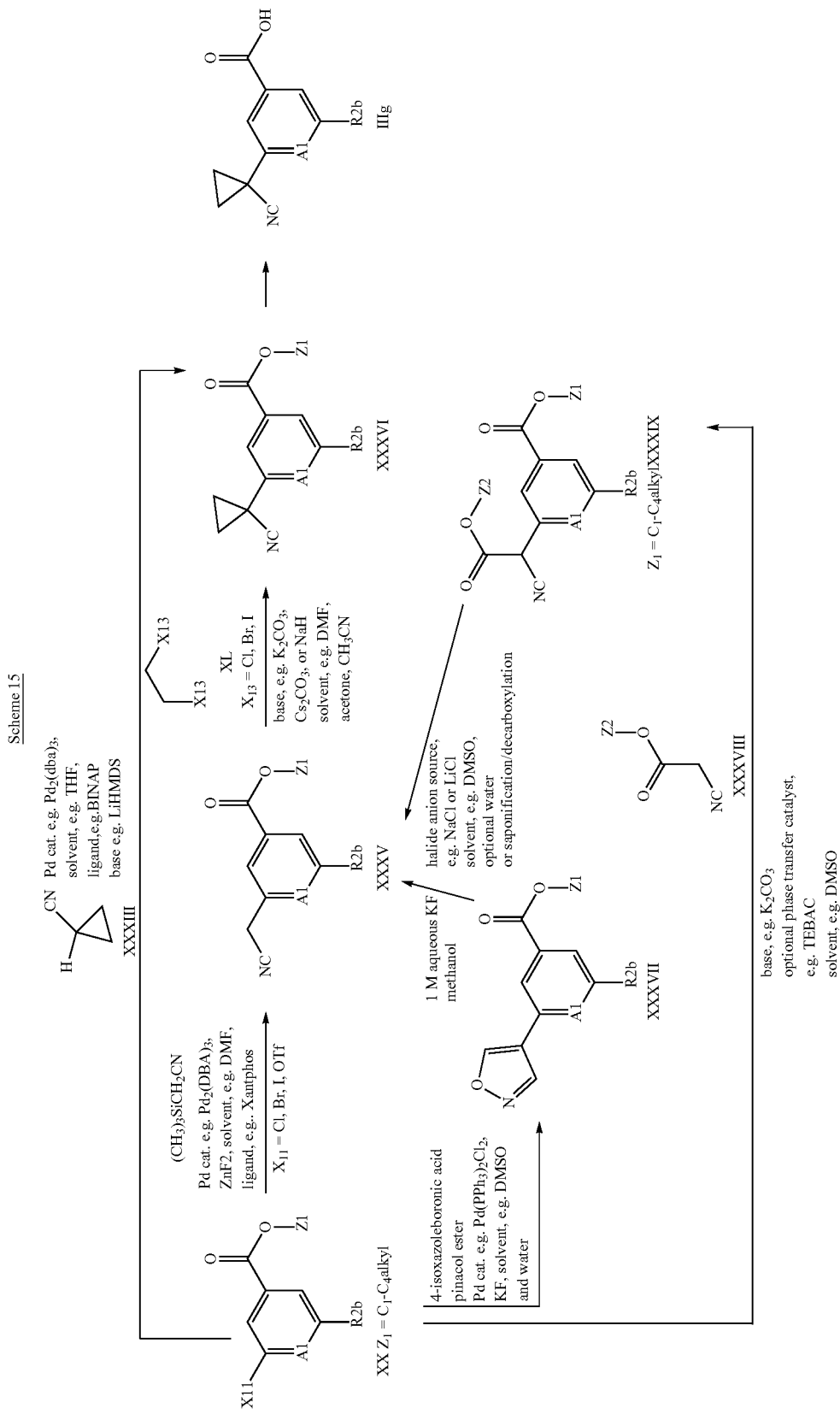

Treatment of compounds of formula XX, wherein $R_{2b}$ and $A_1$ are as defined in formula I, and $X_{11}$ is a leaving group, for example a halogen or a sulfonate, preferably chlorine, bromine, iodine or trifluoromethanesulfonate, and $Z_1$ is $C_1$-$C_4$alkyl, with trimethylsilyl-acetonitrile TMSCN, in the presence of zinc(II)fluoride ($ZnF_2$), and a palladium(0) catalyst such as tris(dibenzylideneacetone)di-palladium(0)-chloroform adduct ($Pd_2(dba)_3$ $CHCl_3$), with a ligand, for example Xantphos, in an inert solvent, such as N,N-dimethylformamide (DMF) at temperatures between 100-180° C., optionally under microwave heating, leads to compounds of formula XXXV, wherein $R_{2b}$, $Z_1$, and $A_1$ are as defined in scheme 15. Such chemistry has been described in the literature, e.g. in Org. Lett. 16(24), 6314-6317, 2014.

Alternatively, reaction of compounds of formula XX with 4-isoxazoleboronic acid or 4-isoxazoleboronic acid pinacol ester, in the presence of potassium fluoride (KF), and a palladium catalyst such as bis(triphenylphosphine)palladium(II) dichloride ($Pd(PPh_3)_2Cl_2$), in an inert solvent, such as dimethylsulfoxide DMSO, optionally in mixture with water, at temperatures between 40-150° C., optionally under microwave heating, leads to compounds of formula XXXVII, wherein $R_{2b}$, $Z_1$, and $A_1$ are as defined in scheme 15. Reaction of compounds of formula XXXVII with aqueous potassium fluoride (KF concentration between 0.5 and 3M, preferably 1 M), in an inert solvent, such as dimethylsulfoxide DMSO or methanol, at temperatures between 20-150° C., optionally under microwave heating, leads to compounds of formula XXXV, wherein $R_{2b}$, $Z_1$ and $A_1$ are as defined in scheme 15. Such chemistry has been described in the literature, e.g. in J. Am. Chem. Soc. 2011, 133, 6948-6951.

Compounds of formula XXXV, wherein $R_{2b}$ $Z_1$, and $A_1$ are as defined in scheme 15, can be further treated with compounds of formula XL, in which $X_{13}$ is a leaving group, such as a halogen (preferably chlorine, bromine or iodine), in the presence of a base such as sodium hydride, sodium carbonate, potassium carbonate $K_2CO_3$, or cesium carbonate $Cs_2CO_3$, in an inert solvent such as N,N-dimethylformamide (DMF), acetone, or acetonitrile, at temperatures between 0-120° C., to give compounds of formula XXXVI, wherein $R_{2b}$, and $A_1$ are as defined in formula I and $Z_1$ is $C_1$-$C_4$alkyl.

Alternatively, compounds of formula XXXVI can be prepared directly from compounds of formula XX by treatment with compounds of formula XXXIII, in presence of a catalyst such as $Pd_2(dba)_3$, with a ligand, such as BINAP, a strong base such as lithium hexamethyldisilazane (LiHMDS), in an inert solvent such as tetrahydrofuran (THF), at temperatures between 30-80° C. Such chemistry has been described in, for example, J. Am. Chem. Soc. 127(45), 15824-15832, 2005.

Yet another method to prepare compounds of formula XXXV from compounds of formula Xb is shown in Scheme 15. Reaction of compounds of formula XX, wherein $R_{2b}$, $Z_1$ and $A_1$ are as defined in scheme 15, and in which $X_{11}$ is a leaving group, for example a halogen or a sulfonate, preferably chlorine, bromine, iodine or trifluoromethanesulfonate, with reagents of the formula XXXVIII, wherein $Z_2$ is $C_1$-$C_4$alkyl, in the presence of a base, such as sodium carbonate, potassium carbonate or cesium carbonate, or sodium hydride, sodium methoxide or ethoxide, potassium tert-butoxide, optionally under palladium (for example involving $Pd(PPh_3)_2Cl_2$) or copper (for example involving CuI) catalysis, in an appropriate solvent such as for example toluene, dioxane, tetrahydrofuran, acetonitrile, N,N-dimethylformamide, N,N-dimethylacetamide, N-methyl-2-pyrrolidone (NMP) or dimethylsulfoxide (DMSO), optionally in presence of a phase transfer catalyst PTC, such as for example tetrabutyl ammonium bromide or triethyl benzyl ammonium chloride TEBAC, at temperatures between room temperature and 180° C., gives compounds of formula XXXIX, wherein $R_{2b}$, and $A_1$ are as defined in formula 1 and $Z_1$ and $Z_2$ are each $C_1$-$C_4$alkyl. Compounds of formula XXXIX can be decarboxylated using conditions such as heating in moist DMSO optionally in the presence of lithium or sodium chloride at temperatures between 50° C. and 180° C. to afford compounds of formula XXXV. Similar chemistry has been described in, for example, Synthesis 2010, No. 19, 3332-3338.

Compounds of formula IIIg, wherein $R_{2b}$ and $A_1$ are as defined in formula I, are finally obtained from compound of formula XXXVI, by treatment with, for example aqueous LiOH, NaOH or KOH, in suitable solvents that may include, for example, THF/MeOH mixture, usually upon heating at temperatures between room temperature and 100° C., preferably between 20° C. to the boiling point of the reaction mixture.

Compounds of Formula I'a

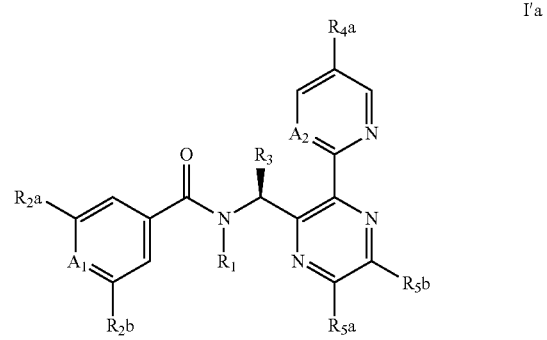

can be prepared by reaction of an amine of formula IIb

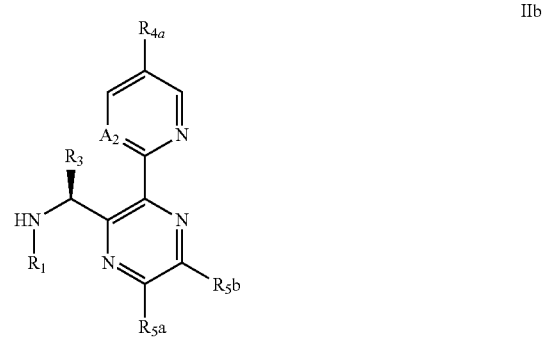

wherein $R_1$, $R_3$, $A_2$, $R_{4a}$, $R_{5a}$, and $R_{5b}$ are described in formula I'a, with a carboxylic acid derivative of formula III wherein $A_1$, $R_{2a}$ and $R_{2b}$ are described as above under formula I.

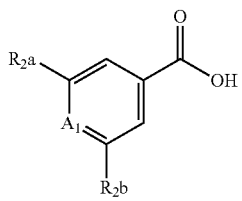

III

The chemistry is described in in more detail in Scheme 16.

Scheme 16

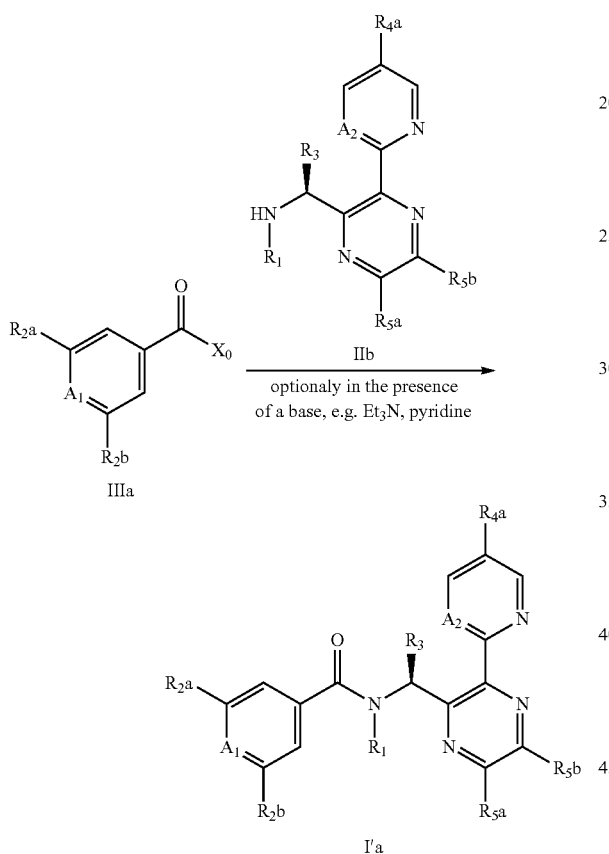

Compounds of formula IIIa, wherein $A_1$, $R_{2a}$, $R_{2b}$ and $X_0$ are described in Scheme 1, can be treated with compounds of formula IIb, wherein $R_1$, $R_3$, $A_2$, $R_{4a}$, $R_{5a}$, and $R_{5b}$ are described in formula I, under the conditions described in detail in Scheme 1 to afford compounds of formula I'a. The formation of compounds of formula IIIa from compounds of formula III is described in Scheme 1.

The formation of compounds of formula IIb is outlined in Scheme 17. Compounds of formula IIb can be prepared by treatment of compounds of formula IIc, wherein $A_2$, $R_3$, $R_{4a}$, $R_{5a}$, and $R_{5b}$ are described in formula I, with compounds of formula XLI (wherein $R_1$ is defined in formula I), e.g. in the presence of NaBH(OAc)$_3$ or NaBH$_3$CN, in a suitable solvent, preferably in acetic acid at room temperature analog to WO2002/088073, page 35. Alternatively, another reagent system for the reductive amination uses a combination of Ti(i-OiPr)$_4$ and NaBH$_4$ (see Synthesis 2003 (14), 2206).

Amines of formula IIc may be obtained by biocatalyzed deracemization of amines of formula IIa. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

Scheme 17

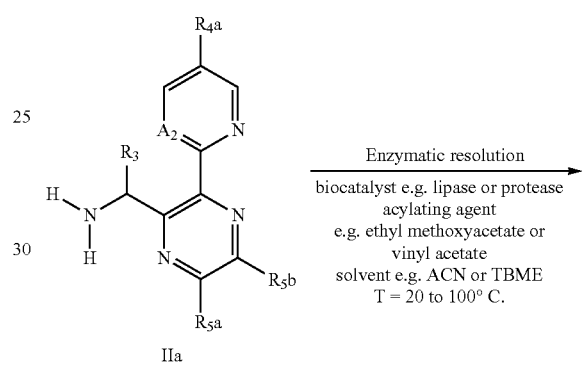

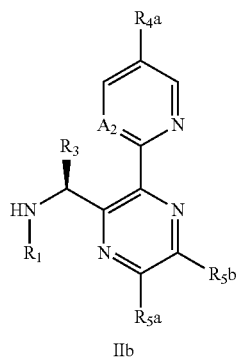

In an alternative process, compounds of formula IIc can be obtained from XVa, wherein $A_2$, $R_3$, $R_{4a}$, $R_{5a}$, and $R_{5b}$ are described in formula I, following the synthesis described in Scheme 18.

Scheme 18

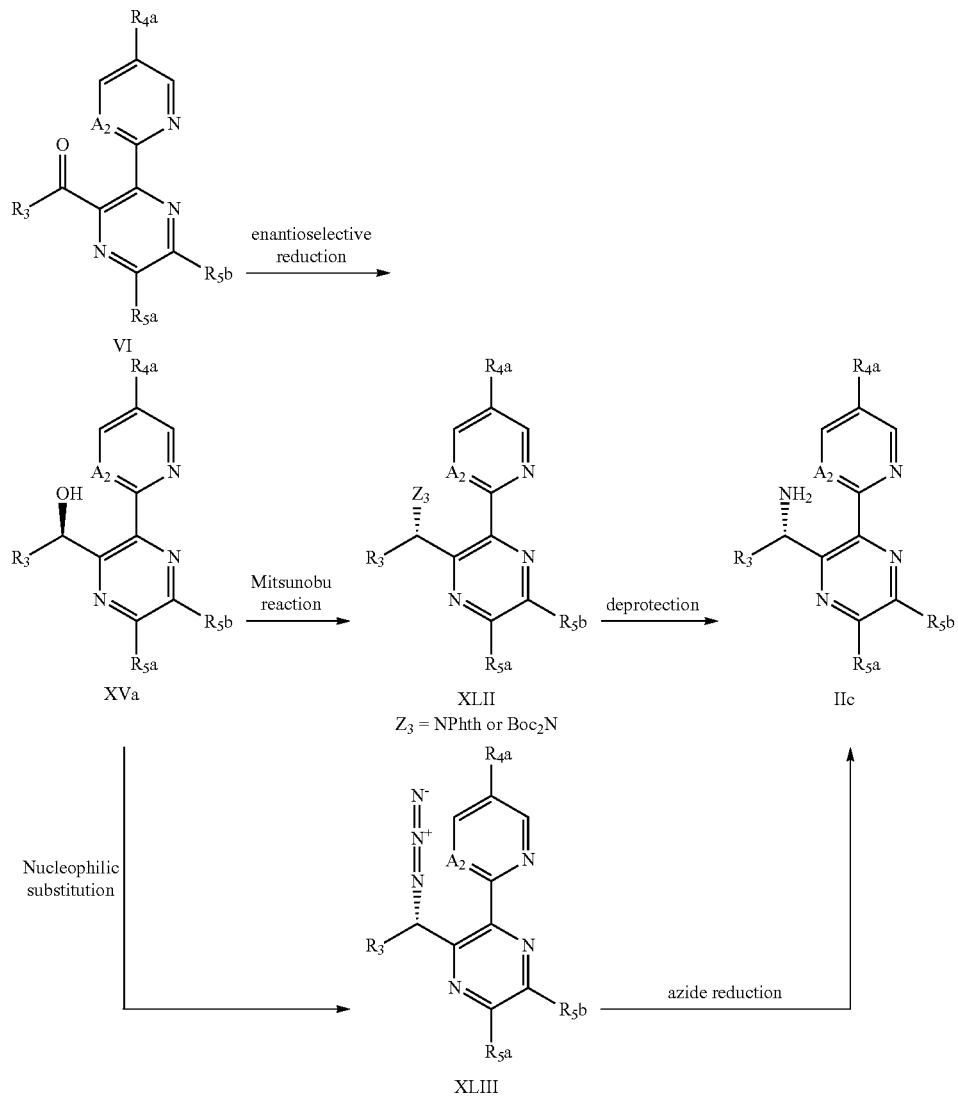

Amines of formula IIc may be obtained from intermediates of formula XLII, wherein $A_2$, $R_3$, $R_{4a}$, $R_{5a}$, and $R_{5b}$ are described in formula I and $Z_3$ is NPhth or NBoc$_2$. Such intermediates can be obtained from alcohols of formula XVa by a Mitsunobu reaction, which involves treating alcohols of formula XVa by diisopropyl azodicarboxylate in the presence of a phosphine such as triphenylphosphine or tributylphosphine and of an amine such as phthalimide or bis(tert-butoxycarbonyl)amine. Mitsunobu reactions are known by those skilled in the art to proceed with inversion of the stereocenter, as described for instance in *Chem. Rev.* 2009, 109, 2551-2651. Amines of formula XLII can then be transformed into amines of formula IIc by treatment with hydrazine if $Z_3$=NPhth or with TFA if $Z_3$=NBoc$_2$.

Alternatively, amines of formula IIc may be obtained by reduction of azides of formula XLIII, wherein $A_2$, $R_3$, $R_{4a}$, $R_{5a}$, and $R_{5b}$ are described in formula I, by treatment with triphenylphosphine and water (Staudinger reaction) or by hydrogenation for example using a palladium catalyst in the presence of hydrogen. Azides of formula XLIII may be obtained by treatment of alcohols of formula XVa, wherein $A_2$, $R_3$, $R_{4a}$, $R_{5a}$, and $R_{5b}$ are described in formula I, with an azidation reagent such as diphenyl phosphoryl azide in a solvent such as toluene or THF in presence of a base such as DBU. Such processes are known by those skilled in the art to proceed with inversion of the stereocenter and are described in the literature for instance in *Adv. Synth. Catal.* 2018, 360, 2157-2165.

Alcohols of formula XVa may be obtained by enantioselective reduction of ketones of formula VI, wherein $A_2$, $R_3$, $R_{4a}$, $R_{5a}$, and $R_{5b}$ are as described in formula I. Such reductions can be done using a catalyst, for instance a ruthenium or a rhodium catalyst with a chiral ligand such as RuCl[(R,R)-TsDPEN](mesitylene) or RuBF$_4$[(R,R)-TsDPEN](p-cymene) in the presence of a hydrogen donor system such as for example HCOOH/Et$_3$N or HCO$_2$NH$_4$. Such processes are described in the literature for instance in *J. Org. Chem.* 2017, 82, 5607.

Alternatively, compounds of formula IIc may also be prepared as outlined in Scheme 19.

Scheme 19

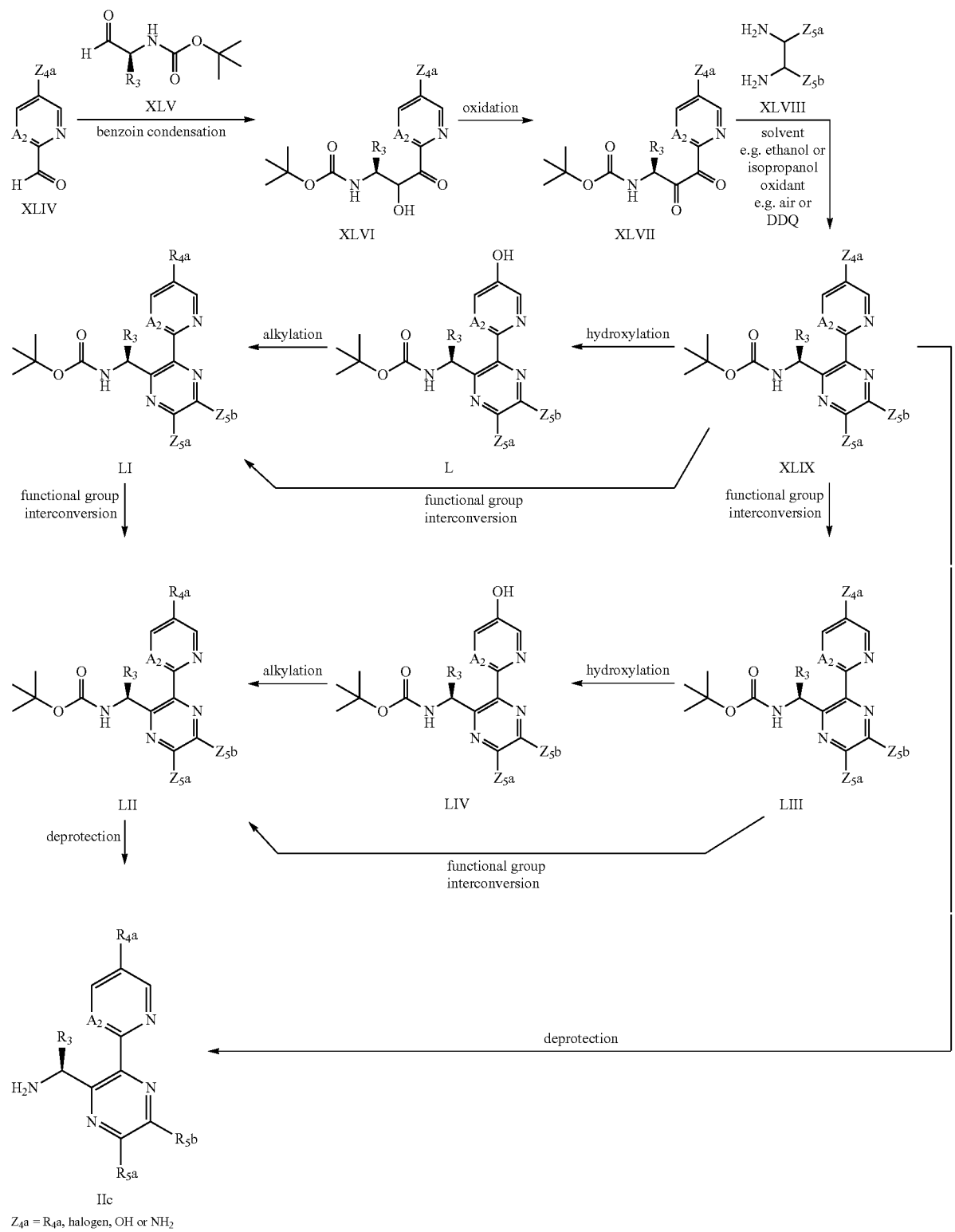

$Z_{4a}$ = $R_{4a}$, halogen, OH or $NH_2$

Amines of formula IIc can be prepared by deprotection of amines of formula LII, wherein $A_2$, $R_3$, $R_{4a}$, $R_{5a}$, and $R_{5b}$ are described in formula I, for instance using an acid such as trifluoroacetic acid or hydrochloric acid. Compounds of formula LII may be synthesized from compounds of formula LI, wherein $A_2$, $R_3$ and $R_{4a}$ are described in formula I and $Z_5a$ and $Z_{5b}$ are, independently of each other, selected from $R_{5a}$, $R_{5b}$, halogen, $NH_2$ or OH. Such functional group interconversions are known to those skilled in the art and examples of such transformations have been described in the literature, for instance in *Eur. J. Org. Chem.* 2005, 19, 4141-4153 or in *J. Org. Chem.* 2008, 73, 7481-7485. Compounds of formula LI can be obtained from compounds of formula L by alkylation, for instance using a base and an electrophile, e.g. chlorodifluoroacetic acid. Compounds of formula L may be prepared by hydroxylation of compounds of formula XLIX, wherein $A_2$ and $R_3$ are described in formula I, $Z_{4a}$ is selected from $R_{4a}$, halogen or $NH_2$, and $Z_{5a}$ and $Z_{5b}$ are, independently of each other, selected from $R_{5a}$, $R_{5b}$, halogen, $NH_2$ or OH. Conversion of XLIX to L can be done following methods referenced in the literature, for instance in *Org. Lett.* 2016, 18, 2244-2247 or *Tetrahedron* 2009, 65, 757-764. Amines of formula XLIX can be obtained by condensation of diamines of formula XLVIII, wherein $Z_{5a}$ and $Z_{5b}$ are, independently of each other, selected from $R_{5a}$, $R_{5b}$, halogen, $NH_2$ or OH, on diketones of formula XLVII, wherein $A_2$ and $R_3$ are described in formula I, and $Z_{4a}$ is selected from $R_{4a}$, halogen or $NH_2$. This condensation can take place in the presence of a suitable solvent such as ethanol or isopropanol in presence of an oxidant such as air or DDQ. Diketones of formula XLVII may be formed by oxidation of hydroxyketones of formula XLVI wherein $A_2$ and $R_3$ are described in formula I, and $Z_{4a}$ is selected from $R_{4a}$, halogen or $NH_2$. This oxidation can involve, for instance, $SO_3$-pyridine in presence of DMSO and a base for instance triethylamine, or also sodium hypochlorite in presence of a catalyst such as TEMPO/$Bu_4NHSO_4$. Examples of such oxidations can be found in the literature, for instance in *Synlett*, 2014, 25, 596 or *J. Am. Chem. Soc.* 1990, 112, 5290-5313. Hydroxyketones of formula XLVI may be synthesized by cross-benzoin condensation between aldehydes of formula XLIV, wherein $A_2$ is described in formula I and $Z_{4a}$ is selected from $R_{4a}$, halogen or $NH_2$, and aldehydes of formula XLV, wherein $R_3$ is as described in formula I. Aldehydes of formula XLV are commercially available in chiral form, like for instance Boc-L-alaninal (CAS 79069-50-4) or tert-butyl N-[(1S)-1-(cyclopropylmethyl)-2-oxo-ethyl]carbamate (CAS 881902-36-9). Cross-benzoin condensations are done in the usual way by employing an organocatalyst such as a triazolium salt or a thiazolium salt in the presence of a base such as potassium tert-butoxide or isopropyldiethylamine in a suitable solvent such as DCM or THF at a temperature between −20° C. and the boiling point of the solvent. Examples of catalysts for such transformations have been described in the literature for instance in *J. Am. Chem. Soc.* 2014, 136, 7539-7542 or in *Org. Lett.* 2016, 18, 4518-4521.

Compounds of formula LI may also be obtained directly from compounds of formula XLIX, for instance using transition metal catalysis or diazonium chemistry. Such functional group interconversions are known to those skilled in the art and examples can be found in the literature, for instance in *J. Am. Chem. Soc.* 2019, 141, 19257-19262, *Angew. Chem. Int. Ed.* 2015, 54, 5736-5739 or *Heterocycles*, 2004, 63, 2735-2746.

Compounds of formula LII may be obtained from compounds of formula LIV, wherein $A_2$, $R_3$, $R_{5a}$ and $R_{5b}$ are described in formula I by alkylation for instance using a base and an electrophile, e.g. chlorodifluoroacetic acid. Compounds of formula LIV may be synthesized from compounds of formula XLIX by hydroxylation reaction, following methods referenced in the literature, for instance in *Org. Lett.* 2016, 18, 2244-2247 or *Tetrahedron* 2009, 65, 757-764. Alternatively, compounds of formula LII may be obtained from compounds of formula LIII, wherein $A_2$, $R_3$, $R_{5a}$ and $R_{5b}$ are described in formula I, and $Z_{4a}$ is selected from $R_{4a}$, halogen or $NH_2$. Such functional group interconversions are known to those skilled in the art and examples can be found in the literature, for instance in *J. Am. Chem. Soc.* 2019, 141, 19257-19262, *Angew. Chem. Int. Ed.* 2015, 54, 5736-5739 or *Heterocycles*, 2004, 63, 2735-2746.

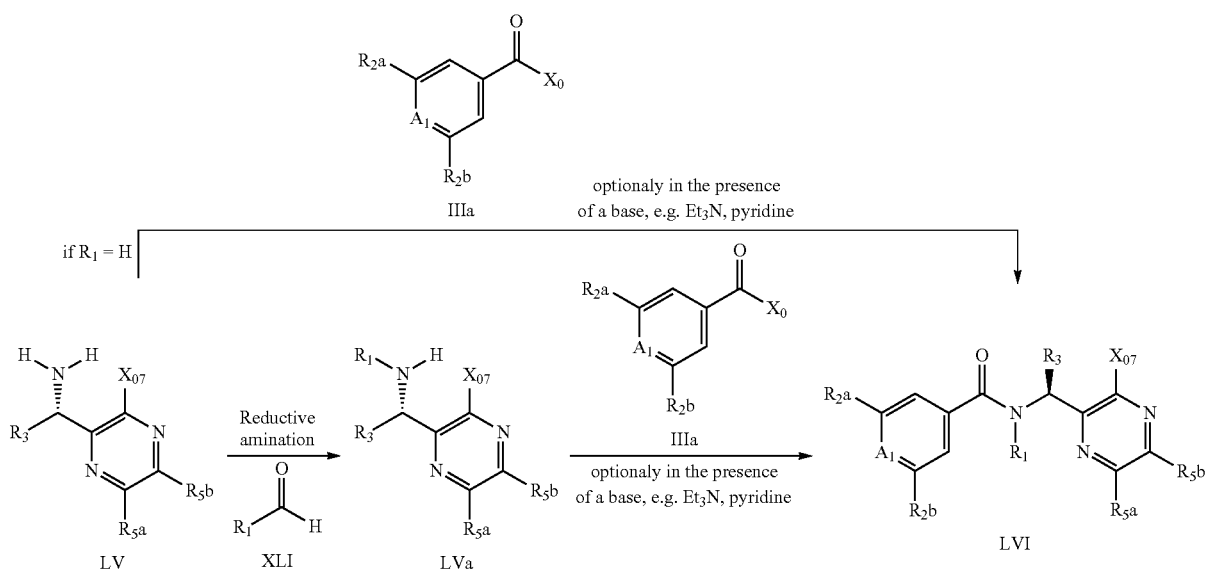

Scheme 20

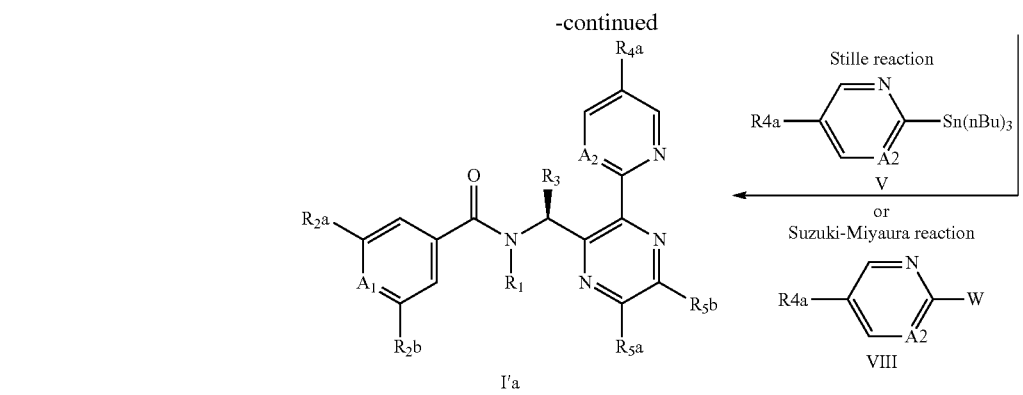

$X_{O7}$ = Cl, Br, I, OMs, OTs or OTf

As shown in Scheme 20, compounds of formula I'a can be alternatively prepared by reaction of compounds of formula LVI (wherein $A_1$, $R_1$, $R_{2a}$, $R_{2b}$, $R_3$, $R_{5a}$, and $R_{5b}$ are defined in formula I, and $X_{O7}$ is a leaving group like, for example, chlorine, bromine, iodine) with compounds of formula V (Stille reaction) or compounds of formula VIII (Suzuki-Miyaura reaction) in the presence of a palladium catalyst as described in detail in Schemes 2 and 3.

Compounds of formula LVI can be prepared by coupling of amines of formula LVa (wherein $R_1$, $R_3$, $R_{5a}$, and $R_{5b}$ are defined in formula I, and $X_{O7}$ is a leaving group like, for example, chlorine, bromine, iodine) and compounds of formula IIIa, wherein $A_1$, $R_{2a}$, $R_{2b}$ and $X_0$ are described in Scheme 1, under the conditions described in detail in Scheme 1. Under the same conditions, if $R_1$=H, compounds of formula LVI may be obtained directly from compounds of formula LV.

Compounds of formula LVa can be prepared by treatment of compounds of formula LV, with compounds of formula XLI (wherein $R_1$ is as defined in formula I), e.g. in the presence of $NaBH(OAc)_3$ or $NaBH_3CN$, in a suitable solvent, preferably in acetic acid at room temperature analog to WO2002/088073, page 35. Alternatively, another reagent system for the reductive amination uses a combination of Ti(i-OiPr)$_4$ and NaBH$_4$ (see Synthesis 2003 (14), 2206).

Amines of formula LV can be prepared by deracemization procedure method, which involves for example, a selective acylation of one enantiomer. Such an example is described more in details in Scheme 21.

-continued $X_{O7}$ = Cl, Br, I, OMs, OTs or OTf

Amines of formula LV may be obtained by biocatalyzed deracemization of amines of formula LVb, wherein $R_3$, $R_{5a}$, and $R_{5b}$ are described in Scheme 1 and $X_{O7}$ is a leaving group such as bromine, chlorine or iodine. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

Alternatively, resolution of amines of formula LVb may be achieved using a chiral auxiliary, as described in Scheme 22.

Scheme 21

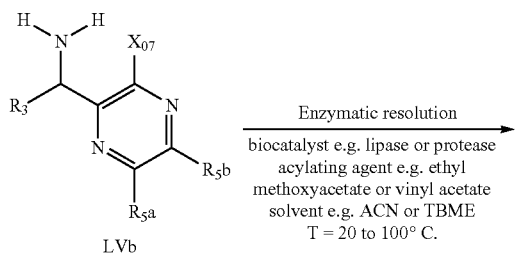

Scheme 22

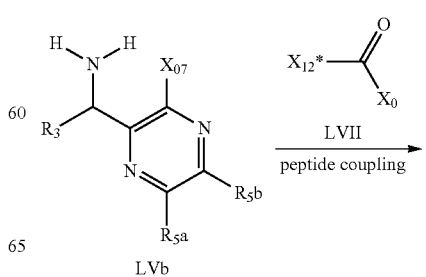

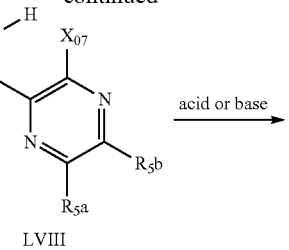

LVIII

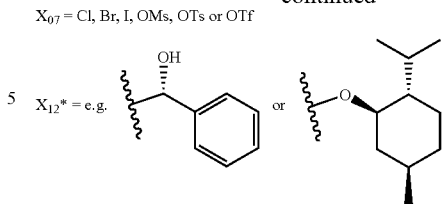

$X_{07}$ = Cl, Br, I, OMs, OTs or OTf $X_{12}^{*}$ = e.g.

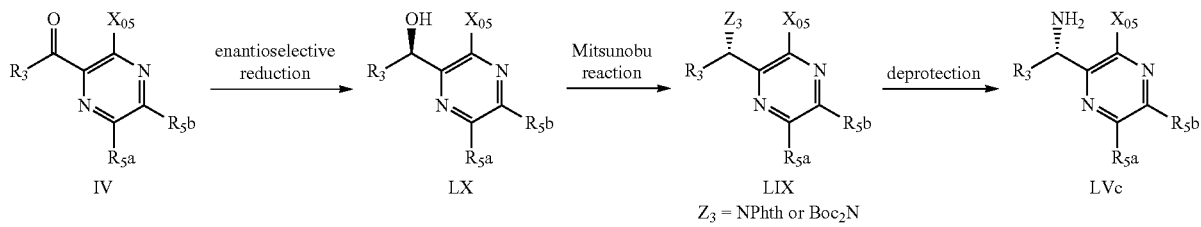

LV

Amines of formula LV can be prepared for intermediates of formula LVIII, wherein $R_3$, $R_{5a}$, and $R_{5b}$ are described in Scheme 1, $X_{07}$ is a leaving group such as bromine, chlorine or iodine and $X_{12}^{*}$ is a chiral auxiliary by treatment with acids such as HCl or bases such as NaOH. Amines of formula LVIII can be formed by coupling of a chiral compound of formula LVII, wherein $X_0$ is described in Scheme 1 and $X_{12}^{*}$ is a chiral moiety of known chirality, with amines of formula LVb following the conditions detailed in Scheme 1. Chiral auxiliaries of formula LVII are for instance derived from mandelic acid or (1R)-menthyl-chloroformate. Examples of such deracemization processes are reported in the literature, for instance in *J. Org. Chem.* 2007, 72, 485-493.

Alternatively, amines of formula LVc (wherein $R_3$, $R_{5a}$, and $R_{5b}$ are defined in formula I, and $X_{05}$ is a leaving group like, for example, chlorine, bromine, iodine), can be formed as described in Scheme 23.

Scheme 23

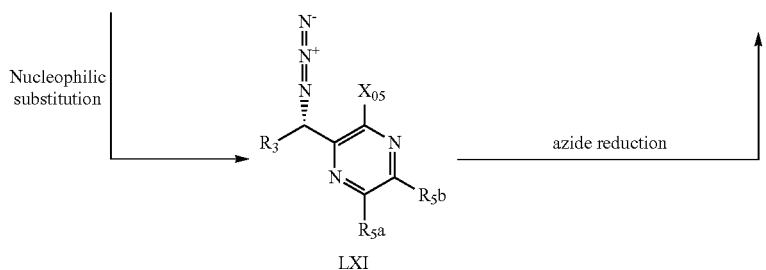

LXI $X_{05}$ = Cl, Br, I, OMs, OTs or OTf

Amines of formula LVc may be obtained from intermediates of formula LIX, wherein $R_3$, $R_{5a}$, and $R_{5b}$ are described in formula I, $X_{05}$ is a leaving group as described in Scheme 3 and $Z_3$ is NPhth or NBoc$_2$. Intermediates of formula LIX can be obtained from alcohols of formula LX, wherein $R_3$, $R_{5a}$, and $R_{5b}$ are as described in formula I and $X_{05}$ is a leaving group as described in Scheme 3, by a Mitsunobu reaction. This involves treating alcohols of formula LX by diisopropyl azodicarboxylate in the presence of a phosphine such as triphenylphosphine or tributylphosphine and of an amine such as phthalimide or bis(tert-butoxycarbonyl)amine. Mitsunobu reactions are known by those skilled in the art to proceed with inversion of the stereocenter, as described for instance in *Chem. Rev.* 2009, 109, 2551-2651. Amines of formula LIX can then be transformed into amines of formula LVc by treatment with hydrazine if $Z_3$=NPhth or with TFA if $Z_3$=NBoc$_2$.

Alternatively, amines of formula LVc may be obtained by reduction of azides of formula LXI, wherein $R_3$, $R_{5a}$, and $R_{5b}$ are as described in formula I and $X_{05}$ is a leaving group as described in Scheme 3, by treatment with triphenylphosphine and water (Staudinger reaction) or by hydrogenation for example using a palladium catalyst in the presence of hydrogen. Azides of formula LXI may be obtained by treatment of alcohols of formula LX with an azidation reagent such as diphenyl phosphoryl azide in a solvent such as toluene or THF in presence of a base such as DBU. Such processes are known by those skilled in the art to proceed with inversion of the stereocenter and are described in the literature for instance in *Adv. Synth. Catal.* 2018, 360, 2157-2165.

Alcohols of formula LX may be obtained by enantioselective reduction of ketones of formula IV, wherein $R_3$, $R_{5a}$, and $R_{5b}$ are as described in formula I and $X_{05}$ is a leaving group as described in Scheme 3. Such reductions can be done using catalysts, for instance a ruthenium or a rhodium catalyst with a chiral ligand such as RuCl[(R,R)-TsDPEN] (mesitylene) or RuBF$_4$[(R,R)-TsDPEN](p-cymene) in the presence of a hydrogen donor system such as for example HCOOH/Et$_3$N or HCO$_2$NH$_4$. Such processes are described in the literature for instance in *J. Org. Chem.* 2017, 82, 5607.

Depending on the procedure or the reaction conditions, the reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the following Tables A-1 to A-27 can be prepared according to the methods described above. The examples which follow are intended to illustrate the invention and show preferred compounds of formula I, in the form of a compound of formula Iaa.

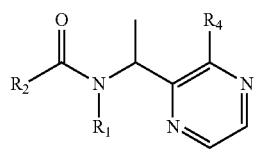

Iaa

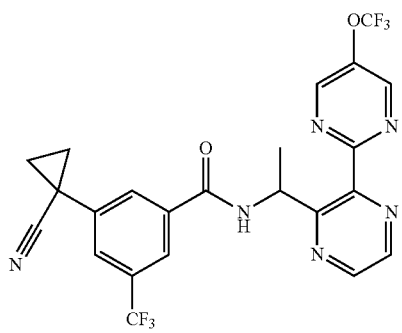

I

TABLE Z

Substituent definitions of $R_2$:

| Index | $R_2$ |
|---|---|
| 1 | (structure) |
| 2 | (structure) |
| 3 | (structure) |
| 4 | (structure) |

Table A-1 provides 16 compounds A-1.001 to A-1.016 of formula Iaa wherein $R_1$ is H, $R_4$ is [5-(trifluoromethoxy) pyrimidin-2-yl] and $R_2$ are as defined in table Z. For example, A-1.002 is TABLE Z-continued Substituent definitions of $R_2$:

| Index | $R_2$ |
|---|---|
| 5 | 3-cyclopropyl-5-(trifluoromethyl)phenyl |
| 6 | 1-cyano-cyclopropyl attached to 6-(trifluoromethyl)pyridin-2-yl (4-position) |
| 7 | 3-(2,2-difluorocyclopropyl)-5-(trifluoromethyl)phenyl |
| 8 | 3-cyclopropoxy-5-(trifluoromethyl)phenyl |
| 9 | 3-[1-methyl-2-(trifluoromethyl)cyclopropyl]-5-(trifluoromethyl)phenyl |
| 10 | 3-[difluoro(cyclopropyl)methyl]-5-(trifluoromethyl)phenyl |
| 11 | 3-[2-(trifluoromethyl)cyclopropyl]-5-(trifluoromethyl)phenyl |
| 12 | 3-(trifluoromethylsulfonyl)-5-(trifluoromethyl)phenyl |
| 13 | 2-cyclopropyl-6-(trifluoromethyl)pyridin-4-yl |
| 14 | 3-(trifluoromethylsulfinyl)-5-(trifluoromethyl)phenyl |
| 15 | 3-(2-methoxycyclopropyl)-5-(trifluoromethyl)phenyl |
| 16 | 2-(2-methoxycyclopropyl)-6-(trifluoromethyl)pyridin-4-yl |

Table A-2 provides 16 compounds A-2.001 to A-2.016 of formula Iaa wherein $R_1$ is H, $R_4$ is [5-(trifluoromethoxy)-2-pyridyl] and $R_2$ is as defined in table Z.

Table A-3 provides 16 compounds A-3.001 to A-3.016 of formula Iaa wherein $R_1$ is H, $R_4$ is [5-(2,2-difluoroethoxy)pyrimidin-2-yl] and $R_2$ is as defined in table Z.

Table A-4 provides 16 compounds A-4.001 to A-4.016 of formula Iaa wherein $R_1$ is H, $R_4$ is [5-(2,2-difluoroethoxy)-2-pyridyl] and $R_2$ is as defined in table Z.

Table A-5 provides 16 compounds A-5.001 to A-5.016 of formula Iaa wherein $R_1$ is H, $R_4$ is [5-(2,2,2-trifluoroethoxy)pyrimidin-2-yl] and $R_2$ is as defined in table Z.

Table A-6 provides 16 compounds A-6.001 to A-6.016 of formula Iaa wherein $R_1$ is H, $R_4$ is [5-(2,2,2-trifluoroethoxy)-2-pyridyl] and $R_2$ is as defined in table Z.

Table A-7 provides 16 compounds A-7.001 to A-7.016 of formula Iaa wherein $R_1$ is H, $R_4$ is [5-(difluoromethoxy)pyrimidin-2-yl] and $R_2$ is as defined in table Z.

Table A-8 provides 16 compounds A-8.001 to A-8.016 of formula Iaa wherein $R_1$ is H, $R_4$ is [5-(difluoromethoxy)-2-pyridyl] and $R_2$ is as defined in table Z.

Table A-9 provides 16 compounds A-9.001 to A-9.016 of formula Iaa wherein $R_1$ is H, $R_4$ is (5-cyano-2-pyridyl) and $R_2$ is as defined in table Z.

Table A-10 provides 16 compounds A-10.001 to A-10.016 of formula Iaa wherein $R_1$ is $CH_3$, $R_4$ is [5-(trifluoromethoxy)pyrimidin-2-yl] and $R_2$ is as defined in table Z.

Table A-11 provides 16 compounds A-11.001 to A-11.016 of formula Iaa wherein $R_1$ is $CH_3$, $R_4$ is [5-(trifluoromethoxy)-2-pyridyl] and $R_2$ is as defined in table Z.

Table A-12 provides 16 compounds A-12.001 to A-12.016 of formula Iaa wherein $R_1$ is $CH_3$, $R_4$ is [5-(2,2-difluoroethoxy)pyrimidin-2-yl] and $R_2$ is as defined in table Z.

Table A-13 provides 16 compounds A-13.001 to A-13.016 of formula Iaa wherein $R_1$ is $CH_3$, $R_4$ is [5-(2,2-difluoroethoxy)-2-pyridyl] and $R_2$ is as defined in table Z.

Table A-14 provides 16 compounds A-14.001 to A-14.016 of formula Iaa wherein $R_1$ is $CH_3$, $R_4$ is [5-(2,2,2-trifluoroethoxy)pyrimidin-2-yl] and $R_2$ is as defined in table Z.

Table A-15 provides 16 compounds A-15.001 to A-15.016 of formula Iaa wherein $R_1$ is $CH_3$, $R_4$ is [5-(2,2,2-trifluoroethoxy)-2-pyridyl] and $R_2$ is as defined in table Z.

Table A-16 provides 16 compounds A-16.001 to A-16.016 of formula Iaa wherein $R_1$ is $CH_3$, $R_4$ is [5-(difluoromethoxy)pyrimidin-2-yl] and $R_2$ is as defined in table Z.

Table A-17 provides 16 compounds A-17.001 to A-17.016 of formula Iaa wherein $R_1$ is $CH_3$, $R_4$ is [5-(difluoromethoxy)-2-pyridyl] and $R_2$ is as defined in table Z.

Table A-18 provides 16 compounds A-18.001 to A-18.016 of formula Iaa wherein $R_1$ is $CH_3$, $R_4$ is (5-cyano-2-pyridyl) and $R_2$ is as defined in table Z.

Table A-19 provides 16 compounds A-19.001 to A-19.016 of formula Iaa wherein $R_1$ is cyclopropyl-$CH_2$—, $R_4$ is [5-(trifluoromethoxy)pyrimidin-2-yl] and $R_2$ is as defined in table Z.

Table A-20 provides 16 compounds A-20.001 to A-20.016 of formula Iaa wherein $R_1$ is cyclopropyl-$CH_2$—, $R_4$ is [5-(trifluoromethoxy)-2-pyridyl] and $R_2$ is as defined in table Z.

Table A-21 provides 16 compounds A-21.001 to A-21.016 of formula Iaa wherein $R_1$ is cyclopropyl-$CH_2$—, $R_4$ is [5-(2,2-difluoroethoxy)pyrimidin-2-yl] and $R_2$ is as defined in table Z.

Table A-22 provides 16 compounds A-22.001 to A-22.016 of formula Iaa wherein $R_1$ is cyclopropyl-$CH_2$—, $R_4$ is [5-(2,2-difluoroethoxy)-2-pyridyl] and $R_2$ is as defined in table Z.

Table A-23 provides 16 compounds A-23.001 to A-23.016 of formula Iaa wherein $R_1$ is cyclopropyl-$CH_2$—, $R_4$ is [5-(2,2,2-trifluoroethoxy)pyrimidin-2-yl] and $R_2$ is as defined in table Z.

Table A-24 provides 16 compounds A-24.001 to A-24.016 of formula Iaa wherein $R_1$ is cyclopropyl-$CH_2$—, $R_4$ is [5-(2,2,2-trifluoroethoxy)-2-pyridyl] and $R_2$ is as defined in table Z.

Table A-25 provides 16 compounds A-25.001 to A-25.016 of formula Iaa wherein $R_1$ is cyclopropyl-$CH_2$—, $R_4$ is [5-(difluoromethoxy)pyrimidin-2-yl] and $R_2$ is as defined in table Z.

Table A-26 provides 16 compounds A-26.001 to A-26.016 of formula Iaa wherein $R_1$ is cyclopropyl-$CH_2$—, $R_4$ is [5-(difluoromethoxy)-2-pyridyl] and $R_2$ is as defined in table Z.

Table A-27 provides 16 compounds A-27.001 to A-27.016 of formula Iaa wherein $R_1$ is cyclopropyl-$CH_2$—, $R_4$ is (5-cyano-2-pyridyl) and $R_2$ is as defined in table Z.

The compounds of formula I according to the following Tables B-1 to B-27 can be prepared according to the methods described above. The examples which follow are intended to illustrate the invention and show preferred compounds of formula I, in the form of a compound of formula Iab.

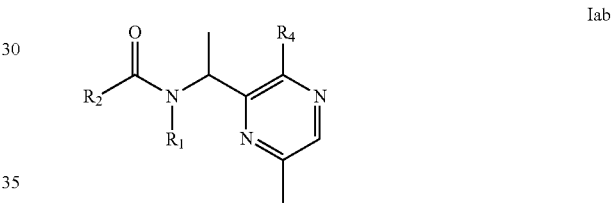

Table B-1 provides 16 compounds B-1.001 to B-1.016 of formula Iab wherein $R_1$ is H, $R_4$ is [5-(trifluoromethoxy)pyrimidin-2-yl] and $R_2$ is as defined in table Z.

Table B-2 provides 16 compounds B-2.001 to B-2.016 of formula Iab wherein $R_1$ is H, $R_4$ is [5-(trifluoromethoxy)-2-pyridyl] and $R_2$ is as defined in table Z.

Table B-3 provides 16 compounds B-3.001 to B-3.016 of formula Iab wherein $R_1$ is H, $R_4$ is [5-(2,2-difluoroethoxy)pyrimidin-2-yl] and $R_2$ is as defined in table Z.

Table B-4 provides 16 compounds B-4.001 to B-4.016 of formula Iab wherein $R_1$ is H, $R_4$ is [5-(2,2-difluoroethoxy)-2-pyridyl] and $R_2$ is as defined in table Z.

Table B-5 provides 16 compounds B-5.001 to B-5.016 of formula Iab wherein $R_1$ is H, $R_4$ is [5-(2,2,2-trifluoroethoxy)pyrimidin-2-yl] and $R_2$ is as defined in table Z.

Table B-6 provides 16 compounds B-6.001 to B-6.016 of formula Iab wherein $R_1$ is H, $R_4$ is [5-(2,2,2-trifluoroethoxy)-2-pyridyl] and $R_2$ is as defined in table Z.

Table B-7 provides 16 compounds B-7.001 to B-7.016 of formula Iab wherein $R_1$ is H, $R_4$ is [5-(difluoromethoxy)pyrimidin-2-yl] and $R_2$ is as defined in table Z.

Table B-8 provides 16 compounds B-8.001 to B-8.016 of formula Iab wherein $R_1$ is H, $R_4$ is [5-(difluoromethoxy)-2-pyridyl] and $R_2$ is as defined in table Z.

Table B-9 provides 16 compounds B-9.001 to B-9.016 of formula Iab wherein $R_1$ is H, $R_4$ is (5-cyano-2-pyridyl) and $R_2$ is as defined in table Z.

Table B-10 provides 16 compounds B-10.001 to B-10.016 of formula Iab wherein $R_1$ is $CH_3$, $R_4$ is [5-(trifluoromethoxy)pyrimidin-2-yl] and $R_2$ is as defined in table Z.

Table B-11 provides 16 compounds B-11.001 to B-11.016 of formula Iab wherein $R_1$ is $CH_3$, $R_4$ is [5-(trifluoromethoxy)-2-pyridyl] and $R_2$ is as defined in table Z.

Table B-12 provides 16 compounds B-12.001 to B-12.016 of formula Iab wherein $R_1$ is $CH_3$, $R_4$ is [5-(2,2-difluoroethoxy)pyrimidin-2-yl] and $R_2$ is as defined in table Z.

Table B-13 provides 16 compounds B-13.001 to B-13.016 of formula Iab wherein $R_1$ is $CH_3$, $R_4$ is [5-(2,2-difluoroethoxy)-2-pyridyl] and $R_2$ is as defined in table Z.

Table B-14 provides 16 compounds B-14.001 to B-14.016 of formula Iab wherein $R_1$ is $CH_3$, $R_4$ is [5-(2,2,2-trifluoroethoxy)pyrimidin-2-yl] and $R_2$ is as defined in table Z.

Table B-15 provides 16 compounds B-15.001 to B-15.016 of formula Iab wherein $R_1$ is $CH_3$, $R_4$ is [5-(2,2,2-trifluoroethoxy)-2-pyridyl] and $R_2$ is as defined in table Z.

Table B-16 provides 16 compounds B-16.001 to B-16.016 of formula Iab wherein $R_1$ is $CH_3$, $R_4$ is [5-(difluoromethoxy)pyrimidin-2-yl] and $R_2$ is as defined in table Z.

Table B-17 provides 16 compounds B-17.001 to B-17.016 of formula Iab wherein $R_1$ is $CH_3$, $R_4$ is [5-(difluoromethoxy)-2-pyridyl] and $R_2$ is as defined in table Z.

Table B-18 provides 16 compounds B-18.001 to B-18.016 of formula Iab wherein $R_1$ is $CH_3$, $R_4$ is (5-cyano-2-pyridyl) and $R_2$ is as defined in table Z.

Table B-19 provides 16 compounds B-19.001 to B-19.016 of formula Iab wherein $R_1$ is cyclopropyl-$CH_2$—, $R_4$ is [5-(trifluoromethoxy)pyrimidin-2-yl] and $R_2$ is as defined in table Z.

Table B-20 provides 16 compounds B-20.001 to B-20.016 of formula Iab wherein $R_1$ is cyclopropyl-$CH_2$—, $R_4$ is [5-(trifluoromethoxy)-2-pyridyl] and $R_2$ is as defined in table Z.

Table B-21 provides 16 compounds B-21.001 to B-21.016 of formula Iab wherein $R_1$ is cyclopropyl-$CH_2$—, $R_4$ is [5-(2,2-difluoroethoxy)pyrimidin-2-yl] and $R_2$ is as defined in table Z.

Table B-22 provides 16 compounds B-22.001 to B-22.016 of formula Iab wherein $R_1$ is cyclopropyl-$CH_2$—, $R_4$ is [5-(2,2-difluoroethoxy)-2-pyridyl] and $R_2$ is as defined in table Z.

Table B-23 provides 16 compounds B-23.001 to B-23.016 of formula Iab wherein $R_1$ is cyclopropyl-$CH_2$—, $R_4$ is [5-(2,2,2-trifluoroethoxy)pyrimidin-2-yl] and $R_2$ is as defined in table Z.

Table B-24 provides 16 compounds B-24.001 to B-24.016 of formula Iab wherein $R_1$ is cyclopropyl-$CH_2$—, $R_4$ is [5-(2,2,2-trifluoroethoxy)-2-pyridyl] and $R_2$ is as defined in table Z.

Table B-25 provides 16 compounds B-25.001 to B-25.016 of formula Iab wherein $R_1$ is cyclopropyl-$CH_2$—, $R_4$ is [5-(difluoromethoxy)pyrimidin-2-yl] and $R_2$ is as defined in table Z.

Table B-26 provides 16 compounds B-26.001 to B-26.016 of formula Iab wherein $R_1$ is cyclopropyl-$CH_2$—, $R_4$ is [5-(difluoromethoxy)-2-pyridyl] and $R_2$ is as defined in table Z.

Table B-27 provides 16 compounds B-27.001 to B-27.016 of formula Iab wherein $R_1$ is cyclopropyl-$CH_2$—, $R_4$ is (5-cyano-2-pyridyl) and $R_2$ is as defined in table Z.

The compounds of formula I according to the following Tables C-1 to C-27 can be prepared according to the methods described above. The examples which follow are intended to illustrate the invention and show preferred compounds of formula I, in the form of a compound of formula Iac.

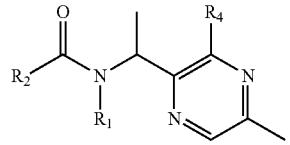

Table C-1 provides 16 compounds C-1.001 to C-1.016 of formula Iac wherein $R_1$ is H, $R_4$ is [5-(trifluoromethoxy)pyrimidin-2-yl] and $R_2$ is as defined in table Z.

Table C-2 provides 16 compounds C-2.001 to C-2.016 of formula Iac wherein $R_1$ is H, $R_4$ is [5-(trifluoromethoxy)-2-pyridyl] and $R_2$ is as defined in table Z.

Table C-3 provides 16 compounds C-3.001 to C-3.016 of formula Iac wherein $R_1$ is H, $R_4$ is [5-(2,2-difluoroethoxy)pyrimidin-2-yl] and $R_2$ is as defined in table Z.

Table C-4 provides 16 compounds C-4.001 to C-4.016 of formula Iac wherein $R_1$ is H, $R_4$ is [5-(2,2-difluoroethoxy)-2-pyridyl] and $R_2$ is as defined in table Z.

Table C-5 provides 16 compounds C-5.001 to C-5.016 of formula Iac wherein $R_1$ is H, $R_4$ is [5-(2,2,2-trifluoroethoxy)pyrimidin-2-yl] and $R_2$ is as defined in table Z.

Table C-6 provides 16 compounds C-6.001 to C-6.016 of formula Iac wherein $R_1$ is H, $R_4$ is [5-(2,2,2-trifluoroethoxy)-2-pyridyl] and $R_2$ is as defined in table Z.

Table C-7 provides 16 compounds C-7.001 to C-7.016 of formula Iac wherein $R_1$ is H, $R_4$ is [5-(difluoromethoxy)pyrimidin-2-yl] and $R_2$ is as defined in table Z.

Table C-8 provides 16 compounds C-8.001 to C-8.016 of formula Iac wherein $R_1$ is H, $R_4$ is [5-(difluoromethoxy)-2-pyridyl] and $R_2$ is as defined in table Z.

Table C-9 provides 16 compounds C-9.001 to C-9.016 of formula Iac wherein $R_1$ is H, $R_4$ is (5-cyano-2-pyridyl) and $R_2$ is as defined in table Z.

Table C-10 provides 16 compounds C-10.001 to C-10.016 of formula Iac wherein $R_1$ is $CH_3$, $R_4$ is [5-(trifluoromethoxy)pyrimidin-2-yl] and $R_2$ is as defined in table Z.

Table C-11 provides 16 compounds C-11.001 to C-11.016 of formula Iac wherein $R_1$ is $CH_3$, $R_4$ is [5-(trifluoromethoxy)-2-pyridyl] and $R_2$ is as defined in table Z.

Table C-12 provides 16 compounds C-12.001 to C-12.016 of formula Iac wherein $R_1$ is $CH_3$, $R_4$ is [5-(2,2-difluoroethoxy)pyrimidin-2-yl] and $R_2$ is as defined in table Z.

Table C-13 provides 16 compounds C-13.001 to C-13.016 of formula Iac wherein $R_1$ is $CH_3$, $R_4$ is [5-(2,2-difluoroethoxy)-2-pyridyl] and $R_2$ is as defined in table Z.

Table C-14 provides 16 compounds C-14.001 to C-14.016 of formula Iac wherein $R_1$ is $CH_3$, $R_4$ is [5-(2,2,2-trifluoroethoxy)pyrimidin-2-yl] and $R_2$ is as defined in table Z.

Table C-15 provides 16 compounds C-15.001 to C-15.016 of formula Iac wherein $R_1$ is $CH_3$, $R_4$ is [5-(2,2,2-trifluoroethoxy)-2-pyridyl] and $R_2$ is as defined in table Z.

Table C-16 provides 16 compounds C-16.001 to C-16.016 of formula Iac wherein $R_1$ is $CH_3$, $R_4$ is [5-(difluoromethoxy)pyrimidin-2-yl] and $R_2$ is as defined in table Z.

Table C-17 provides 16 compounds C-17.001 to C-17.016 of formula Iac wherein $R_1$ is $CH_3$, $R_4$ is [5-(difluoromethoxy)-2-pyridyl] and $R_2$ is as defined in table Z.

Table C-18 provides 16 compounds C-18.001 to C-18.016 of formula Iac wherein $R_1$ is $CH_3$, $R_4$ is (5-cyano-2-pyridyl) and $R_2$ is as defined in table Z.

Table C-19 provides 16 compounds C-19.001 to C-19.016 of formula Iac wherein $R_1$ is cyclopropyl-$CH_2$—, $R_4$ is [5-(trifluoromethoxy)pyrimidin-2-yl] and $R_2$ is as defined in table Z.

Table C-20 provides 16 compounds C-20.001 to C-20.016 of formula Iac wherein $R_1$ is cyclopropyl-$CH_2$—, $R_4$ is [5-(trifluoromethoxy)-2-pyridyl] and $R_2$ is as defined in table Z.

Table C-21 provides 16 compounds C-21.001 to C-21.016 of formula Iac wherein $R_1$ is cyclopropyl-$CH_2$—, $R_4$ is [5-(2,2-difluoroethoxy)pyrimidin-2-yl] and $R_2$ is as defined in table Z.

Table C-22 provides 16 compounds C-22.001 to C-22.016 of formula Iac wherein $R_1$ is cyclopropyl-$CH_2$—, $R_4$ is [5-(2,2-difluoroethoxy)-2-pyridyl] and $R_2$ is as defined in table Z.

Table C-23 provides 16 compounds C-23.001 to C-23.016 of formula Iac wherein $R_1$ is cyclopropyl-$CH_2$—, $R_4$ is [5-(2,2,2-trifluoroethoxy)pyrimidin-2-yl] and $R_2$ is as defined in table Z.

Table C-24 provides 16 compounds C-24.001 to C-24.016 of formula Iac wherein $R_1$ is cyclopropyl-$CH_2$—, $R_4$ is [5-(2,2,2-trifluoroethoxy)-2-pyridyl] and $R_2$ is as defined in table Z.

Table C-25 provides 16 compounds C-25.001 to C-25.016 of formula Iac wherein $R_1$ is cyclopropyl-$CH_2$—, $R_4$ is [5-(difluoromethoxy)pyrimidin-2-yl] and $R_2$ is as defined in table Z.

Table C-26 provides 16 compounds C-26.001 to C-26.016 of formula Iac wherein $R_1$ is cyclopropyl-$CH_2$—, $R_4$ is [5-(difluoromethoxy)-2-pyridyl] and $R_2$ is as defined in table Z.

Table C-27 provides 16 compounds C-27.001 to C-27.016 of formula Iac wherein $R_1$ is cyclopropyl-$CH_2$—, $R_4$ is (5-cyano-2-pyridyl) and $R_2$ is as defined in table Z.

The compounds of formula I according to the following Tables D-1 to D-27 can be prepared according to the methods described above. The examples which follow are intended to illustrate the invention and show preferred compounds of formula I, in the form of a compound of formula Iad.

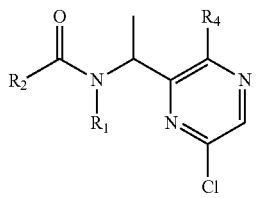

Iad

Table D-1 provides 16 compounds D-1.001 to D-1.016 of formula Iad wherein $R_1$ is H, $R_4$ is [5-(trifluoromethoxy)pyrimidin-2-yl] and $R_2$ is as defined in table Z.

Table D-2 provides 16 compounds D-2.001 to D-2.016 of formula Iad wherein $R_1$ is H, $R_4$ is [5-(trifluoromethoxy)-2-pyridyl] and $R_2$ is as defined in table Z.

Table D-3 provides 16 compounds D-3.001 to D-3.016 of formula Iad wherein $R_1$ is H, $R_4$ is [5-(2,2-difluoroethoxy)pyrimidin-2-yl] and R: is as defined in table Z.

Table D-4 provides 16 compounds D-4.001 to D-4.016 of formula Iad wherein $R_1$ is H, $R_4$ is [5-(2,2-difluoroethoxy)-2-pyridyl] and $R_2$ is as defined in table Z.

Table D-5 provides 16 compounds D-5.001 to D-5.016 of formula Iad wherein $R_1$ is H, $R_4$ is [5-(2,2,2-trifluoroethoxy)pyrimidin-2-yl] and $R_2$ is as defined in table Z.

Table D-6 provides 16 compounds D-6.001 to D-6.016 of formula Iad wherein $R_1$ is H, $R_4$ is [5-(2,2,2-trifluoroethoxy)-2-pyridyl] and $R_2$ is as defined in table Z.

Table D-7 provides 16 compounds D-7.001 to D-7.016 of formula Iad wherein $R_1$ is H, $R_4$ is [5-(difluoromethoxy)pyrimidin-2-yl] and $R_2$ is as defined in table Z.

Table D-8 provides 16 compounds D-8.001 to D-8.016 of formula Iad wherein $R_1$ is H, $R_4$ is [5-(difluoromethoxy)-2-pyridyl] and $R_2$ is as defined in table Z.

Table D-9 provides 16 compounds D-9.001 to D-9.016 of formula Iad wherein $R_1$ is H, $R_4$ is (5-cyano-2-pyridyl) and $R_2$ is as defined in table Z.

Table D-10 provides 16 compounds D-10.001 to D-10.016 of formula Iad wherein $R_1$ is $CH_3$, $R_4$ is [5-(trifluoromethoxy)pyrimidin-2-yl] and $R_2$ is as defined in table Z.

Table D-11 provides 16 compounds D-11.001 to D-11.016 of formula Iad wherein $R_1$ is $CH_3$, $R_4$ is [5-(trifluoromethoxy)-2-pyridyl] and $R_2$ is as defined in table Z.

Table D-12 provides 16 compounds D-12.001 to D-12.016 of formula Iad wherein $R_1$ is $CH_3$, $R_4$ is [5-(2,2-difluoroethoxy)pyrimidin-2-yl] and $R_2$ is as defined in table Z.

Table D-13 provides 16 compounds D-13.001 to D-13.016 of formula Iad wherein $R_1$ is $CH_3$, $R_4$ is [5-(2,2-difluoroethoxy)-2-pyridyl] and $R_2$ is as defined in table Z.

Table D-14 provides 16 compounds D-14.001 to D-14.016 of formula Iad wherein $R_1$ is $CH_3$, $R_4$ is [5-(2,2,2-trifluoroethoxy)pyrimidin-2-yl] and $R_2$ is as defined in table Z.

Table D-15 provides 16 compounds D-15.001 to D-15.016 of formula Iad wherein $R_1$ is $CH_3$, $R_4$ is [5-(2,2,2-trifluoroethoxy)-2-pyridyl] and $R_2$ is as defined in table Z.

Table D-16 provides 16 compounds D-16.001 to D-16.016 of formula Iad wherein $R_1$ is $CH_3$, $R_4$ is [5-(difluoromethoxy)pyrimidin-2-yl] and $R_2$ is as defined in table Z.

Table D-17 provides 16 compounds D-17.001 to D-17.016 of formula Iad wherein $R_1$ is $CH_3$, $R_4$ is [5-(difluoromethoxy)-2-pyridyl] and $R_2$ is as defined in table Z.

Table D-18 provides 16 compounds D-18.001 to D-18.016 of formula Iad wherein $R_1$ is $CH_3$, $R_4$ is (5-cyano-2-pyridyl) and $R_2$ is as defined in table Z.

Table D-19 provides 16 compounds D-19.001 to D-19.016 of formula Iad wherein $R_1$ is cyclopropyl-$CH_2$—, $R_4$ is [5-(trifluoromethoxy)pyrimidin-2-yl] and $R_2$ is as defined in table Z.

Table D-20 provides 16 compounds D-20.001 to D-20.016 of formula Iad wherein $R_1$ is cyclopropyl-$CH_2$—, $R_4$ is [5-(trifluoromethoxy)-2-pyridyl] and $R_2$ is as defined in table Z.

Table D-21 provides 16 compounds D-21.001 to D-21.016 of formula Iad wherein $R_1$ is cyclopropyl-$CH_2$—, $R_4$ is [5-(2,2-difluoroethoxy)pyrimidin-2-yl] and $R_2$ is as defined in table Z.

Table D-22 provides 16 compounds D-22.001 to D-22.016 of formula Iad wherein $R_1$ is cyclopropyl-$CH_2$—, $R_4$ is [5-(2,2-difluoroethoxy)-2-pyridyl] and $R_2$ is as defined in table Z.

Table D-23 provides 16 compounds D-23.001 to D-23.016 of formula Iad wherein $R_1$ is cyclopropyl-$CH_2$—, $R_4$ is [5-(2,2,2-trifluoroethoxy)pyrimidin-2-yl] and $R_2$ is as defined in table Z.

Table D-24 provides 16 compounds D-24.001 to D-24.016 of formula Iad wherein $R_1$ is cyclopropyl-$CH_2$—, $R_4$ is [5-(2,2,2-trifluoroethoxy)-2-pyridyl] and $R_2$ is as defined in table Z.

Table D-25 provides 16 compounds D-25.001 to D-25.016 of formula Iad wherein $R_1$ is cyclopropyl-$CH_2$—, $R_4$ is [5-(difluoromethoxy)pyrimidin-2-yl] and $R_2$ is as defined in table Z.

Table D-26 provides 16 compounds D-26.001 to D-26.016 of formula Iad wherein $R_1$ is cyclopropyl-$CH_2$—, $R_4$ is [5-(difluoromethoxy)-2-pyridyl] and $R_2$ is as defined in table Z.

Table D-27 provides 16 compounds D-27.001 to D-27.016 of formula Iad wherein $R_1$ is cyclopropyl-$CH_2$—, $R_4$ is (5-cyano-2-pyridyl) and $R_2$ is as defined in table Z.

The compounds of formula I according to the following Tables D-1 to D-27 can be prepared according to the methods described above. The examples which follow are intended to illustrate the invention and show preferred compounds of formula I, in the form of a compound of formula Iae.

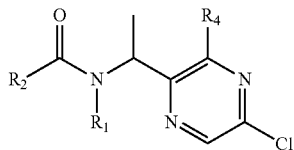
Iae

Table E-1 provides 16 compounds E-1.001 to E-1.016 of formula Iae wherein $R_1$ is H, $R_4$ is [5-(trifluoromethoxy)pyrimidin-2-yl] and $R_2$ is as defined in table Z.

Table E-2 provides 16 compounds E-2.001 to E-2.016 of formula Iae wherein $R_1$ is H, $R_4$ is [5-(trifluoromethoxy)-2-pyridyl] and $R_2$ is as defined in table Z.

Table E-3 provides 16 compounds E-3.001 to E-3.016 of formula Iae wherein $R_1$ is H, $R_4$ is [5-(2,2-difluoroethoxy)pyrimidin-2-yl] and $R_2$ is as defined in table Z.

Table E-4 provides 16 compounds E-4.001 to E-4.016 of formula Iae wherein $R_1$ is H, $R_4$ is [5-(2,2-difluoroethoxy)-2-pyridyl] and $R_2$ is as defined in table Z.

Table E-5 provides 16 compounds E-5.001 to E-5.016 of formula Iae wherein $R_1$ is H, $R_4$ is [5-(2,2,2-trifluoroethoxy)pyrimidin-2-yl] and $R_2$ is as defined in table Z.

Table E-6 provides 16 compounds E-6.001 to E-6.016 of formula Iae wherein $R_1$ is H, $R_4$ is [5-(2,2,2-trifluoroethoxy)-2-pyridyl] and $R_2$ is as defined in table Z.

Table E-7 provides 16 compounds E-7.001 to E-7.016 of formula Iae wherein $R_1$ is H, $R_4$ is [5-(difluoromethoxy)pyrimidin-2-yl] and $R_2$ is as defined in table Z.

Table E-8 provides 16 compounds E-8.001 to E-8.016 of formula Iae wherein $R_1$ is H, $R_4$ is [5-(difluoromethoxy)-2-pyridyl] and $R_2$ is as defined in table Z.

Table E-9 provides 16 compounds E-9.001 to E-9.016 of formula Iae wherein $R_1$ is H, $R_4$ is (5-cyano-2-pyridyl) and $R_2$ is as defined in table Z.

Table E-10 provides 16 compounds E-10.001 to E-10.016 of formula Iae wherein $R_1$ is $CH_3$, $R_4$ is [5-(trifluoromethoxy)pyrimidin-2-yl] and $R_2$ is as defined in table Z.

Table E-11 provides 16 compounds E-11.001 to E-11.016 of formula Iae wherein $R_1$ is $CH_3$, $R_4$ is [5-(trifluoromethoxy)-2-pyridyl] and $R_2$ is as defined in table Z.

Table E-12 provides 16 compounds E-12.001 to E-12.016 of formula Iae wherein $R_1$ is $CH_3$, $R_4$ is [5-(2,2-difluoroethoxy)pyrimidin-2-yl] and $R_2$ is as defined in table Z.

Table E-13 provides 16 compounds E-13.001 to E-13.016 of formula Iae wherein $R_1$ is $CH_3$, $R_4$ is [5-(2,2-difluoroethoxy)-2-pyridyl] and $R_2$ is as defined in table Z.

Table E-14 provides 16 compounds E-14.001 to E-14.016 of formula Iae wherein $R_1$ is $CH_3$, $R_4$ is [5-(2,2,2-trifluoroethoxy)pyrimidin-2-yl] and $R_2$ is as defined in table Z.

Table E-15 provides 16 compounds E-15.001 to E-15.016 of formula Iae wherein $R_1$ is $CH_3$, $R_4$ is [5-(2,2,2-trifluoroethoxy)-2-pyridyl] and $R_2$ is as defined in table Z.

Table E-16 provides 16 compounds E-16.001 to E-16.016 of formula Iae wherein $R_1$ is $CH_3$, $R_4$ is [5-(difluoromethoxy)pyrimidin-2-yl] and $R_2$ is as defined in table Z.

Table E-17 provides 16 compounds E-17.001 to E-17.016 of formula Iae wherein $R_1$ is $CH_3$, $R_4$ is [5-(difluoromethoxy)-2-pyridyl] and $R_2$ is as defined in table Z.

Table E-18 provides 16 compounds E-18.001 to E-18.016 of formula Iae wherein $R_1$ is $CH_3$, $R_4$ is (5-cyano-2-pyridyl) and $R_2$ is as defined in table Z.

Table E-19 provides 16 compounds E-19.001 to E-19.016 of formula Iae wherein $R_1$ is cyclopropyl-$CH_2$—, $R_4$ is [5-(trifluoromethoxy)pyrimidin-2-yl] and $R_2$ is as defined in table Z.

Table E-20 provides 16 compounds E-20.001 to E-20.016 of formula Iae wherein $R_1$ is cyclopropyl-$CH_2$—, $R_4$ is [5-(trifluoromethoxy)-2-pyridyl] and $R_2$ is as defined in table Z.

Table E-21 provides 16 compounds E-21.001 to E-21.016 of formula Iae wherein $R_1$ is cyclopropyl-$CH_2$—, $R_4$ is [5-(2,2-difluoroethoxy)pyrimidin-2-yl] and $R_2$ is as defined in table Z.

Table E-22 provides 16 compounds E-22.001 to E-22.016 of formula Iae wherein $R_1$ is cyclopropyl-$CH_2$—, $R_4$ is [5-(2,2-difluoroethoxy)-2-pyridyl] and $R_2$ is as defined in table Z.

Table E-23 provides 16 compounds E-23.001 to E-23.016 of formula Iae wherein $R_1$ is cyclopropyl-$CH_2$—, $R_4$ is [5-(2,2,2-trifluoroethoxy)pyrimidin-2-yl] and $R_2$ is as defined in table Z.

Table E-24 provides 16 compounds E-24.001 to E-24.016 of formula Iae wherein $R_1$ is cyclopropyl-$CH_2$—, $R_4$ is [5-(2,2,2-trifluoroethoxy)-2-pyridyl] and $R_2$ is as defined in table Z.

Table E-25 provides 16 compounds E-25.001 to E-25.016 of formula Iae wherein $R_1$ is cyclopropyl-$CH_2$—, $R_4$ is [5-(difluoromethoxy)pyrimidin-2-yl] and $R_2$ is as defined in table Z.

Table E-26 provides 16 compounds E-26.001 to E-26.016 of formula Iae wherein $R_1$ is cyclopropyl-$CH_2$—, $R_4$ is [5-(difluoromethoxy)-2-pyridyl] and $R_2$ is as defined in table Z.

Table E-27 provides 16 compounds E-27.001 to E-27.016 of formula Iae wherein $R_1$ is cyclopropyl-$CH_2$—, $R_4$ is (5-cyano-2-pyridyl) and $R_2$ is as defined in table Z.

Also made available are certain intermediate compounds of the amine of formulae IIaa to IIae, some of which are novel, wherein $R_1$ and $R_4$ (corresponding to the ring having $R_{4a}$ and $A_2$ in formula I) are as defined in the first aspect. The stereogenic centre is indicated with an asterisk in the structures below; and accordingly the invention makes available both racemates and the individual enantiomers; especially preferred is the enantiomer having the same spatial arrangement at the stereogenic centre as depicted in formula I'a.

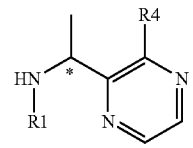
IIaa

-continued

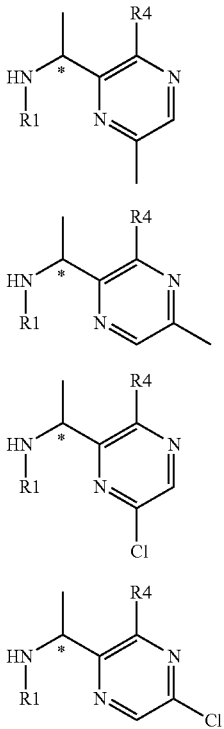

IIab

IIac

IIad

IIae

Specific examples of compounds of formula IIaa to IIae are where $R_1$ and $R_4$ are as defined in Tables A-1 to $A_{27}$.

Specific examples of compound of formula IIIab are where $R_2$ (corresponding to the ring having $R_{2a}$, $A_1$ and $R_{2b}$) is as defined in table Z.

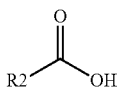

IIIab

Also made available are compounds of formulae III, VI, XV, XVa, XLII, XLIII, XLVI, XLVII, XLIX, L, LI, LII, LIII, LIV, LV, LVa, LVc, LVI, LIX, LX, and LXI, wherein, as applicable, the substituents $R_1$, $A_1$, $R_{2a}$, $R_{2b}$, $R_3$, $R_{5a}$, $R_{5b}$ and $R_4$ (corresponding to the ring having $R_{4a}$ and $A_2$), are as defined in any one of rows Tables A-1 to A-27, B-1 to B-27, C-1 to C-27, D-1 to D-27 and E-1 to E-27. An especially preferred enantiomer of the compounds of formulae III, VI, XV, XVa, XLII, XLIII, XLVI, XLVII, XLIX, L, LI, LII, LIII, LIV, LV, LVa, LVc, LVI, LIX, LX, and LXI, as applicable, is the enantiomer having the same spatial arrangement at the stereogenic centre as depicted in formula I'a.

The present invention also makes available
a compound of formula II, wherein $A_2$, $R_1$, $R_3$, $R_{4a}$, $R_{5a}$, and $R_{5b}$ are as defined for formula I;
accordingly preferred embodiments of $A_2$, $R_1$, $R_3$, $R_{4a}$, $R_{5a}$, and $R_{5b}$ for a compound of formula I are likewise preferred embodiments of $A_2$, $R_1$, $R_3$, $R_{4a}$, $R_{5a}$, and $R_{5b}$ for a compound of formula II;
a compound of formulae IIaa, IIab, IIac, IIad and IIae, wherein $R_1$ is as defined formula I. and $R_4$ is the cyclic group containing $A_2$ and the substituent $R_{4a}$ in formula I, wherein $A_2$ and $R_{4a}$ are as defined as defined formula I; accordingly preferred embodiments of $R_1$, $A_2$ and $R_{4a}$ for a compound of formula I are likewise preferred embodiments of $R_1$, $A_2$ and $R_{4a}$ for a any one of a compound of formulae IIaa, IIab, IIac, IIad and IIae;
a compound of formula III, wherein $A_1$, $R_{2a}$ and $R_{2b}$ are as defined for formula I; accordingly preferred embodiments of $A_1$, $R_{2a}$ and $R_{2b}$ for a compound of formula I are likewise preferred embodiments of $A_1$, $R_{2a}$ and $R_{2b}$ for a compound of formula III;
a compound of formula VI, wherein $A_2$, $R_3$, $R_{4a}$, $R_{5a}$, and $R_{5b}$ are are as defined for formula I; accordingly preferred embodiments of $A_2$, $R_3$, $R_{4a}$, $R_{5a}$, and $R_{5b}$ for a compound of formula I are likewise preferred embodiments of $A_2$, $R_3$, $R_{4a}$, $R_{5a}$, and $R_{5b}$ for a compound of formula VI;
a compound of formula XV, wherein $A_2$, $R_3$, $R_{4a}$, $R_{5a}$, and $R_{5b}$ are are as defined for formula I; accordingly preferred embodiments of $A_2$, $R_3$, $R_{4a}$, $R_{5a}$, and $R_{5b}$ for a compound of formula I are likewise preferred embodiments of $A_2$, $R_3$, $R_{4a}$, $R_{5a}$, and $R_{5b}$ for a compound of formula XV;
a compound of formula XVa, wherein $A_2$, $R_3$, $R_{4a}$, $R_{5a}$, and $R_{5b}$ are are as defined for formula I; accordingly preferred embodiments of $A_2$, $R_3$, $R_{4a}$, $R_{5a}$, and $R_{5b}$ for a compound of formula I are likewise preferred embodiments of $A_2$, $R_3$, $R_{4a}$, $R_{5a}$, and $R_{5b}$ for a compound of formula XVa;
a compound of formula XLII, wherein $A_2$, $R_3$, $R_{4a}$, $R_{5a}$, and $R_{5b}$ are are as defined for formula I and $Z_3$ is NPhth or $NBoc_2$; accordingly preferred embodiments of $A_2$, $R_3$, $R_{4a}$, $R_{5a}$, and $R_{5b}$ for a compound of formula I are likewise preferred embodiments of $A_2$, $R_3$, $R_{4a}$, $R_{5a}$, and $R_{5b}$ for a compound of formula XLII;
a compound of formula XLIII, wherein $A_2$, $R_3$, $R_{4a}$, $R_{5a}$, and $R_{5b}$ are are as defined for formula I; accordingly preferred embodiments of $A_2$, $R_3$, $R_{4a}$, $R_{5a}$, and $R_{5b}$ for a compound of formula I are likewise preferred embodiments of $A_2$, $R_3$, $R_{4a}$, $R_{5a}$, and $R_{5b}$ for a compound of formula XLIII;
a compound of formula XLVI, wherein $A_2$ and $R_3$ are are as defined for formula I and $Z_{4a}$ is $R_{4a}$, halogen or $NH_2$; accordingly preferred embodiments of $A_2$, $R_3$, and $R_{4a}$ for a compound of formula I are likewise preferred embodiments of $A_2$, $R_3$ and $R_{4a}$ for a compound of formula XLVI;
a compound of formula XLVII, wherein $A_2$ and $R_3$ are are as defined for formula I and $Z_{4a}$ is $R_{4a}$, halogen or $NH_2$; accordingly preferred embodiments of $A_2$, $R_3$, and $R_{4a}$ for a compound of formula I are likewise preferred embodiments of $A_2$, $R_3$ and $R_{4a}$ for a compound of formula XLVII;
a compound of formula XLIX, wherein $A_2$ and $R_3$ are are as defined for formula I, $Z_{4a}$ is $R_{4a}$, halogen or $NH_2$, and $Z_{5a}$ and $Z_{5b}$ are independent of each other selected from $R_{5a}$, $R_{5b}$, halogen, $NH_2$ and OH; accordingly preferred embodiments of $A_2$, $R_3$, $R_{4a}$, $R_{5a}$ and $R_{5b}$ for a compound of formula I are likewise preferred embodiments of $A_2$, $R_3$, $R_{4a}$, $R_{5a}$ and $R_{5b}$ for a compound of formula XLIX;
a compound of formula L, wherein $A_2$ and $R_3$ are are as defined for formula I, and $Z_{5a}$ and $Z_{5b}$ are independent of each other selected from $R_{5a}$, $R_{5b}$, halogen, $NH_2$ and OH; accordingly preferred embodiments of $A_2$, $R_3$, $R_{5a}$ and $R_{5b}$ for a compound of formula I are likewise preferred embodiments $A_2$, $R_3$, $R_{5a}$ and $R_{5b}$ for a compound of formula L;

a compound of formula LI, wherein $A_2$, $R_3$ and $R_{4a}$ are are as defined for formula I, and $Z_{5a}$ and $Z_{5b}$ are independent of each other selected from $R_{5a}$, $R_{5b}$, halogen, $NH_2$ and OH; accordingly preferred embodiments of $A_2$, $R_3$, $R_{4a}$, $R_{5a}$ and $R_{5b}$ for a compound of formula I are likewise preferred embodiments $A_2$, $R_3$, $R_{4a}$, $R_{5a}$ and $R_{5b}$ for a compound of formula LI;

a compound of formula LII, wherein $A_2$, $R_3$, $R_{4a}$, $R_{5a}$ and $R_{5b}$ are are as defined for formula I; accordingly preferred embodiments of $A_2$, $R_3$, $R_{4a}$, $R_{5a}$ and $R_{5b}$ for a compound of formula I are likewise preferred embodiments $A_2$, $R_3$, $R_{4a}$, $R_{5a}$ and $R_{5b}$ for a compound of formula LII;

a compound of formula LIII, wherein $A_2$, $R_3$, $R_{5a}$ and $R_{5b}$ are are as defined for formula I, and $Z_{4a}$ is $R_{4a}$, halogen or $NH_2$; accordingly preferred embodiments of $A_2$, $R_3$, $R_{4a}$, $R_{5a}$ and $R_{5b}$ for a compound of formula I are likewise preferred embodiments $A_2$, $R_3$, $R_{4a}$, $R_{5a}$ and $R_{5b}$ for a compound of formula LIII;

a compound of formula LIV, wherein $A_2$, $R_3$, $R_{5a}$ and $R_{5b}$ are are as defined for formula I, and $Z_{4a}$ is $R_{4a}$, halogen or $NH_2$; accordingly preferred embodiments of $A_2$, $R_3$, $R_{4a}$, $R_{5a}$ and $R_{5b}$ for a compound of formula I are likewise preferred embodiments $A_2$, $R_3$, $R_{4a}$, $R_{5a}$ and $R_{5b}$ for a compound of formula LIV;

a compound of formula LV, wherein $R_3$, $R_{5a}$ and $R_{5b}$ are are as defined for formula I, and $X_{07}$ is a leaving group, for example, chlorine, bromine, iodine; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LV;

a compound of formula LVa, wherein $R_1$, $R_3$, $R_{5a}$ and $R_{5b}$ are are as defined for formula I, and $X_{07}$ is a leaving group, for example, chlorine, bromine, iodine; accordingly preferred embodiments of $R_1$, $R_3$, $R_{5a}$ and $R_{5b}$ for a compound of formula I are likewise preferred embodiments $R_1$, $R_3$, $R_{5a}$ and $R_{5b}$ for a compound of formula LVa;

a compound of formula LVc, wherein $R_3$, $R_{5a}$ and $R_{5b}$ are are as defined for formula I, and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LVc;

a compound of formula LVI, wherein $A_1$, $R_{2a}$, $R_{2b}$ $R_1$, $R_3$, $R_{5a}$ and $R_{5b}$ are are as defined for formula I, and $X_{07}$ is a leaving group, for example, chlorine, bromine, iodine; accordingly preferred embodiments of $A_1$, $R_{2a}$, $R_{2b}$ $R_1$, $R_3$, $R_{5a}$ and $R_{5b}$ for a compound of formula I are likewise preferred embodiments $A_1$, $R_{2a}$, $R_{2b}$ $R_1$, $R_3$, $R_{5a}$ and $R_{5b}$ for a compound of formula LVI;

a compound of formula LIX, wherein $R_3$, $R_{5a}$ and $R_{5b}$ are are as defined for formula I, $Z_3$ is NPhth or $NBoc_2$ and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LIX;

a compound of formula LX, wherein $R_3$, $R_{5a}$ and $R_{5b}$ are are as defined for formula I and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LX; and a compound of formula LXI, wherein $R_3$, $R_{5a}$ and $R_{5b}$ are are as defined for formula I and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LXI.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the above mentioned animal pests are:

from the order Acarina, for example,

*Acalitus* spp., *Aculus* spp., *Acaricalus* spp., *Aceria* spp., *Acarus siro*, *Amblyomma* spp., *Argas* spp., *Boophilus* spp., *Brevipalpus* spp., *Bryobia* spp., *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemlineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp. *Drosophila melanogaster*, *Fannia* spp., *Gastrophilus* spp., *Geomyza tripunctata*, *Glossina* spp., *Hypoderma* spp.,

*Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Aleurodes* spp., *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simularis*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp., *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp, *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Elasmopalpus lignosellus*, *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes,

*Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina*; *Deroceras* (*D. agrestis, D. empiricorum, D. laeve, D. reticulatum*); *Discus* (*D. rotundatus*); *Euomphalia*; *Galba* (*G. trunculata*); *Helicelia* (*H. itala, H. obvia*); *Helicidae Helicigona arbustorum*); *Helicodiscus*; *Helix* (*H. aperta*); *Limax* (*L. cinereoniger, L. flavus, L. marginatus, L. maximus, L. tenellus*); *Lymnaea*; *Milax* (*M. gagates, M. marginatus, M. sowerbyi*); *Opeas*; *Pomacea* (*P. canaticulata*); *Vallonia* and *Zanitoides*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The compounds of formula I are particularly suitable for control of
    a pest of the order Hemiptera, for example, one or more of the species *Bemisia tabaci, Aphis craccivora, Myzus persicae, Rhopalosiphum Padi, Nilaparvata lugens*, and *Euschistus heros* (preferably in vegetables, soybeans, and sugarcane);
    a pest of the order Lepidoptera, for example, one or more of the species *Spodoptera littoralis, Spodoptera frugiperda, Plutella xylostella, Cnaphalocrocis medinalis, Cydia pomonella, Chrysodeixis includes, Chilo sup-*

*pressalis, Elasmopalpus lignosellus, Pseudoplusia includens*, and *Tuta absoluta* (preferably in vegetables and corn);

a pest of the order Thysanoptera, such as the family Thripidae, for example, one or more of *Thrips tabaci* and *Frankliniella occidentalis* (preferably in vegetables); and soil pests (such as of the order Coleoptera), for example, the species *Diabrotica balteata, Agriotes* spp. and *Leptinotarsa decemlineata* (preferably in vegetables and corn).

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A$_{055}$, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard 1® (cotton variety that expresses a Cry1Ac toxin); Bollgard 11® (cotton variety that expresses a Cry1Ac and a Cry2Ab toxin); VipCot® (cotton variety that expresses a Vip3A and a Cry1Ab toxin); New-Leaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A$_{055}$ modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603x MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603 x MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention provides a compound of the first aspect for use in therapy. The present invention provides a compound of the first aspect, for use in controlling parasites in or on an animal. The present invention further provides a compound of the first aspect, for use in controlling ectoparasites on an animal. The present invention further provides a compound of the first aspect, for use in preventing and/or treating diseases transmitted by ectoparasites.

The present invention provides the use of a compound of the first aspect, for the manufacture of a medicament for controlling parasites in or on an animal. The present invention further provides the use of a compound of the first aspect, for the manufacture of a medicament for controlling ectoparasites on an animal. The present invention further provides the use of a compound of the first aspect, for the manufacture of a medicament for preventing and/or treating diseases transmitted by ectoparasites.

The present invention provides the use of a compound of the first aspect, in controlling parasites in or on an animal. The present invention further provides the use of a compound of the first aspect, in controlling ectoparasites on an animal.

The term "controlling" when used in context of parasites in or on an animal refers to reducing the number of pests or parasites, eliminating pests or parasites and/or preventing further pest or parasite infestation.

The term "treating" when used used in context of parasites in or on an animal refers to restraining, slowing, stopping or reversing the progression or severity of an existing symptom or disease. The term "preventing" when used used in context of parasites in or on an animal refers to the avoidance of a symptom or disease developing in the animal.

The term "animal" when used used in context of parasites in or on an animal may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camellids, pigs, sheep, goats and horses. Companion animals include, but are not limited to, dogs, cats and rabbits.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, acari, insects and crustaceans (e.g. sea lice). The Acari (or Acarina) sub-class comprises ticks and mites. Ticks include, but are not limited to, members of the following genera: *Rhipicaphalus*, for example, *Rhipicaphalus* (*Boophilus*) *microplus* and *Rhipicephalus sanguineus*; *Amblyomrna*; *Dermacentor*; *Haemaphysalis*; *Hyalomma*; *Ixodes*; *Rhipicentor*; *Margaropus*; *Argas*; *Otobius*; and *Ornithodoros*. Mites include, but are not limited to, members of the following genera: *Chorioptes*, for example *Chorioptes bovis*; *Psoroptes*, for example *Psoroptes ovis*; *Cheyletiella*; *Dermanyssus*; for example *Dermanyssus gallinae*; *Ortnithonyssus*; *Demodex*, for example *Demodex canis*; *Sarcoptes*, for example *Sarcoptes scabiei*; and *Psorergates*. Insects include, but are not limited to, members of the orders: Siphonaptera, Diptera, Phthiraptera, Lepidoptera, Coleoptera and Homoptera. Members of the Siphonaptera order include, but are not limited to, *Ctenocephalides felis* and *Ctenocephatides canis*. Members of the Diptera order include, but are not limited to, *Musca* spp.; bot fly, for example *Gasterophilus intestinalis* and *Oestrus ovis*; biting flies; horse flies, for example *Haematopota* spp. and *Tabunus* spp.; haematobia, for example *Haematobia irritans*; *Stomoxys*; *Lucilia*; midges; and mosquitoes. Members of the Phthiraptera class include, but are not limited to, blood sucking lice and chewing lice, for example *Bovicola Ovis* and *Bovicola Bovis*.

The term "effective amount" when used used in context of parasites in or on an animal refers to the amount or dose of the compound of the invention, or a salt thereof, which, upon single or multiple dose administration to the animal, provides the desired effect in or on the animal. The effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age, and general health; the parasite to be controlled and the degree of infestation; the specific disease or disorder involved; the degree of or involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts, which can be different to agrochemically acceptable salts.

Pharmaceutically and veterinary acceptable salts and common methodology for preparing them are well known in the art. See, for example, Gould, P. L., "Salt selection for basic drugs", International Journal of Pharmaceutics, 33: 201-217 (1986); Bastin, R. J., et al. "Salt Selection and Optimization Procedures for Pharmaceutical New Chemical Entities", Organic Process Research and Development, 4: 427-435 (2000); and Berge, S. M., et al., "Pharmaceutical Salts", Journal of Pharmaceutical Sciences, 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipemis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, |

TABLE B-continued

Examples of native woodborers of economic importance.

| Family | Species | Host or Crop Infested |
|---|---|---|
| | Texania campestris | Quince, Redbud, Serviceberry, Sycamore, Walnut, Willow Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs, ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus* verstitus and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecti cornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*. The compounds of formulae I, and I'a, or salts thereof, are especially suitable for controlling one or more pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae. In a preferred embodiment of each aspect, a compound TX (where the abbreviation "TX" means "one compound selected from the compounds defined in the Tables A-1 to A-27, B-1 to B-27, C-1 to C-27, D-1 to D-27 and E-1 to E-27, and Table P") controls one or more of pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae.

The compounds of formulae I, and I'a, or salts thereof, are especially suitable for controlling one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp. In a preferred embodiment of each aspect, a compound TX (where the abbreviation "TX" means "one compound selected from the compounds defined in the Tables A-1 to A-27, B-1 to B-27, C-1 to C-27, D-1 to D-27 and E-1 to E-27, and Table P") controls one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp.

The compounds of formulae I, and I'a, or salts thereof, are especially suitable for controlling one or more of *Spodoptera littoralis*, *Plutella xylostella*, *Frankliniella occidentalis*, *Thrips tabaci*, *Euschistus heros*, *Cydia pomonella*, *Nilaparvata lugens*, *Myzus persicae*, *Chrysodeixis includens*, *Aphis craccivora*, *Diabrotica balteata*, *Rhopalosiphum padi*, and *Chilo suppressalis*.

In a preferred embodiment of each aspect, a compound TX (where the abbreviation "TX" means "one compound selected from the compounds defined in the Tables A-1 to A-27, B-1 to B-27, C-1 to C-27, D-1 to D-27 and E-1 to E-27, and Table P") controls one or more of *Spodoptera littoralis*, *Plutella xylostella*, *Frankliniella occidentalis*, *Thrips tabaci*, *Euschistus heros*, *Cydia pomonella*, *Nilaparvata lugens*, *Myzus persicae*, *Chrysodeixis includens*, *Aphis craccivora*, *Diabrotica balteata*, *Rhopalosiphum Padia*, and *Chilo Suppressalis*, such as *Spodoptera littoralis*+TX, *Plutella xylostella*+TX; *Frankliniella occidentalis*+TX, *Thrips tabaci*+TX, *Euschistus heros*+TX, *Cydia pomonella*+TX, *Nilaparvata lugens*+TX, *Myzus persicae*+TX, *Chrysodeixis includens*+TX, *Aphis craccivora*+TX, *Diabrotica balteata*+TX, *Rhopalosiphum Padi*+TX, and *Chilo suppressalis*+TX.

In an embodiment, of each aspect, one compound selected from the compounds defined in the Tables A-1 to A-27, B-1 to B-27, C-1 to C-27, D-1 to D-27 and E-1 to E-27, and Table P, is suitable for controlling *Spodoptera littoralis*, *Plutella xylostella*, *Frankliniella occidentalis*, *Thrips tabaci*,

*Euschistus heros, Cydia pomonella, Nilaparvata lugens, Myzus persicae, Chrysodeixis includens, Aphis craccivora, Diabrotica balteata, Rhopalosiphum Padia*, and *Chilo Suppressalis* in cotton, vegetable, maize, cereal, rice and soya crops.

In an embodiment, one compound from selected from the compounds defined in the Tables A-1 to A-27, B-1 to B-27, C-1 to C-27, D-1 to D-27 and E-1 to E-27, and Table P, is suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile (against non-target organisms above and below ground such as fish, birds and bees), improved physico-chemical properties, or increased biodegradability). In particular, it has been surprisingly found that certain compounds of formula I may show an advantageous safety profile with respect to non-target arthropods, in particular pollinators such as honey bees, solitary bees, and bumble bees. Most particularly, *Apis mellifera*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use.

The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$—$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance.

Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
  active ingredient: 1 to 95%, preferably 60 to 90%
  surface-active agent: 1 to 30%, preferably 5 to 20%
  liquid carrier: 1 to 80%, preferably 1 to 35%
Dusts:
  active ingredient: 0.1 to 10%, preferably 0.1 to 5%
  solid carrier: 99.9 to 90%, preferably 99.9 to 99%
Suspension Concentrates:
  active ingredient: 5 to 75%, preferably 10 to 50%
  water: 94 to 24%, preferably 88 to 30%
  surface-active agent: 1 to 40%, preferably 2 to 30%

Wettable Powders:
  active ingredient: 0.5 to 90%, preferably 1 to 80%
  surface-active agent: 0.5 to 20%, preferably 1 to 15%
  solid carrier: 5 to 95%, preferably 15 to 90%
Granules:
  active ingredient: 0.1 to 30%, preferably 0.1 to 15%
  solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.
Suspension Concentrate

| active ingredients | 40% |
|---|---|
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.
Flowable Concentrate for Seed Treatment

| active ingredients | 40% |
|---|---|
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.
Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

LCMS Methods:
Method 1:
Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 4.00 kV, Fragmentor: 100 V, Desolvatation Temperature: 350° C., Gas Flow: 11 L/min, Nebulizer Gas: 45 psi, Mass range: 110 to 1000 Da) and a 1200 Series HPLC from Agilent: quaternary pump, heated column compartment and diode-array detector. Column: KINETEX EVO C18, 2.6 µm, 50×4.6 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 0% B, 100% A; 0.9-1.8 min 100% B; Flow (mL/min) 1.8.
Method 2:
Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: Binary pump, heated column compartment and diode-array detector. Column: Waters UPLC HSS T3 C18, 1.8 µm, 30×2.1 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 10% B; 0.-0.2 min 10-50% B; 0.2-0.7 min 50-100% B; Flow (mL/min) 0.8.

Chiral SFC method 1: Spectra were recorded on a SFC from Waters (Waters Acquity UPC$^2$/QDa) equipped with a PDA Detector Waters Acquity UPC$^2$. Column: Daicel SFC CHIRALPAK® IC, (3 µm, 0.3 cm×10 cm, 40° C.; Mobile phase: A: CO2 B: MeOH isocratic: 10% B in 2.0 min; ABPR: 1800 psi; Flow rate: 2.0 ml/min; Detection: 220 nm; Sample concentration: 1 mg/mL in ACN; Injection: 1 µL Chiral SFC method 2: Spectra were recorded on a SFC from Waters (Waters Acquity UPC$^2$/QDa) equipped with a PDA Detector Waters Acquity UPC$^2$. Column: Daicel SFC CHIRALPAK® IG, (3 µm, 0.3 cm×10 cm, 40° C.; Mobile phase: A: CO2 B: MeOH isocratic: 15% B in 4.8 min;

ABPR: 1800 psi; Flow rate: 2.0 ml/min; Detection: 270 nm; Sample concentration: 1 mg/mL in ACN/MeOH (1:1); Injection: 1 μL

Preparation of methyl 2-chloro-6-(trifluoromethyl)pyridine-4-carboxylate (intermediate I1)

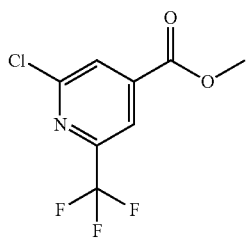

(I1)

Sulfuric acid (2.46 mL, 44.3 mmol, 1.00 equiv.) was added dropwise at room temperature to a solution of 2-chloro-6-(trifluoromethyl)pyridine-4-carboxylic acid (CAS 796090-23-8, 10.0 g, 44.3 mmol) in methanol (266 mL). The reaction mixture was heated up to 65° C. and stirred overnight. After cooling fown to room temperature, the reaction mixture was poured over a saturated sodium hydrogenocarbonate aqueous solution and the aqueous phase was extracted three times with dichloromethane. The combined organic layers were dried over sodium sulfate, filtered and evaporated to afford the desired product (10.2 g, 42.70 mmol) which was used without further purification.
$^1$H NMR (400 MHz, chloroform-d) δ ppm: 4.04 (s, 3H) 8.11 (s, 1H) 8.17 (d, J=1.10 Hz, 1H).

Preparation of methyl 2-cyclopropyl-6-(trifluoromethyl)pyridine-4-carboxylate (intermediate I2) and 2-cyclopropyl-6-(trifluoromethyl)pyridine-4-carboxylic acid (intermediate I3)

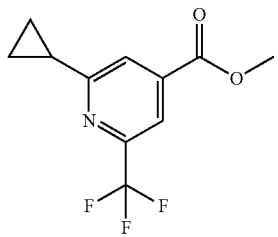

(I2)

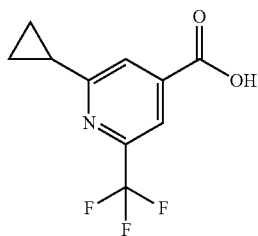

(I3)

Cyclopropylboronic acid (1.43 g, 16.7 mmol, 2.00 equiv.) and sodium hydrogenocarbonate (2.10 g, 25.1 mmol, 3.00 equiv.) were added to a solution of methyl 2-chloro-6-(trifluoromethyl)pyridine-4-carboxylate (intermediate I1 prepared as described above) (2.00 g, 8.35 mmol) in 1,4-dioxane (20.9 mL) and water (8.35 mL), and the resulting suspension was flushed with argon for 10 min. [1,1'-bis(diphenylphosphino)ferrocene] dichloropalladium (II) (0.322 g, 0.417 mmol, 0.05 equiv.) was added and the resulting suspension was stirred at 100° C. for 1 hour under argon. After cooling down to room temperature, the reaction mixture was quenched with water and extracted twice with ethyl acetate. The combined organic phases were dried over sodium sulfate, filtered and evaporated to give of first crude material, which gave after purification by flash chromatography over silica gel (ethyl acetate in cyclohexane) the desired intermediate I2 (0.706 g, 2.88 mmol).
$^1$H NMR (400 MHz, chloroform-d) δ ppm: 1.04-1.23 (m, 4H) 2.14-2.28 (m, 1H) 4.00 (s, 3H) 7.88 (s, 1H) 7.95 (d, J=1.47 Hz, 1H).
LC-MS (method 1): retention time 1.12 min, m/z 246 [M+H]$^+$.

After acidification to pH 1, the aqueous layer was extracted again twice with ethyl acetate, the combined organic phases were dried over sodium sulfate, filtered and evaporated to give a second crude material, which upon purification by flash chromatography over silica gel (methanol in dichloromethane) afforded the intermediate I3 (0.166 g, 0.718 mmol).
$^1$H NMR (400 MHz, dimethylsulfoxide-d6) δ ppm: 0.94-1.03 (m, 2H) 1.06-1.15 (m, 2H) 2.37-2.46 (m, 1H) 7.88 (d, J=1.10 Hz, 1H) 8.05 (d, J=0.73 Hz, 1H) 13.89-14.33 (m, 1H).
LC-MS (method 1): retention time 0.94 min, m/z 232 [M+H]$^+$.

Preparation of 2-cyclopropyl-6-(trifluoromethyl)pyridine-4-carboxylic acid (intermediate I3)

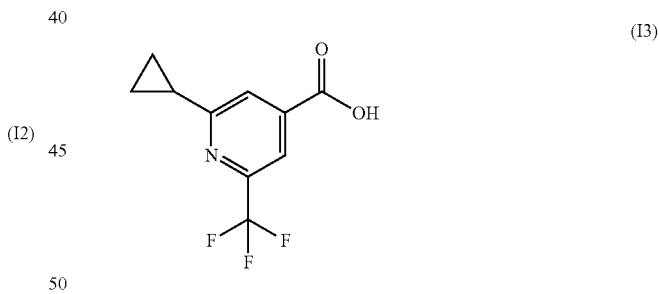

(I3)

Lithium hydroxide monohydrate (0.147 g, 3.43 mmol, 1.20 equiv.) was added to a solution of methyl 2-cyclopropyl-6-(trifluoromethyl)pyridine-4-carboxylate (intermediate I2 prepared as described above) in a 3:1 tetrahydrofuran/water mixture (24.5 mL). After stirring for 2 hours at room temperature, the reaction mixture was concentrated, and the remaining aqueous phase was acidified to pH 1 by addition of a 1 M hydrochloric acid aqueous solution (3.43 mL). The aqueous layer was extracted three times with ethyl acetate, the combined organic phases were dried over sodium sulfate, filtered and concentrated to afford 2-cyclopropyl-6-(trifluoromethyl)pyridine-4-carboxylic acid.
$^1$H NMR (400 MHz, dimethylsulfoxide-d6) δ ppm: 0.96-1.02 (m, 2H) 1.07-1.15 (m, 2H) 2.40 (tt, J$_1$=8.12 Hz, J$_2$=4.72 Hz, 1H) 7.88 (d, J=1.10 Hz, 1H) 8.04 (s, 1H) 13.90-14.36 (m, 1H)

LC-MS (method 1): retention time 0.94 min, m/z 232 [M+H]+.

Preparation of methyl 3-cyclopropyl-5-(trifluoromethyl)benzoate (intermediate I4)

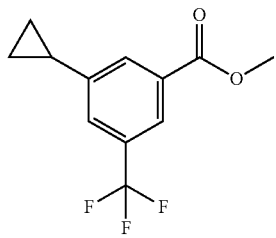

(I4)

A solution of propargyl bromide in toluene (80% weight, 0.89 g, 0.67 mL) was added to a white suspension of 9-BBN dimer (3.0 g, 12 mmol) in 26 mL of dry tetrahydrofuran under argon to give a pale yellow solution. The mixture was refluxed for 2 hours and then cooled to room temperature. A previously degassed sodium hydroxide 4M aqueous solution (4.4 mL, 18 mmol) was added to give a cloudy colorless solution. The mixture obtained was stirred for 1 hour at room temperature under argon. The resulting very pale yellow solution was then added to a previously degassed light yellow solution of methyl 3-bromo-5-(trifluoromethyl)benzoate (187331-46-0, 1.5 g, 5.2 mmol) and tetrakis(triphenylphosphine) palladium(0) (0.30 g, 0.26 mmol) in 52 mL of dry tetrahydrofuran to give a light yellow solution. The resulting mixture was stirred for 19 hours at reflux. The mixture was cooled down at room temperature, diluted with ethyl acetate, quenched with water (+few drops of brine) and the aqueous layer was extracted twice with ethyl acetate. Organic layers were combined, washed once with brine, dried over sodium sulfate, filtered and evaporated under vacuum at 60° C. The crude was purified by chromatography over silica gel to afford methyl 3-cyclopropyl-5-(trifluoromethyl)benzoate as a colorless liquid.

$^1$H NMR (400 MHz, chloroform-d) δ ppm: 0.76-0.85 (m, 2H) 1.06-1.15 (m, 2H) 2.03 (tt, $J_1$=8.39 Hz, $J_2$=5.00 Hz, 1H) 3.96 (s, 3H) 7.52 (s, 1H) 7.91 (s, 1H) 8.08 (d, J=0.73 Hz, 1H).

$^{19}$F NMR (377 MHz, chloroform-d) δ ppm: −62.75 (s, 3F).

Preparation of 3-cyclopropyl-5-(trifluoromethyl)benzoic acid (intermediate I5)

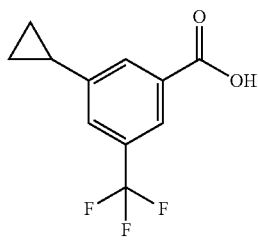

(I5)

Methyl 3-cyclopropyl-5-(trifluoromethyl)benzoate (7.00 g, 28.7 mmol) was dissolved in tetrahydrofuran (57.3 mL) and water (28.7 mL). Then lithium hydroxide (1.21 g, 28.7 mmol) was added and the resulting pale yellow cloudy solution was stirred for 4 hours at room temperature. The reaction mixture was diluted in ethyl acetate and water. The organic phase was washed twice with water. The combined aqueous layers were acidified with 1N aqueous hydrochloric acid until pH 1-2 and extracted three times with ethyl acetate. The combined organic layers were washed once with brine, dried over sodium sulfate, filtered and concentrated under reduced pressure at 60° C. to afford 3-cyclopropyl-5-(trifluoromethyl)benzoic acid, which was used without further purification.

$^1$H NMR (400 MHz, dimethylsulfoxide-d6) δ ppm: 0.79-0.85 (m, 2H) 1.03-1.10 (m, 2H) 2.12-2.22 (m, 1H) 7.70 (s, 1H) 7.88 (s, 1H) 7.93 (s, 1H) 13.47 (br s, 1H).

LC-MS (method 1): retention time 0.99 min, m/z 229 [M−H]−.

Preparation of methyl 3-(trifluoromethyl)-5-vinyl-benzoate (intermediate I6)

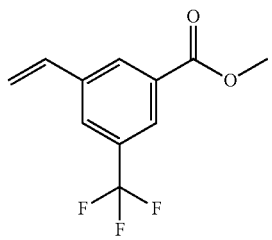

(I6)

In a three neck flask under argon, methyl 3-bromo-5-(trifluoromethyl)benzoate (CAS: 187331-46-0, 20 g, 69.24 mmol) was dissolved in toluene (312 mL). Then Tributyl (vinyl)Tin (25.56 mL, 83.09 mmol) was added and the resulting solution was degassed with argon for 10 min. Tetrakis(triphenylphosphine) palladium(0) (0.816543 g, 0.69 mmol) was added, and the resulting mixture was stirred at 110° C. for 2 hours. After cooling at room temperature, the mixture was diluted with ethyl acetate (100 mL), filtered though a pad of Celite, washed with ethyl acetate and the filtrate was concentrated under vacuum. The crude was purified by chromatography over silica gel to afford methyl 3-(trifluoromethyl)-5-vinyl-benzoate.

$^1$H NMR (400 MHz, chloroform-d) δ ppm: 3.98 (s, 3H) 5.47 (d, J=11.00 Hz, 1H) 5.93 (d, J=17.61 Hz, 1H) 6.79 (dd, $J_1$=17.42 Hz, $J_2$=10.82 Hz, 1H) 7.82 (s, 1H) 8.19 (s, 1H) 8.24-8.29 (m, 1H).

Preparation of diphenyl(2,2,2-trifluoroethyl)sulfonium trifluoromethanesulfonate

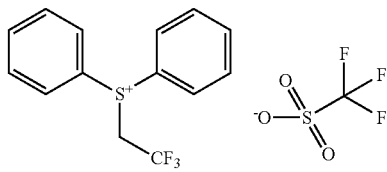

In an autoclave, diphenyl sulfide (36.43 mL, 211.1 mmol) and 2,2,2-trifluoroethyl trifluoromethanesulfonate (6.207 mL, 42.22 mmol) were mixed. The mixture was stirred for 2 min at room temperature then the autoclave was closed and heated at 150° C. for 20 hours. The reaction was cooled at room temperature and a white precipitate was formed. 75 ml of diethyl ether was added, then the white solid was filtered. It was washed four times with 30 mL of diethyl ether and then dried under reduced pressure.

$^1$H NMR (400 MHz, chloroform-d) δ ppm: 5.78 (d, J=8.80 Hz, 2H) 7.89 (d, J=8.07 Hz, 4H) 7.93-8.00 (m, 2H) 8.37 (dd, J$_1$=8.62 Hz, J$_2$=1.28 Hz, 4H).

$^{19}$F NMR (377 MHz, chloroform-d) δ ppm: −78.91 (s, 3F) −61.26 (s, 3F).

Preparation of methyl 3-(trifluoromethyl)-5-[2-(trifluoromethyl)cyclopropyl]benzoate (intermediate I7)

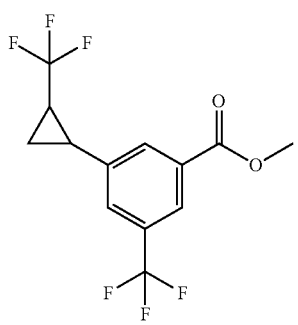

(I7)

In a vial under argon, 3-(trifluoromethyl)-5-vinyl-benzoate (1.9 g, 8.3 mmol) and cesium fluoride (1.5 g, 9.9 mmol) were dissolved in dimethylacetamide (33 mL) to give a colorless solution which was degassed under argon for 20 min. 5,10,15,20-Tetraphenyl-21H,23H-porphine Iron(III) chloride (0.31 g, 0.41 mmol) was added. The reaction became a green suspension and diphenyl(2,2,2-trifluoroethyl)sulfonium trifluoromethanesulfonic acid (3.8 g, 9.1 mmol) was also added portionwise. The reaction was stirred at room temperature overnight. The resulting mixture was diluted with dichloromethane, then water was added. The organic layer was washed four times with water, dried over sodium sulfate, filtered and concentrated under reduced pressure at 40° C. under 160 mbar. The crude was purified by chromatography over silica gel to afford methyl 3-(trifluoromethyl)-5-[2-(trifluoromethyl)cyclopropyl]benzoate.

$^1$H NMR (400 MHz, chloroform-d) δ ppm: 1.25-1.34 (m, 1H) 1.48-1.55 (m, 1H) 1.88-2.00 (m, 1H) 2.46-2.53 (m, 1H) 3.98 (s, 3H) 7.60 (s, 1H) 7.98 (s, 1H) 8.19 (s, 1H).

Preparation of 3-(trifluoromethyl)-5-[2-(trifluoroethyl)cyclopropyl]benzoic acid (I8)

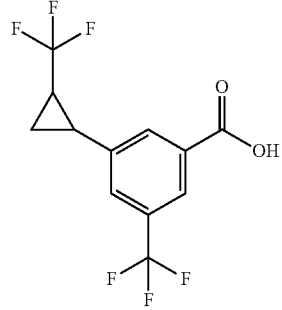

(I8)

3-(trifluoromethyl)-5-[2-(trifluoromethyl)cyclopropyl]benzoate (1.43 g, 3.80 mmol) was dissolved in tetrahydrofuran (11.4 mL) and water (7.60 mL). Lithium hydroxide monohydrate (0.322 g, 7.60 mmol) was added and the resulting mixture was stirred 3 hours 30 min at room temperature. The reaction mixture was cooled to 0° C. then it was acidified with a 2M hydrochloric acid solution. The aqueous layer was extracted twice with ethyl acetate, the organic layer was washed with brine, dried over sodium sulfate, filtered and concentrated under reduced pressure to afford 3-(trifluoromethyl)-5-[2-(trifluoromethyl)cyclopropyl]benzoic acid.

$^1$H NMR (400 MHz, dimethylsulfoxide-d6) δ ppm 1.40-1.47 (m, 2H) 2.53-2.60 (m, 1H) 2.72 (td, J$_1$=7.70 Hz, J$_2$=4.77 Hz, 1H) 7.87 (s, 1H) 8.02 (s, 1H) 8.05-8.08 (m, 1H) 13.54 (br s, 1H).

LC-MS (method 1): retention time 1.04 min, m/z 297 [M−H]$^-$.

Preparation of methyl 3-(trifluoromethyl)-5-(trifluoromethylsulfanyl)benzoate (intermediate I9)

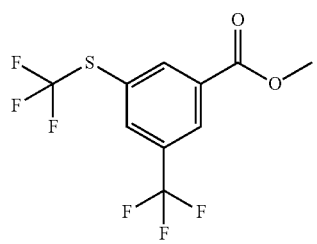

(I9)

(2,2'-bipyridine)(trifluoromethanethiolato) copper (CAS 1413732-47-4) (3.9 g, 12 mmol, 2.0 equiv.) was added to a solution of methyl 3-iodo-5-(trifluoromethyl)benzoate (2.0 g, 6.1 mmol) in acetonitrile (18 mL) under argon. The reaction mixture was heated up to 90° C. and stirred overnight. After cooling down to room temperature, the reaction mixture was filtered over a pad of Celite and concentrated. The crude material was purified by two flash chromatographies over silica gel (ethyl acetate in cyclohexane) to afford the desired product as a yellow gum (1.5 g, 4.9 mmol).

$^1$H NMR (400 MHz, chloroform-d) δ ppm: 4.02 (s, 3H), 8.11 (s, 1H), 8.44 (s. 1H), 8.53 (s, 1H).

LC-MS (method 1): retention time 1.21 min, m/z 279 [M−MeO+H]⁺.

Preparation of methyl 3-(trifluoromethyl)-5-(trifluoromethylsulfonyl)benzoate (intermediate I10)

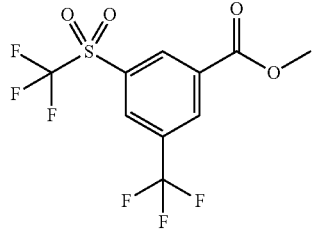

(I10)

3-Chloroperbenzoic acid (2.3 g, 11 mmol, 2.1 equiv.) was added portionwise to a 0° C. cooled solution of methyl 3-(trifluoromethyl)-5-(trifluoromethylsulfanyl)benzoate (intermediate I13 prepared as described above) (1.8 g, 5.3 mmol) in dichloromethane (16 mL). After stirring for 1 hour at room temperature, more 3-chloroperbenzoic acid (2.3 g, 11 mmol, 2.1 equiv.) was added and the reaction mixture was stirred overnight. The precipitate formed was filtered. The filtrate was washed with 10% aqueous solution of sodium thiosulfate and with NaHCO₃ sat solution. The organic phase was dried over sodium sulfate, filtered and concentrated under reduced pressure. The crude was purified by chromatography over silica gel to afford methyl 3-(trifluoromethyl)-5-(trifluoromethylsulfonyl) benzoate.

$^1$H NMR (400 MHz, Chloroform) δ ppm 4.07 (s, 3H) 8.43-8.51 (m, 1H) 8.70-8.80 (m, 1H) 8.84-8.91 (m, 1H).

$^{19}$F NMR (377 MHz, chloroform-d) δ ppm: −77.49 (s, 3F) −62.96 (s, 3F)

Preparation of 3-(trifluoromethyl)-5-(trifluoromethylsulfonyl)benzoic acid (I11)

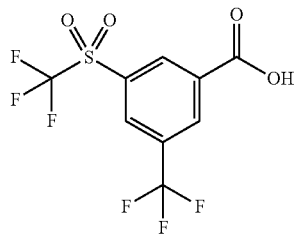

(I11)

Methyl 3-(trifluoromethyl)-5-(trifluoromethylsulfonyl)benzoate (1.8 g, 5.4 mmol) was charged in a flask and dissolved in tetrahydrofuran (16 mL) and water (11 mL). To this mixture was added lithium hydroxide monohydrate (0.26 g, 11 mmol) and the reaction was stirred for 1 hour at room temperature. The reaction mixture was acidified with 1 M hydrochloric acid, and the aqueous phase was extracted with ethyl acetate twice. The combined organic phases were dried over sodium sulfate, filtered and then concentrated to afford 3-(trifluoromethyl)-5-(trifluoromethylsulfonyl)benzoic acid which was used without further purification.

$^1$H NMR (400 MHz, dimethylsulfoxide-d6) δ ppm: 8.68 (s, 2H) 8.71-8.76 (m, 1H) 13.33-15.22 (m, 1H).

Preparation of methyl 3-(cyclopropanecarbonyl)-5-(trifluoromethyl)benzoate (intermediate I12)

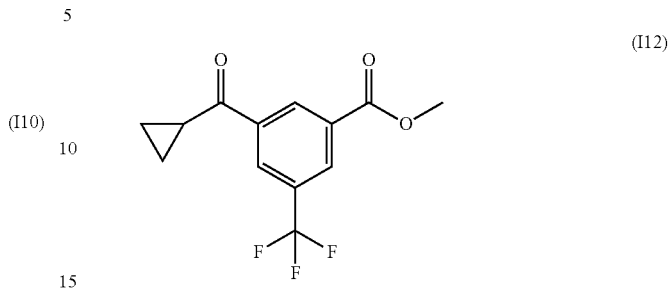

(I12)

Methyl 3-iodo-5-(trifluoromethyl)benzoate (10 g, 28.78 mmol) was taken in tetrahydrofuran (115 mL) under argon. The resulting pale brown solution was cooled down to −78° C. with a dry ice/acetone bath. The Turbo-Grignard 1.3 M in tetrahydrofuran solution (31 mL, 40.29 mmol) was added dropwise with a syringe over 20 minutes to give directly a dark solution while maintaining the temperature below −65° C. The resulting mixture was stirred at −78° C. for 15 minutes. Cuprous cyanide (3.125 g, 34.5 mmol) and anhydrous lithium chloride (1.479 g, 34.5 mmol) were added simultaneously at once to give a dark suspension. The resulting mixture was stirred again at −78° C. for 15 minutes. Cyclopropanecarbonyl chloride (5.340 mL, 57.5 mmol) was finally added dropwise over 5 minutes (temperature reached −68° C. maximum). The resulting mixture was stirred at −78° C. for 1 hour, warmed up to room temperature and stirred for 30 minutes to give a brown suspension. The reaction mixture was cooled down to −78° C. and quenched slowly with 20 ml of methanol. The resulting mixture was allowed to reach room temperature and the suspension obtained was filtered over Celite. Saturated aqueous ammonium chloride and ethyl acetate were added to the filtrate. The aqueous layer was extracted twice with ethyl acetate. The combined organic layers were dried over sodium sulfate, filtered and concentrated under reduced pressure at 40° C. The crude material was purified by chromatography over silica gel to afford methyl 3-(cyclopropanecarbonyl)-5-(trifluoromethyl)benzoate.

$^1$H NMR (400 MHz, chloroform-d) δ ppm: 1.16-1.22 (m, 2H) 1.35 (quin, J=3.76 Hz, 2H) 2.74 (tt, $J_1$=7.84 Hz, $J_2$=4.45 Hz, 1H) 4.02 (s, 3H) 8.45 (d, J=0.73 Hz, 1H) 8.51 (d, J=0.73 Hz, 1H) 8.86 (s, 1H).

Preparation of methyl 3-[cyclopropyl(difluoro)methyl]-5-(trifluoromethyl)benzoate (intermediate I13)

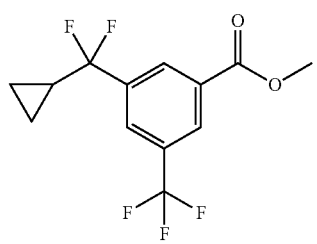

(I13)

Methyl 3-(cyclopropanecarbonyl)-5-(trifluoromethyl)benzoate (5.5 g, 20 mmol) was taken in 2,2-difluoro-1,3-dimethyl-imidazolidine (36 mL, 280 mmol) under argon to give a light yellow solution. The resulting mixture was stirred for 5 hours at 110° C. to give a light brown solution. The reaction mixture was cooled down to room temperature and added dropwise to 1.0 L of a vigorously stirred saturated aqueous sodium hydrogenocarbonate solution at 0° C. (temperature was maintained below 10° C.). The resulting mixture (pH 8-9) was then extracted 3 times with ethyl acetate. The combined organic layers were dried over sodium sulfate, filtered and concentrated under reduced pressure at 50° C. The crude material was purified by chromatography over silica gel to afford methyl 3-[cyclopropyl(difluoro)methyl]-5-(trifluoromethyl)benzoate.

$^1$H NMR (400 MHz, chloroform-d) δ ppm: 0.73-0.79 (m, 2H) 0.82-0.89 (m, 2H) 1.47-1.60 (m, 1H) 8.00 (d, J=0.73 Hz, 1H) 8.39 (s, 1H) 8.42 (s, 1H).

$^{19}$F NMR (377 MHz, chloroform-d) δ ppm: −98.40 (s, 3F) −62.81 (s, 2 F).

Preparation of 3-[cyclopropyl(difluoro)methyl]-5-(trifluoromethyl)benzoic acid (I14)

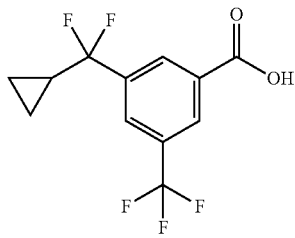

(I14)

Methyl 3-[cyclopropyl(difluoro)methyl]-5-(trifluoromethyl)benzoate (4.45 g, 15.1 mmol) was taken in tetrahydrofuran (30.3 mL) and water (15.1 mL). Lithium hydroxide monohydrate (0.833 g, 19.7 mmol) was added and the resulting colourless cloudy solution was stirred for 1 hour at room temperature. The reaction mixture was diluted with ethyl acetate and water. The organic phase was washed twice with water. The combined aqueous layers were acidified with 1N aqueous hydrochloric acid until pH 1-2 and extracted three times with ethyl acetate. The combined organic layers were washed once with brine, dried over sodium sulfate, filtered and concentrated under reduced pressure at 60° C. to afford 3-[cyclopropyl(difluoro)methyl]-5-(trifluoromethyl)benzoic, which was used without further purification.

$^1$H NMR (400 MHz, dimethylsulfoxide-d6) δ ppm: 0.62-0.84 (m, 4H) 1.65-1.97 (m, 1H) 7.93-8.23 (m, 1H) 8.23-8.51 (m, 2H) 13.24-14.48 (m, 1H).

LC-MS (method 1): retention time 1.03 min, m/z 279 [M−H]$^-$.

Preparation of methyl 2-(1-cyano-2-ethoxy-2-oxo-ethyl)-6-(trifluoromethyl)pyridine-4-carboxylate (intermediate I15)

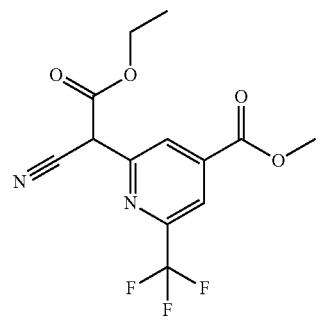

(I15)

Methyl 2-chloro-6-(trifluoromethyl)pyridine-4-carboxylate (1.05 g, 4.40 mmol) was dissolved in dimethylsulfoxide (13.2 mL). Then ethyl 2-cyanoacetate (0.702 mL, 6.60 mmol), potassium carbonate (1.535 g, 11.00 mmol) and tetrabutylammonium bromide (0.145 g, 0.440 mmol) were added successively at room temperature. The resulting suspension was stirred 1 hour at 90° C. and then let stirred overnight at room temperature. The reaction mass was diluted with 50 mL of water and 100 mL of ethyl acetate, cooled to 0-10° C. and slowly quenched with 1N hydrochloric acid via dropping funnel until pH 3. The aqueous phase was extracted with ethyl acetate. The combined organic layers were dried over sodium sulfate and concentrated under reduced pressure at 50° C. The crude material was purified by chromatography over silica gel with ethyl acetate in cyclohexane to afford methyl 2-(1-cyano-2-ethoxy-2-oxo-ethyl)-6-(trifluoromethyl)pyridine-4-carboxylate.

$^1$H NMR (400 MHz, chloroform-d) δ ppm: 1.36-1.43 (m, 3H) 4.01 (s, 3H) 4.34 (q, J=7.58 Hz, 2H) 7.34 (s, 1H) 8.06 (s, 1H) 14.46-14.67 (m, 1H).

LC-MS (method 1): retention time 1.01 min, m/z 317 [M+H]$^+$.

Preparation of methyl 2-(cyanomethyl)-6-(trifluoromethyl)pyridine-4-carboxylate (I16)

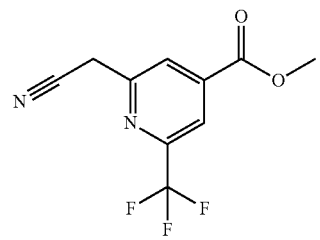

(I16)

To a solution of methyl 2-(1-cyano-2-ethoxy-2-oxo-ethyl)-6-(trifluoromethyl)pyridine-4-carboxylate (0.800 g, 2.53 mmol) in dimethyl sulfoxide (20 mL) was added sodium chloride (0.299 g, 5.06 mmol) in water (10 mL). The resulting mixture was stirred for 4 hours at 95° C. After cooling down to room temperature, the reaction mixture was diluted with water (50 mL) and extracted with ethyl acetate (3*50 mL). The combined organic layers were dried over sodium sulfate, filtered and contracted under reduced pressure to afford methyl 2-(cyanomethyl)-6-(trifluoromethyl)pyridine-4-carboxylate which was used without further purification.

¹H NMR (400 MHz, chloroform-d) δ ppm: 4.05 (s, 3H) 4.13 (s, 2H) 8.24 (s, 1H) 8.26 (s, 1H).

LC-MS (method 1): retention time 0.89 min, m/z 243 [M−H]⁻.

Preparation of 2-(1-cyanocyclopropyl)-6-(trifluoromethyl)pyridine-4-carboxylic acid (I17)

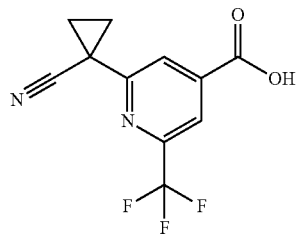

(I17)

Methyl 2-(cyanomethyl)-6-(trifluoromethyl)pyridine-4-carboxylate (0.05 g, 0.20 mmol) was dissolved in dimethylformamide (2 mL). Sodium hydride (24 mg, 0.61 mmol) was added at room temperature and the colorless solution became a dark purple suspension. After 10 min, 1,2-dibromoethane (0.02 mL, 0.24 mmol) was added and the resulting suspension was stirred for 15 min at room temperature. The reaction mixture was quenched with a saturated ammonium chloride solution at 0-5° C. and diluted with ethyl acetate. The aqueous layer was acidified to pH 2-3 with 1N hydrochloric acid and extracted twice with ethyl acetate. The combined organic layers were dried over sodium sulfate, filtered and evaporated under reduced pressure. The crude was purified by reverse phase chromatography to afford 2-(1-cyanocyclopropyl)-6-(trifluoromethyl)pyridine-4-carboxylic acid.

¹H NMR (400 MHz, dimethylsulfoxide-d6) δ ppm: 1.76-1.83 (m, 2H) 1.96-2.03 (m, 2H) 8.07 (d, J=1.10 Hz, 1H) 8.17 (s, 1H) 13.35-15.45 (m, 1H).

LC-MS (method 1): retention time 0.89 min, m/z 255 [M−H]⁻.

Preparation of methyl 3-(cyanomethyl)-5-(trifluoromethyl)benzoate (intermediate I18)

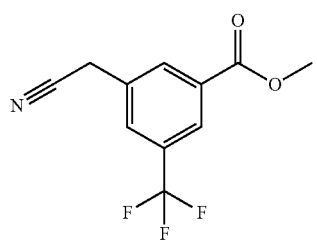

(I18)

Methyl 3-bromo-5-(trifluoromethyl)benzoate (0.600 g, 2.08 mmol) was dissolved in N,N-dimethylformamide (4.2 mL). (Trimethylsilyl)acetonitrile (0.862 mL, 6.23 mmol) was added dropwise with a syringe. The solution was degassed under Ar for 5 min. Then ZnF₂ (0.130 g, 1.25 mmol), Xantphos (0.0481 g, 0.0831 mmol) and Pd₂(dba)₃ (0.0384 g, 0.0415 mmol) were added. The resulting black suspension was stirred at 100° C. for 22 hours then cooled down to room temperature. The mixture was concentrated under reduced pressure at 50° C. The crude material was purified by chromatography over silica gel with ethyl acetate in cyclohexane to afford methyl 3-(cyanomethyl)-5-(trifluoromethyl)benzoate.

¹H NMR (400 MHz, chloroform-d) δ=8.30 (1H, s), 8.23 (1H, s), 7.81 (1H, s), 3.99 (3H, s), 3.90 (2H, s) ppm.

LC-MS (method 1): retention time 0.92 min, m/z 242 [M−H]⁻.

Preparation of methyl 3-(1-cyanocyclopropyl)-5-(trifluoromethyl)benzoate (intermediate I19)

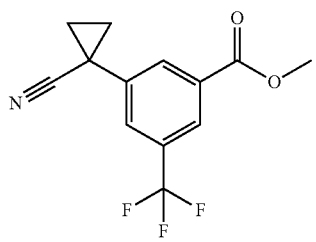

(I19)

Methyl 3-(cyanomethyl)-5-(trifluoromethyl)benzoate (2.15 g, 7.07 mmol) was dissolved in N,N-dimethylformamide (32.3 mL). Cesium carbonate (7.13 g, 21.2 mmol) was added to the stirred solution and the mixture was stirred at room temperature for 10 min. 1,2-dibromoethane (0.68 mL 7.78 mmol) was added and the mixture was stirred at 60° C. for 3 hours then cooled down to room temperature. Water (30 mL) was added, then the aqueous layer was extracted with ethyl acetate (60 mL). The combined organic layers were dried over sodium sulfate, filtered and concentrated in vacuo. The crude material was purified by flash chromatography (silica gel, ethyl acetate in hexanes) to afford methyl 3-(1-cyanocyclopropyl)-5-(trifluoromethyl)benzoate.

¹H NMR (400 MHz, chloroform-d) δ=8.23 (1H, s), 8.09 (1H, s), 7.79 (1H, s), 3.98 (3H, s), 1.84-1.92 (2H, m), 1.47-1.57 (m, 2H) ppm.

Preparation of 3-(1-cyanocyclopropyl)-5-(trifluoromethyl)benzoic acid (intermediate I20)

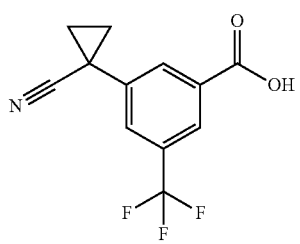

(I20)

Methyl 3-(1-cyanocyclopropyl)-5-(trifluoromethyl)benzoate (59 mg, 0.22 mmol) was dissolved in tetrahydrofuran (0.66 mL) and water (0.33 ml). Lithium hydroxide monohydrate (9.3 mg, 0.22 mmol) was added and the mixture was stirred at room temperature for 42 hours. 1N hydrochloric acid was added until pH=2. The aqueous layer was extracted three times with ethyl acetate. The combined organic layers were dried over sodium sulfate, filtered and concentrated in vacuo to afford 3-(1-cyanocyclopropyl)-5-(trifluoromethyl)benzoic acid.

$^1$H NMR (400 MHz, chloroform-d) δ=8.60-9.90 (1H, br s), 8.29 (1H, s), 8.15 (1H, s), 7.84 (1H, s), 1.84-1.93 (2H, m), 1.50-1.60 (2H, m) ppm.

LC-MS (method 1): retention time 0.86 min, m/z 254 [M−H]$^−$.

Preparation of 1-[3-bromo-5-(trifluoromethyl)phenyl]ethanol

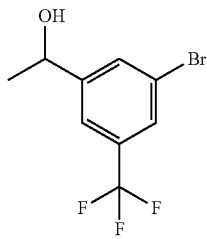

Methyl magnesium bromide (1.00 M in THF, 63.2 mL, 63.2 mmol) was added to a solution of 3-bromo-5-(trifluoromethyl)benzaldehyde (8.00 g, 31.6 mmol) in tetrahydrofuran (100 mL) at 0° C. under nitrogen. resulting brown reaction mixture was stirred at room temperature for 30 min. The reaction mixture was quenched with saturated ammonium chloride solution. The aqueous layer was extracted with ethyl acetate, dried over sodium sulfate and concentrated under reduced pressure to obtain 1-[3-bromo-5-(trifluoromethyl)phenyl]ethanol as a light yellow liquid.

$^1$H NMR (400 MHz, DMSO-d) δ ppm: 7.78-7.88 (m, 2H), 7.71 (s, 1H), 5.52 (d, 1H), 4.81 (m, 1H), 1.35 (d, 3H).

Preparation of 1-[3-bromo-5-(trifluoromethyl)phenyl]ethanone

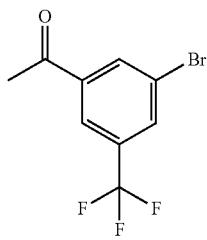

Pyridinium chlorochromate (5.05 g, 23.4 mmol) was added portionwise to a stirred solution of 1-[3-bromo-5-(trifluoromethyl)phenyl]ethanol (7.00 g, 15.6 mmol) in dichloromethane (150 mL) at 0° C. The resulting brown colour reaction mixture was stirred at room temperature for 2 hours. The reaction mixture was filtered through celite pad then the filtrate was evaporated under reduced pressure. The crude residue was purified by flash chromatography over silica gel (eluting with ethyl acetate in hexanes) to afford 1-[3-bromo-5-(trifluoromethyl)phenyl]ethanone as a colorless oil.

$^1$H NMR (400 MHz, DMSO-d) δ ppm: 8.38 (1H, s), 8.26 (1H, s), 8.19 (1H, s), 2.69 (s, 1H).

Preparation of 1-[3-bromo-5-(trifluoromethyl)phenyl]cyclopropanol

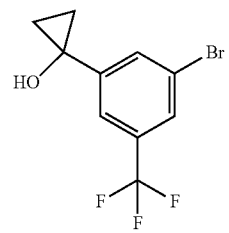 [SMILES: OC1(c2cc(Br)cc(C(F)(F)F)c2)CC1]

A solution of 1-[3-bromo-5-(trifluoromethyl)phenyl]ethanone (5.00 g, 18.3 mmol) in dichloromethane (30 mL) at 0° C. was treated with triethylamine (3.84 mL, 27.5 mmol) and trimethylsilyl trifluoromethanesulfonate (6.12 g, 27.5 mmol). The mixture was stirred for 2 hours at room temperature. The reaction mixture was quenched with saturated sodium bicarbonate solution (100 mL). The aqueous layer was extracted with dichloromethane. The organic layer was dried over sodium sulfate and concentrated under reduced pressure. The crude silyl enol ether was dissolved in dichloromethane and cooled down to 0° C. Di-iodomethane (7.37 g, 27.5 mmol) and diethylzinc (1.00 M in hexane, 27.5 mL, 27.5 mmol) were added dropwise and the mixture was stirred for 16 hours at room temperature. The reaction mixture was quenched with saturated ammonium chloride solution. The aqueous layer was extracted with dichloromethane. The organic layer was dried over sodium sulfate and concentrated under reduced pressure. The residue was dissolved in methanol at 0° C. and potassium carbonate (0.254 g, 1.83 mmol) was added. The resulting light yellow reaction mixture was stirred at 0° C. for 1 hour. The reaction mixture was concentrated under reduced pressure. The residue was purified by flash chromatography over silica gel (eluting with ethyl acetate in hexanes) to afford 1-[3-bromo-5-(trifluoromethyl)phenyl]cyclopropanol as an off-white solid.

$^1$H NMR (400 MHz, chloroform-d) δ ppm: 7.75 (1H, s), 7.65 (1H, s), 7.58 (1H, s), 6.30 (s, 1H), 1.15-1.25 (m, 2H), 1.05-1.15 (m, 2H).

Preparation of 1-bromo-3-(1-methoxycyclopropyl)-5-(trifluoromethyl)benzene (140)

(I40)

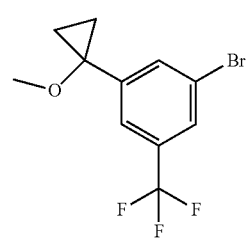

A solution of 1-[3-bromo-5-(trifluoromethyl)phenyl]cyclopropanol (500 mg, 1.74 mmol) in tetrahydrofuran (2.0 mL) was added dropwise to a suspension of sodium hydride (60% in oil, 139 mg, 3.49 mmol) in tetrahydrofuran (2.0 mL). The mixture was stirred at 0° C. for 10 minutes. Methyl iodide (371 mg, 2.62 mmol) was added dropwise and the resulting mixture was stirred at 0° C. for 1 hour. Saturated ammonium chloride solution was added. The aqueous layer was extracted with ethyl acetate. The combined organic layers were dried over sodium sulfate and concentrated under reduced pressure. The crude residue was purified by flash chromatography over silica gel (gradient of ethyl acetate in hexanes) to afford 1-bromo-3-(1-methoxycyclopropyl)-5-(trifluoromethyl)benzene as a colorless liquid.

$^1$H NMR (400 MHz, DMSO-d) δ ppm: 7.82 (s, 1H), 7.69 (s, 1H), 7.55 (s, 1H), 3.27 (s, 3H), 1.20-1.28 (m, 2H), 1.09-1.18 (m, 2H).

Preparation of methyl 3-(1-methoxycyclopropyl)-5-(trifluoromethyl)benzoate (I38)

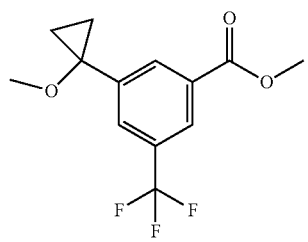

(I38)

An autoclave was charged with 1-bromo-3-(1-methoxycyclopropyl)-5-(trifluoromethyl)benzene (1.50 g, 4.83 mmol), triethylamine (1.02 mL, 7.24 mmol) and methanol (30 mL). The reaction mixture was purged with argon. [1,1'-bis(diphenylphosphino)ferrocene]dichloropalladium (II) (353 mg, 0.483 mmol) was added. The autoclave was placed under carbon monoxide atmosphere (200 psi) and heated to 100° C. for 16 hours. The autoclave was cooled down to room temperature and filled with argon. The reaction mixture was filtered through celite. Water and ethyl acetate were added to the filtrate and the aqueous layer was extracted with ethyl acetate. The combined organic layers were dried over sodium sulfate and concentrated in vacuo. The crude residue was purified by flash chromatography over silica gel (gradient of ethyl acetate in hexanes) to afford methyl 3-(1-methoxycyclopropyl)-5-(trifluoromethyl)benzoate as a pale yellow liquid.

$^1$H NMR (400 MHz, chloroform-d) δ ppm: 8.17 (s, 1H), 8.05 (s, 1H), 7.78 (s, 1H), 3.95 (s, 3H), 3.25 (s, 3H), 1.30 (t, 2H), 1.05 (t, 2H).

Preparation of 3-(1-methoxycyclopropyl)-5-(trifluoromethyl)benzoic acid (I39)

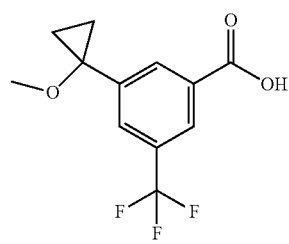

(I39)

Methyl 3-(1-methoxycyclopropyl)-5-(trifluoromethyl)benzoate (1.00 g, 3.46 mmol) was dissolved in tetrahydrofuran (6.0 mL) and water (3.0 mL). Lithium hydroxide monohydrate (291 mg, 6.93 mmol) was added and the mixture was stirred at room temperature for 3 hours. The mixture was concentrated and 2N hydrochloric acid was added at 0° C. The precipitate that formed was filtered off, washed with water and dried to afford 3-(1-methoxycyclopropyl)-5-(trifluoromethyl)benzoic acid as a white solid.

$^1$H NMR (400 MHz, chloroform-d) δ ppm: 13.4-13.7 (br. S, 1H), 8.00-8.10 (m, 2H), 7.72 (s, 1H), 3.19 (s, 3H), 1.25-1.35 (m, 2H), 1.08-1.15 (m, 2H).

Preparation of 2-chloro-5-(2,2-difluoroethoxy)pyrimidine

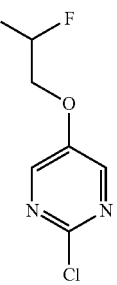

2-Chloropyrimidin-5-ol ([CAS: 4983-28-2] 5.00 g, 38.3 mmol) was dissolved in DMF (30.0 mL). Potassium carbonate (10.6 g, 76.6 mmol) and 1,1-difluoro-2-iodoethane (8.8 g, 46.0 mmol) were added. The resulting reaction mixture was stirred at 80° C. for 12 h before being cooled to room temperature. It was then poured into a mixture ice cold water and extracted twice with ethyl acetate (200 mL each). The combined organic layers were dried over sodium sulfate, filtered and concentrated in vacuo. The crude material was purified by flash chromatography (silica gel, 0-50% ethyl acetate in hexanes) to afford 2-chloro-5-(2,2-difluoroethoxy)pyrimidine.

LC-MS (method 1): m/z 195.1 [M+H]$^+$.

Preparation of tributyl-[5-(2,2-difluoroethoxy)pyrimidin-2-yl]stannane

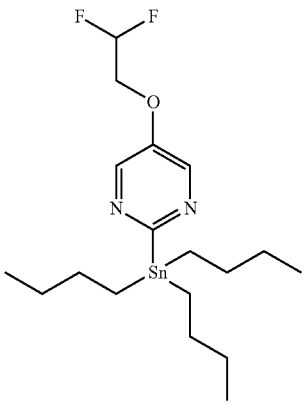 [SMILES: CCC[CH2][Sn]([CH2]CCC)([CH2]CCC)[c]1ncc(OCC(F)F)cn1]

2-Chloro-5-(2,2-difluoroethoxy)pyrimidine (2.00 g, 9.251 mmol) was dissolved in toluene (40.0 mL) and hexa-n-butylditin (8.05 g, 13.877 mmol) was added. The reaction mixture was purged with argon for 5 minutes, tetrakis (triphenylphosphine)palladium(0) (0.5345 g, 0.4626 mmol) was added, the reaction mixture was purged with argon for another 5 minutes and subsequently stirred at 100° C. for 16 h. It was filtered through a pad of Celite and the filtrate was concentrated in vacuo. The crude material was purified by neutral alumina chromatography (0-20% ethyl acetate in hexanes) to afford tributyl-[5-(2,2-difluoroethoxy)pyrimidin-2-yl]stannane.

$^1$H NMR (400 MHz, chloroform-d) δ ppm: 0.87 (t, 9H) 1.15 (t, 6H) 1.30-1.35 (q, 6H) 1.54-1.62 (m, 6H) 4.21-4.30 (dt, 2H) 5.95-6.26 (br tt, 1H) 8.47 (s, 2H)

Preparation of 1-[3-[5-(2,2-difluoroethoxy)pyrimidin-2-yl]pyrazin-2-yl]ethenone (I22)

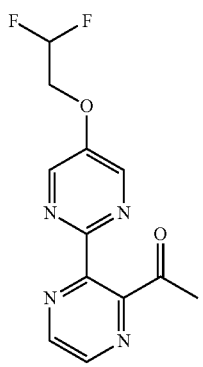

Tributyl-[5-(2,2-difluoroethoxy)pyrimidin-2-yl]stannane (1.00 g, 2.00 mmol) was dissolved in toluene (15 mL), then 1-(3-chloropyrazin-2-yl)ethanone ([CAS: 121246-90-0] 0.439 g, 2.52 mmol) was added. The mixture was purged with argon fir 5 minutes, then copper(I) iodide (0.0763 g, 0.401 mmol) and tetrakis(triphenylphosphine)palladium(0) (0.232 g, 0.200 mmol) were added and the resulting reaction mixture was stirred at 100° C. for 4 h. After cooling to room temperature, it was filtered through a pad of Celite and the filtrate was concentrated in vacuo. The crude product was purified by flash chromate-graphy (combiflash, silica gel, 0-100% ethyl acetate in hexanes) to afford 1-[3-[5-(2,2-difluoroethoxy)-pyrimidin-2-yl]pyrazin-2-yl]ethanone.

LC-MS (method 1): m/z 281.1 [M+H]$^+$.
$^1$H NMR (400 MHz, DMSO-d6) δ ppm: 8.90 (s, 1H), 8.70-8.90 (m, 3H), 6.48 (t, 1H), 4.63 (td, 2H), 2.62 (s, 3H).

Preparation of 1-[3-[5-(2,2-difluoroethoxy)pyrimidin-2-yl]pyrazin-2-yl]ethanamine (I28)

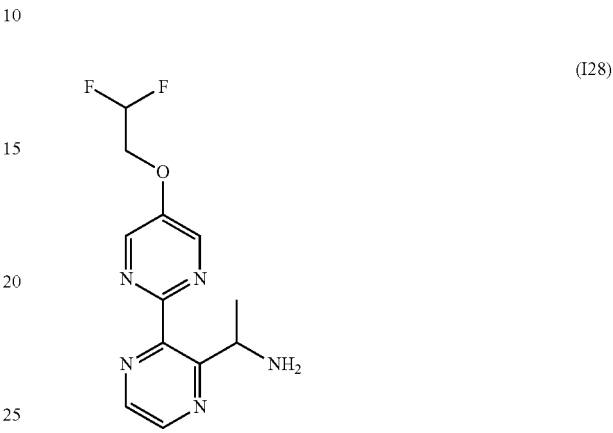

1-[3-[5-(2,2-Difluoroethoxy)pyrimidin-2-yl]pyrazin-2-yl]ethanone (0.80 g, 0.285 mmol) was dissolved in a saturated solution of ammonium acetate in ethanol (10 mL). Ammonia solution 30% in water (5.0 mL) and sodium cyanoborohydride (0.0538 g, 0.856 mmol) were added and the reaction mixture was stirred at reflux for 18 h. The reaction mixture was cooled to room temperature and washed with dichloromethane (50 mL). The aqueous layer was concentrated in vacuo to afford a crude product which was purified by reverse phase chromatography (C$_{18}$ column, 0 to 50% acetonitrile in water) to afford 1-[3-[5-(2,2-difluoroethoxy)pyrimidin-2-yl]pyrazin-2-yl]ethanamine.

LC-MS (method 1): m/z 282.1 [M+H]$^+$.
$^1$H NMR (400 MHz, DMSO-d6) δ ppm: 8.80-9.00 (m, 4H), 6.50 (tt, 1H), 4.90 (m, 1H), 4.78 (td, 2H), 1.45 (d, 3H)

Preparation of 2-(1-cyanocyclopropyl)-N-[1-[3-[5-(2,2-difluoroethoxy)pyrimidin-2-yl]pyrazin-2-yl]ethyl]-6-(trifluoromethyl)pyridine-4-carboxamide (compound P40)

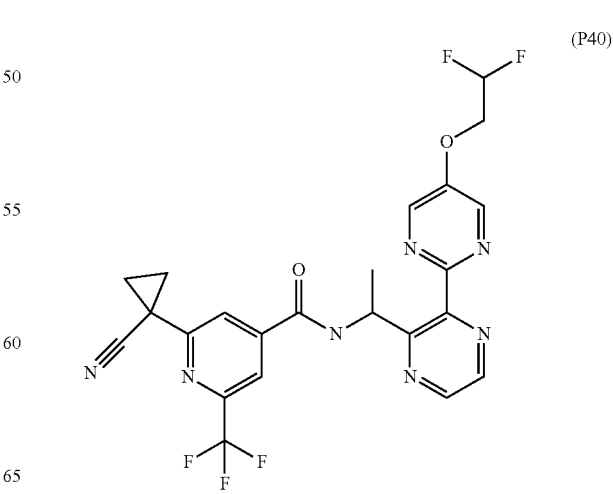

To a stirred solution of 1-[3-[5-(2,2-difluoroethoxy)pyrimidin-2-yl]pyrazin-2-yl]ethanamine (80%, 50 mg, 0.142 mmol) in DMF (2 mL) at 0° C. was added 2-(1-cyanocyclopropyl)-6-(trifluoromethyl)pyridine-4-carboxylic acid (90%, 0.0486 g, 0.171 mmol), propanephosphonic acid anhydride (T3P, 0.136 g, 0.427 mmol) and N,N-diisopropylethylamine (0.0551 g, 0.427 mmol). After addition the reaction mixture was allowed to stir at room temperature for 5 h. The reaction mixture was diluted with water (30 mL) and extracted twice with dichloromethane (150 mL each). The combined organic layers were washed with brine (30 mL), dried over sodium sulfate, filtered and concentrated in vacuo. The crude was purified by reversed phase chromatography (0-80% acetonitrile in water) to afford 2-(1-cyanocyclopropyl)-N-[1-[3-[5-(2,2-difluoroethoxy)pyrimidin-2-yl]pyrazin-2-yl]ethyl]-6-(trifluoromethyl)pyridine-4-carboxamide.

¹H NMR (400 MHz, DMSO-d6) δ ppm: 1.62 (d, 3H) 1.75 (m, 2H) 1.93 (m, 2H) 4.63 (t, 2H) 5.66 (t, 1H) 6.35-6.62 (br t, 1H) 7.98 (s, 1H) 8.11 (s, 1H) 8.69 (s, 1H) 8.78 (s, 1H) 8.82 (s, 2H) 9.48 (d, 1H) LC-MS (method 1): retention time 7.32 min, m/z 520.2 [M+H]⁺.

Preparation of
2-chloro-5-(difluoromethoxy)pyrimidine

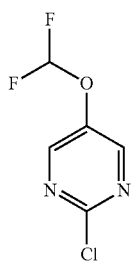

2-Chloropyrimidin-5-ol ([CAS: 4983-28-2] 5.00 g, 38.3 mmol) was dissolved in DMF (20.0 mL). Potassium carbonate (10.6 g, 76.6 mmol) and sodium 2-chloro-2,2-difluoroacetate (8.76 g, 57.5 mmol) were added. The resulting reaction mixture was stirred at 80° C. for 4 h before being cooled to room temperature and diluted with ethyl acetate. This organic layer was washed twice with cold water (100 mL each), dried over sodium sulfate, filtered and concentrated in vacuo. The crude material was purified by flash chromatography (combiflash, silica gel, 0-50% ethyl acetate in hexanes) to afford 2-chloro-5-(difluoromethoxy)pyrimidine.

¹H NMR (400 MHz, chloroform-d) δ ppm: 6.45-6.82 (br t, 1H) 8.55 (s, 2H)

Preparation of tributyl-[5-(difluoromethoxy)pyrimidin-2-yl]stannane

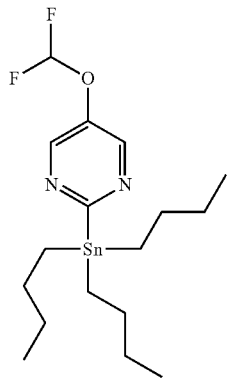 [SMILES: CCC[CH2][Sn]([CH2]CCC)([CH2]CCC)[c]1ncc(OC(F)F)cn1]

To a solution of 2-chloro-5-(difluoromethoxy)pyrimidine (2.70 g, 13.5 mmol) in toluene (50 mL) was added bis(tributyltin) (10.2 mL, 20.2 mmol). The reaction mixture was purged with argon for 5 minutes then tetrakis(triphenylphosphine)palladium(0) (778 mg, 0.673 mmol) was added and the reaction mixture was purged again with argon for another 2 minutes. The resulting reaction mixture was stirred at 100° C. for 16 h. The reaction mixture was cooled to 0° C., diluted with water and extracted twice with ethyl acetate. The combined organic layers were dried over sodium sulfate, filtered and concentrated under reduced pressure. Purification of the crude material by flash chromatography over silica gel (eluting with ethyl acetate in n-hexane) afforded tributyl-[5-(difluoromethoxy)pyrimidin-2-yl]stannane.

¹H-NMR (400 MHz, CDCl₃): δ=8.60 (s, 1H), 7.26 (s, 1H), 6.57 (t, 1H), 1.50-1.70 (m, 6H), 1.25-1.40 (m, 6H), 1.10-1.20 (m, 6H), 0.88 (m, 9H) ppm.

Preparation of 1-[3-[5-(difluoromethoxy)pyrimidin-2-yl]pyrazin-2-yl]ethanone (I23)

(I23)

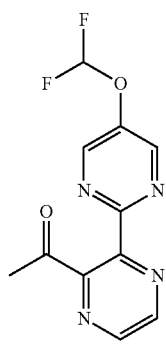

To a mixture of tributyl-[5-(difluoromethoxy)pyrimidin-2-yl]stannane (3.20 g, 6.62 mmol) in toluene (50.0 mL) was added 1-(4-chloropyrimidin-5-yl)ethanone (1267 mg, 7.28 mmol). The reaction mixture was purged with argon for 5 minutes. Tetrakis(triphenylphosphine)palladium(0) (382 mg, 0.331 mmol) and copper iodide (252 mg, 1.32 mmol) were added to the reaction mixture and purged again with argon for another 2 minutes. The resulting reaction mixture was stirred at 100° C. for 16 h. The reaction mixture was cooled to 0° C., diluted with water (100 mL) and extracted with ethyl acetate (2×100 mL). The combined organic layers were dried over sodium sulfate and concentrated in vacuo. The crude material was purified by flash chromatography (silica gel, gradient of ethyl acetate in hexanes) to afford 1-[3-[5-(difluoromethoxy)pyrimidin-2-yl]pyrazin-2-yl]ethenone as a light brown solid.

$^1$H NMR (400 MHz, DMSO-d6) δ ppm: 8.80-9.00 (m, 4H), 7.50 (t, 1H), 2.65 (s, 3H)

Preparation of 1-[3-[5-(difluoromethoxy)pyrimidin-2-yl]pyrazin-2-yl]ethanamine (I29)

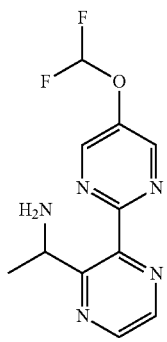

(I29)

To a solution of 1-[3-[5-(difluoromethoxy)pyrimidin-2-yl]pyrazin-2-yl]ethanone (1.70 g, 6.39 mmol) in a solution of saturated ammonium acetate in ethanol (130 mL) were added sodium cyanoborohydride (1.19 g, 19.2 mmol) and 30% aqueous ammonia (50 mL). The mixture was stirred at reflux for 16 h, cooled to room temperature, and concentrated in vacuo. The crude material was purified by reverse phase chromatography (C$_{18}$ column, gradient of acetonitrile in water) to give 1-[3-[5-(difluoromethoxy)pyrimidin-2-yl]pyrazin-2-yl]ethanamine as a light brown gum.

$^1$H NMR (400 MHz, DMSO-d6) δ ppm: 8.80-9.10 (m, 4H), 7.51 (t, 1H), 4.88 (m, 1H), 1.50 (d, 3H)

Preparation of 3-cyclopropyl-N-[1-[3-[5-(difluoromethoxy)pyrimidin-2-yl]pyrazin-2-yl]ethyl]-5-(trifluoro-methyl)benzamide (compound P7)

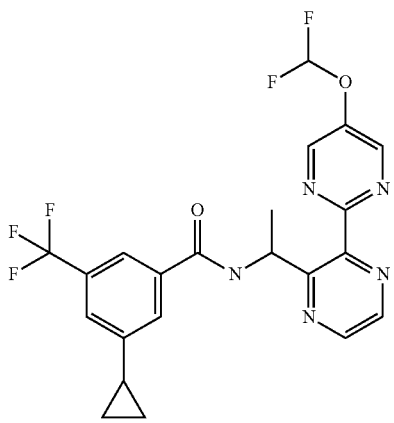

(P7)

To a stirred solution of 3-cyclopropyl-5-(trifluoromethyl)benzoic acid (90%, 0.0861 g, 0.337 mmol) in toluene (5 mL) was added dropwise thionyl chloride (0.0737 mL, 1.01 mmol). The reaction mixture was stirred at reflux for 2 h, then cooled to room temperature and concentrated in vacuo to afford the corresponding acid chloride.

To a solution of 1-[3-[5-(difluoromethoxy)pyrimidin-2-yl]pyrazin-2-yl]ethanamine (90%, 0.100 g, 0.337 mmol) in dichloromethane (2 mL) and triethylamine (0.284 mL, 0.202 mmol) was added dropwise a solution of the previously prepared acid chloride in dichloromethane (3 mL) over 5 minutes. After addition, the reaction mixture was stirred for 2 h at room temperature. It was cooled to 0° C., quenched with water (10 mL) and extracted twice with ethyl acetate (50 mL each). The combined organic layers were dried over sodium sulfate, filtered and concentrated in vacuo. The crude product was purified by flash chromatography (combiflash, silica gel, 0-100% ethyl acetate in hexanes) to afford 3-cyclopropyl-N-[1-[3-[5-(difluoromethoxy)pyrimidin-2-yl]pyrazin-2-yl]ethyl]-5-(trifluoromethyl)benzamide.

$^1$H NMR (400 MHz, chloroform-d) δ ppm: 0.75-0.82 (m, 2H) 1.02 (d, 2H) 1.30 (d, 3H) 2.03-2.12 (m, 1H) 5.54-5.62 (m, 1H) 7.29-7.67 (br t, 1H) 7.61 (d, 2H) 7.80 (s, 1H) 8.70 (s, 1H) 8.79 (s, 1H) 8.94 (s, 2H) 9.06 (d, 1H)

LC-MS (method 1): retention time 7.65 min, m/z 480.1 [M+H]$^+$.

Preparation of 3-[cyclopropyl(difluoro)methyl]-N-[1-[3-[5-(difluoromethoxy)pyrimidin-2-yl]pyrazin-2-yl]ethyl]-5-(trifluoromethyl)benzamide (P29)

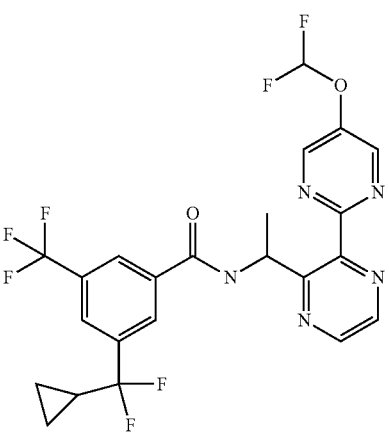

(P29)

To a solution of 3-[cyclopropyl(difluoro)methyl]-5-(trifluoromethyl)benzoic acid (4.72 mg, 0.0168 mmol) in toluene (2.0 mL) was added thionyl chloride (0.0037 mL, 0.051 mmol) dropwise at room temperature. The reaction mixture was stirred at reflux for 2 hours, cooled to room temperature, and concentrated in vacuo. The crude material was dissolved in dichloromethane (1 mL), and a solution of 1-[3-[5-(difluoromethoxy)pyrimidin-2-yl]pyrazin-2-yl]ethanamine (5.0 mg, 0.017 mmol) in dichloromethane (2.0 mL) was added followed by addition of triethylamine (0.0071 mL, 0.051 mmol). The reaction mixture was stirred at room temperature for 2 hours, then cooled down to 0° C. Water was added, the aqueous layer was extracted with ethyl acetate, the combined organic layers were dried over sodium sulfate and concentrated in vacuo. The crude product was purified by flash chromatography (silica gel, gradient of ethyl acetate in hexanes) to afford 3-[cyclopropyl(difluoro) methyl]-N-[1-[3-[5-(difluoromethoxy)pyrimidin-2-yl]pyrazin-2-yl]ethyl]-5-(trifluoromethyl)benzamide as an off-white solid.

¹H-NMR (400 MHz, chloroform-d) δ=0.65-0.75 (m, 4H), 1.10 (t, 1H), 1.63 (d, 3H), 1.70-1.90 (m, 1H), 5.61 (m, 1H), 7.48 (t, 1H), 7.95 (s, 1H), 8.20 (d, 2H), 8.70 (m, 1H), 8.79 (m, 1H), 8.92 (m, 2H), 9.28 (d, 1H) ppm Preparation of N-[1-[3-[5-(difluoromethoxy)pyrimidin-2-yl]pyrazin-2-yl]ethyl]-3-(trifluoromethyl)-5-(trifluoromethylsulfonyl)benzamide (P19)

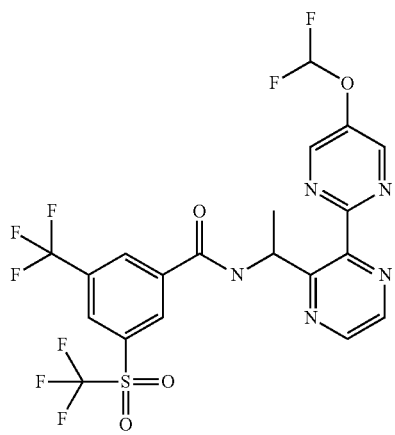

(P19)

To a solution of 3-(trifluoromethyl)-5-(trifluoromethylsulfonyl)benzoic acid (121 mg, 0.337 mmol) in toluene (2.0 mL) was added thionyl chloride (0.0737 mL, 1.01 mmol) dropwise at room temperature. The reaction mixture was stirred at reflux for 2 hours, cooled to room temperature, and concentrated in vacuo. The crude acid chloride was dissolved in dichloromethane (10 mL), and a solution of 1-[3-[5-(difluoromethoxy)pyrimidin-2-yl]pyrazin-2-yl]ethanamine (100.0 mg, 0.337 mmol) in dichloromethane (10.0 mL) was added followed by addition of triethylamine (0.142 mL, 1.01 mmol). The reaction mixture was stirred at room temperature for 2 hours, then cooled down to 0° C. Water was added, the aqueous layer was extracted with ethyl acetate, the combined organic layers were dried over sodium sulfate and concentrated in vacuo. The crude product was purified by flash chromatography (silica gel, gradient of ethyl acetate in hexanes) to afford N-[1-[3-[5-(difluoromethoxy)pyrimidin-2-yl]pyrazin-2-yl]ethyl]-3-(trifluoromethyl)-5-(trifluoromethylsulfonyl)benzamide as an off-white solid.

¹H-NMR (400 MHz, chloroform-d) δ=1.63 (d, 3H), 5.61 (m, 1H), 7.48 (t, 1H), 8.52 (s, 1H), 8.65-8.73 (m, 3H), 8.79 (d, 1H), 8.92 (s, 2H), 9.57 (s, 1H) ppm Preparation of 2-bromo-5-(2,2,2-trifluoroethoxy)pyridine

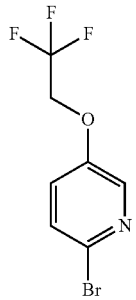

To a solution of 6-bromopyridin-3-ol (20.0 g, 115 mmol) and potassium carbonate (31.8 g, 230 mmol) in acetonitrile (200 mL), stirred at room temperature for 5 min, was added 2,2,2-Trifluoroethyl trifluoromethanesulfonate (29.3 g, 126 mmol). The reaction mixture was stirred at room temperature for 16 h. The reaction mixture was poured in ice cold water and extracted with ethyl acetate. The combined organic layers were washed with brine, dried over sodium sulfate, filtered and concentrated under reduced pressure. Purification of the crude material by flash chromatography over silica gel (eluting with ethyl acetate in n-hexane) afforded 2-bromo-5-(2,2,2-trifluoroethoxy)pyridine.

¹H-NMR (400 MHz, CDCl₃): δ=8.15 (d, 1H), 7.45 (d, 1H), 7.2 (dd, 1H), 4.4 (q, 2H) ppm.

Preparation of tributyl-[5-(2,2,2-trifluoroethoxy)-2-pyridyl]stannane

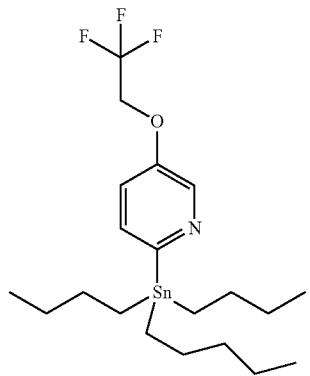 [SMILES: CCCC[CH2][Sn]([CH2]CCC)([CH2]CCC)[c]1ccc(OCC(F)(F)F)cn1]

To a solution of 2-bromo-5-(2,2,2-trifluoroethoxy)pyridine (9.00 g, 31.6 mmol) in toluene (300 mL) was added bis(tributyltin) (20.7 mL, 41.1 mmol). The reaction mixture was purged with argon for 20 minutes then tetrakis(triphenylphosphine)palladium(0) (2.74 g, 2.37 mmol) was added and the reaction mixture was purged again with argon for another 2 minutes. The resulting reaction mixture was stirred at 100° C. for 48 h. The reaction mixture was cooled to 0° C., diluted with water and extracted with ethyl acetate. Combined organic layers were dried over sodium sulfate, filtered and concentrated under reduced pressure. Purification of the crude material by flash chromatography over silica gel (eluting with ethyl acetate in n-hexane) afforded tributyl-[5-(2,2,2-trifluoroethoxy)-2-pyridyl]stannane.

¹H-NMR (400 MHz, CDCl₃): δ=8.55 (d, 1 h), 7.4 (dd, 1H), 7.15 (m, 1H), 4.4 (q, 2H), 1.55 (m, 6H), 1.35 (m, 6H), 1.15 (m, 6H), 0.95 (m, 9H) ppm.

Preparation of 1-[3-[5-(2,2,2-trifluoroethoxy)-2-pyridyl]pyrazin-2-yl]ethanone (I25)

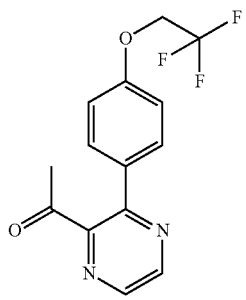

To a solution of tributyl-[5-(2,2,2-trifluoroethoxy)-2-pyridyl]stannane (550 mg, 1.06 mmol) in toluene (20 mL) were added 1-(3-chloropyrazin-2-yl)ethanone (203 mg, 1.17 mmol) and copper(I) iodide (40.4 mg, 0.212 mmol). The reaction mixture was purged with argon for 10 min and tetrakis(triphenylphosphine)palladium(0) (61.4 mg, 0.0531 mmol) was added. The reaction was stirred at 100° C. for 2 h. The reaction mixture was cooled to 0° C., diluted with water and extracted with ethyl acetate. Organic phase was dried over sodium sulfate, filtered and concentrated under reduced pressure. Purification of the crude material by flash chromatography over silica gel (eluting with ethyl acetate in n-hexane) afforded 1-[3-[5-(2,2,2-trifluoroethoxy)-2-pyridyl]pyrazin-2-yl]ethanone.

¹H-NMR (400 MHz, DMSO-d6): δ=8.85 (d, 1H), 8.7 (m, 1H), 8.45 (s, 1H), 8.25 (d, 1H), 7.75 (d, 1H), 5 (q, 2H), 2.6 (s, 3H) ppm.

Preparation of 1-[3-[5-(2,2,2-trifluoroethoxy)-2-pyridyl]pyrazin-2-yl]ethanamine (I31)

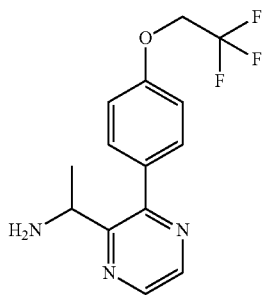

To a solution of 1-[3-[5-(2,2,2-trifluoroethoxy)-2-pyridyl]pyrazin-2-yl]ethanone (1.80 g, 5.45 mmol) in a saturated solution of ammonium acetate in ethanol (120 mL) were added at room temperature sodium cyanoborohydride (1.01 g, 16.4 mmol) and ammonia (30% in water, 50 mL). The reaction mixture was stirred at reflux for 18 hours. After cooling down to room temperature, it was concentrated under reduced pressure. Purification of the crude material by reverse-phase chromatography (eluting acetonitrile in water) afforded 1-[3-[5-(2,2,2-trifluoroethoxy)-2-pyridyl]pyrazin-2-yl]ethanamine.

¹H-NMR (400 MHz, DMSO-d6): δ=8.8 (s, 2H), 8.65 (d, 1H), 8.15 (d, 1H), 7.8 (m, 1H), 7.45 (br s, 2H), 7.25 (m, 1H), 7.15 (m, 1H), 5.2 (br s, 1H), 5 (q, 2H), 1.5 (m, 3H) ppm.

Preparation of 2-(1-cyanocyclopropyl)-N-[1-[3-[5-(2,2,2-trifluoroethoxy)-2-pyridyl]pyrazin-2-yl]ethyl]-6-(trifluoromethyl)pyridine-4-carboxamide (compound P23)

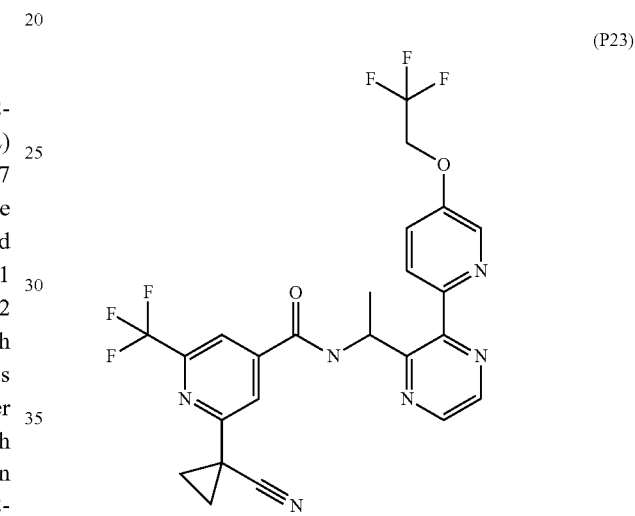

To a solution of 2-(1-cyanocyclopropyl)-6-(trifluoromethyl)pyridine-4-carboxylic acid (85.9 mg, 0.302 mmol) in toluene (5 mL) was added dropwise at 0° C. thionyl chloride (66 µL, 0.0905 mmol). The reaction mixture was stirred at 90° C. for 20 hours. After cooling down to room temperature, it was concentrated under reduced pressure. The resulting residue was dissolved in dichloromethane (10 mL) and added at 0° C. to a solution of 1-[3-[5-(2,2,2-trifluoroethoxy)-2-pyridyl]pyrazin-2-yl]ethanamine (100 mg, 0.302 mmol) and triethylamine (0.127 mL, 0.905 mmol) in dichloromethane (10 mL). The reaction mixture was stirred at room temperature for 2 hours. It was then diluted with dichloromethane and washed with water. The organic layer was dried over sodium sulfate, filtered and concentrated under reduced pressure. Purification of the crude material by flash chromatography over silica gel (eluting with ethyl acetate in n-hexane) afforded 2-(1-cyanocyclopropyl)-N-[1-[3-[5-(2,2,2-trifluoroethoxy)-2-pyridyl]pyrazin-2-yl]ethyl]-6-(trifluoromethyl)pyridine-4-carboxamide.

¹H-NMR (400 MHz, DMSO-d6): δ=9.5 (d, 1H), 8.75 (dd, 2H), 8.55 (m, 1H), 8.15 (s, 1H), 8.05 (d, 1 h), 8 (s, 1H), 7.75 (dd, 1H), 5.9 (t, 1H), 5 (q, 2H), 1.95 (m, 2H), 1.75 (m, 2H), 1.65 (dd, 3H) ppm.

Preparation of
2-chloro-5-(2,2,2-trifluoroethoxy)pyrimidine

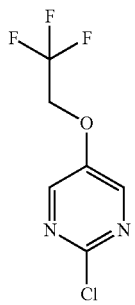

To a solution of 2-chloropyrimidin-5-ol (1.0 g, 7.7 mmol) in N,N-dimethylformamide (7.7 mL), was added cesium carbonate (3.2 g, 10 mmol). 2,2,2-trifluoroethyl trifluoromethanesulfonate (2.2 g, 9.2 mmol) was added dropwise to the mixture. The mixture was stirred at room temperature for 18 hours. The reaction mixture was poured into ice-water then extracted with ethyl acetate. The combined organic layers were washed four times with water, then with brine, They were dried over sodium sulfate and concentrated in vacuo. Purification of the crude material by flash chromatography over silica gel (eluting with ethyl acetate in n-hexane) afforded 2-chloro-5-(2,2,2-trifluoroethoxy)pyrimidine as a light yellow oil.

$^1$H NMR (400 MHz, Chloroform) δ ppm 4.46-4.52 (m, 2H) 8.40 (s, 2H)

$^{19}$F NMR (377 MHz, Chloroform) δ ppm −73.74 (s)

Preparation of tributyl-[5-(2,2,2-trifluoroethoxy)pyrimidin-2-yl]stannane

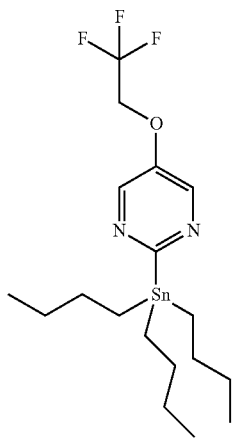 [SMILES: CCC[CH2][Sn]([CH2]CCC)([CH2]CCC)[c]1ncc(OCC(F)(F)F)cn1]

To a solution of 2-chloro-5-(2,2,2-trifluoroethoxy)pyrimidine (1.00 g, 4.70 mmol) in toluene (10 mL) was added bis(tributyltin) (4.09 g, 7.06 mmol). The reaction mixture was purged with argon for 5 minutes then tetrakis(triphenylphosphine)palladium(0) (0.544 g, 0.470 mmol) was added and the reaction mixture was purged again with argon for another 5 minutes. The resulting reaction mixture was stirred at 100° C. for 16 hours. The reaction mixture was filtered over Celite and the filtrate was concentrated under reduced pressure. Purification of the crude material by flash chromatography over neutral alumina (eluting with ethyl acetate in n-hexane) afforded tributyl-[5-(2,2,2-trifluoroethoxy)pyrimidin-2-yl]stannane.

$^1$H-NMR (400 MHz, CDCl$_3$): δ=8.50 (s, 1H), 8.40 (s, 1H), 4.43 (m, 2H), 4.12 (q, 2H), 1.50-1.70 (m, 6H), 1.20-1.45 (m, 6H), 1.10-1.20 (m, 6H), 0.83-0.98 (m, 9H) ppm.

Preparation of 1-[3-[5-(2,2,2-trifluoroethoxy)pyrimidin-2-yl]pyrazin-2-yl]ethanone (I24)

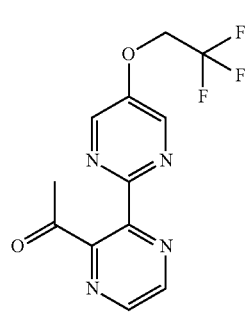

(I24)

To a solution of tributyl-[5-(2,2,2-trifluoroethoxy)-2-pyridyl]stannane (1.00 g, 2.14 mmol) in toluene (20 mL) were added 1-(3-chloropyrazin-2-yl)ethanone (0.402 g, 2.57 mmol). The reaction mixture was purged with argon for 5 min then copper(I) iodide (0.0815 g, 0.428 mmol) and [1,1'-bis(diphenylphosphino)ferrocene] dichloropalladium (II) (1.57 g, 2.14 mmol) were added. The reaction was stirred at 100° C. for 4 hours. The reaction mixture was cooled to 0° C., filtered through celite and the filtrate was concentrated under reduced pressure. Purification of the crude material by flash chromatography over silica gel (eluting with ethyl acetate in n-hexane) afforded 1-[3-[5-(2,2,2-trifluoroethoxy)pyrimidin-2-yl]pyrazin-2-yl]ethanone. m/z=299.1 [M+H]$^+$ Preparation of 1-[3-[5-(2,2,2-trifluoroethoxy)pyrimidin-2-yl]pyrazin-2-yl]ethanamine (I30)

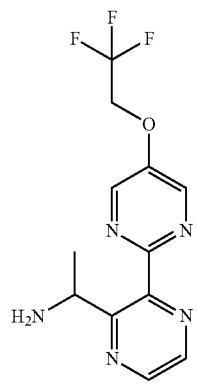

(I30)

To a solution of 1-[3-[5-(2,2,2-trifluoroethoxy)pyrimidin-2-yl]pyrazin-2-yl]ethanone (700 mg, 1.88 mmol) in a saturated solution of ammonium acetate in ethanol (100 mL) were added at room temperature sodium cyanoborohydride (0.354 g, 5.63 mmol) and ammonia (30% in water, 30 mL). The reaction mixture was stirred at reflux for 18 hours. After cooling down to room temperature, the mixture was washed with dichloromethane. The aqeuous layer was concentrated in vacuo. Purification of the crude material by reverse-phase chromatography (eluting acetonitrile in water) afforded 1-[3-[5-(2,2,2-trifluoroethoxy)pyrimidin-2-yl]pyrazin-2-yl] ethanamine.

$^1$H-NMR (400 MHz, DMSO-d6): δ=8.95 (s, 2H), 8.60-9.00 (m, 2H), 7.8-8.30 (br s, 2H), 5.08-5.20 (m, 2H), 4.95-5.05 (m, 1H), 1.5 (m, 3H) ppm.

Preparation of 2-(1-cyanocyclopropyl)-N-[1-[3-[5-(2,2,2-trifluoroethoxy)pyrimidin-2-yl]pyrazin-2-yl] ethyl]-6-(trifluoromethyl)pyridine-4-carboxamide (compound P34)

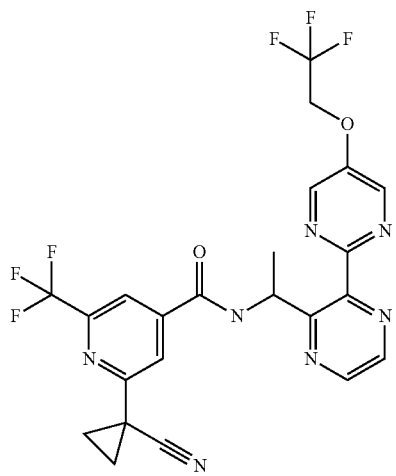

(P34)

To a stirred solution of 1-[3-[5-(2,2,2-trifluoroethoxy) pyrimidin-2-yl]pyrazin-2-yl]ethanamine (30.0 mg, 0.100 mmol) in N,N-dimethylformamide (2.0 mL) was added 2-(1-cyanocyclopropyl)-6-(trifluoromethyl)pyridine-4-carboxylic acid (0.0257 g, 0.100 mmol), propanephosphonic acid anhydride (T3P®) (0.0957 g, 0.301 mmol) and N,N-Diisopropylethylamine (0.0389 g, 0.301 mmol) at 0° C. The mixture was stirred at room temperature for 5 h. The reaction mixture was diluted with water (30 mL) and extracted twice with dichloromethane. The combined organic layers were washed with brine (30 mL), dried over sodium sulfate and concentrated in vacuo. Purification of the crude material by reverse phase chromatography ($C_{18}$ column, gradient of acetonitrile in water) afforded 2-(1-cyanocyclopropyl)-N-[1-[3-[5-(2,2,2-trifluoroethoxy)pyrimidin-2-yl]pyrazin-2-yl] ethyl]-6-(trifluoromethyl)pyridine-4-carboxamide as an off-white solid.

$^1$H-NMR (400 MHz, DMSO-d6): δ=9.45 (d, 1H), 8.82-8.90 (m, 2H), 8.75-8.80 (m, 1H), 8.68-8.75 (m, 1H), 8.16-8.22 (m, 1H), 7.95-8.15 (m, 1H), 5.60-5.70 (m, 1H), 5.00-5.15 (m, 2H), 1.90-1.98 (m, 2H), 1.70-1.80 (m, 2H), 1.56-1.65 (d, 3H) ppm.

Preparation of 6-tributylstannylpyridine-3-carbonitrile

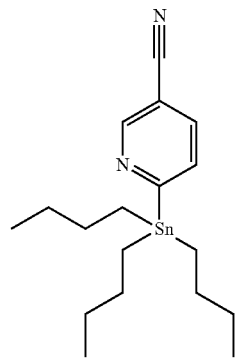 [SMILES: CCC[CH2][Sn]([CH2]CCC)([CH2]CCC)[c]1ccc(C#N)cn1]

To a solution of 6-chloropyridine-3-carbonitrile (250 mg, 1.80 mmol) in toluene (10 mL) was added hexa-n-butylditin (1.00 mL, 1.98 mmol). The reaction mixture was purged with argon for 2 minutes. Then tetrakis(triphenylphosphine) palladium(0) (146 mg, 0.126 mmol) was added and it was purged again with argon for additional 2 minutes. The resulting reaction mixture was heated up to 130° C. and stirred for 16 hours. After cooling down to room temperature, the reaction mixture was filtered through Celite. The filtrate was concentrated under reduced pressure. Purification of the crude material by neutral alumina flash chromatography (eluting with ethyl acetate in hexane) afforded 6-tributylstannylpyridine-3-carbonitrile.

$^1$H-NMR (400 MHz, CDCl$_3$): δ=8.90-9.00 (m, 1H), 7.65-7.75 (m, 1H), 7.50-7.60 (m, 1H), 7.25-7.40 (m, 2H), 1.45-1.65 (m, 4H), 1.25-1.40 (m, 7H), 1.10-1.20 (m, 5H), 0.80-0.95 (m, 9H) ppm.

Preparation of 6-(3-acetylpyrazine-2-yl)pyridine-3-carbonitrile (I21)

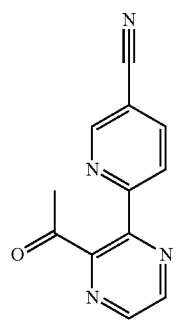

(I21)

To a solution of 6-tributylstannylpyridine-3-carbonitrile (24.0 g, 48.8 mmol) in toluene (600 mL) were added 1-(4-chloropyrimidin-5-yl)ethanone (9.18 g, 52.7 mmol) and copper(I) iodide (1.86 g, 9.77 mmol). The reaction mixture was purged with argon for 10 minutes. Then tetrakis (triphenylphosphine)palladium(0) (2.82 g, 2.44 mmol) was added. The reaction mixture was heated up to 95° C. and stirred for 5 hours. After cooling down to room temperature, it was filtered through Celite and the filtrate was concentrated under reduced pressure. Purification of the crude material by flash chromatography over silica gel (eluting with ethyl acetate in hexane) afforded 6-(3-acetylpyrazin-2-yl)pyridine-3-carbonitrile.

$^1$H-NMR (400 MHz, d6-DMSO): δ=9.1 (m, 2H), 8.92 (m, 1H), 8.83 (m, 1H) 8.53 (d, 1H) 8.32 (d, 1H) 2.65 (s, 3H) ppm.

Preparation of 6-[3-(1-aminoethyl)pyrazin-2-yl]pyridine-3-carbonitrile (I27)

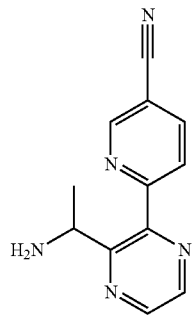

(I27)

To a solution of 6-(3-acetylpyrazin-2-yl)pyridine-3-carbonitrile (0.200 g, 0.803 mmol) in a saturated solution of ammonium acetate in ethanol (30 mL) were added at room temperature aqueous ammonia (20 mL) and sodium cyanoborohydride (154 mg, 2.41 mmol). The reaction mixture was heated up to reflux and stirred for 12 hours. After cooling down to room temperature, it was concentrated under reduced pressure. Purification of the crude material by reverse-phase chromatography (eluting acetonitrile in water) afforded 6-[3-(1-aminoethyl)pyrazin-2-yl]pyridine-3-carbonitrile.

$^1$H-NMR (400 MHz, d6-DMSO): δ=9.22 (s, 1H), 8.85-8.95 (m, 2H), 8.50-8.60 (m, 1H), 8.30-8.40 (m, 1H) 7.80-8.10 (br. s, 2H), 5.25-5.35 (m, 1H), 1.52 (d, 3H) ppm.

Preparation of 3-(1-cyanocyclopropyl)-N-[1-[3-(5-cyano-2-pyridyl)pyrazin-2-yl]ethyl]-5-(trifluoromethyl)benzamide (P25)

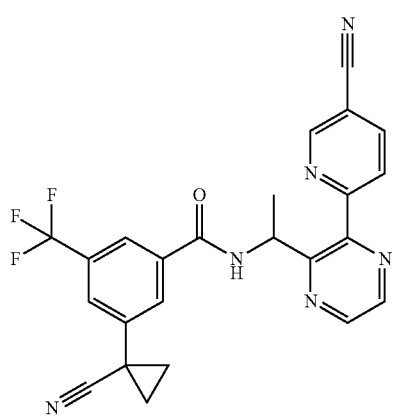

(P25)

To a solution of 3-[cyano(cyclopropyl)methyl]-5-(trifluoromethyl)benzoic acid (0.130 g, 0.459 mmol) in toluene (20 mL) was added dropwise at 0° C. thionyl chloride (0.134 mL, 1.83 mmol). The reaction mixture was heated up to 90° C. and stirred for 20 hours. After cooling down to room temperature, it was concentrated under reduced pressure. The resulting residue was dissolved in dichloromethane (10 mL) and added at 0° C. to a solution of 6-[3-(1-aminoethyl)pyrazin-2-yl]pyridine-3-carbonitrile (0.126 g, 0.505 mmol) and triethylamine (0.258 mL, 1.83 mmol) in dichloromethane (5 mL). The reaction mixture was stirred at room temperature for 2 hours. It was then diluted with dichloromethane and washed with water. The organic layer was dried over sodium sulfate, filtered and concentrated under reduced pressure. Purification of the crude material by flash chromatography over silica gel (eluting with ethyl acetate in hexane) afforded 3-(1-cyanocyclopropyl)-N-[1-[3-(5-cyano-2-pyridyl)pyrazin-2-yl]ethyl]-5-(trifluoromethyl)benzamide.

$^1$H-NMR (400 MHz, d6-DMSO): δ=9.28 (d, 1H), 9.15-9.20 (m, 1H), 8.72-8.80 (d, 1H), 8.65-8.72 (d, 1H), 8.45-8.55 (m, 1H), 8.19 (d, 1H), 8.06 (s, 1H), 7.95 (s, 1H), 7.75 (s, 1H), 5.78 (t, 1H), 1.80-1.87 (m, 2H), 1.60-1.75 (m, 5H) ppm.

Preparation of 2-(1-cyanocyclopropyl)-N-[1-[3-(5-cyano-2-pyridyl)pyrazin-2-yl]ethyl]-6-(trifluoromethyl)pyridine-4-carboxamide (compound P16)

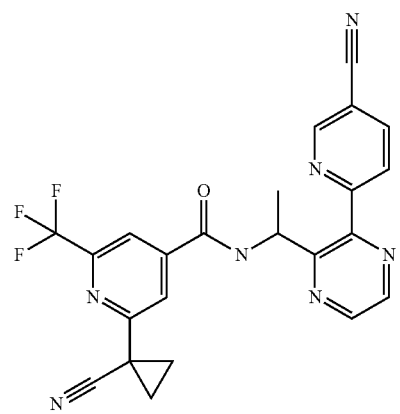

(P16)

Under argon, thionyl chloride (0.14 mL, 1.93 mmol) was added dropwise to a stirred solution of 2-(1-cyanocyclopropyl)-6-(trifluoromethyl)pyridine-4-carboxylic acid (I17, 130 mg, 0.482 mmol) in toluene (20 mL) at 0° C. The solution was heated at 90° C. for 2 h then the reaction mixture was concentrated in vacuo. The residue was diluted in dichloromethane (10 mL) and added to a stirred solution of 6-[3-(1-aminoethyl)pyrazin-2-yl]pyridine-3-carbonitrile (121 mg, 0.482 mmol) and triethylamine (0.271 mL, 1.93 mmol) in dichloromethane (10 mL) at 0° C. The reaction mixture was stirred for 2 hours at room temperature, then diluted with dichloromethane and washed with water. The organic layer was dried over sodium sulfate, filtered and concentrated under reduced pressure. The crude material was purified by reverse phase chromatography ($C_{18}$ column, gradient of acetonitrile in water) to afford 2-(1-cyanocyclopropyl)-N-[1-[3-(5-cyano-2-pyridyl)pyrazin-2-yl]ethyl]-6-(trifluoromethyl)pyridine-4-carboxamide as a white solid.

$^1$H-NMR (400 MHz, d6-DMSO): δ=9.55 (d, 1H), 9.18 (m, 1H), 8.78 (d, 1H), 8.71 (d, 1H), 8.52 (dd, 1H), 8.20 (d,

1H), 8.11 (s, 1H), 7.96 (s, 1H), 5.81 (m, 1H), 1.91 (m, 2H), 1.71-1.80 (m, 2H), 1.67 (d, 3H) ppm.

$^{19}$F NMR (377 MHz, d6-DMSO) δ=−66.70 (s) ppm

Preparation of N-[1-[3-(5-cyano-2-pyridyl)pyrazin-2-yl]ethyl]-3-(1-methoxycyclopropyl)-5-(trifluoromethyl)benzamide (P50)

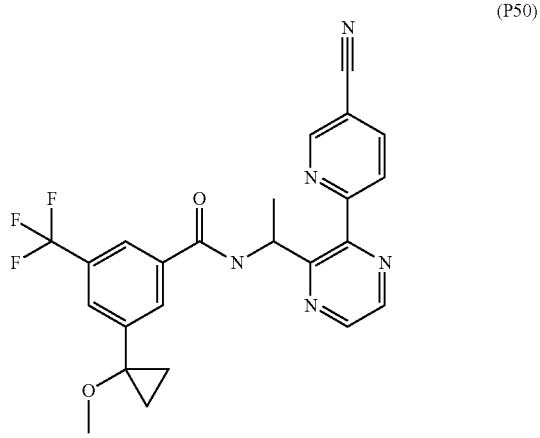 [SMILES: COC1(c2cc(C(=O)NC(C)c3nccnc3-c3ccc(C#N)cn3)cc(C(F)(F)F)c2)CC1]

Thionyl chloride (0.108 mL, 1.48 mmol) was added dropwise to a stirred solution of 3-(1-methoxycyclopropyl)-5-(trifluoromethyl)benzoic acid (I39, 130 mg, 0.493 mmol) in toluene (3 mL) at 0° C. The reaction mixture was heated up to 90° C. and stirred for 2 hours. After cooling down to room temperature, it was concentrated under reduced pressure. The resulting residue was dissolved in dichloromethane (2 mL) and added to a solution of 6-[3-(1-aminoethyl)pyrazin-2-yl]pyridine-3-carbonitrile (0.125 g, 0.542 mmol) and triethylamine (0.208 mL, 1.48 mmol) in dichloromethane (2 mL). The reaction mixture was stirred at room temperature for 2 hours. It was then diluted with dichloromethane and washed with water. The organic layer was dried over sodium sulfate, filtered and concentrated under reduced pressure. Purification of the crude material by reverse phase chromatography ($C_{18}$ column, gradient of acetonitrile in water) afforded N-[1-[3-(5-cyano-2-pyridyl)pyrazin-2-yl]ethyl]-3-(1-methoxycyclopropyl)-5-(trifluoromethyl)benzamide as an off-white solid. 1H-NMR (400 MHz, d6-DMSO): δ=9.12-9.35 (m, 2H), 8.75-8.80 (d, 1H), 8.68-8.75 (d, 1H), 8.46-8.52 (m, 1H), 8.19 (d, 1H), 7.97 (s, 1H), 7.82 (s, 1H), 7.66 (s, 1H), 5.71-5.82 (m, 1H), 3.13 (s, 3H), 1.68 (d, 2H), 1.20-1.28 (m, 2H), 1.08-1.12 (m, 2H) ppm.

Preparation of 1-(3-chloropyrazin-2-yl)ethanamine

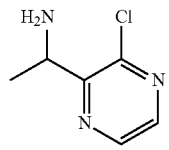

To a of 1-(3-chloropyrazin-2-yl)ethanone (0.200 g, 1.28 mmol) in methanol (4.5 mL) were added at room temperature ammonium acetate (0.995 g, 12.8 mmol) and sodium cyanoborohydride (0.0591 g, 0.894 mmol). The resulting suspension was stirred at room temperature for 18 hours, then concentrated in vacuo. The crude material was purified by reverse phase chromatography ($C_{18}$ column, gradient of acetonitrile in water) to afford 1-(3-chloropyrazin-2-yl)ethanamine.

$^{1}$H NMR (400 MHz, CDCl$_3$) δ=8.49 (d, 1H), 8.26 (d, 1H), 4.56 (q, 1H), 1.95 (br s, 2H), 1.44 (d, 3H) ppm Preparation of (1S)-1-(3-chloropyrazin-2-yl)ethanamine (I34)

To a solution if 1-(3-chloropyrazin-2-yl)ethanamine (202.2 mg, 1.20 mmol) in tert-butyl methyl ether (11 mL) was added Novozym® 435 (240 mg), followed by ethyl methoxyacetate (1.44 mL, 12.0 mmol) at room temperature. The mixture was stirred at 40° C. for 5.5 hours. The reaction mixture was diluted with dichloromethane and filtered. The filtrate was concentrated in vacuo. The crude material was purified by flash chromatography over silica gel (eluting with a gradient of methanol in dichloromethane) to afford (1S)-1-(3-chloropyrazin-2-yl)ethanamine.

$^{1}$H NMR (400 MHz, CDCl$_3$) δ=8.49 (d, 1H), 8.27 (d, 1H), 4.56 (q, 1H), 1.73 (br s, 2H), 1.44 (d, 3H) ppm [α]$_D^{20}$: −32.3° (c: 1.157, CHCl$_3$)

Preparation of (1R)-1-(3-chloropyrazin-2-yl)ethanol (I26)

1-(3-chloropyrazin-2-yl)ethanone (157 mg, 1.00 mmol) was dissolved in dichloromethane (10.0 mL) and the flask was evacuated and backfilled with argon three times. Then RuBF$_4$[(R,R)-TsDPEN](p-cymene) (0.0362 g, 0.0526 mmol) was added. A cooled solution of triethylamine (0.348 mL, 2.50 mmol.) and formic acid (0.160 mL, 4.29 mmol) was added dropwise to the reaction mixture, which was stirred at room temperature for 4 hours. The reaction mixture was concentrated in vacuo. The crude material was purified by flash chromatography over silica gel (eluting with a gradient of ethyl acetate in cyclohexane) to afford (1R)-1-(3-chloropyrazin-2-yl)ethanol.

$^{1}$H-NMR (400 MHz, CDCl$_3$) δ=8.49 (d, 1H), 8.34 (d, 1H), 5.18 (m, 1H), 3.81 (d, 1H), 1.52 (d, 3H) ppm Chiral SFC (method 2): 1.98 min (minor enantiomer), 2.55 min (major enantiomer); ee=85%

Preparation of (1S)-1-(3-chloropyrazin-2-yl) ethanamine (I34)

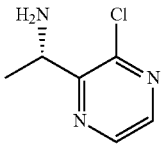

(1R)-1-(3-chloropyrazin-2-yl)ethanol (87.8 mg, 0.554 mmol) was dissolved in tetrahydrofuran (1.9 mL). Then, 1,8-diazabicyclo[5.4.0]undec-7-ene (0.10 mL, 0.66 mmol) was added dropwise to the reaction mixture followed by diphenylphosphine azide (0.130 mL, 0.585 mmol). The reaction mixture was stirred at rt for 19 hours. Tetrahydrofuran (1.4 mL) was added, followed by triphenylphosphine (179.4 mg, 0.677 mmol). The reaction mixture was stirred at room temperature for 2 hours. Water (0.15 mL) was added, and the reaction mixture was stirred at room temperature for 46 hours. The reaction mixture was concentrated to a volume of 1 mL then diluted with dichloromethane. 1 M hydrochloric acid was added, then the aqueous layer was washed with dichloromethane. The aqueous layer was basified to pH=14 with 4 M sodium hydroxide solution and extracted with dichloromethane. The combined organic layers were dried over magnesium sulfate and concentrated in vacuo. The crude material was purified by flash chromatography over silica gel (eluting with a gradient of methanol in dichloromethane) to afford (1S)-1-(3-chloropyrazin-2-yl) ethanamine.

$^1$H NMR (400 MHz, CDCl$_3$) δ=8.49 (d, 1H), 8.27 (d, 1H), 4.56 (q, 1H), 1.84 (s, 2H), 1.44 (d, 3H) ppm [α]$_D^{20}$: −26.0° (c: 0.960, CHCl$_3$)

Preparation of (2R)—N-[(1S)-1-(3-chloropyrazin-2-yl)ethyl]-2-hydroxy-2-phenyl-acetamide

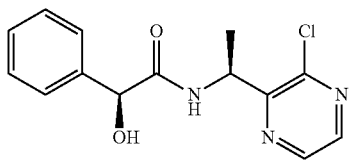 [SMILES: C[C@H](NC(=O)[C@@H](O)c1ccccc1)c1nccnc1Cl]

To a solution of 1-(3-chloropyrazin-2-yl)ethanamine;hydrochloride (700 mg, 3.61 mmol) in dichloromethane (18 mL) were added (R)-(−)-mandelic acid (610 mg, 3.97 mmol), N-ethyldiisopropylamine (1.26 mL, 7.21 mmol), 1-hydroxybenzotriazole (50.8 mg, 0.361 mmol) and N,N'-dicylohexylcarbodiimide (844 mg, 3.97 mmol). The reaction mixture was stirred at room temperature for 18 hours. The reaction mixture was diluted with saturated aqueous sodium carbonate solution and extracted with dichloromethane. The organic layers were dried over magnesium sulfate and concentrated in vacuo. Purification of the crude material by flash chromatography over silica gel (eluting with methanol in dichloromethane) afforded (2R)—N-[(1R)-1-(3-chloropyrazin-2-yl)ethyl]-2-hydroxy-2-phenyl-acetamide and (2R)—N-[(1R)-1-(3-chloropyrazin-2-yl)ethyl]-2-hydroxy-2-phenyl-acetamide. The relative stereochemistry of (2R)—N-[(1R)-1-(3-chloropyrazin-2-yl)ethyl]-2-hydroxy-2-phenyl-acetamide was determined by X-ray crystallography (crystallized from acetonitrile/water).

Analytical data for (2R)—N-[(1R)-1-(3-chloropyrazin-2-yl)ethyl]-2-hydroxy-2-phenyl-acetamide:
LCMS: Rt 0.74, m/z=291 (M+H$^+$)

Preparation of (1S)-1-(3-chloropyrazin-2-yl) ethanamine;hydrochloride

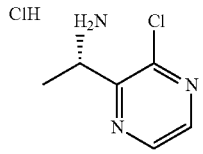

A solution of (2R)—N-[(1S)-1-(3-chloropyrazin-2-yl) ethyl]-2-hydroxy-2-phenyl-acetamide (0.93 g, 3.2 mmol) in hydrochloric acid (32% in water, 13 mL) was heated up to reflux and stirred for 2 hours. After cooling down to room temperature, the reaction mixture was basified with 3 N sodium hydroxide and diluted and extracted with ethyl acetate. The aqueous layer was freeze-dried overnight and the resulting solid was suspended in acetone. The suspension was filtered and the filtrate was concentrated under reduced pressure. The resulting oil was dissolved in ethyl acetate and 1 N hydrochloric acid was added. A precipitate appeared, it was filtered and dried under reduced pressure to afford the desired product. LCMS: Rt 0.19, m/z=158 (M+H+).

Preparation of (1S)-1-(3-chloropyrazin-2-yl)-N-(cyclopropylmethyl)ethanamine (I35)

(I35)

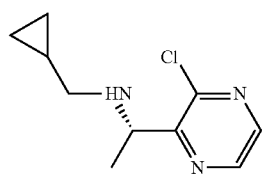

Sodium triacetoxyborohydride (59.4 mg, 0.267 mmol) was added to a stirred solution of (1S)-1-(3-chloropyrazin-2-yl)ethanamine (30.0 mg, 0.190 mmol), cyclopropanecarboxyladehyde (15.0 mg, 0.209 mmol) and acetic acid (0.0109 mL, 0.190 mmol) in 1,2-dichloroethane (0.95 mL). The mixture was stirred at room temperature for 4 hours. Saturated aqueous sodium carbonate solution was added, the aqueous layer was extracted with dichloromethane. The organic layer was dried over magnesium sulfate and concentrated in vacuo. The crude material was purified by flash chromatography over silica gel (eluting with ethyl acetate in cyclohexane) to afford (1S)-1-(3-chloropyrazin-2-yl)-N-(cyclopropylmethyl)ethanamine. $^1$H NMR (400 MHz, Solvent) δ=−0.03-0.10 (m, 2H) 0.38-0.52 (m, 2H) 0.83-1.00 (m, 1H) 1.40 (d, 3H) 2.07 (dd, 1H) 2.15-2.29 (m, 1H) 2.53 (dd, 1H) 4.39 (q, 1H) 8.26 (d, 1H) 8.51 (d, 1H) ppm

[α]$_D^{20}$=−54° (c 0.327, CHCl$_3$)

Preparation of tert-butyl N-[(1S)-3-(5-bromo-2-pyridyl)-2-hydroxy-1-methyl-3-oxo-propyl]carbamate

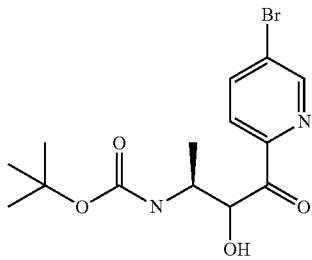 [SMILES: C[C@H](NC(=O)OC(C)(C)C)C(O)C(=O)c1ccc(Br)cn1]

In a round-bottomed flask was prepared a solution of tert-butyl N-[(1S)-1-methyl-2-oxo-ethyl]carbamate (CAS 79069-50-4, 1.07 g, 6.18 mmol) in dichloromethane (12 mL). The flask was evacuated and refilled with argon three times. Then, 2-(3-benzyl-4-methyl-thiazol-3-ium-5-yl)ethanol;bromide (0.388 g, 1.24 mmol), 5-bromopyridine-2-carbaldehyde (CAS 31181-90-5, 1.81 g, 9.27 mmol) and dichloromethane (6 mL) were added successively, followed by N,N-diisopropylethylamine (2.16 mL, 12.4 mmol). The reaction mixture was stirred for 1 hour at room temperature. It was quenched with ammonium chloride sat. aq. and extracted three times with dichloromethane. The combined organic layers were dried over magnesium sulfate, filtered and concentrated under reduced pressure. Purification of the crude material by flash chromatography over silica gel (eluting with ethyl acetate in cyclohexane) afforded tert-butyl N-[(1S)-3-(5-bromo-2-pyridyl)-2-hydroxy-1-methyl-3-oxo-propyl]carbamate as an orange gum.

LCMS: Rt 0.98, m/z=359-361 (M+H$^+$) (Bromo pattern); $^1$H-NMR (400 MHz, CDCl$_3$) δ=1.37-1.40 (m, 3H) 1.43-1.44 (m, 9H) 4.34-4.69 (m, 2H) 5.22-5.36 (m, 1H) 7.86-8.08 (m, 2H) 8.73 (d, J=2.20 Hz, 1H) ppm.

Preparation of tert-butyl N-[(1S)-3-(5-bromo-2-pyridyl)-1-methyl-2,3-dioxo-propyl]carbamate

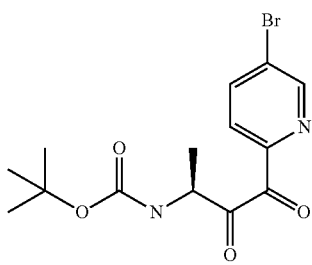 [SMILES: C[C@H](NC(=O)OC(C)(C)C)C(=O)C(=O)c1ccc(Br)cn1]

To a solution of tert-butyl N-[(1S)-3-(5-bromo-2-pyridyl)-2-hydroxy-1-methyl-3-oxo-propyl]carbamate (15.2 g, 42.3 mmol) in dichloromethane (100 mL) and dimethyl sulfoxide (20 mL) were added at 0° C. N,N-diisopropylethylamine (21.8 mL, 127 mmol, 3.00 equiv.) and in two portions sulfur trioxide pyridine complex (13.9 g, 84.6 mmol, 2.00 equiv.). The reaction mixture was stirred at 0° C. for 1 hour. It was quenched water and diluted with dichloromethane and 1 N hydrochloric acid. The aqueous layer was extracted twice with dichloromethane. The combined organic layers were dried over magnesium sulfate, filtered and concentrated under reduced pressure. Purification of the crude material by flash chromatography over silica gel (eluting with ethyl acetate in cyclohexane) afforded tert-butyl N-[(1S)-3-(5-bromo-2-pyridyl)-1-methyl-2,3-dioxo-propyl]carbamate as an orange oil.

1H-NMR (400 MHz, CDCl$_3$) δ=1.36-1.41 (m, 9H) 1.45-1.48 (m, 3H) 4.82-4.96 (m, 1H) 5.10 (br s, 1H) 7.91-8.00 (m, 1H) 8.01-8.11 (m, 1H) 8.79 (d, J=1.83 Hz, 1H) ppm.

Preparation of tert-butyl N-[(1S)-1-[3-(5-bromo-2-pyridyl)pyrazin-2-yl]ethyl]carbamate (I33)

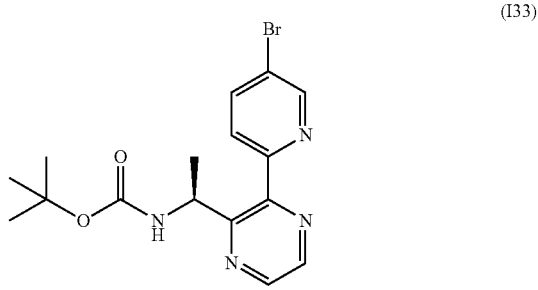 [SMILES: C[C@H](NC(=O)OC(C)(C)C)c1nccnc1-c1ccc(Br)cn1]

(I33)

To a solution of tert-butyl N-[(1S)-3-(5-bromo-2-pyridyl)-1-methyl-2,3-dioxo-propyl]carbamate (375 mg, 1.05 mmol) in ethanol (22 mL) was added ethylenediamine (0.36 mL, 5.24 mmol). The reaction mixture was stirred at room temperature for 60 hours in the presence of air. It was concentrated under reduced pressure. Purification of the crude material by flash chromatography over silica gel (eluting with ethyl acetate in cyclohexane) afforded tert-butyl N-[(1S)-1-[3-(5-bromo-2-pyridyl)pyrazin-2-yl]ethyl]carbamate as a colorless gum.

LCMS: Rt 1.09, m/z=379-381 (M+H+) (Bromo pattern); $^1$H-NMR (400 MHz, CDCl$_3$) δ=1.33-1.45 (m, 9H) 1.52-1.56 (m, 3H) 5.65-5.83 (m, 2H) 7.96-8.02 (m, 2H) 8.53-8.60 (m, 2H) 8.79 (dd, J=2.20, 1.10 Hz, 1H) ppm.

Chiral SFC (method 1): 1.80 min (major enantiomer), 1.11 min (minor enantiomer); ee=92%

Preparation of tert-butyl N-[(1S)-1-[6-amino-3-(5-bromo-2-pyridyl)pyrazin-2-yl]ethyl]carbamate (I37)

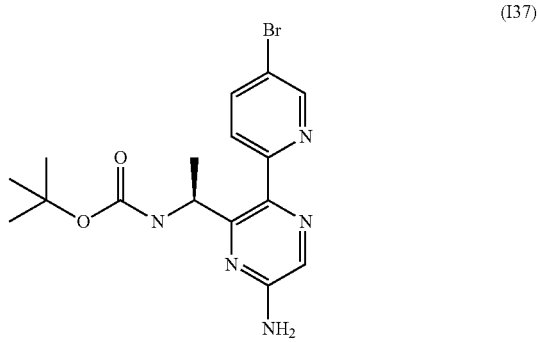 [SMILES: C[C@H](NC(=O)OC(C)(C)C)c1nc(N)cnc1-c1ccc(Br)cn1]

(I37)

To a solution of tert-butyl N-[(1S)-3-(5-bromo-2-pyridyl)-1-methyl-2,3-dioxo-propyl]carbamate (500 mg, 0.894 mmol) in isopropanol (13.4 mL) was added 2-aminoacetamidine dihydrobromide (1.21 g, 4.11 mmol). Potassium acetate (266 mg, 2.68 mmol) was added. The reaction mixture was stirred at room temperature for 2.5 hours in the presence of air. The reaction was quenched with water and the aqueous layer was extracted with ethyl acetate. The combined organic layers were washed with brine, dried over magnesium sulfate, filtered and concentrated under reduced pressure. Purification of the crude material by reverse phase chromatography (C18, eluting with ACN in water) afforded tert-butyl N-[(1S)-1-[6-amino-3-(5-bromo-2-pyridyl)pyrazin-2-yl]ethyl]carbamate.

LCMS: Rt 1.00, m/z=394-396 (M+H+) (Bromo pattern);
$^1$H-NMR (600 MHz, CDCl$_3$) δ=1.45 (br s, 9H) 1.47 (d, J=6.7 Hz, 3H) 4.84 (br s, 2H) 5.66-5.74 (m, 1H) 5.89 (br s, 1H) 7.86-7.88 (m, 1H) 7.89 (br d, J=2.0 Hz, 1H) 7.90 (s, 1H) 8.72 (s, 1H) ppm Preparation of tert-butyl N-[(1S)-1-[3-(5-cyano-2-pyridyl)pyrazin-2-yl]ethyl]carbamate (I36)

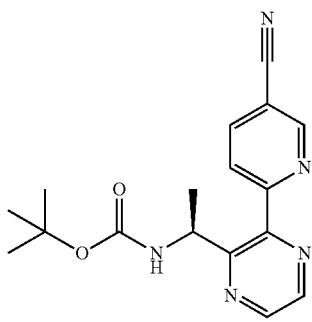

(I36)

Degassed 1,4-dioxane (9.20 mL) was added to a mixture of tert-butyl N-[(1S)-1-[3-(5-bromo-2-pyridyl)pyrazin-2-yl]ethyl]carbamate (1.396 g, 3.681 mmol), potassium ferricyanide (1.224 g, 3.681 mmol), tBuXPhos Pd-G3 (0.151 g, 0.184 mmol) and tBuXPhos (0.082 g, 0.18 mmol) at room temperature under argon. A degassed solution of potassium acetate (0.05 M in water, 9.20 mL, 0.500 mmol) was added and the mixture was stirred at 100° C. for 5 hours. The reaction mixture was diluted with water, then extracted three times with ethyl acetate. The combined organic layers were concentrated in vacuo. The crude material was purified by flash chromatography over silica gel (eluting with ethyl acetate in cyclohexane) to afford tert-butyl N-[(1S)-1-[3-(5-cyano-2-pyridyl)pyrazin-2-yl]ethyl]carbamate as a white solid.

$^1$H-NMR (400 MHz, CDCl$_3$) δ=1.38 (br s, 9H), 1.55 (d, 3H), 5.66-5.78 (m, 2H), 8.11 (dd, 1H), 8.30 (d, 1H), 8.59 (d, 1H), 8.63 (d, 1H), 8.93-9.04 (m, 1H) ppm.

Preparation of 6-[3-[(1S)-1-aminoethyl]pyrazin-2-yl]pyridine-3-carbonitrile (I32)

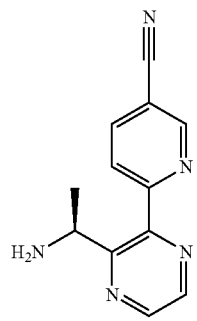

(I32)

Trifluoroacetic acid (0.69 mL, 8.7 mmol) was added to a solution of tert-butyl N-[(1S)-1-[3-(5-cyano-2-pyridyl)pyrazin-2-yl]ethyl]carbamate (0.520 g, 1.60 mmol) in dichloromethane (3.5 mL). The mixture was stirred at room temperature for 18 hours. The reaction mixture was concentrated in vacuo. The residue was dissolved in dichloromethane, then washed with saturated aqueous sodium carbonate, dried over magnesium sulfate and concentrated in vacuo to afford 6-[3-[(1S)-1-aminoethyl]pyrazin-2-yl]pyridine-3-carbonitrile.

LCMS (method 1): Rt 0.28, m/z=226 [M+H]$^+$
$^1$H-NMR (400 MHz, CDCl$_3$) δ=1.48 (d, J=6.60 Hz, 3H) 1.96 (s, 2H) 4.74 (q, J=6.60 Hz, 1H) 8.09-8.14 (m, 1H) 8.19-8.23 (m, 1H) 8.55 (d, J=2.57 Hz, 1H) 8.65 (d, J=2.20 Hz, 1H) 8.97 (dd, J=2.20, 0.73 Hz, 1H) ppm Preparation of 6-[3-[(1S)-1-(cyclopropylmethylamino)ethyl]pyrazin-2-yl]pyridine-3-carbonitrile (I33)

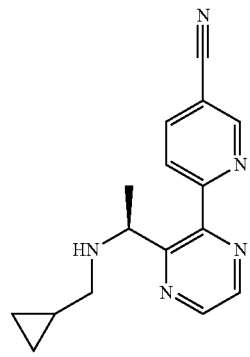

(I33)

To a solution of 6-[3-[(1S)-1-aminoethyl]pyrazin-2-yl]pyridine-3-carbonitrile (0.200 g, 0.888 mmol) in 1,2-dichloroethane (4.4 mL) were added cyclopropanecarboxaldehyde (0.0745 mL, 0.977 mmol), acetic acid (0.051 mL, 0.89 mmol) and sodium triacetoxyborohydride (0.277 g, 1.24 mmol). The mixture was stirred at room temperature for 1.5 hour. Saturated aqueous sodium carbonate was added, the aqueous layer was extracted with ethyl acetate. The combined organic layers were dried over magnesium sulfate and concentrated in vacuo. Purification of the crude material by flash chromatography over silica gel (eluting with ethyl acetate in cyclohexane) afforded 6-[3-[(1S)-1-(cyclopropylmethylamino)ethyl]pyrazin-2-yl]pyridine-3-carbonitrile as a yellow oil.

$^1$H-NMR (400 MHz, CDCl$_3$) δ=−0.05 (dd, 2H) 0.39 (td, 2H) 0.81-0.94 (m, 1H) 1.50 (d, 3H) 1.98 (dd, 1H) 2.44 (dd, 1H) 2.49-2.89 (m, 1H) 4.73 (q, 1H) 8.11-8.18 (m, 1H) 8.20-8.27 (m, 1H) 8.57 (d, 1H) 8.69 (d, 1H) 9.00 (dd, 1H) ppm Preparation of N-[(1S)-1-[3-(5-cyano-2-pyridyl)pyrazin-2-yl]ethyl]-3-[cyclopropyl(difluoro)methyl]-N-(cyclopropylmethyl)-5-(trifluoromethyl)benzamide (P43)

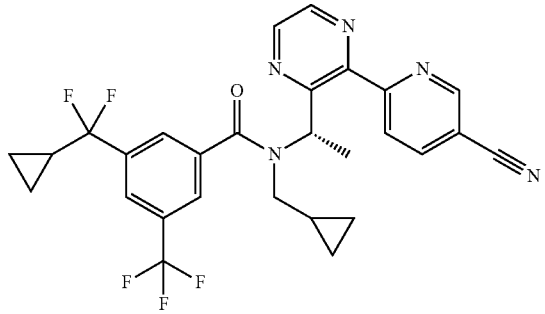

(P43)

Oxalyl chloride (0.0375 mL, 0.428 mmol) was added to a solution of 3-[cyclopropyl(difluoro)methyl]-5-(trifluoromethyl)benzoic acid (0.0800 g, 0.286 mmol) in dichloromethane (0.87 mL) containing one drop of N,N-dimethylformamide. After one hour, the reaction mixture was concentrated in vacuo. The crude acyl chloride was dissolved in ethyl acetate (1.1 mL), and 6-[3-[(1S)-1-(cyclopropylmethylamino)ethyl]pyrazin-2-yl]pyridine-3-carbonitrile (0.0797 g, 0.286 mmol) and aqueous sodium bicarbonate (1N, 1.14 mL, 1.14 mmol) were added. The mixture was stirred at room temperature for 45 minutes. The layers were separated, the aqueous layer was extracted with ethyl acetate. The combined organic layers were dried over magnesium sulfate and concentrated in vacuo. Purification of the crude material by flash chromatography over silica gel (eluting with ethyl acetate in cyclohexane) afforded N-[(1S)-1-[3-(5-cyano-2-pyridyl)pyrazin-2-yl]ethyl]-3-[cyclopropyl(difluoro)methyl]-N-(cyclopropylmethyl)-5-(trifluoromethyl)benzamide.

$^1$H NMR (400 MHz, TFA-d1) δ=−0.23-0.05 (m, 2H) 0.35-0.57 (m, 2H) 0.60-0.78 (m, 3H) 0.76-1.04 (m, 2H) 1.14-1.31 (m, 1H) 1.32-1.47 (m, 1H) 1.53-1.68 (m, 1H) 2.03-2.17 (m, 3H) 3.29-3.46 (m, 1H) 3.54-3.73 (m, 1H) 1.32-6.50 (m, 1H) 7.67-7.83 (m, 2H) 7.90-8.06 (m, 1H) 8.61-8.82 (m, 2H) 9.08 (br s, 1H) 9.18-9.38 (m, 2H) ppm; LCMS (method 1): Rt 1.21, m/z=542 [M+H]$^+$; [α]$_D^{20}$: +1520 (c: 0.477, CHCl$_3$)

Preparation of N-[(1S)-1-[3-(5-cyano-2-pyridyl)pyrazin-2-yl]ethyl]-3-[cyclopropyl(difluoro)methyl]-5-(trifluoromethyl)benzamide (P42)

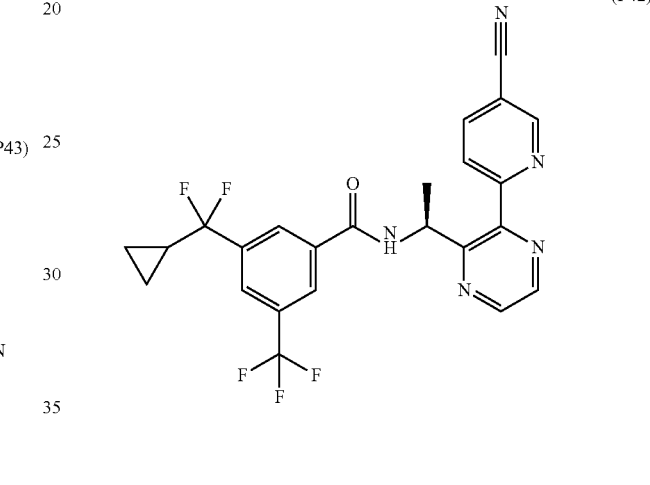

(P42)

Oxalyl chloride (0.0375 mL, 0.428 mmol) was added to a solution of 3-[cyclopropyl(difluoro)methyl]-5-(trifluoromethyl)benzoic acid (0.0800 g, 0.286 mmol) in dichloromethane (0.87 mL) containing one drop of N,N-dimethylformamide. After one hour, the reaction mixture was concentrated in vacuo. The crude acyl chloride was dissolved in ethyl acetate (1.1 mL), and 6-[3-[(1S)-1-aminoethyl]pyrazin-2-yl]pyridine-3-carbonitrile (0.0643 g, 0.286 mmol) and aqueous sodium bicarbonate (1N, 1.14 mL, 1.14 mmol) were added. The mixture was stirred at room temperature for 45 minutes. The layers were separated, the aqueous layer was extracted with ethyl acetate. The combined organic layers were dried over magnesium sulfate and concentrated in vacuo. Purification of the crude material by flash chromatography over silica gel (eluting with ethyl acetate in cyclohexane) afforded N-[(1S)-1-[3-(5-cyano-2-pyridyl)pyrazin-2-yl]ethyl]-3-[cyclopropyl(difluoro)methyl]-5-(trifluoromethyl)benzamide.

$^1$H NMR (400 MHz, CDCl$_3$) δ=0.71-0.79 (m, 2H) 0.81-0.88 (m, 2H) 1.47-1.60 (m, 1H) 1.72 (d, 3H) 1.27-6.37 (m, 1H) 7.63 (br d, 1H) 7.93 (s, 1H) 8.10 (s, 1H) 8.15 (s, 1H) 8.17-8.22 (m, 1H) 8.38 (dd, 1H) 8.69 (q, 2H) 9.08 (dd, 1H) ppm; LCMS (method 1): Rt 1.13, m/z=488 [M+H]$^+$; [α]$_D^{20}$: +1450 (c: 0.707, CHCl$_3$)

TABLE P

Examples of compounds of formula I

| Entry | IUPAC name | STRUCTURE | RT (min) | [M + H] (measured) | Method | MP °C. |
|---|---|---|---|---|---|---|
| P1 | 2-(1-cyanocyclopropyl)-N-[1-[3-[5-(difluoromethoxy)-2-pyridyl]pyrazin-2-yl]ethyl]-6-(trifluoromethyl)pyridine-4-carboxamide | 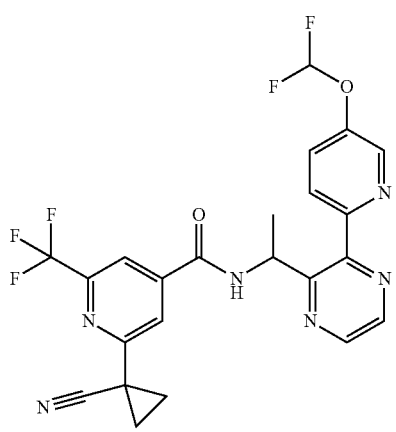 [SMILES: CC(NC(=O)c1cc(C(F)(F)F)nc(C2(C#N)CC2)c1)c1nccnc1-c1ccc(OC(F)F)cn1] | | | | 140-150 |
| P2 | 3-(1-cyanocyclopropyl)-N-[1-[3-[5-(2,2,2-trifluoroethoxy)pyrimidin-2-yl]pyrazin-2-yl]ethyl]-5-(trifluoromethyl)benzamide | 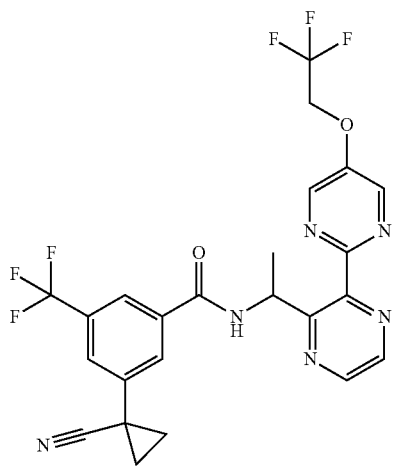 [SMILES: CC(NC(=O)c1cc(C(F)(F)F)cc(C2(C#N)CC2)c1)c1nccnc1-c1ncc(OCC(F)(F)F)cn1] | | | | 160-164 |
| P3 | 3-(1-cyanocyclopropyl)-N-[1-[3-[5-(difluoromethoxy)-2-pyridyl]pyrazin-2-yl]ethyl]-5-(trifluoromethyl)benzamide | 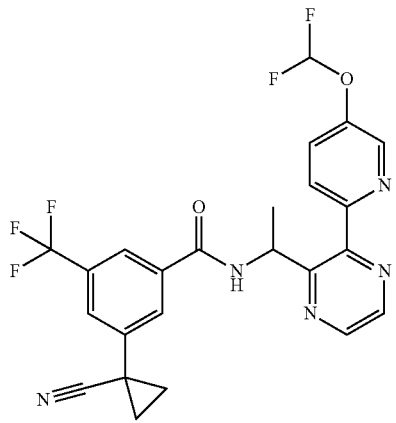 [SMILES: CC(NC(=O)c1cc(C(F)(F)F)cc(C2(C#N)CC2)c1)c1nccnc1-c1ccc(OC(F)F)cn1] | | | | 120-130 |

TABLE P-continued

Examples of compounds of formula I

| Entry | IUPAC name | STRUCTURE | RT (min) | [M + H] (measured) | Method | MP ° C. |
|---|---|---|---|---|---|---|
| P4 | 3-[cyclopropyl(difluoro)methyl]-N-[1-[3-[5-(2,2,2-trifluoroethoxy)pyrimidin-2-yl]pyrazin-2-yl]ethyl]-5-(trifluoromethyl)benzamide | 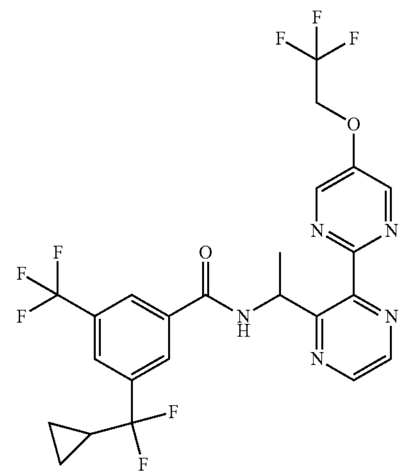 [SMILES: CC(NC(=O)c1cc(C(F)(F)F)cc(C(F)(F)C2CC2)c1)c1nccnc1-c1ncc(OCC(F)(F)F)cn1] | | | | 145-150 |
| P5 | 3-[cyclopropyl(difluoro)methyl]-N-[1-[3-[5-(difluoromethoxy)-2-pyridyl]pyrazin-2-yl]ethyl]-5-(trifluoromethyl)benzamide | 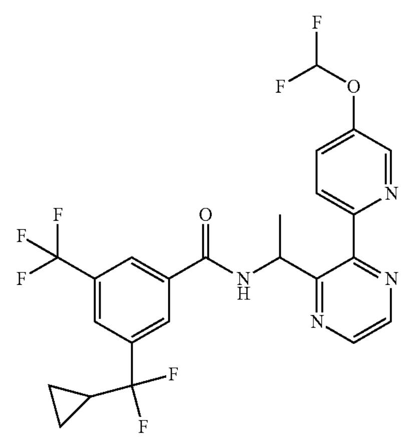 [SMILES: CC(NC(=O)c1cc(C(F)(F)F)cc(C(F)(F)C2CC2)c1)c1nccnc1-c1ccc(OC(F)F)cn1] | | | | 120-130 |
| P6 | 3-cyclopropyl-N-[1-[3-[5-(2,2,2-trifluoroethoxy)pyrimidin-2-yl]pyrazin-2-yl]ethyl]-5-(trifluoromethyl)benzamide | 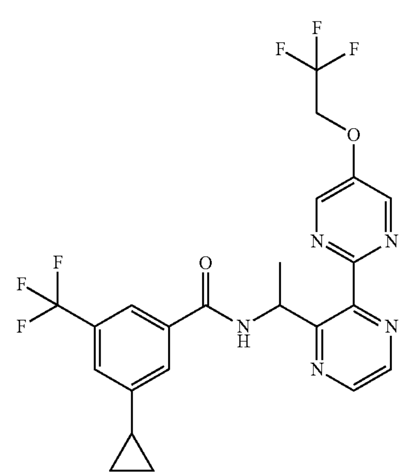 [SMILES: CC(NC(=O)c1cc(C2CC2)cc(C(F)(F)F)c1)c1nccnc1-c1ncc(OCC(F)(F)F)cn1] | | | | 66-70 |

TABLE P-continued

Examples of compounds of formula I

| Entry | IUPAC name | STRUCTURE | RT (min) | [M + H] (measured) | Method | MP ° C. |
|---|---|---|---|---|---|---|
| P7 | 3-cyclopropyl-N-[1-[3-[5-(difluoromethoxy)-2-pyridyl]pyrazin-2-yl]ethyl]-5-(trifluoromethyl)benzamide | 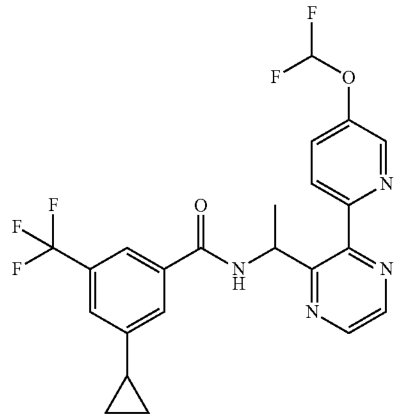 [SMILES: CC(NC(=O)c1cc(C2CC2)cc(C(F)(F)F)c1)c1nccnc1-c1ccc(OC(F)F)cn1] | | | | 130-140 |
| P8 | 3-(1-cyano-1-methyl-ethyl)-N-[1-[3-[5-(difluoromethoxy)pyrimidin-2-yl]pyrazin-2-yl]ethyl]-5-(trifluoromethyl)benzamide | 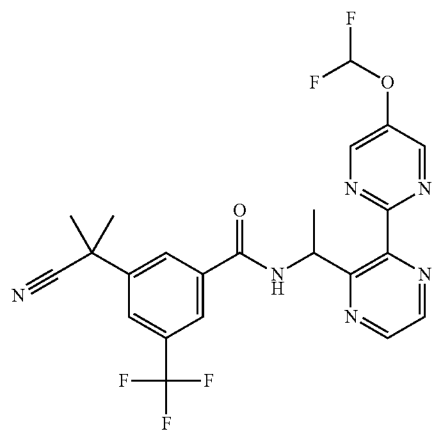 [SMILES: CC(NC(=O)c1cc(C(F)(F)F)cc(C(C)(C)C#N)c1)c1nccnc1-c1ncc(OC(F)F)cn1] | | | | 130-140 |
| P9 | 3-(1-cyano-1-methyl-ethyl)-N-[1-[3-(5-cyano-2-pyridyl)pyrazin-2-yl]ethyl]-5-(trifluoromethyl)benzamide | 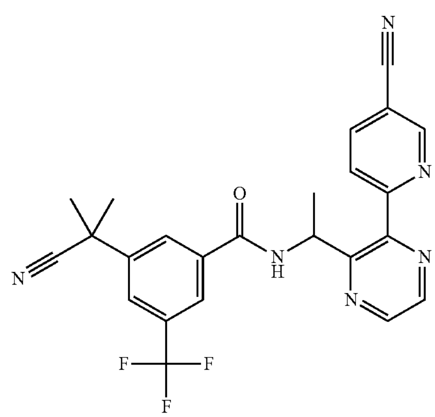 [SMILES: CC(NC(=O)c1cc(C(F)(F)F)cc(C(C)(C)C#N)c1)c1nccnc1-c1ccc(C#N)cn1] | | | | 135-140 |

TABLE P-continued

Examples of compounds of formula I

| Entry | IUPAC name | STRUCTURE | RT (min) | [M + H] (measured) | Method | MP ° C. |
|---|---|---|---|---|---|---|
| P10 | 3-(1-cyano-1-methyl-ethyl)-N-[1-[3-[5-(2,2,2-trifluoroethoxy)-2-pyridyl]pyrazin-2-yl]ethyl]-5-(trifluoromethyl)benzamide | 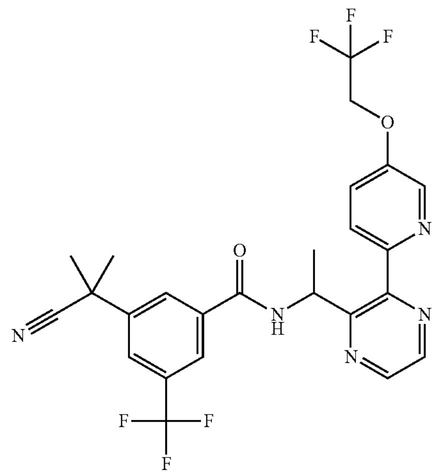 [SMILES: CC(NC(=O)c1cc(C(F)(F)F)cc(C(C)(C)C#N)c1)c1nccnc1-c1ccc(OCC(F)(F)F)cn1] | | | | 120-125 |
| P11 | N-[1-[3-[5-(difluoromethoxy)-2-pyridyl]pyrazin-2-yl]ethyl]-3-(trifluoromethyl)-5-(trifluoromethylsulfonyl)benzamide | 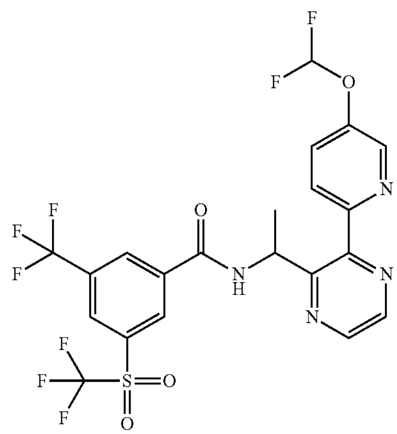 [SMILES: CC(NC(=O)c1cc(C(F)(F)F)cc(S(=O)(=O)C(F)(F)F)c1)c1nccnc1-c1ccc(OC(F)F)cn1] | | | | 180-190 |
| P12 | N-[1-[3-[5-(2,2,2-trifluoroethoxy)pyrimidin-2-yl]pyrazin-2-yl]ethyl]-3-(trifluoromethyl)-5-(trifluoromethylsulfonyl)benzamide | 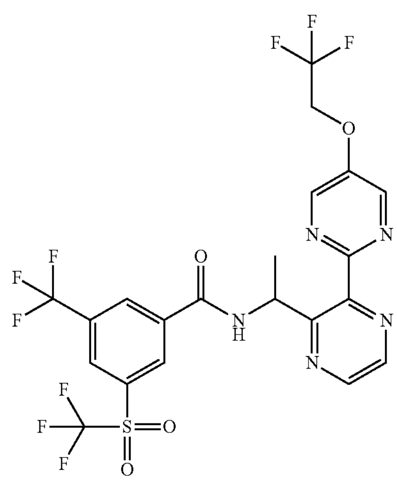 [SMILES: CC(NC(=O)c1cc(C(F)(F)F)cc(S(=O)(=O)C(F)(F)F)c1)c1nccnc1-c1ncc(OCC(F)(F)F)cn1] | | | | 180-185 |

TABLE P-continued

Examples of compounds of formula I

| Entry | IUPAC name | STRUCTURE | RT (min) | [M + H] (measured) | Method | MP ° C. |
|---|---|---|---|---|---|---|
| P13 | 3-(1-cyano-1-methyl-ethyl)-N-[1-[3-[5-(difluoromethoxy)-2-pyridyl]pyrazin-2-yl]ethyl]-5-(trifluoromethyl)benzamide | 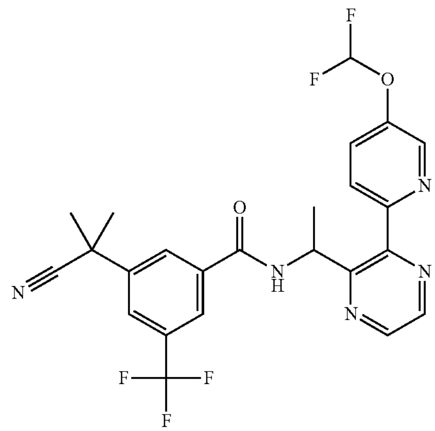 [SMILES: CC(NC(=O)c1cc(C(F)(F)F)cc(C(C)(C)C#N)c1)c1nccnc1-c1ccc(OC(F)F)cn1] | | | | 130-140 |
| P14 | N-[1-[3-(5-cyano-2-pyridyl)pyrazin-2-yl]ethyl]-3-cyclopropyl-5-(trifluoromethyl)benzamide | 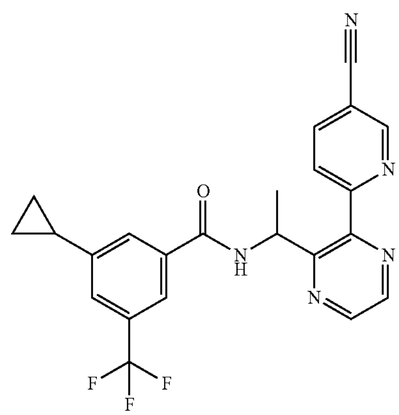 [SMILES: CC(NC(=O)c1cc(C2CC2)cc(C(F)(F)F)c1)c1nccnc1-c1ccc(C#N)cn1] | | | | 190-195 |
| P15 | N-[1-[3-(5-cyano-2-pyridyl)pyrazin-2-yl]ethyl]-3-(trifluoromethyl)-5-(trifluoromethylsulfonyl)benzamide | 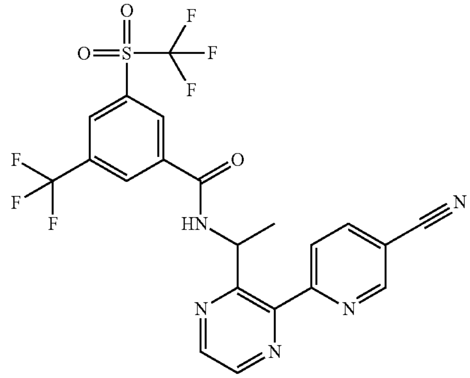 [SMILES: CC(NC(=O)c1cc(C(F)(F)F)cc(S(=O)(=O)C(F)(F)F)c1)c1nccnc1-c1ccc(C#N)cn1] | | | | 165-170 |

TABLE P-continued

Examples of compounds of formula I

| Entry | IUPAC name | STRUCTURE | RT (min) | [M + H] (measured) | Method | MP ° C. |
|---|---|---|---|---|---|---|
| P16 | 2-(1-cyanocyclopropyl)-N-[1-[3-(5-cyano-2-pyridyl)pyrazin-2-yl]ethyl]-6-(trifluoromethyl)pyridine-4-carboxamide | 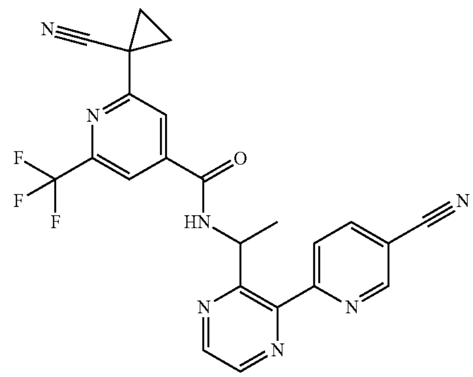 [SMILES: CC(NC(=O)c1cc(C(F)(F)F)nc(C2(C#N)CC2)c1)c1nccnc1-c1ccc(C#N)cn1] | | | | 150-155 |
| P17 | N-[1-[3-(5-cyano-2-pyridyl)pyrazin-2-yl]ethyl]-2-cyclopropyl-6-(trifluoromethyl)pyridine-4-carboxamide | 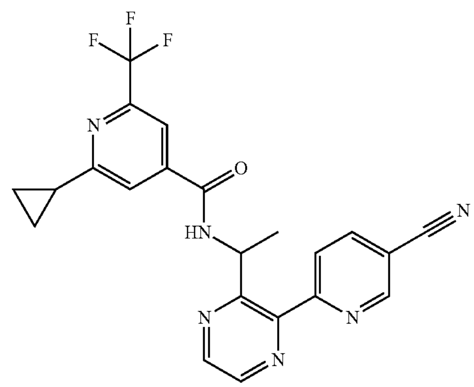 [SMILES: CC(NC(=O)c1cc(C2CC2)nc(C(F)(F)F)c1)c1nccnc1-c1ccc(C#N)cn1] | | | | 210-215 |
| P18 | N-[1-[3-(5-cyano-2-pyridyl)pyrazin-2-yl]ethyl]-3-[cyclopropyl(difluoro)methyl]-5-(trifluoromethyl)benzamide | 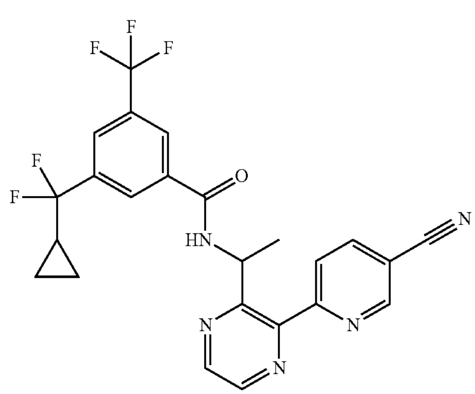 [SMILES: CC(NC(=O)c1cc(C(F)(F)F)cc(C(F)(F)C2CC2)c1)c1nccnc1-c1ccc(C#N)cn1] | | | | 160-165 |

TABLE P-continued

Examples of compounds of formula I

| Entry | IUPAC name | STRUCTURE | RT (min) | [M + H] (measured) | Method | MP ° C. |
|---|---|---|---|---|---|---|
| P19 | N-[1-[3-[5-(difluoromethoxy)pyrimidin-2-yl]pyrazin-2-yl]ethyl]-3-(trifluoromethyl)-5-(trifluoromethylsulfonyl)benzamide | 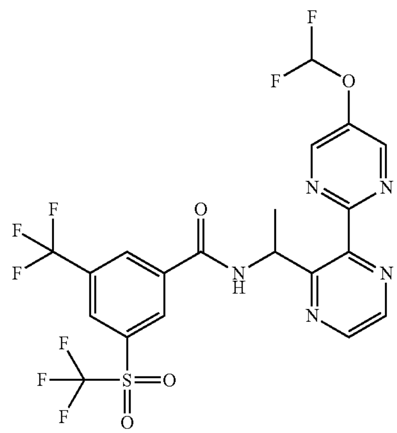 [SMILES: CC(NC(=O)c1cc(C(F)(F)F)cc(S(=O)(=O)C(F)(F)F)c1)c1nccnc1-c1ncc(OC(F)F)cn1] | | | | 130-135 |
| P20 | N-[1-[3-[5-(2,2-difluoroethoxy)-2-pyridyl]pyrazin-2-yl]ethyl]-3-(trifluoromethyl)-5-(trifluoromethylsulfonyl)benzamide | 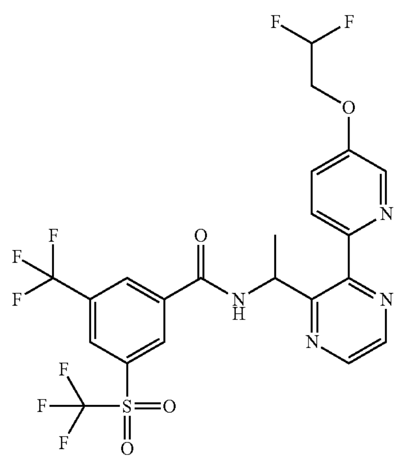 [SMILES: CC(NC(=O)c1cc(C(F)(F)F)cc(S(=O)(=O)C(F)(F)F)c1)c1nccnc1-c1ccc(OCC(F)F)cn1] | | | | 140-145 |
| P21 | N-[1-[3-[5-(2,2,2-trifluoroethoxy)-2-pyridyl]pyrazin-2-yl]ethyl]-3-(trifluoromethyl)-5-(trifluoromethylsulfonyl)benzamide | 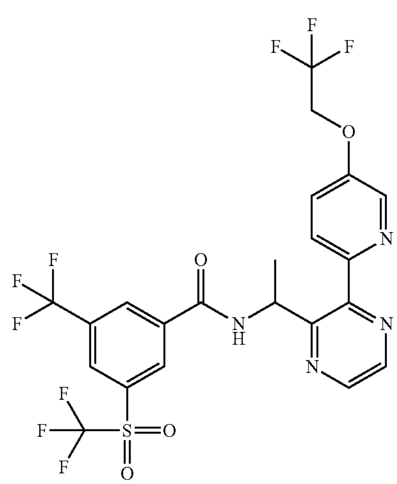 [SMILES: CC(NC(=O)c1cc(C(F)(F)F)cc(S(=O)(=O)C(F)(F)F)c1)c1nccnc1-c1ccc(OCC(F)(F)F)cn1] | | | | 130-135 |

TABLE P-continued

Examples of compounds of formula I

| Entry | IUPAC name | STRUCTURE | RT (min) | [M + H] (measured) | Method | MP ° C. |
|---|---|---|---|---|---|---|
| P22 | 2-(1-cyanocyclopropyl)-N-[1-[3-[5-(2,2-difluoroethoxy)-2-pyridyl]pyrazin-2-yl]ethyl]-6-(trifluoromethyl)pyridine-4-carboxamide | 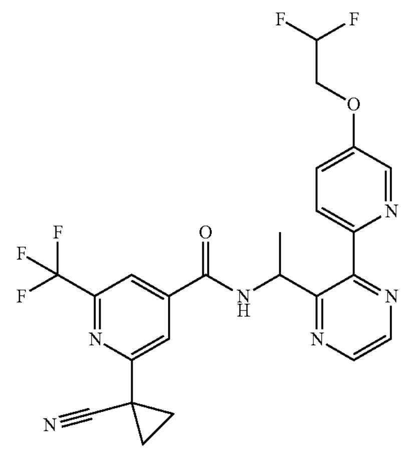 [SMILES: CC(NC(=O)c1cc(C(F)(F)F)nc(C2(C#N)CC2)c1)c1nccnc1-c1ccc(OCC(F)F)cn1] | | | | 115-120 |
| P23 | 2-(1-cyanocyclopropyl)-N-[1-[3-[5-(2,2,2-trifluoroethoxy)-2-pyridyl]pyrazin-2-yl]ethyl]-6-(trifluoromethyl)pyridine-4-carboxamide | 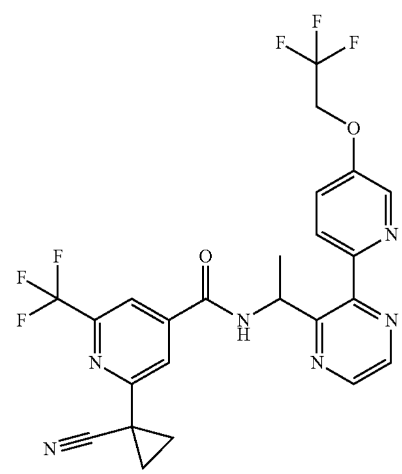 [SMILES: CC(NC(=O)c1cc(C(F)(F)F)nc(C2(C#N)CC2)c1)c1nccnc1-c1ccc(OCC(F)(F)F)cn1] | | | | 120-125 |
| P24 | 3-(1-cyanocyclopropyl)-N-[1-[3-[5-(2,2,2-trifluoroethoxy)-2-pyridyl]pyrazin-2-yl]ethyl]-5-(trifluoromethyl)benzamide | 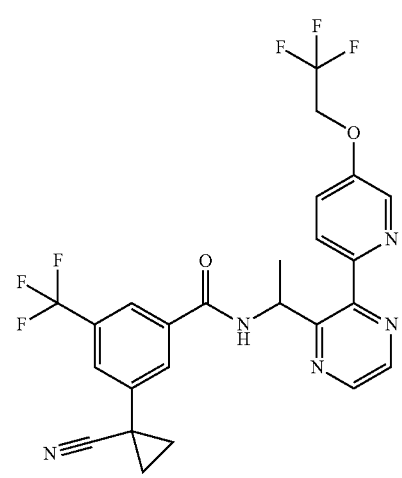 [SMILES: CC(NC(=O)c1cc(C(F)(F)F)cc(C2(C#N)CC2)c1)c1nccnc1-c1ccc(OCC(F)(F)F)cn1] | | | | 140-145 |

TABLE P-continued

Examples of compounds of formula I

| Entry | IUPAC name | STRUCTURE | RT (min) | [M + H] (measured) | Method | MP ° C. |
|---|---|---|---|---|---|---|
| P25 | 3-(1-cyanocyclopropyl)-N-[1-[3-(5-cyano-2-pyridyl)pyrazin-2-yl]ethyl]-5-(trifluoromethyl)benzamide | 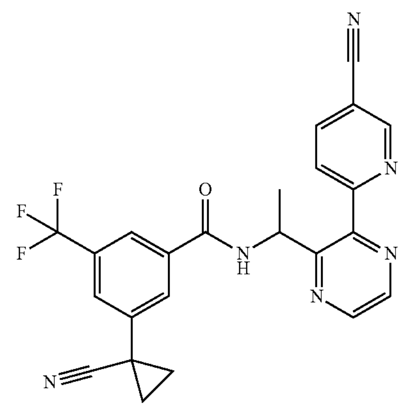 [SMILES: CC(NC(=O)c1cc(C(F)(F)F)cc(C2(C#N)CC2)c1)c1nccnc1-c1ccc(C#N)cn1] | | | | 170-175 |
| P26 | 3-cyclopropyl-N-[1-[3-[5-(2,2-difluoroethoxy)-2-pyridyl]pyrazin-2-yl]ethyl]-5-(trifluoromethyl)benzamide | 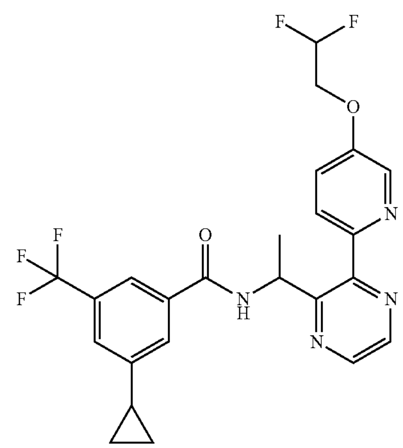 [SMILES: CC(NC(=O)c1cc(C2CC2)cc(C(F)(F)F)c1)c1nccnc1-c1ccc(OCC(F)F)cn1] | | | | 100-105 |
| P27 | 3-cyclopropyl-N-[1-[3-[5-(2,2,2-trifluoroethoxy)-2-pyridyl]pyrazin-2-yl]ethyl]-5-(trifluoromethyl)benzamide | 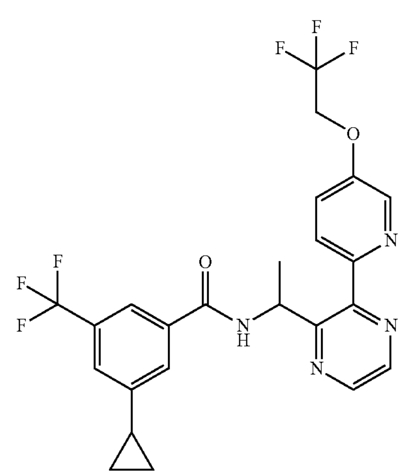 [SMILES: CC(NC(=O)c1cc(C2CC2)cc(C(F)(F)F)c1)c1nccnc1-c1ccc(OCC(F)(F)F)cn1] | | | | 110-115 |

TABLE P-continued

Examples of compounds of formula I

| Entry | IUPAC name | STRUCTURE | RT (min) | [M + H] (measured) | Method | MP ° C. |
|---|---|---|---|---|---|---|
| P28 | N-[1-[3-[5-(2,2-difluoroethoxy)pyrimidin-2-yl]pyrazin-2-yl]ethyl]-3-(trifluoromethyl)-5-(trifluoromethylsulfonyl)benzamide | 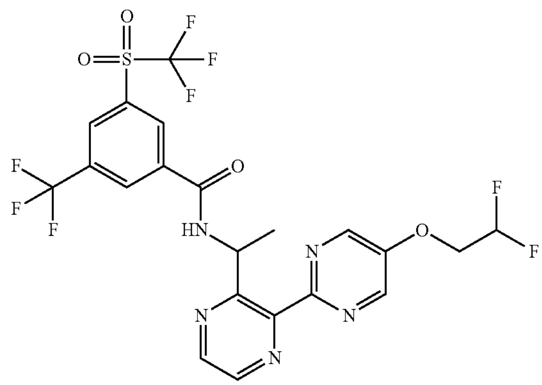 [SMILES: CC(NC(=O)c1cc(C(F)(F)F)cc(S(=O)(=O)C(F)(F)F)c1)c1nccnc1-c1ncc(OCC(F)F)cn1] | | | | 185-188 |
| P29 | 3-[cyclopropyl(difluoro)methyl]-N-[1-[3-[5-(difluoromethoxy)pyrimidin-2-yl]pyrazin-2-yl]ethyl]-5-(trifluoromethyl)benzamide | 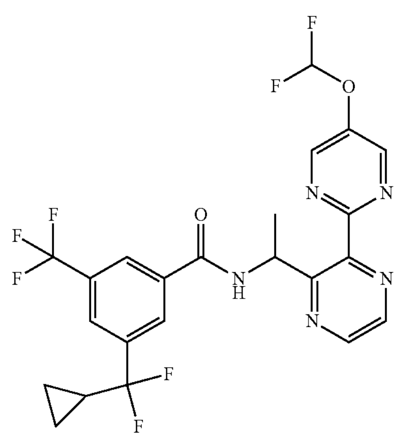 [SMILES: CC(NC(=O)c1cc(C(F)(F)F)cc(C(F)(F)C2CC2)c1)c1nccnc1-c1ncc(OC(F)F)cn1] | | | | 120-125 |
| P30 | 3-[cyclopropyl(difluoro)methyl]-N-[1-[3-[5-(2,2-difluoroethoxy)-2-pyridyl]pyrazin-2-yl]ethyl]-5-(trifluoromethyl)benzamide | 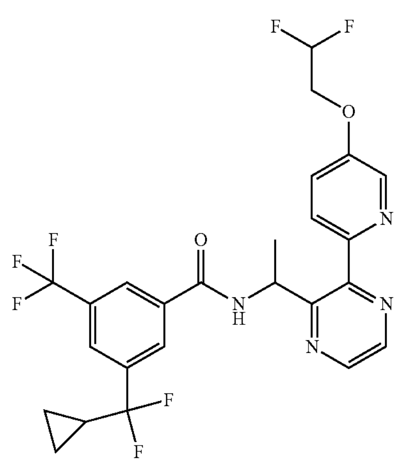 [SMILES: CC(NC(=O)c1cc(C(F)(F)F)cc(C(F)(F)C2CC2)c1)c1nccnc1-c1ccc(OCC(F)F)cn1] | | | | 130-135 |

TABLE P-continued

Examples of compounds of formula I

| Entry | IUPAC name | STRUCTURE | RT (min) | [M + H] (measured) | Method | MP °C. |
|---|---|---|---|---|---|---|
| P31 | 3-[cyclopropyl(difluoro)methyl]-N-[1-[3-[5-(2,2,2-trifluoroethoxy)-2-pyridyl]pyrazin-2-yl]ethyl]-5-(trifluoromethyl)benzamide | 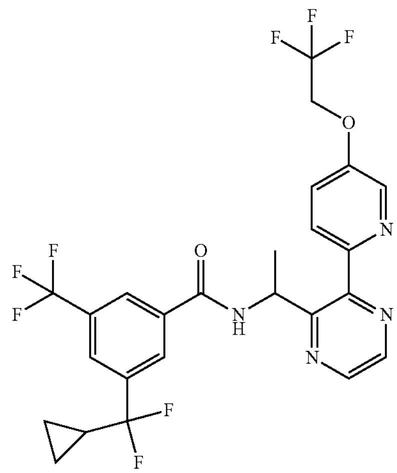 [SMILES: CC(NC(=O)c1cc(C(F)(F)F)cc(C(F)(F)C2CC2)c1)c1nccnc1-c1ccc(OCC(F)(F)F)cn1] | | | | 130-135 |
| P32 | 3-(1-cyanocyclopropyl)-N-[1-[3-[5-(difluoromethoxy)pyrimidin-2-yl]pyrazin-2-yl]ethyl]-5-(trifluoromethyl)benzamide | 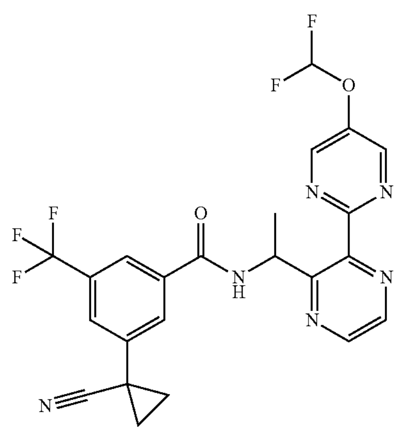 [SMILES: CC(NC(=O)c1cc(C(F)(F)F)cc(C2(C#N)CC2)c1)c1nccnc1-c1ncc(OC(F)F)cn1] | | | | 100-105 |
| P33 | 3-(1-cyanocyclopropyl)-N-[1-[3-[5-(2,2-difluoroethoxy)-2-pyridyl]pyrazin-2-yl]ethyl]-5-(trifluoromethyl)benzamide | 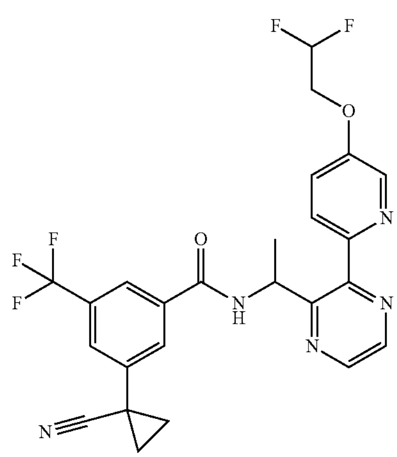 | | | | 130-135 |

TABLE P-continued

Examples of compounds of formula I

| Entry | IUPAC name | STRUCTURE | RT (min) | [M + H] (measured) | Method | MP ° C. |
|---|---|---|---|---|---|---|
| P34 | 2-(1-cyanocyclopropyl)-N-[1-[3-[5-(2,2,2-trifluoroethoxy)pyrimidin-2-yl]pyrazin-2-yl]ethyl]-6-(trifluoromethyl)pyridine-4-carboxamide | 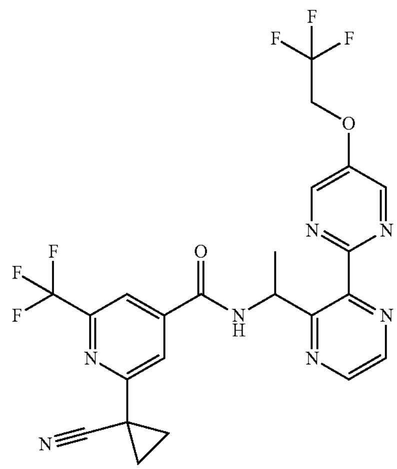 [SMILES: CC(NC(=O)c1cc(C(F)(F)F)nc(C2(C#N)CC2)c1)c1nccnc1-c1ncc(OCC(F)(F)F)cn1] | | | | 68-72 |
| P35 | 2-cyclopropyl-N-[1-[3-[5-(2,2-difluoroethoxy)pyrimidin-2-yl]pyrazin-2-yl]ethyl]-6-(trifluoromethyl)pyridine-4-carboxamide | 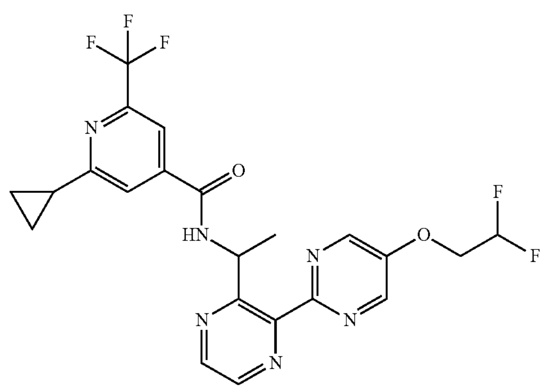 [SMILES: CC(NC(=O)c1cc(C2CC2)nc(C(F)(F)F)c1)c1nccnc1-c1ncc(OCC(F)F)cn1] | | | | 132-135 |
| P36 | 2-(1-cyanocyclopropyl)-N-[1-[3-[5-(difluoromethoxy)pyrimidin-2-yl]pyrazin-2-yl]ethyl]-6-(trifluoromethyl)pyridine-4-carboxamide | 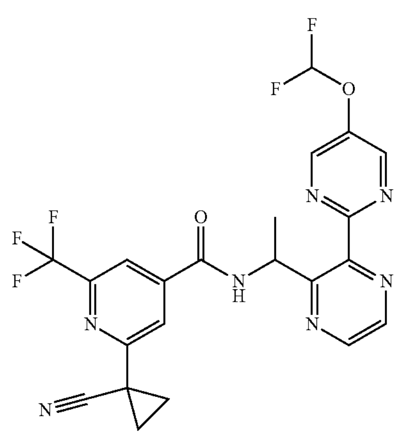 [SMILES: CC(NC(=O)c1cc(C(F)(F)F)nc(C2(C#N)CC2)c1)c1nccnc1-c1ncc(OC(F)F)cn1] | | | | 70-75 |

TABLE P-continued

Examples of compounds of formula I

| Entry | IUPAC name | STRUCTURE | RT (min) | [M + H] (measured) | Method | MP ° C. |
|---|---|---|---|---|---|---|
| P37 | 3-cyclopropyl-N-[1-[3-[5-(2,2-difluoroethoxy)pyrimidin-2-yl]pyrazin-2-yl]ethyl]-5-(trifluoromethyl)benzamide | 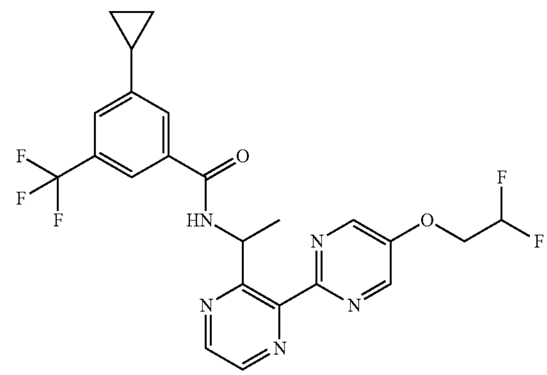 [SMILES: CC(NC(=O)c1cc(C2CC2)cc(C(F)(F)F)c1)c1nccnc1-c1ncc(OCC(F)F)cn1] | | | | 54-58 |
| P38 | N-[1-[3-[5-(2,2-difluoroethoxy)pyrimidin-2-yl]pyrazin-2-yl]ethyl]-3-(trifluoromethyl)-5-[2-(trifluoromethyl)cyclopropyl]benzamide | 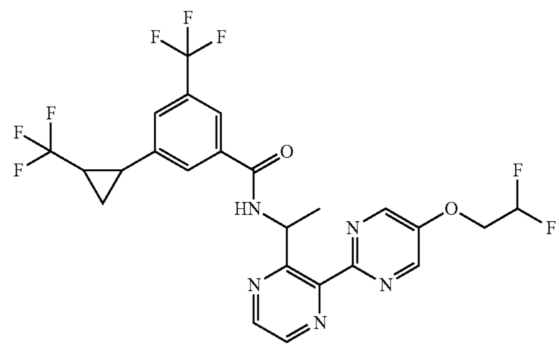 [SMILES: CC(NC(=O)c1cc(C2CC2C(F)(F)F)cc(C(F)(F)F)c1)c1nccnc1-c1ncc(OCC(F)F)cn1] | | | | 115-120 |
| P39 | 3-[cyclopropyl(difluoro)methyl]-N-[1-[3-[5-(2,2-difluoroethoxy)pyrimidin-2-yl]pyrazin-2-yl]ethyl]-5-(trifluoromethyl)benzamide | 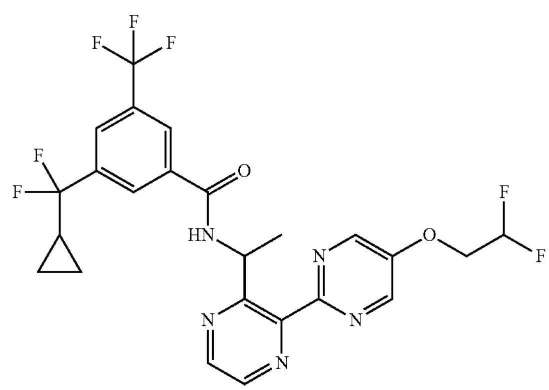 [SMILES: CC(NC(=O)c1cc(C(F)(F)F)cc(C(F)(F)C2CC2)c1)c1nccnc1-c1ncc(OCC(F)F)cn1] | | | | 118-123 |
| P40 | 2-(1-cyanocyclopropyl)-N-[1-[3-[5-(2,2-difluoroethoxy)pyrimidin-2-yl]pyrazin-2-yl]ethyl]-6-(trifluoromethyl)pyridine-4-carboxamide | 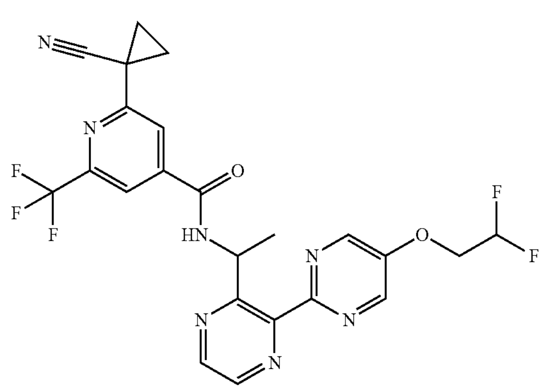 [SMILES: CC(NC(=O)c1cc(C(F)(F)F)nc(C2(C#N)CC2)c1)c1nccnc1-c1ncc(OCC(F)F)cn1] | | | | 58-63 |

TABLE P-continued

Examples of compounds of formula I

| Entry | IUPAC name | STRUCTURE | RT (min) | [M + H] (measured) | Method | MP ° C. |
|---|---|---|---|---|---|---|
| P41 | 3-cyclopropyl-N-[1-[3-[5-(difluoromethoxy)pyrimidin-2-yl]pyrazin-2-yl]ethyl]-5-(trifluoromethyl)benzamide | 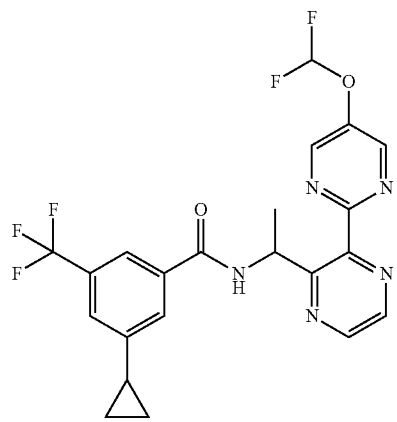 [SMILES: CC(NC(=O)c1cc(C2CC2)cc(C(F)(F)F)c1)c1nccnc1-c1ncc(OC(F)F)cn1] | | | | 90-95 |
| P42 | N-[(1S)-1-[3-(5-cyano-2-pyridyl)pyrazin-2-yl]ethyl]-3-[cyclopropyl(difluoro)methyl]-5-(trifluoromethyl)benzamide | 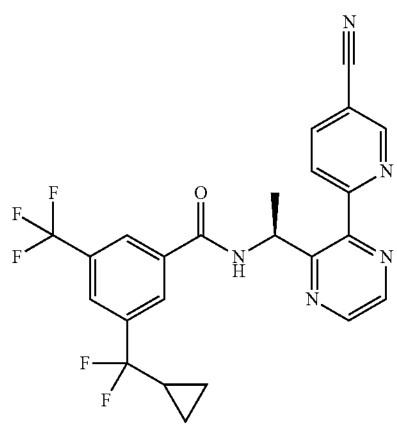 [SMILES: C[C@H](NC(=O)c1cc(C(F)(F)F)cc(C(F)(F)C2CC2)c1)c1nccnc1-c1ccc(C#N)cn1] | 1.13 | 488.0 | 1 | |
| P43 | N-[(1S)-1-[3-(5-cyano-2-pyridyl)pyrazin-2-yl]ethyl]-3-[cyclopropyl(difluoro)methyl]-N-(cyclopropylmethyl)-5-(trifluoromethyl)benzamide | 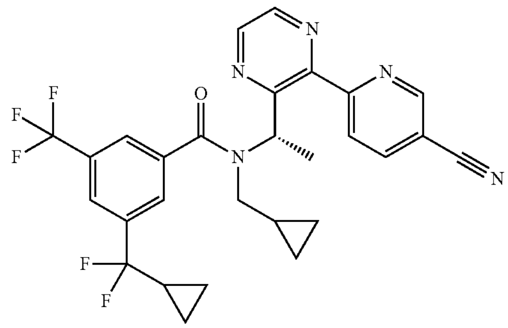 [SMILES: C[C@@H](c1nccnc1-c1ccc(C#N)cn1)N(CC1CC1)C(=O)c1cc(C(F)(F)F)cc(C(F)(F)C2CC2)c1] | 1.21 | 542.6 | 1 | |

TABLE P-continued

Examples of compounds of formula I

| Entry | IUPAC name | STRUCTURE | RT (min) | [M + H] (measured) | Method | MP ° C. |
|---|---|---|---|---|---|---|
| P44 | 3-(1-cyanocyclopropyl)-N-[1-[3-(5-cyano-2-pyridyl)pyrazin-2-yl]ethyl]-5-(difluoromethoxy)benzamide | 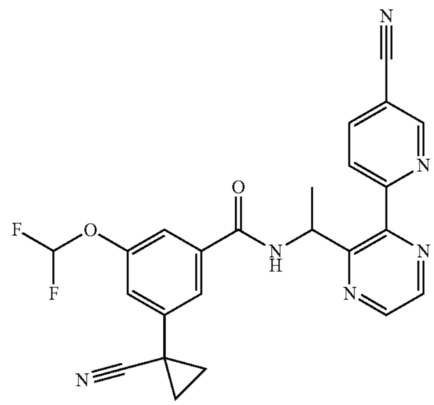 [SMILES: CC(NC(=O)c1cc(OC(F)F)cc(C2(C#N)CC2)c1)c1nccnc1-c1ccc(C#N)cn1] | | | | 140-150 |
| P45 | 3-(1-cyanocyclopropyl)-N-[1-[3-(5-cyano-2-pyridyl)pyrazin-2-yl]ethyl]-5-(trifluoromethoxy)benzamide | 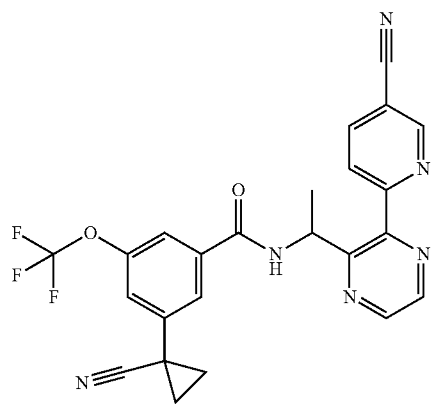 [SMILES: CC(NC(=O)c1cc(OC(F)(F)F)cc(C2(C#N)CC2)c1)c1nccnc1-c1ccc(C#N)cn1] | | | | 160-170 |
| P46 | N-[1-[3-(5-cyano-2-pyridyl)pyrazin-2-yl]ethyl]-3-(1-methoxycyclopropyl)-5-(trifluoromethyl)benzamide | 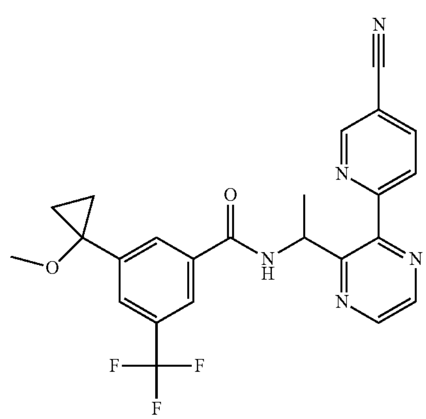 [SMILES: COC1(c2cc(C(=O)NC(C)c3nccnc3-c3ccc(C#N)cn3)cc(C(F)(F)F)c2)CC1] | | | | 140-150 |

TABLE P-continued

Examples of compounds of formula I

| Entry | IUPAC name | STRUCTURE | RT (min) | [M + H] (measured) | Method | MP ° C. |
|---|---|---|---|---|---|---|
| P47 | 3-(1-cyano-1-methyl-ethyl)-N-[1-[3-[5-(2,2,2-trifluoroethoxy)pyrimidin-2-yl]pyrazin-2-yl]ethyl]-5-(trifluoromethyl)benzamide | 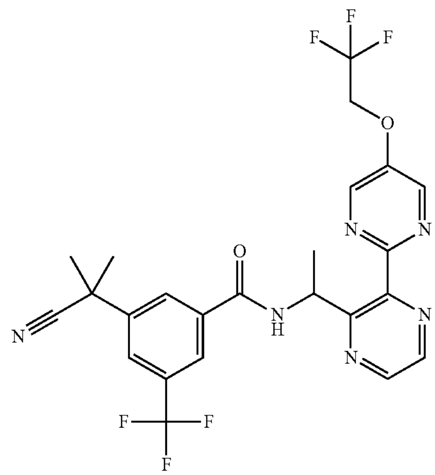 [SMILES: CC(NC(=O)c1cc(C(F)(F)F)cc(C(C)(C)C#N)c1)c1nccnc1-c1ncc(OCC(F)(F)F)cn1] | | | | 170-175 |
| P48 | 3-(1-cyano-1-methyl-ethyl)-N-[1-[3-[5-(2,2-difluoroethoxy)pyrimidin-2-yl]pyrazin-2-yl]ethyl]-5-(trifluoromethyl)benzamide | 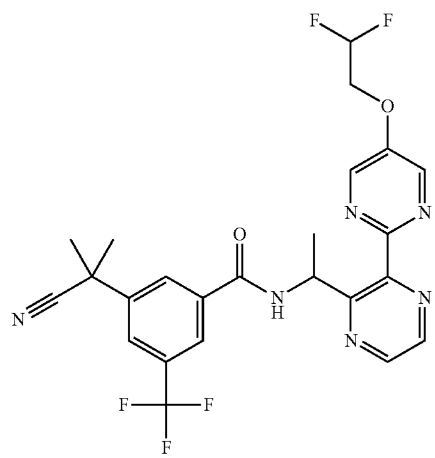 [SMILES: CC(NC(=O)c1cc(C(F)(F)F)cc(C(C)(C)C#N)c1)c1nccnc1-c1ncc(OCC(F)F)cn1] | | | | 145-148 |
| P49 | 3-(1-cyanocyclopropyl)-N-[1-[3-[5-(2,2-difluoroethoxy)pyrimidin-2-yl]pyrazin-2-yl]ethyl]-5-(trifluoromethyl)benzamide | 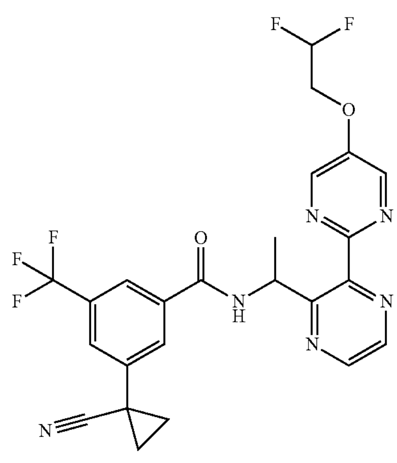 [SMILES: CC(NC(=O)c1cc(C(F)(F)F)cc(C2(C#N)CC2)c1)c1nccnc1-c1ncc(OCC(F)F)cn1] | | | | 65-70 |

TABLE P-continued

Examples of compounds of formula I

| Entry | IUPAC name | STRUCTURE | RT (min) | [M + H] (measured) | Method | MP ° C. |
|---|---|---|---|---|---|---|
| P50 | N-[1-[3-(5-cyano-2-pyridyl)pyrazin-2-yl]ethyl]-3-(1-methoxycyclopropyl)-5-(trifluoromethyl)benzamide | 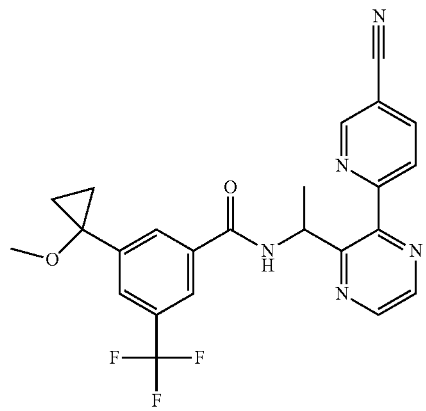 [SMILES: COC1(c2cc(C(=O)NC(C)c3nccnc3-c3ccc(C#N)cn3)cc(C(F)(F)F)c2)CC1] | | | | 140-150 |

TABLE I

Table of Intermediates

| Index | IUPAC name | STRUCTURE | RT (min) | m/z (measured) | Method | NMR |
|---|---|---|---|---|---|---|
| I1 | methyl 2-chloro-6-(trifluoromethyl)pyridine-4-carboxylate | 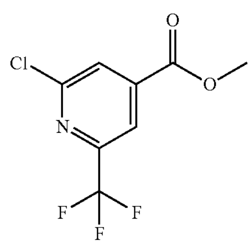 | | | | 1) |
| I2 | methyl 2-cylcopropyl-6-(trifluoromethyl)pyridine-4-carboxylate | 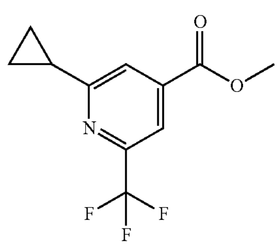 [SMILES: COC(=O)c1cc(C2CC2)nc(C(F)(F)F)c1] | 1.12 | 246 [M + H]$^+$ | 1 | |
| I3 | 2-cyclopropyl-6-(trifluoromethyl)pyridine-4-carboxylic acid | 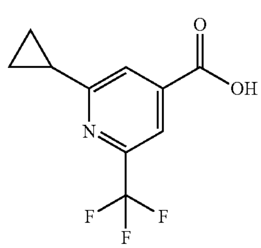 [SMILES: O=C(O)c1cc(C2CC2)nc(C(F)(F)F)c1] | 0.94 | 232 [M + H]$^+$ | 1 | |

TABLE I-continued

Table of Intermediates

| Index | IUPAC name | STRUCTURE | RT (min) | m/z (measured) | Method | NMR |
|---|---|---|---|---|---|---|
| I4 | methyl 3-cyclopropyl-5-(trifluoromethyl)benzoate | 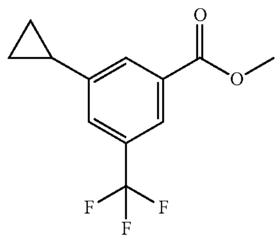 [SMILES: COC(=O)c1cc(C2CC2)cc(C(F)(F)F)c1] | | | | 2) |
| I5 | 3-cyclopropyl-5-(trifluoromethyl)benzoic acid | 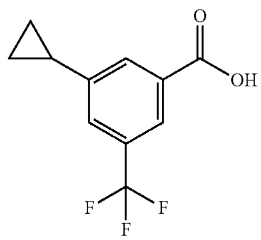 [SMILES: O=C(O)c1cc(C2CC2)cc(C(F)(F)F)c1] | 0.99 | 229 [M − H]⁻ | 1 | |
| I6 | methyl 3-(trifluoromethyl)-5-vinyl-benzoate | 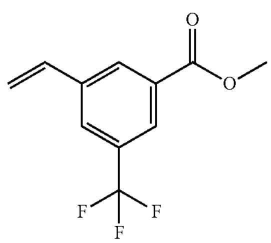 [SMILES: C=Cc1cc(C(=O)OC)cc(C(F)(F)F)c1] | | | | 3) |
| I7 | methyl 3-(trifluoromethyl)-5-[2-(trifluoromethyl)cyclopropyl]benzoate | 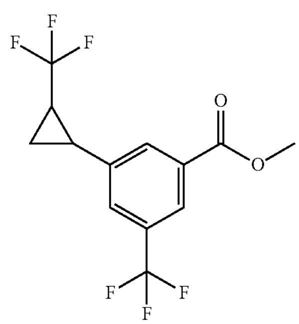 [SMILES: COC(=O)c1cc(C2CC2C(F)(F)F)cc(C(F)(F)F)c1] | | | | 4) |
| I8 | 3-(trifluoromethyl)-5-[2-(trifluoromethyl)cyclopropyl]benzoic acid | 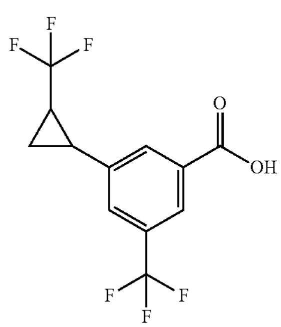 [SMILES: O=C(O)c1cc(C2CC2C(F)(F)F)cc(C(F)(F)F)c1] | 1.04 | 297 [M − H]⁻ | 1 | |

TABLE I-continued

Table of Intermediates

| Index | IUPAC name | STRUCTURE | RT (min) | m/z (measured) | Method | NMR |
|---|---|---|---|---|---|---|
| I9 | methyl 3-(trifluoromethyl)-5-(trifluoromethylsulfanoyl) benzoate | 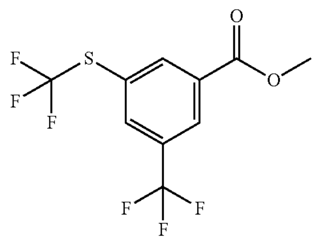 [SMILES: COC(=O)c1cc(SC(F)(F)F)cc(C(F)(F)F)c1] | | | | 5) |
| I10 | methyl 3-(trifluoromethyl)-5-(trifluoromethylsulfonyl) benzoate | 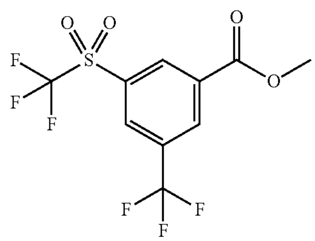 [SMILES: COC(=O)c1cc(C(F)(F)F)cc(S(=O)(=O)C(F)(F)F)c1] | | | | 6) |
| I11 | 3-(trifluoromethyl)-5-(trifluoromethylsulfonyl) benzoic acid | 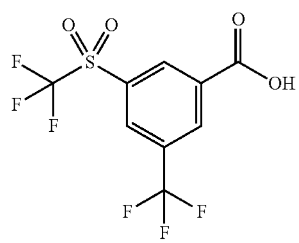 [SMILES: O=C(O)c1cc(C(F)(F)F)cc(S(=O)(=O)C(F)(F)F)c1] | | | | 7) |
| I12 | methyl 3-(cyclopropanecarbonyl)-5-(trifluoromethyl)benzoate | 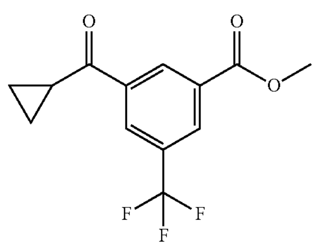 [SMILES: COC(=O)c1cc(C(=O)C2CC2)cc(C(F)(F)F)c1] | | | | 8) |
| I13 | methyl 3-[cyclopropyl(difluoro)methyl]-5-(trifluoromethyl)benzoate | 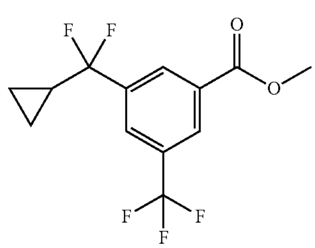 [SMILES: COC(=O)c1cc(C(F)(F)F)cc(C(F)(F)C2CC2)c1] | | | | 9) |
| I14 | 3-[cyclopropyl(difluoro)methyl]-5-(trifluoromethyl)benzoic acid | 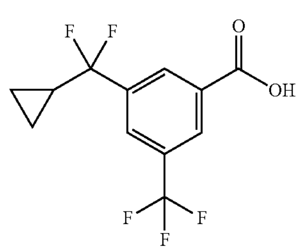 [SMILES: O=C(O)c1cc(C(F)(F)F)cc(C(F)(F)C2CC2)c1] | 1.03 | 279 [M − H]− | 1 | |

TABLE I-continued

Table of Intermediates

| Index | IUPAC name | STRUCTURE | RT (min) | m/z (measured) | Method | NMR |
|---|---|---|---|---|---|---|
| I15 | methyl 2-(1-cyano-2-ethoxy-2-oxo-ethyl)-6-(trifluoromethyl)pyridine-4-carboxylate | 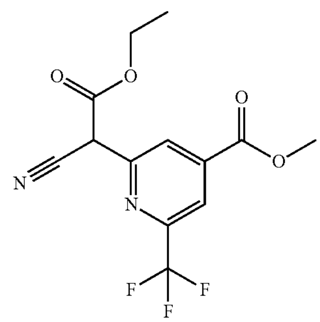 [SMILES: CCOC(=O)C(C#N)c1cc(C(=O)OC)cc(C(F)(F)F)n1] | 1.01 | 317 [M + H]⁺ | 1 | |
| I16 | methyl 2-(cyanomethyl)-6-(trifluoromethyl)pyridine-4-carboxylate | 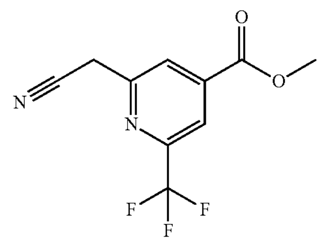 [SMILES: COC(=O)c1cc(CC#N)nc(C(F)(F)F)c1] | | | | 10) |
| I17 | 2-(1-cyanocyclopropyl)-6-(trifluoromethyl)pyridine-4-carboxylic acid | 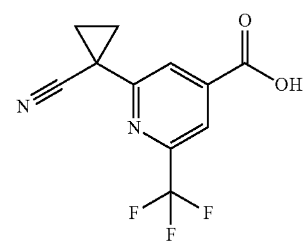 [SMILES: N#CC1(c2cc(C(=O)O)cc(C(F)(F)F)n2)CC1] | 0.89 | 255 [M − H]⁻ | 1 | |
| I18 | methyl 3-(cyanomethyl)-5-(trifluoromethyl)benzoate | 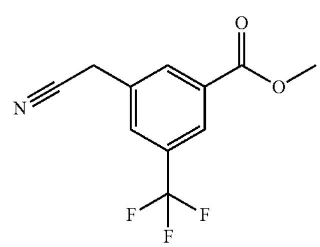 [SMILES: COC(=O)c1cc(CC#N)cc(C(F)(F)F)c1] | | | | 11) |
| I19 | methyl 3-(1-cyanocyclopropyl)-5-(trifluoromethyl)benzoate | 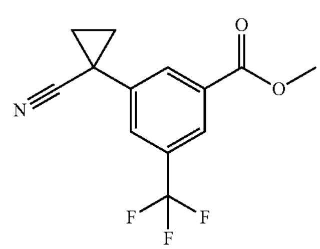 [SMILES: COC(=O)c1cc(C(F)(F)F)cc(C2(C#N)CC2)c1] | | | | 12) |
| I20 | 3-(1-cyanocyclopropyl)-5-(trifluoromethyl)benzoic acid | 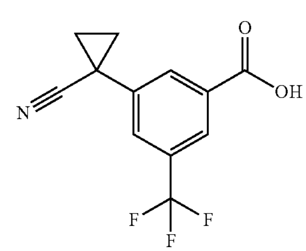 [SMILES: N#CC1(c2cc(C(=O)O)cc(C(F)(F)F)c2)CC1] | | | | 13) |

TABLE I-continued

Table of Intermediates

| Index | IUPAC name | STRUCTURE | RT (min) | m/z (measured) | Method | NMR |
|---|---|---|---|---|---|---|
| I21 | 6-(3-acetylpyrazin-2-yl)pyridine-3-carbonitrile | 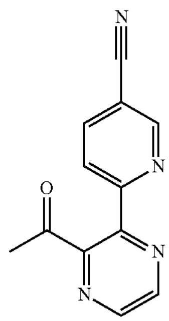 [SMILES: CC(=O)c1nccnc1-c1ccc(C#N)cn1] | 0.73 | 225.1 | 1 | |
| I22 | 1-[3-[5-(2,2-difluoroethoxy)pyrimidin-2-yl]pyrazin-2-yl]ethanone | 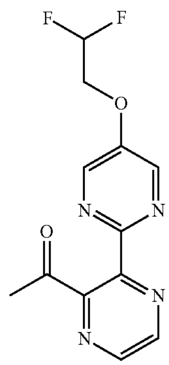 [SMILES: CC(=O)c1nccnc1-c1ncc(OCC(F)F)cn1] | | | | 14) |
| I23 | 1-[3-[5-(difluoromethoxy)pyrimidin-2-yl]pyrazin-2-yl]ethanone | 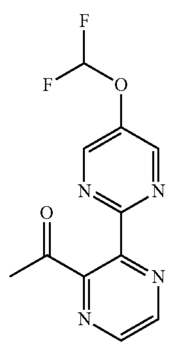 [SMILES: CC(=O)c1nccnc1-c1ncc(OC(F)F)cn1] | | | | 15) |
| I24 | 1-[3-[5-(2,2,2-trifluoroethoxy)pyrimidin-2-yl]pyrazin-2-yl]ethanone | 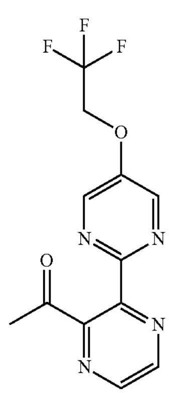 [SMILES: CC(=O)c1nccnc1-c1ncc(OCC(F)(F)F)cn1] | | 299.1 [M + H]⁺ | | |

TABLE I-continued

Table of Intermediates

| Index | IUPAC name | STRUCTURE | RT (min) | m/z (measured) | Method | NMR |
|---|---|---|---|---|---|---|
| I25 | 1-[3-[5-(2,2,2-trifluoroethoxy)-2-pyridyl]pyrazin-2-yl]ethanone | 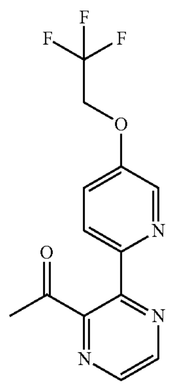 [SMILES: CC(=O)c1nccnc1-c1ccc(OCC(F)(F)F)cn1] | | | | 16) |
| I26 | (1R)-1-(3-chloropyrazin-2-yl)ethanol | 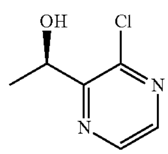 | 0.40 | 159/160 [M + H]⁺ | 1 | |
| I27 | 6-[3-(1-aminoethyl)pyrazin-2-yl]pyridine-3-carbonitrile | 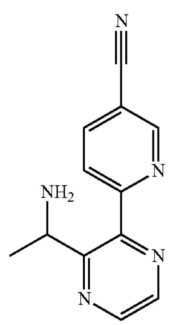 [SMILES: CC(N)c1nccnc1-c1ccc(C#N)cn1] | | | | 17) |
| I28 | 1-[3-[5-(2,2-difluoroethoxy)pyrimidin-2-yl]pyrazin-2-yl]ethanamine | 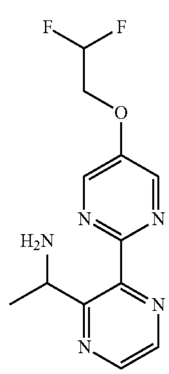 [SMILES: CC(N)c1nccnc1-c1ncc(OCC(F)F)cn1] | | | | 18) |

TABLE I-continued
Table of Intermediates
| Index | IUPAC name | STRUCTURE | RT (min) | m/z (measured) | Method | NMR |
|---|---|---|---|---|---|---|
| I29 | 1-[3-[5-(difluoromethoxy)pyrimidin-2-yl]pyrazin-2-yl]ethanamine | 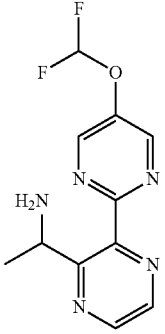 | | | | 19) |
| I30 | 1-[3-[5-(2,2,2-trifluoroethoxy)pyrimidin-2-yl]pyrazin-2-yl]ethanamine | 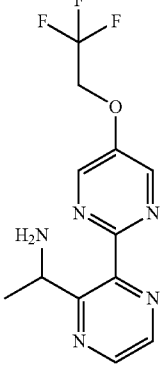 | | | | 20) |
| I31 | 1-[3-[5-(2,2,2-trifluoroethoxy)-2-pyridyl]pyrazin-2-yl]ethanamine | 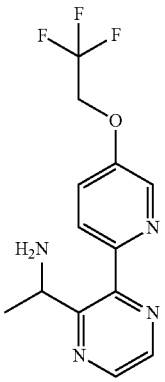 | | | | 21) |
| I32 | 6-[3-[(1S)-1-aminoethyl]pyrazin-2-yl]pyridine-3-carbonitrile | 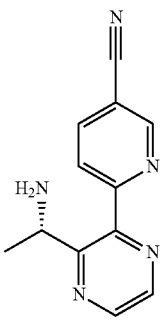 | 0.28 | 226 [M + H]⁺ | 1 | |

TABLE I-continued

Table of Intermediates

| Index | IUPAC name | STRUCTURE | RT (min) | m/z (measured) | Method | NMR |
|---|---|---|---|---|---|---|
| I33 | 6-[3-[(1S)-1-(cyclopropylmethylamino)ethyl]pyrazin-2-yl]pyridine-3-carbonitrile | 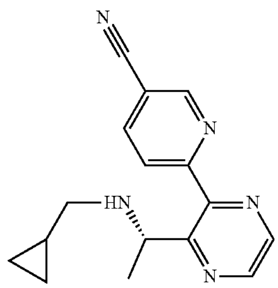 [SMILES: C[C@H](NCC1CC1)c1nccnc1-c1ccc(C#N)cn1] | | | | 22) |
| I34 | (1S)-1-(3-chloropyrazin-2-yl)ethanamine | 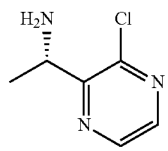 | 0.17 | 158 [M + H]⁺ | 1 | |
| I35 | (1S)-1-(3-chloropyrazin-2-yl)-N-(cyclopropylmethyl)ethanamine | 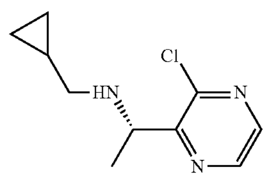 | 0.26 | 212 [M + H]⁺ | 1 | |
| I36 | tert-butyl N-[(1S)-1-[3-(5-cyano-2-pyridyl)pyrazin-2-yl]ethyl]carbamate | 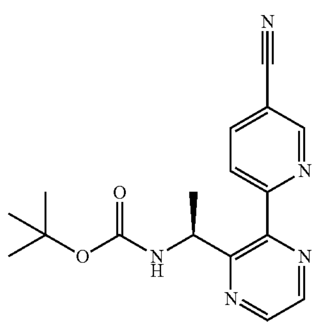 [SMILES: C[C@H](NC(=O)OC(C)(C)C)c1nccnc1-c1ccc(C#N)cn1] | | | | 23) |
| I37 | tert-butyl N-[(1S)-1-[6-amino-3-(5-bromo-2-pyridyl)pyrazin-2-yl]ethyl]carbamate | 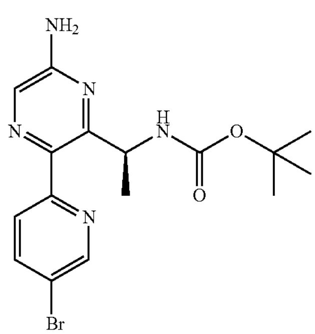 [SMILES: C[C@H](NC(=O)OC(C)(C)C)c1nc(N)cnc1-c1ccc(Br)cn1] | 0.99 | 394/396 [M + H]⁺ (bromo pattern) | 1 | |
| I38 | methyl 3-(1-methoxycyclopropyl)-5-(trifluoromethyl)benzoate | 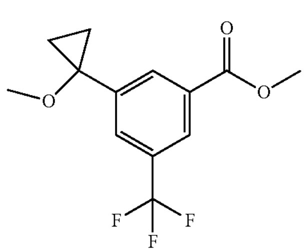 | | | | 24) |

TABLE I-continued

Table of Intermediates

| Index | IUPAC name | STRUCTURE | RT (min) | m/z (measured) | Method | NMR |
|---|---|---|---|---|---|---|
| I39 | 3-(1-methoxycyclopropyl)-5-(trifluoromethyl)benzoic acid | 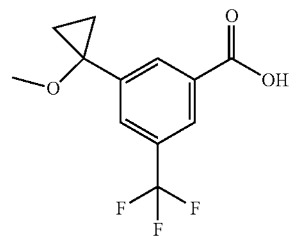 [SMILES: COC1(c2cc(C(=O)O)cc(C(F)(F)F)c2)CC1] | | | | 25) |
| I40 | 1-bromo-3-(1-methoxycyclopropyl)-5-(trifluoromethyl)benzene | 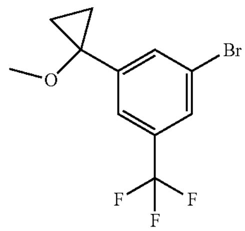 [SMILES: COC1(c2cc(Br)cc(C(F)(F)F)c2)CC1] | | | | 26) |

[1] $^1$H NMR (400 MHz, chloroform-d) δ ppm: 4.04 (s, 3 H) 8.11 (s, 1 H) 8.17 (d, J = 1.10 Hz, 1 H).
[2] $^1$H NMR (400 MHz, chloroform-d) δ ppm: 0.76-0.85 (m, 2 H) 1.06-1.15 (m, 2 H) 2.03 (tt, J$_1$ = 8.39 Hz, J$_2$ = 5.00 Hz, 1 H 3.96 (s, 3 H) 7.52 (s, 1 H) 7.91 (s, 1 H) 8.08 (d, J = 0.73 Hz, 1 H). $^{19}$F NMR (377 MHz, chloroform-d) δ ppm: −62.75 (s, 3 F).
[3] $^1$H NMR (400 MHz, chloroform-d) δ ppm: 3.98 (s, 3 H) 5.47 (d, J = 11.00 Hz, 1 H) 5.93 (d, J = 17.61 Hz, 1 H) 6.79 (dd, J$_1$ = 17.42 Hz, J$_2$ = 10.82 Hz, 1 H) 7.82 (s, 1 H) 8.19 (s, 1 H) 8.24-8.29 (m, 1 H).
[4] $^1$H NMR (400 MHz, chloroform-d) δ ppm: 1.25-1.34 (m, 1 H) 1.48-1.55 (m, 1 H) 1.88-2.00 (m, 1 H) 2.46-2.53 (m, 1 H) 3.98 (s, 3 H) 7.60 (s, 1 H) 7.98 (s, 1 H) 8.19 (s, 1 H).
[5] $^1$H NMR (400 MHz, chloroform-d) δ ppm: 4.02 (s, 3 H), 8.11 (s, 1 H), 8.44 (s, 1H), 8.53 (s, 1 H).
[6] $^1$H NMR (400 MHz, Chloroform) δ ppm 4.07 (s, 3 H) 8.43-8.51 (m, 1 H) 8.70-8.80 (m, 1 H) 8.84-8.91 (m, 1 H). $^{19}$F NMR (377 MHz, chloroform-d) δ ppm: −77.49 (s, 3 F) −62.96 (s, 3 F)
[7] $^1$H NMR (400 MHz, dimethylsulfoxide-d6) δ ppm: 8.68 (s, 2 H) 8.71-8.76 (m, 1 H) 13.33-15.22 (m, 1 H).
[8] $^1$H NMR (400 MHz, chloroform-d) δ ppm: 1.16-1.22 (m, 2 H) 1.35 (quin, J = 3.76 Hz, 2 H) 2.74 (tt, J$_1$ = 7.84 Hz, J$_2$ = 4.45 Hz, 1 H) 4.02 (s, 3 H) 8.45 (d, J = 0.73 Hz, 1 H) 8.51 (d, J = 0.73 Hz, 1 H) 8.86 (s, 1 H).
[9] $^1$H NMR (400 MHz, chloroform-d) δ ppm: 0.73-0.79 (m, 2 H) 0.82-0.89 (m, 2 H) 1.47-1.60 (m, 1 H) 8.00 (d, J = 0.73 Hz, 1 H) 8.39 (s, 1 H) 8.42 (s, 1 H). $^{19}$F NMR (377 MHz, chloroform-d) δ ppm: −98.40 (s, 3 F) −62.81 (s, 2 F).
[10] $^1$H NMR (400 MHz, chloroform-d) δ ppm: 4.05 (s, 3 H) 4.13 (s, 2 H) 8.24 (s, 1 H) 8.26 (s, 1 H).
[11] $^1$H NMR (400 MHz, chloroform-d) δ ppm: 8.30 (1 H, s), 8.23 (1 H, s), 7.81 (1 H, s), 3.99 (3 H, s), 3.90 (2 H, s).
[12] $^1$H NMR (400 MHz, chloroform-d) δ ppm: 8.23 (1 H, s), 8.09 (1 H, s), 7.79 (1 H, s), 3.98 (3 H, s), 1.84-1.92 (2 H, m), 1.47-1.57 (m, 2H).
[13] $^1$H NMR (400 MHz, chloroform-d) δ ppm: 8.60-9.90 (1 H, br s), 8.29 (1 H, s), 8.15 (1 H, s), 7.84 (1 H, s), 1.84-1.93 (2 H, m), 1.50-1.60 (2 H, m)
[14] $^1$H NMR (400 MHz, DMSO-d6) δ ppm: 8.90 (s, 1H), 8.70-8.90 (m, 3H), 6.48 (t, 1H), 4.63 (td, 2H), 2.62 (s, 3H).
[15] $^1$H NMR (400 MHz, DMSO-d6) δ ppm: 8.80-9.00 (m, 4H), 7.50 (t, 1H), 2.65 (s, 3H).
[16] $^1$H-NMR (400 MHz, DMSO-d6): δ ppm 8.85 (d, 1H), 8.70 (m, 1H), 8.45 (s, 1H), 8.25 (d, 1H), 7.75 (d, 1H), 5 (q, 2H), 2.6 (s, 3H).
[17] $^1$H-NMR (400 MHz, DMSO-d6): δ ppm 9.22 (s, 1H), 8.85-8.95 (m, 2H), 8.50-8.60 (m, 1H), 8.30-8.40 (m, 1H) 7.80-8.10 (br. s, 2H), 5.25-5.35 (m, 1 H), 1.52 (d, 3H)
[18] $^1$H NMR (400 MHz, DMSO-d6) δ ppm: 8.80-9.00 (m, 4H), 6.50 (tt, 1H), 4.90 (m, 1H), 4.78 (td, 2H), 1.45 (d, 3H)
[19] $^1$H NMR (400 MHz, DMSO-d6) δ ppm: 8.80-9.10 (m, 4H), 7.51 (t, 1H), 4.88 (m, 1H), 1.50 (d, 3H)
[20] $^1$H-NMR (400 MHz, DMSO-d6): δ ppm: 8.95 (s, 2H), 8.60-9.00 (m, 2H), 7.8-8.30 (br s, 2H), 5.08-5.20 (m, 2H), 4.95-5.05 (m, 1H), 1.5 (m, 3H)
[21] $^1$H-NMR (400 MHz, DMSO-d6): δ ppm: 8.8 (s, 2H), 8.65 (d, 1H), 8.15 (d, 1H), 7.8 (m, 1H), 7.45 (br s, 2H), 7.25 (m, 1H), 7.15 (m, 1H), 5.2 (br s, 1H), 5 (q, 2H), 1.5 (m, 3H)
[22] $^1$H NMR (400 MHz, chloroform-d) δ ppm −0.05 (dd, 2H) 0.39 (td, 2H) 0.81-0.94 (m, 1H) 1.50 (d, 3H) 1.98 (dd, 1H) 2.44 (dd, 1H) 2.49-2.89 (m, 1H) 4.73 (q, 1H) 8.11-8.18 (m, 1H) 8.20-8.27 (m, 1H) 8.57 (d, 1H) 8.69 (d, 1H) 9.00 (dd, 1H)
[23] $^1$H NMR (400 MHz, chloroform-d) δ ppm 1.38 (br s, 9H), 1.55 (s, 3H), 5.66-5.78 (m, 2H), 8.11 (dd, 1H), 8.30 (d, 1H), 8.59 (d, 1H), 8.63 (d, 1H), 8.93-9.04 (m, 1H)
[24] $^1$H NMR (400 MHz, chloroform-d) δ ppm: 13.4-13.7 (br. s, 1H), 8.00-8.10 (m, 2H), 7.72 (s, 1H), 3.19 (s, 3H), 1.25-1.35 (m, 2H), 1.08-1.15 (m, 2H).
[25] $^1$H NMR (400 MHz, chloroform-d) δ ppm: 8.17 (s, 1H), 8.05 (s, 1H), 7.78 (s, 1H), 3.95 (s, 3H), 3.25 (s, 3H), 1.30 (t, 2H), 1.05 (t, 2H).
[26] $^1$H NMR (400 MHz, DMSO-d) δ ppm: 7.82 (s, 1H), 7.69 (s, 1H), 7.55 (s, 1H), 3.27 (s, 3H), 1.20-1.28 (m, 2H), 1.09-1.18 (m, 2H).

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (where the abbreviation "TX" means "one compound selected from the compounds defined in the Tables A-1 to A-27, B-1 to B-27, C-1 to C-27, D-1 to D-27 and E-1 to E-27, and Table P"):

an adjuvant selected from the group of substances consisting of petroleum oils (alternative name) (628)+TX, an insect control active substance selected from Abamectin+TX, Acequinocyl+TX, Acetamiprid+TX, Acetoprole+TX, Acrinathrin+TX, Acynonapyr+TX, Afidopyropen+TX, Afoxalaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Beta-cypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1472050-04-6+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2249718-27-0+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cyclobutrifluram+TX, Cycloprothrin+TX, Cycloxaprid+TX, Cycloxaprid+TX, Cyenopyrafen+TX, Cyetpyrafen (or Etpyrafen)+TX, Cyflumetofen+TX, Cyfluthrin+TX, Cyhalodiamide+TX, Cyhalothrin+TX, Cypermethrin+TX, Cyphenothrin+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin+TX, Empenthrin+TX, Epsilon-momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupentiofenox+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halofenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nitenpyram+TX, Nithiazine+TX, Omethoate+TX, Oxamyl+TX, Oxazosufyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyrimostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachloraniliprole+TX, Tetradiphon+TX, Tetramethrin+TX, Tetramethylfluthrin+TX, Tetranactin+TX, Tetraniliprole+TX, Thetacypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, Azadirachtin+TX, *Bacillus aizawai*+TX, *Bacillus chitinosporus* AQ746 (NRRL Accession No B-21 618)+TX, *Bacillus firmus*+TX, *Bacillus kurstaki*+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A₃-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, pyrethrum+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+

TX, *Spodoptera frugiperda* Nucleopolyhedrovirus+ TX, *Streptomyces galbus* (NRRL Accession No. 30232)+TX, *Streptomyces* sp. (NRRL Accession No. B-30145)+TX, Terpenoid blend+TX, and *Verticillium* spp., an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, Cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca- 9,11-dien-1-yl acetate (IUPAC name) (780)+TX, (9Z, 12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure 11 (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, Cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methylpropyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure 11+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquinbutyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl) aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, El 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone 11+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methyl-rhodanine+TX, 5-methyl-6-thioxo-1,3,5-thiadiazinan-3-ylacetic acid+TX, 6-isopentenylaminopurine+TX, 2-fluoro-N-(3-methoxyphenyl)-9H-purin-6-amine+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, –sodium fluoroacetate+TX, thallium sulfate+TX, warfarin+TX, -2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, mercuric oxide+TX, thiophanate-methyl+TX, azaconazole+TX, bitertanol+TX, bromuconazole+TX, cyproconazole+TX, difenoconazole+TX, diniconazole–+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, –simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidine+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, –metalaxyl–+TX, Rmetalaxyl+TX, ofurace+TX, oxadixyl+TX, carbendazim+TX, debacarb+TX, fuberidazole–+TX, thiabendazole+TX, chlozolinate+TX, dichlozoline+TX, myclozoline–+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb–+TX, chloro-thalonil+TX, cyflufenamid+TX, cymoxanil+TX, cyclobutrifluram+TX, diclocymet+TX, diclomezine–+TX, dicloran+TX, diethofencarb+TX, dimethomorph–+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, –fenhexamid+TX, fosetyl-aluminium–+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]

pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1, 1, 3-trimethylindan-4-yl) pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1, 1, 3-trimethylindan-4-yl) pyridine-3-carboxamide+TX, α-(1, 1-dimethylethyl)-α-[4'-(trifluoromethoxy) [1,1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy] benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[2-trifluoromethyl)oxetan-2-yl]phenyl]-N-methyl-formamidine+TX, N-ethyl-N'-[5-methoxy-2-methyl-4-[2-trifuoromethyl)tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1S)-1-benzyl-1,3-dimethyl-butyl]-7,8-difluoro-quinoline-3-carboxamide+TX, 8-fluoro-N-[1-[(3-fluorophenyl)methyl]-1,3-dimethyl-butyl]quinoline-3-carboxamide+TX, N-(1-benzyl-1,3-dimethyl-butyl)-8-fluoro-quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-(1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinolyl+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085);

N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N—[(E)-methoxyiminomethyl]-4-[5-(trifluoromethyl)-1,2,4-oxadiazol-3-yl]benzamide+TX, N—[(Z)-methoxyiminomethyl]-4-[5-(trifluoromethyl)-1,2,4-oxadiazol-3-yl]benzamide+TX, N—[N-methoxy-C-methyl-carbonimidoyl]-4-[5-(trifluoromethyl)-1,2,4-oxadiazol-3-yl]benzamide+TX (these compounds may be prepared from the methods described in WO 2018/202428); microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, *Bacteria* spp. (GROWMEND®+TX, GROW-SWEET®+TX, Shootup®)+TX, bacteriophage of Clavibacter michiganensis (AgriPhage®)+TX, Bakflor®+TX, Beauveria bassiana (Beaugenic®+TX, Brocaril WP®)+TX, Beauveria bassiana GHA (Mycotrol ES®+TX, Mycotrol O®+TX, BotaniGuard®)+TX, Beauveria brongniartii (Engerlingspilz®+TX, Schweizer Beauveria®+TX, Melocont®)+TX, Beauveria spp.+TX, Botrytis cineria+TX, Bradyrhizobium japonicum (TerraMax®)+TX, Brevibacillus brevis+TX, Bacillus thuringiensis tenebrionis (Novodor®)+TX, BtBooster+TX, Burkholderia cepacia (Deny®+TX, Intercept®+TX, Blue Circle®)+TX, Burkholderia gladii+TX, Burkholderia gladioli+TX, Burkholderia spp.+TX, Canadian thistle fungus (CBH Canadian Bioherbicide®)+TX, Candida butyri+TX, Candida famata+TX, Candida fructus+TX, Candida glabrata+TX, Candida guilliermondii+TX, Candida melibiosica+TX, Candida oleophila strain O+TX, Candida parapsilosis+TX, Candida pelliculosa+TX, Candida pulcherrima+TX, Candida reukaufii+TX, Candida saitoana (Bio-Coat®+TX, Biocure®)+TX, Candida sake+TX, Candida spp.+TX, Candida tenius+TX, Cedecea dravisae+TX, Cellulomonas flavigena+TX, Chaetomium cochliodes (Nova-Cide®)+TX, Chaetomium globosum (Nova-Cide®)+TX, Chromobacterium subtsugae strain PRAA4-1T (Grandevo®)+TX, Cladosporium cladosporioides+TX, Cladosporium oxysporum+TX, Cladosporium chlorocephalum+TX, Cladosporium spp.+TX, Cladosporium tenuissimum+TX, Clonostachys rosea (EndoFine®)+TX, Colletotrichum acutatum+TX, Coniothyrium minitans (Cotans WG®)+TX, Coniothyrium spp.+TX, Cryptococcus albidus (YIELDPLUS®)+TX, Cryptococcus humicola+TX, Cryptococcus infirmo-miniatus+TX, Cryptococcus laurentii+TX, Cryptophlebia leucotreta granulovirus (Cryptex®)+TX, Cupriavidus campinensis+TX, Cydia pomonella granulovirus (CYD-X®)+TX, Cydia pomonella granulovirus (Madex®+TX, Madex Plus®+TX, Madex Max/Carpovirusine®)+TX, Cylindrobasidium laeve (Stumpout®)+TX, Cylindrocladium+TX, Debaryomyces hansenii+TX, Drechslera hawaiinensis+TX, Enterobacter cloacae+TX, Enterobacteriaceae+TX, Entomophtora virulenta (Vektor®)+TX, Epicoccum nigrum+TX, Epicoccum purpurascens+TX, Epicoccum spp.+TX, Filobasidium floriforme+TX, Fusarium acuminatum+TX, Fusarium chlamydosporum+TX, Fusarium oxysporum (Fusaclean®/Biofox C®)+TX, Fusarium proliferatum+TX, Fusarium spp.+TX, Galactomyces geotrichum+TX, Gliocladium catenulatum (Primastop®+TX, Prestop®)+TX, Gliocladium roseum+TX, Gliocladium spp. (SoilGard®)+TX, Gliocladium virens (Soilgard®)+TX, Granulovirus (Granupom®)+TX, Halobacillus halophilus+TX, Halobacillus litoralis+TX, Halobacillus trueperi+TX, Halomonas spp.+TX, Halomonas subglaciescola+TX, Halovibrio variabilis+TX, Hanseniaspora uvarum+TX, Helicoverpa armigera nucleopolyhedrovirus (Helicovex®)+TX, Helicoverpa zea nuclear polyhedrosis virus (Gemstar®)+TX, Isoflavone-formononetin (Myconate®)+TX, Kloeckera apiculata+TX, Kloeckera spp.+TX, Lagenidium giganteum (Laginex®)+TX, Lecanicillium longisporum (Vertiblast®)+TX, Lecanicillium muscarium (Vertikil®)+TX, Lymantria Dispar nucleopolyhedrosis virus (Disparvirus®)+TX, Marinococcus halophilus+TX, Meira geulakonigii+TX, Metarhizium anisopliae (Met52®)+TX, Metarhizium anisopliae (Destruxin WP®)+TX, Metschnikowia fruticola (Shemer®)+TX, Metschnikowia pulcherrima+TX, Microdochium dimerum (Antibot®)+TX, Micromonospora coerulea+TX, Microsphaeropsis ochracea+TX, Muscodor albus 620 (Muscudor®)+TX, Muscodor roseus strain $A_3$-5+TX, Mycorrhizae spp. (AMykor®+TX, Root Maximizer®)+TX, Myrothecium verrucaria strain AARC-0255 (DiTera®)+TX, BROS PLUS®+TX, Ophiostoma piliferum strain D97 (Sylvanex®)+TX, Paecilomyces farinosus+TX, Paecilomyces fumosoroseus (PFR-97®+TX, PreFeRal®)+TX, Paecilomyces linacinus (Biostat WP®)+TX, Paecilomyces lilacinus strain 251 (MeloCon WG®)+TX, Paenibacillus polymyxa+TX, Pantoea agglomerans (BlightBan $C_9$-1®)+TX, Pantoea spp.+TX, Pasteuria spp. (Econem®)+TX, Pasteuria nishizawae+TX, Penicillium aurantiogriseum+TX, Penicillium billai (Jumpstart®+TX, TagTeam®)+TX, Penicillium brevicompactum+TX, Penicillium frequentans+TX, Penicillium griseofulvum+TX, Penicillium purpurogenum+TX, Penicillium spp.+TX, Penicillium viridicatum+TX, Phlebiopsis gigantean (Rotstop®)+TX, phosphate solubilizing bacteria (Phosphomeal®)+TX, Phytophthora cryptogea+TX, Phytophthora palmivora (Devine®)+TX, Pichia anomala+TX, Pichia guilermondii+TX, Pichia membranaefaciens+TX, Pichia onychis+TX, Pichia stipites+TX, Pseudomonas aeruginosa+TX, Pseudomonas aureofasciens (Spot-Less Biofungicide®)+TX, Pseudomonas cepacia+TX, Pseudomonas chlororaphis (AtEze®)+TX, Pseudomonas corrugate+TX, Pseudomonas fluorescens strain $A_{506}$ (BlightBan $A_{506}$®)+TX, Pseudomonas putida+TX, Pseudomonas reactans+TX, Pseudomonas spp.+TX, Pseudomonas syringae (Bio-Save®)+TX, Pseudomonas viridiflava+TX, Pseudomons fluorescens (Zequanox®)+TX, Pseudozyma flocculosa strain PF-$A_{22}$ UL (Sporodex L®)+TX, Puccinia canaliculata+TX, Puccinia thlaspeos (Wood Warrior®)+TX, Pythium paroecandrum+TX, Pythium oligandrum (Polygandron®+TX, Polyversum®)+TX, Pythium periplocum+TX, Rhanella aquatilis+TX, Rhanella spp.+TX, Rhizobia (Dormal®+TX, Vault®)+TX, Rhizoctonia+TX, Rhodococcus globerulus strain AQ719+TX, Rhodosporidium diobovatum+TX, Rhodosporidium toruloides+TX, Rhodotorula spp.+TX, Rhodotorula glutinis+TX, Rhodotorula graminis+TX, Rhodotorula mucilagnosa+TX, Rhodotorula rubra+TX, Saccharomyces cerevisiae+TX, Salinococcus roseus+TX, Sclerotinia minor+TX, Sclerotinia minor (SARRITOR®)+TX, Scytalidium spp.+TX, Scytalidium uredinicola+TX, Spodoptera exigua nuclear polyhedrosis virus (Spod-X®+TX, Spexit®)+TX, Serratia marcescens+TX, Serratia plymuthica+TX, Serratia spp.+TX, Sordaria fimicola+TX, Spodoptera littoralis nucleopolyhedrovirus (Littovir®)+TX, Sporobolomyces roseus+TX, Stenotrophomonas maltophilia+TX, Streptomyces ahygroscopicus+TX, Streptomyces albaduncus+TX, Streptomyces exfoliates+TX, Streptomyces galbus+TX, Streptomyces griseoplanus+TX, Streptomyces griseoviridis (Mycostop®)+TX, Streptomyces lydicus (Actinovate®)+TX, Streptomyces lydicus WYEC-108 (ActinoGrow®)+TX, Streptomyces violaceus+TX, Tilletiopsis minor+TX, Tilletiopsis spp.+TX, Trichoderma asperellum (T34 Biocontrol®)+TX, Trichoderma gamsii (Tenet®)+TX, Trichoderma atroviride (Plantmate®)+TX, Trichoderma hamatum TH 382+TX, Trichoderma harzianum rifai (Mycostar®)+TX, Trichoderma harzianum T-22 (Trianum-P®+TX, PlantShield HCO+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*;

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline 1®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *PsyIIaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homobrassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected selected from the compounds defined in the Tables A-1 to A-27, B-1 to B-27, C-1 to C-27, D-1 to D-27 and E-1 to E-27 and with active ingredients described above comprises a compound selected from one compound defined in the Tables A-1 to A-27, B-1 to B-27, C-1 to C-27, D-1 to D-27 and E-1 to E-27 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from the compounds defined in the Tables A-1 to A-27, B-1 to B-27, C-1 to C-27, D-1 to D-27 and E-1 to E-27 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil for example in the form of granules (soil application). In the case of paddy rice crops, such granules can be metered into the flooded paddy-field.

The compounds of formula I of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The disclosure in the present application makes available each and every combination of embodiments disclosed herein.

It should be noted that the disclosure herein in respect of a compound of formula I applies equally in respect of a compound of each of formulae I*, I'a, I-A, I'-A and Tables A-1 to A-27, B-1 to B-27, C-1 to C-27, D-1 to D-27 and E-1 to E-27. Further the preferred enantiomer of formula I'a applies also to compounds in the Tables A-1 to A-27, B-1 to B-27, C-1 to C-27, D-1 to D-27 and E-1 to E-27.

The compounds of the invention can be distinguished from other similar compounds by virtue of greater efficacy at low application rates and/or different pest control, which can be verified by the person skilled in the art using the experimental procedures, using lower concentrations if necessary, for example 10 ppm, δ ppm, 2 ppm, 1 ppm or 0.2 ppm; or lower application rates, such as 300, 200 or 100, mg of AI per m$^2$. The greater efficacy can be observed by an increased safety profile (against non-target organisms above and below ground (such as fish, birds and bees), improved physico-chemical properties, or increased biodegradability).

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, 6 ppm, 3 ppm, 1.5 ppm, 0.8 ppm or 0.2 ppm.

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% control in at least one of the two categories (mortality or growth inhibition) at an application rate of 200 ppm: P1, P2, P3, P4, P6, P7, P8, P9, P13, P16, P19, P22, P23, P24, P25, P27, P28, P29, P32, P33, P34, P36, P37, P38, P40, P41, P42, P43, P44, P46, P47, P48, P49, P50

Example B2: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% control in at least one of the two categories (mortality or growth inhibition) at an application rate of 200 ppm: P2, P28, P29, P32, P34, P36, P40, P47, P48, P49

Example B3: *Frankliniella occidentalis* (Western Flower Thrips): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P44, P48

Example B4: *Chilo suppressalis* (Striped Rice Stemborer)

24-well microtiter plates with artificial diet were treated with aqueous test solutions prepared from 10'000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control in at least one of the three categories (mortality, anti-feedant or growth inhibition) at an application rate of 200 ppm: P1, P2, P3, P4, P5, P6, P7, P8, P9, P10, P11, P12, P13, P14, P15, P16, P17, P18, P19, P20, P22, P23, P24, P25, P26, P27, P28, P29, P32, P33, P34, P35, P36, P37, P38, P39, P40, P41, P42, P43, P44, P45, P46, P47, P48, P49, P50

Example B5: *Plutella xylostella* (Diamond Back Moth)

24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% control in at least one of the two categories (mortality or growth inhibition) at an application rate of 200 ppm: P1, P2, P3, P4, P5, P6, P7, P8, P9, P10, P11, P12, P13, P14, P15, P16, P17, P18, P19, P22, P23, P24, P25, P26, P27, P28, P29, P30, P32, P33, P34, P35, P36, P37, P38, P39, P40, P41, P42, P43, P44, P45, P46, P47, P48, P49, P50

Example B6: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: 49

Example B7: *Myzus persicae* (Green Peach Aphid): Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

Example B8: *Myzus persicae* (Green Peach Aphid): Intrinsic Activity

Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm: P2, P9, P32, P34, P37, P40, P44, P47, P48, P49

Example B9: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control in at least one of the three categories (mortality, anti-feedant or growth inhibition) at an application rate of 200 ppm: P1, P2, P3, P4, P5, P6, P7, P8, P9, P10, P11, P12, P13, P14, P15, P16, P17, P18, P19, P22, P23, P24, P25, P26, P28, P29, P32, P33, P34, P35, P36, P37, P38, P39, P40, P41, P42, P43, P44, P46, P47, P48, P49, P50

Example B10: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% control in at least one of the three categories (mortality, anti-feeding, or growth inhibition) at a test rate of 12.5 ppm: P32, P34, P36, P40

Example B11: *Tetranychus urticae* (Two-Spotted Spider Mite)

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: P22

Example B12: *Myzus persicae* (Green Peach Aphid)

Test compounds prepared from 10'000 ppm DMSO stock solutions were applied by a liquid handling robot into 96-well microtiter plates and mixed with a sucrose solution. Parafilm was stretched over the 96-well microtiter plate and a plastic stencil with 96 holes was placed onto the plate. Aphids were sieved into the wells directly onto the Parafilm. The infested plates were closed with a gel blotting card and a second plastic stencil and then turned upside down. The samples were assessed for mortality 5 days after infestation.

The following compounds resulted in at least 80% mortality at an application rate of 50 ppm: P25, P32, P34, P36, P40

Example B13: *Plutella xylostella* (Diamondback Moth)

96-well microtiter plates containing artificial diet were treated with aqueous test solutions, prepared from 10'000 ppm DMSO stock solutions, by a liquid handling robot. After drying, eggs (~30 per well) were infested onto a netted lid which was suspended above the diet. The eggs hatch and L1 larvae move down to the diet. The samples were assessed for mortality 9 days after infestation.

The following compounds gave an effect of at least 80% mortality at an application rate of 500 ppm: P19, P20, P22, P23, P24, P25, P26, P27, P28, P29, P31, P32, P33, P34, P36, P37, P38, P39, P40, P41.

The invention claimed is:
1. A compound of the formula I

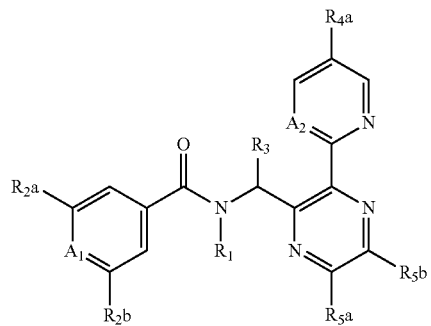

wherein
$R_1$ is H, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_6$haloalkyl, $C_2$-$C_6$alkenyl, $C_2$-$C_6$haloalkeny, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halo atoms, oxetan-3-yl-$CH_2$—, benzyl or benzyl substituted with halo or $C_1$-$C_6$haloalkyl;
$A_1$ is N or C—$R_{2c}$;
$R_{2c}$ is H, halogen, $C_1$-$C_3$alkyl, $C_1$-$C_3$haloalkyl, $C_1$-$C_3$alkoxy, or $C_1$-$C_3$haloalkoxy;
$R_{2a}$ is $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkoxy substituted with one to three substituents independently selected from $C_1$-$C_3$alkyl, $C_1$-$C_3$haloalkyl, cyano, and halogen, $C_3$-$C_6$cycloalkyl$C_1$-$C_4$alkyl, $C_3$-$C_6$cycloalkyl$C_1$-$C_4$alkoxy, $C_3$-$C_6$cycloalkyl$C_1$-$C_4$alkyl substituted with one to five substituents independently selected from $C_1$-$C_3$alkyl, $C_1$-$C_3$haloalkyl, $C_1$-$C_3$alkoxy, cyano, and halogen, $C_3$-$C_6$cycloalkyl$C_1$-$C_4$alkoxy substituted with one to five substituents independently selected from $C_1$-$C_3$alkyl, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, or $C_1$-$C_4$haloalkylsulfinyl;
$R_{2b}$ is H, halogen, $C_1$-$C_3$alkyl, $C_1$-$C_3$haloalkyl, $C_1$-$C_3$haloalkylthio, $C_1$-$C_3$alkoxy, $C_1$-$C_3$haloalkoxy, $SF_5$, or CN;
$R_3$ is $C_1$-$C_3$alkyl or $C_1$-$C_3$haloalkyl;
$A_2$ is $CR_{4b}$ or N;
$R_{4b}$ is hydrogen, or halogen;
$R_{4a}$ is cyano, or $C_1$-$C_3$haloakoxy;
$R_{5a}$ and $R_{5b}$ are, independently of each other, selected from hydrogen, halogen, CN, $C_1$-$C_3$alkyl, $C_1$-$C_3$haloalkyl, $C_3$-$C_4$cycloalkyl, $C_1$-$C_3$alkoxy, and $C_1$-$C_3$haloalkoxy; or agrochemically acceptable salts, stereoisomers, enantiomers, tautomers and N-oxides of the compounds of formula I.

2. The compound according to claim 1 wherein $R_3$ is methyl.

3. The compound according to claim 1, wherein $A_1$ is N.

4. The compound according to claim 1, wherein $A_1$ is C—$R_{2c}$, where $R_{2c}$ is hydrogen or halogen.

5. The compound according to claim 4, wherein R2c is hydrogen.

6. The compound according to claim 1, wherein $R_1$ is hydrogen, methyl, ethyl, n-propyl, isobutyl, cyclopropylmethyl or HC≡CCH$_2$—.

7. The compound according to claim 1, wherein $R_{2a}$ is $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkylC$_1$-C$_4$alkyl substituted with one to five substituents independently selected from halogen and $C_1$-$C_3$haloalkyl, $C_1$-$C_5$cyanoalkyl, $C_3$-$C_6$cycloalkoxy, $C_1$-$C_4$haloalkylsulfonyl or $C_1$-$C_4$haloalkylsulfinyl.

8. The compound according to claim 1, wherein $R_{2b}$ is halogen, $C_1$-$C_3$haloalkyl, $C_1$-$C_3$haloalkylthio, $C_1$-$C_3$alkoxy, $C_1$-$C_3$haloalkoxy, or CN.

9. The compound according to claim 1, wherein $R_{4a}$ is cyano, or $C_1$-$C_3$fluoroalkoxy.

10. The compound according to claim 1, wherein $A_2$ is N.

11. The compound according to claim 1, wherein $A_2$ is CH.

12. The compound according to claim 1, wherein $R_{5a}$ and $R_{5b}$, independent of each other, are selected from hydrogen, halogen, and methyl.

13. A composition comprising the compound according to claim 1, one or more auxiliaries and diluent, and optionally one more other active ingredient.

14. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of the compound according to claim 1, or of a composition comprising said compound, one or more auxiliaries and diluent, and optionally one more other active ingredient.

15. A plant propagation material, comprising, or treated with or adhered thereto, the compound according to claim 1, or of a composition comprising said compound, one or more auxiliaries and diluent, and optionally one more other active ingredient.

16. The plant propagation material according to claim 15, wherein said plant propagation material is a seed.

17. A compound of formulae IIaa to IIae

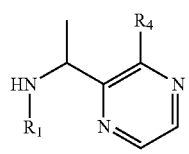

IIaa

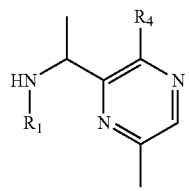

IIab

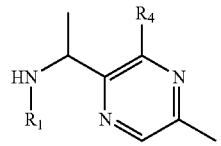

IIac

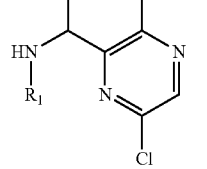

IIad

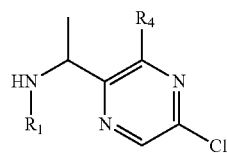

IIae wherein $R_1$ is H, $C_1$-$C_6$alkyl, $C_1$-$C_6$cyanoalkyl, aminocarbonylC$_1$-$C_6$alkyl, hydroxycarbonylC$_1$-$C_6$alkyl, $C_1$-$C_6$nitroalkyl, trimethylsilaneC$_1$-$C_6$alkyl, $C_1$-$C_6$haloalkyl, $C_2$-$C_6$alkenyl, $C_2$-$C_6$haloalkeny, $C_2$-$C_6$alkynyl, $C_2$-$C_6$haloalkynyl, $C_3$-$C_4$cycloalkylC$_1$-$C_2$alkyl-, $C_3$-$C_4$cycloalkylC$_1$-$C_2$alkyl- wherein the $C_3$-$C_4$cycloalkyl group is substituted with 1 or 2 halo atoms, oxetan-3-yl-CH$_2$—, benzyl or benzyl substituted with halo or $C_1$-$C_6$haloalkyl; and R4 is

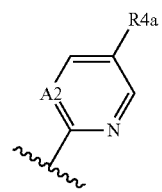

wherein $R_{4a}$ is cyano or $C_1$-$C_3$haloakoxy, and $A_2$ is $CR_{4b}$ or N; wherein $R_{4b}$ is hydrogen, or halogen.

18. The compound according to claim 17, wherein $R_1$ is hydrogen, methyl, ethyl, n-propyl, isobutyl, cyclopropylmethyl or HC≡CCH$_2$—.

19. The compound according to claim 17, wherein $R_{4a}$ is cyano, or $C_1$-$C_3$fluoroalkoxy.

20. The compound according to claim 17, wherein and $A_2$ is CH.

21. A method for the protection of plant propagation material from the attack by insects, acarines, nematodes or molluscs, which comprises treating the propagation material or the site, where the propagation material is planted, with an effective amount of the compound according to claim 1, or of a composition comprising said compound, one or more auxiliaries and diluent, and optionally one more other active ingredient.

22. A method of controlling parasites in or on an animal in need thereof comprising administering an effective amount of the compound according to claim 1, or of a composition comprising said compound, one or more auxiliaries and diluent, and optionally one more other active ingredient.

* * * * *